US010332623B2

(12) United States Patent
Edwards et al.

(10) Patent No.: US 10,332,623 B2
(45) Date of Patent: Jun. 25, 2019

(54) MEDICAMENT DELIVERY DEVICES WITH WIRELESS CONNECTIVITY AND EVENT DETECTION

(71) Applicant: kaleo, Inc., Richmond, VA (US)

(72) Inventors: Eric S. Edwards, Moseley, VA (US); Evan T. Edwards, Charlottesville, VA (US); Paul F. Meyers, Fishers, IN (US); Samuel Jefferson Briggs, London (GB); George McGee Perkins, Cambridge (GB); Eugene Johannes Van Wyk, Cambridge (GB); Mitchell Frederick Burke, Cambridge, MA (US); Eric William Scammell, Cambridge (GB)

(73) Assignee: kaleo, Inc., Richmond, VA (US)

( * ) Notice: Subject to any disclaimer, the term of this patent is extended or adjusted under 35 U.S.C. 154(b) by 0 days.

(21) Appl. No.: 15/872,162

(22) Filed: Jan. 16, 2018

(65) Prior Publication Data
US 2018/0204636 A1    Jul. 19, 2018

Related U.S. Application Data

(60) Provisional application No. 62/447,351, filed on Jan. 17, 2017, provisional application No. 62/559,066, filed on Sep. 15, 2017.

(51) Int. Cl.
*A61M 5/20* (2006.01)
*G16H 20/17* (2018.01)
*G16H 40/67* (2018.01)

(52) U.S. Cl.
CPC .............. *G16H 20/17* (2018.01); *G16H 40/67* (2018.01); *A61M 5/20* (2013.01); *A61M 5/2053* (2013.01);
(Continued)

(58) Field of Classification Search
CPC ...... A61M 5/31; A61M 5/008; A61M 5/1413; A61M 5/1452; A61M 5/20; A61M 5/32;
(Continued)

(56) References Cited

U.S. PATENT DOCUMENTS 2,960,087 A    11/1960   Uytenbogaart
3,055,362 A     9/1962   Uytenbogaart
(Continued)

FOREIGN PATENT DOCUMENTS

AU    2004231230       6/2006
EP     1287840 A1      3/2003
(Continued)

OTHER PUBLICATIONS

"Solutions for Medical Devices," 3M Brochure, ® 3M, (2006), 80-6201-3490-0, 8 pages.
(Continued)

*Primary Examiner* — Hoi C Lau
(74) *Attorney, Agent, or Firm* — ReavesColey PLLC

(57) ABSTRACT

A computer-implemented method includes establishing a communications link, via a short-range wireless protocol, between a mobile computing device and a medicament delivery device. A user input selecting a motion profile of the medicament delivery device is then received in response to an input prompt. A wireless signal is received from the medicament delivery device, the wireless signal associated with an actual motion profile of the medicament delivery device. A notification is produced to indicate a motion difference between the actual motion profile and the target motion profile. In some embodiments, the method optionally includes modifying the target motion profile based on the motion profile over a time period of at least one week, the notification indicating a motion difference between the motion profile and the modified target motion profile.

20 Claims, 70 Drawing Sheets

(52) U.S. Cl.
CPC .......... *A61M 2005/206* (2013.01); *A61M 2005/2013* (2013.01); *A61M 2005/2073* (2013.01); *A61M 2205/18* (2013.01); *A61M 2205/3368* (2013.01); *A61M 2205/3553* (2013.01); *A61M 2205/3569* (2013.01); *A61M 2205/3592* (2013.01); *A61M 2205/50* (2013.01); *A61M 2205/52* (2013.01); *A61M 2205/581* (2013.01); *A61M 2205/8206* (2013.01); *Y02A 90/26* (2018.01)

(58) Field of Classification Search
CPC .......... A61M 5/31528; A61M 5/14244; A61M 5/14; H04W 4/80; H04W 4/008; A61B 6/547; G06F 19/3468; G06F 3/167; G08B 21/185; G09B 9/00; G16H 20/17; A16M 2205/52; A16M 2205/3592; A16M 2205/3569; A16M 2205/3368; A16M 2205/18; A16M 2205/581; A16M 2205/3553
See application file for complete search history.

(56) References Cited

U.S. PATENT DOCUMENTS

| | | |
|---|---|---|
| 3,115,133 A | 12/1963 | Morando |
| 3,426,448 A | 2/1969 | Sarnoff |
| 3,688,765 A | 9/1972 | Gasaway |
| 3,768,472 A | 10/1973 | Hodosh et al. |
| 3,795,061 A | 3/1974 | Sarnoff et al. |
| 3,945,379 A | 3/1976 | Pritz et al. |
| 4,108,177 A | 8/1978 | Pistor |
| 4,226,235 A | 10/1980 | Sarnoff et al. |
| 4,360,019 A | 11/1982 | Portner et al. |
| 4,424,057 A | 1/1984 | House |
| 4,441,629 A | 4/1984 | Mackal |
| 4,484,910 A | 11/1984 | Sarnoff |
| 4,524,243 A | 6/1985 | Shapiro |
| 4,573,976 A | 3/1986 | Sampson et al. |
| 4,596,556 A | 6/1986 | Morrow et al. |
| 4,610,666 A | 9/1986 | Pizzino |
| 4,613,328 A | 9/1986 | Boyd |
| 4,617,557 A | 10/1986 | Gordon |
| 4,624,660 A | 11/1986 | Mijers et al. |
| 4,640,686 A | 2/1987 | Dalling et al. |
| 4,643,721 A | 2/1987 | Brunet |
| 4,666,430 A | 5/1987 | Brown et al. |
| 4,673,657 A | 6/1987 | Christian |
| 4,689,042 A | 8/1987 | Sarnoff et al. |
| 4,693,708 A | 9/1987 | Wanderer et al. |
| 4,781,697 A | 11/1988 | Slaughter |
| 4,782,841 A | 11/1988 | Lopez |
| 4,784,652 A | 11/1988 | Wikström |
| 4,795,433 A | 1/1989 | Sarnoff |
| 4,853,521 A | 8/1989 | Claeys et al. |
| 4,865,582 A | 9/1989 | Sibalis |
| 4,874,382 A | 10/1989 | Lindemann et al. |
| 4,894,054 A | 1/1990 | Miskinyar |
| 4,906,235 A | 3/1990 | Roberts |
| 4,915,695 A | 4/1990 | Koobs |
| 4,941,880 A | 7/1990 | Burns |
| 4,959,056 A | 9/1990 | Dombrowski et al. |
| 4,968,302 A | 11/1990 | Schluter et al. |
| 4,983,164 A | 1/1991 | Hook et al. |
| 5,000,736 A | 3/1991 | Kaufhold, Jr. et al. |
| 5,024,656 A | 6/1991 | Gasaway et al. |
| 5,037,306 A | 8/1991 | van Schoonhoven |
| 5,038,023 A | 8/1991 | Saliga |
| 5,041,088 A | 8/1991 | Ritson et al. |
| 5,062,603 A | 11/1991 | Smith et al. |
| 5,064,413 A | 11/1991 | McKinnon et al. |
| 5,071,353 A | 12/1991 | van der Wal |
| 5,085,642 A | 2/1992 | Sarnoff et al. |
| 5,092,843 A | 3/1992 | Monroe et al. |
| 5,125,898 A | 6/1992 | Kaufhold, Jr. et al. |
| 5,167,625 A | 12/1992 | Jacobsen et al. |
| 5,167,641 A | 12/1992 | Schmitz |
| 5,199,949 A | 4/1993 | Haber et al. |
| 5,224,936 A | 7/1993 | Gallagher |
| 5,240,146 A | 8/1993 | Smedley et al. |
| 5,281,198 A | 1/1994 | Haber et al. |
| 5,286,258 A | 2/1994 | Haber et al. |
| 5,298,023 A | 3/1994 | Haber et al. |
| 5,312,326 A | 5/1994 | Myers et al. |
| 5,314,412 A | 5/1994 | Rex |
| 5,314,502 A | 5/1994 | McNichols et al. |
| 5,343,519 A | 8/1994 | Feldman |
| 5,344,407 A | 9/1994 | Ryan |
| 5,354,284 A | 10/1994 | Haber et al. |
| 5,356,376 A | 10/1994 | Milijasevic et al. |
| 5,363,842 A | 11/1994 | Mishelevich et al. |
| 5,380,281 A | 1/1995 | Tomellini et al. |
| 5,383,851 A | 1/1995 | McKinnon, Jr. et al. |
| 5,394,866 A | 3/1995 | Ritson et al. |
| 5,399,163 A | 3/1995 | Peterson et al. |
| 5,405,362 A | 4/1995 | Kramer et al. |
| 5,417,660 A | 5/1995 | Martin |
| 5,466,217 A | 11/1995 | Myers et al. |
| 5,505,192 A | 4/1996 | Samiotes et al. |
| 5,514,135 A | 5/1996 | Earle |
| 5,544,647 A | 8/1996 | Jewett et al. |
| 5,558,679 A | 9/1996 | Tuttle |
| 5,567,160 A | 10/1996 | Massino |
| 5,568,555 A | 10/1996 | Shamir |
| 5,569,192 A | 10/1996 | van der Wal |
| 5,584,815 A | 12/1996 | Pawelka et al. |
| 5,610,992 A | 3/1997 | Hickman |
| 5,615,771 A | 4/1997 | Hollister |
| 5,616,132 A | 4/1997 | Newman |
| 5,642,731 A | 7/1997 | Kehr |
| 5,645,534 A | 7/1997 | Chanoch |
| 5,662,612 A | 9/1997 | Niehoff |
| 5,681,291 A | 10/1997 | Galli |
| 5,692,492 A | 12/1997 | Bruna et al. |
| 5,695,476 A | 12/1997 | Harris |
| 5,697,916 A | 12/1997 | Schraga |
| 5,716,338 A | 2/1998 | Hjertman et al. |
| 5,728,074 A | 3/1998 | Castellano et al. |
| 5,740,794 A | 4/1998 | Smith et al. |
| 5,752,235 A | 5/1998 | Kehr et al. |
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,346 A | 10/1998 | Weiner |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,905,653 A | 5/1999 | Higham et al. |
| 5,925,021 A | 7/1999 | Castellano et al. |
| 5,928,195 A | 7/1999 | Malamud |
| 5,941,857 A | 8/1999 | Nguyen et al. |
| 5,954,641 A | 9/1999 | Kehr et al. |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,002,781 A | 12/1999 | Takayama et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |

(56) References Cited

U.S. PATENT DOCUMENTS

| | | |
|---|---|---|
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,144,310 A | 11/2000 | Morris |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |
| 6,190,326 B1 | 2/2001 | McKinnon et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,249,717 B1 | 6/2001 | Nicholson et al. |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,285,757 B1 | 9/2001 | Carroll et al. |
| 6,297,737 B1 | 10/2001 | Irvin |
| 6,312,412 B1 | 11/2001 | Saied et al. |
| 6,317,630 B1 | 11/2001 | Gross et al. |
| 6,321,070 B1 | 11/2001 | Clark et al. |
| 6,321,654 B1 | 11/2001 | Robinson |
| 6,323,780 B1 | 11/2001 | Morris |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |
| 6,411,567 B1 | 6/2002 | Niemiec et al. |
| 6,413,236 B1 | 7/2002 | Van Dyke |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,482,185 B1 | 11/2002 | Hartmann |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 | 3/2003 | de la Huerga |
| 6,530,900 B1 | 3/2003 | Daily et al. |
| 6,530,904 B1 | 3/2003 | Edwards et al. |
| 6,535,714 B2 | 3/2003 | Melker et al. |
| 6,539,281 B2 | 3/2003 | Wan et al. |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,509 B1 | 5/2003 | Say |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,589,229 B1 | 7/2003 | Connelly et al. |
| 6,595,956 B1 | 7/2003 | Gross et al. |
| 6,597,794 B2 | 7/2003 | Cole et al. |
| 6,633,796 B1 | 10/2003 | Pool et al. |
| 6,641,566 B2 | 11/2003 | Douglas et al. |
| 6,645,171 B1 | 11/2003 | Robinson et al. |
| 6,645,181 B1 | 11/2003 | Lavi et al. |
| 6,648,850 B2 | 11/2003 | Landau |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,784,798 B2 | 8/2004 | Morris |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,945,961 B2 | 9/2005 | Miller et al. |
| 6,946,299 B2 | 9/2005 | Neel et al. |
| 6,949,082 B2 | 9/2005 | Langley et al. |
| 6,950,028 B2 | 9/2005 | Zweig |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,048,141 B2 | 5/2006 | Abdulhay |
| 7,072,738 B2 | 7/2006 | Bonney et al. |
| 7,074,211 B1 | 7/2006 | Heiniger et al. |
| 7,093,595 B2 | 8/2006 | Nesbitt |
| 7,102,526 B2 | 9/2006 | Zweig |
| 7,104,972 B2 | 9/2006 | Moller et al. |
| 7,113,101 B2 | 9/2006 | Peterson et al. |
| 7,116,233 B2 | 10/2006 | Zhurin |
| 7,118,553 B2 | 10/2006 | Scherer |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,299,981 B2 | 11/2007 | Hickle et al. |

(56) References Cited

U.S. PATENT DOCUMENTS

| | | |
|---|---|---|
| 7,343,914 B2 | 3/2008 | Abrams et al. |
| 7,351,223 B2 | 4/2008 | Call |
| 7,416,540 B2 | 8/2008 | Edwards et al. |
| 7,544,188 B2 | 6/2009 | Edwards et al. |
| 7,630,788 B1 | 12/2009 | Reese |
| 7,648,482 B2 | 1/2010 | Edwards et al. |
| 7,648,483 B2 | 1/2010 | Edwards et al. |
| 7,657,849 B2 | 2/2010 | Chaudhri et al. |
| 7,670,328 B2 | 3/2010 | Miller et al. |
| 7,682,155 B2 | 3/2010 | Raven et al. |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,871,393 B2 | 1/2011 | Monroe |
| 7,938,802 B2 | 5/2011 | Bicknell et al. |
| 7,947,017 B2 | 5/2011 | Edwards et al. |
| 8,021,344 B2 | 9/2011 | Edwards et al. |
| 8,123,719 B2 | 2/2012 | Edwards et al. |
| 8,149,111 B2 | 4/2012 | Monroe |
| 8,206,360 B2 | 6/2012 | Edwards et al. |
| 8,212,658 B2 | 7/2012 | Monroe |
| 8,226,610 B2 | 7/2012 | Edwards et al. |
| 8,229,392 B2 | 7/2012 | Bumiller et al. |
| 8,231,573 B2 | 7/2012 | Edwards et al. |
| 8,424,517 B2 | 4/2013 | Sutherland et al. |
| 8,544,645 B2 | 10/2013 | Edwards et al. |
| 8,556,865 B2 | 10/2013 | Krulevitch et al. |
| 8,556,867 B2 | 10/2013 | Krulevitch et al. |
| 8,627,816 B2 | 1/2014 | Edwards et al. |
| 8,639,288 B1 | 1/2014 | Friedman |
| 8,670,865 B2 | 3/2014 | Coe |
| 8,690,827 B2 | 4/2014 | Edwards et al. |
| 8,789,748 B2 | 6/2014 | Waugh et al. |
| 8,807,131 B1 | 8/2014 | Tunnell et al. |
| 8,849,449 B2 | 9/2014 | Waugh et al. |
| 8,910,299 B2 | 12/2014 | Michalske |
| 8,922,367 B2 | 12/2014 | Denny et al. |
| 8,926,594 B2 | 1/2015 | Edwards et al. |
| 8,939,943 B2 | 1/2015 | Edwards et al. |
| 9,022,980 B2 | 5/2015 | Edwards et al. |
| 9,035,765 B2 | 5/2015 | Engelhard et al. |
| 9,053,530 B2 | 6/2015 | Vik et al. |
| 9,084,849 B2 | 7/2015 | Edwards et al. |
| 9,173,999 B2 | 11/2015 | Edwards et al. |
| 9,179,260 B2 | 11/2015 | Ostrander et al. |
| 9,542,826 B2* | 1/2017 | Edwards .................. A61M 5/31 |
| 9,566,395 B2 | 2/2017 | Denny et al. |
| 9,643,770 B2 | 5/2017 | Denny et al. |
| 9,671,241 B2 | 6/2017 | Tang |
| 9,672,328 B2 | 6/2017 | Saint et al. |
| 9,836,948 B2* | 12/2017 | Edwards .................. A61M 5/31 |
| 9,911,308 B2* | 3/2018 | Edwards .................. A61M 5/31 |
| 2001/0005781 A1 | 6/2001 | Bergens et al. |
| 2002/0000225 A1 | 1/2002 | Schuler et al. |
| 2002/0016567 A1 | 2/2002 | Hochman et al. |
| 2002/0025267 A1* | 2/2002 | Lieber .................. A61M 5/1452 |
| | | 417/572 |
| 2002/0042596 A1 | 4/2002 | Hartlaub et al. |
| 2002/0072784 A1 | 6/2002 | Sheppard, Jr. et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1 | 7/2002 | Juselius |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0065536 A1 | 4/2003 | Hansen et al. |
| 2003/0106824 A1 | 6/2003 | Wilmot et al. |
| 2003/0120212 A1 | 6/2003 | Dedig et al. |
| 2003/0130853 A1 | 7/2003 | Maire |
| 2003/0132128 A1 | 7/2003 | Mazur |
| 2003/0135388 A1 | 7/2003 | Martucci et al. |
| 2003/0171717 A1 | 9/2003 | Farrugia et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0042596 A1 | 3/2004 | Kim et al. |
| 2004/0054327 A1 | 3/2004 | Gillespie, III |
| 2004/0069667 A1 | 4/2004 | Tomellini et al. |
| 2004/0078001 A1 | 4/2004 | Langley et al. |
| 2004/0084047 A1 | 5/2004 | Hickle |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0210199 A1 | 10/2004 | Atterbury et al. |
| 2004/0215369 A1 | 10/2004 | Rosenblum |
| 2004/0220524 A1 | 11/2004 | Sadowski et al. |
| 2004/0225255 A1 | 11/2004 | Ono |
| 2004/0249358 A1 | 12/2004 | McWethy et al. |
| 2004/0267204 A1 | 12/2004 | Brustowiez |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0150488 A1 | 7/2005 | Dave |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0190941 A1 | 9/2005 | Yang |
| 2005/0192530 A1 | 9/2005 | Castellano |
| 2005/0197654 A1 | 9/2005 | Edman et al. |
| 2005/0209558 A1 | 9/2005 | Marx |
| 2005/0209569 A1 | 9/2005 | Ishikawa et al. |
| 2005/0261742 A1 | 11/2005 | Nova et al. |
| 2005/0267403 A1 | 12/2005 | Landau et al. |
| 2005/0273059 A1 | 12/2005 | Mernoe et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0074519 A1 | 4/2006 | Barker et al. |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0169611 A1 | 8/2006 | Prindle |
| 2006/0169773 A1 | 8/2006 | Lyons et al. |
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0247578 A1 | 11/2006 | Arguedas et al. |
| 2006/0247579 A1 | 11/2006 | Friedman |
| 2006/0265186 A1 | 11/2006 | Holland et al. |
| 2007/0008113 A1 | 1/2007 | Spoonhower et al. |
| 2007/0074722 A1 | 4/2007 | Giroux et al. |
| 2007/0111175 A1 | 5/2007 | Raven et al. |
| 2007/0149954 A1 | 6/2007 | Hood et al. |
| 2007/0184847 A1 | 8/2007 | Hansen et al. |
| 2007/0186923 A1 | 8/2007 | Poutiatine et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0239140 A1 | 10/2007 | Checheiski et al. |
| 2007/0260210 A1 | 11/2007 | Conroy |
| 2007/0285238 A1 | 12/2007 | Batra |
| 2007/0285258 A1 | 12/2007 | Hartman |

(56) References Cited

U.S. PATENT DOCUMENTS

| | | |
|---|---|---|
| 2008/0097311 A1 | 4/2008 | Dacquay et al. |
| 2008/0111685 A1 | 5/2008 | Olson et al. |
| 2008/0160492 A1 | 7/2008 | Campbell et al. |
| 2008/0228143 A1 | 9/2008 | Stamp |
| 2008/0230057 A1 | 9/2008 | Sutherland |
| 2008/0234625 A1 | 9/2008 | Dacquay et al. |
| 2009/0030285 A1 | 1/2009 | Andersen |
| 2009/0062728 A1 | 3/2009 | Woo |
| 2009/0067973 A1* | 3/2009 | Eliuk .................. B66C 1/42 414/729 |
| 2009/0069787 A1* | 3/2009 | Estes .................. A61M 5/1413 604/503 |
| 2009/0131875 A1 | 5/2009 | Green |
| 2009/0143761 A1 | 6/2009 | Cantor et al. |
| 2009/0194104 A1 | 8/2009 | Van Sickle |
| 2009/0299156 A1 | 12/2009 | Simpson et al. |
| 2010/0111066 A1 | 5/2010 | Mehta |
| 2010/0169111 A1 | 7/2010 | Brue et al. |
| 2010/0192948 A1 | 8/2010 | Sutherland et al. |
| 2010/0211005 A1 | 8/2010 | Edwards et al. |
| 2010/0214095 A1 | 8/2010 | Davide |
| 2010/0250280 A1 | 9/2010 | Sutherland |
| 2010/0250697 A1 | 9/2010 | Hansen et al. |
| 2010/0267357 A1 | 10/2010 | Holmstrom et al. |
| 2010/0268303 A1 | 10/2010 | Mitchell et al. |
| 2010/0286612 A1 | 11/2010 | Cirillo |
| 2011/0046698 A1 | 2/2011 | Kivi et al. |
| 2011/0144574 A1 | 6/2011 | Kamen et al. |
| 2011/0264033 A1 | 10/2011 | Jensen et al. |
| 2011/0295215 A1 | 12/2011 | Nielsen et al. |
| 2012/0001750 A1* | 1/2012 | Monroe .................. A61M 5/002 340/539.11 |
| 2012/0015335 A1 | 1/2012 | Smith et al. |
| 2012/0046613 A1 | 2/2012 | Plumptre |
| 2012/0052837 A1 | 3/2012 | Reich et al. |
| 2012/0071819 A1 | 3/2012 | Bruggemann et al. |
| 2012/0081225 A1 | 4/2012 | Waugh et al. |
| 2012/0083666 A1 | 4/2012 | Waugh et al. |
| 2012/0101444 A1 | 4/2012 | Muller-Pathle et al. |
| 2012/0107783 A1 | 5/2012 | Julian et al. |
| 2012/0165747 A1 | 6/2012 | Lanin et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2013/0072897 A1 | 3/2013 | Day et al. |
| 2013/0079708 A1 | 3/2013 | Wimpenny et al. |
| 2013/0079725 A1 | 3/2013 | Shang et al. |
| 2013/0110050 A1 | 5/2013 | Boyd et al. |
| 2013/0131601 A1 | 5/2013 | Pommereau et al. |
| 2013/0138040 A1 | 5/2013 | Weinandy |
| 2013/0138444 A1 | 5/2013 | George |
| 2013/0151162 A1 | 6/2013 | Harris et al. |
| 2013/0236872 A1 | 9/2013 | Laurusonis et al. |
| 2013/0266919 A1 | 10/2013 | Baker et al. |
| 2014/0004808 A1 | 1/2014 | Li et al. |
| 2014/0082501 A1* | 3/2014 | Bae .................. G06F 3/167 715/728 |
| 2014/0155827 A1 | 6/2014 | Ostrander et al. |
| 2014/0207099 A1* | 7/2014 | Nagar .................. A61M 5/14244 604/503 |
| 2014/0243749 A1* | 8/2014 | Edwards .................. A61M 5/31 604/187 |
| 2014/0276385 A1 | 9/2014 | Baker et al. |
| 2014/0296824 A1 | 10/2014 | Edwards et al. |
| 2014/0354998 A1 | 12/2014 | Bock et al. |
| 2014/0371714 A1 | 12/2014 | Edwards et al. |
| 2014/0379874 A1 | 12/2014 | Starr et al. |
| 2015/0045729 A1 | 2/2015 | Denzer et al. |
| 2015/0051538 A1* | 2/2015 | Hata .................. A61M 5/20 604/67 |
| 2015/0112707 A1 | 4/2015 | Manice et al. |
| 2015/0196711 A1 | 7/2015 | Edwards et al. |
| 2015/0202367 A1 | 7/2015 | Plaschkes et al. |
| 2015/0208981 A1* | 7/2015 | Oh .................. G01R 33/283 600/411 |
| 2015/0294551 A1* | 10/2015 | Edwards .................. A61M 5/31 340/635 |
| 2016/0012205 A1* | 1/2016 | Saint .................. A61M 5/31528 604/154 |
| 2016/0021470 A1* | 1/2016 | Gustafsson .......... H04R 25/558 381/315 |
| 2016/0121056 A1 | 5/2016 | Edwards et al. |
| 2016/0129182 A1 | 5/2016 | Schuster et al. |
| 2016/0157816 A1 | 6/2016 | Denny |
| 2016/0166768 A1 | 6/2016 | Edwards et al. |
| 2016/0184535 A1 | 6/2016 | Edwards et al. |
| 2016/0235916 A1 | 8/2016 | Edwards et al. |
| 2016/0256639 A1* | 9/2016 | Van Sickle .......... A61M 15/008 |
| 2016/0296716 A1* | 10/2016 | Cabiri .................. A61M 5/20 |
| 2016/0320210 A1* | 11/2016 | Nelson .................. A61B 5/062 |
| 2016/0342748 A1 | 11/2016 | Gulfo et al. |
| 2017/0049954 A1 | 2/2017 | Edwards et al. |
| 2017/0068799 A1 | 3/2017 | Mesinger et al. |
| 2017/0092101 A1* | 3/2017 | Edwards .................. A61M 5/31 |
| 2017/0109498 A1* | 4/2017 | Childress ............ G06F 19/3462 |
| 2017/0196771 A1 | 7/2017 | Hooven et al. |
| 2017/0270276 A1 | 9/2017 | Saint et al. |
| 2018/0028142 A1* | 2/2018 | Bhatia .................. A61B 6/547 |
| 2018/0028755 A1 | 2/2018 | Philip et al. |
| 2018/0033286 A1* | 2/2018 | Edwards .................. A61M 5/31 |
| 2018/0102066 A1 | 4/2018 | Edwards et al. |
| 2018/0110923 A1* | 4/2018 | Kaplan .................. A61K 31/485 |
| 2018/0151053 A1* | 5/2018 | Edwards .................. A61M 5/31 |
| 2018/0204636 A1* | 7/2018 | Edwards .................. G16H 20/17 |
| 2018/0289901 A1* | 10/2018 | Boggild-Damkvist .................. A61M 5/427 |

FOREIGN PATENT DOCUMENTS

| | | |
|---|---|---|
| EP | 1712178 A2 | 10/2006 |
| EP | 1095668 | 4/2007 |
| EP | 1777984 A1 | 4/2007 |
| EP | 1883268 A2 | 1/2008 |
| WO | WO 93/02720 | 2/1993 |
| WO | WO 95/26009 | 9/1995 |
| WO | WO 96/25965 | 8/1996 |
| WO | WO 98/52632 | 11/1998 |
| WO | WO 99/07425 | 2/1999 |
| WO | WO 99/10031 | 3/1999 |
| WO | WO 99/43283 | 9/1999 |
| WO | WO 2001/003758 | 1/2001 |
| WO | WO 2001/024690 | 4/2001 |
| WO | WO 2001/026020 | 4/2001 |
| WO | WO 2001/088828 | 11/2001 |
| WO | WO 2001/093926 | 12/2001 |
| WO | WO 2003/095001 | 11/2003 |
| WO | WO 2004/022138 | 3/2004 |
| WO | WO 2005/050526 | 6/2005 |
| WO | WO 2005/074790 | 8/2005 |
| WO | WO 2006/045525 | 5/2006 |
| WO | WO 2006/109778 | 10/2006 |
| WO | WO 2006/123956 | 11/2006 |
| WO | WO 2006/125692 | 11/2006 |
| WO | WO 2007/087304 | 8/2007 |
| WO | WO 2008/005315 | 1/2008 |
| WO | WO 2008/008451 | 1/2008 |
| WO | WO 2008/148864 | 12/2008 |
| WO | WO 2010/114392 | 10/2010 |
| WO | WO 2012/063172 | 5/2012 |
| WO | WO 2013/033467 A1 | 3/2013 |
| WO | WO 2013/043063 | 3/2013 |
| WO | WO 2013/154954 | 10/2013 |
| WO | WO 2013/164628 A1 | 11/2013 |
| WO | WO 2014/008393 A1 | 1/2014 |
| WO | WO 2014/036308 A2 | 3/2014 |
| WO | WO 2014/089083 A1 | 6/2014 |
| WO | WO 2014/116987 A1 | 7/2014 |
| WO | WO 2014/143815 A2 | 9/2014 |
| WO | WO 2014/144096 A1 | 9/2014 |
| WO | WO 2015/044112 A1 | 4/2015 |
| WO | WO 2016/151042 A1 | 9/2016 |

(56) References Cited

FOREIGN PATENT DOCUMENTS

| WO | WO 2016/210404 | 12/2016 |
|----|----------------|---------|
| WO | WO 2017/013463 | 1/2017  |
| WO | WO 2017/013464 | 1/2017  |
| WO | WO 2017/132577 | 8/2017  |
| WO | WO 2017/178865 | 10/2017 |
| WO | WO 2018/013419 | 1/2018  |

OTHER PUBLICATIONS

Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint&ArticleID=CA6332947>, 3 pages.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.

"Flexible circuits capabilities of Flexible Technology Limited," Our Flexible Circuits Capabilities [online] Retrieved from the internet <URL: http://www.flexibletechnology.com/Flexible circuitsCapabilit.htm >, 2 pages.

"Flex Circuits/flexible circuits design guide", [online] [retrieved on Aug. 28, 2006] Retrieved from the Internet URL: http://flexiblecircuit.co.uk/Flex Circuits Design Guide.htm >, 7 pages.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.

"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.

Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.

RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.

"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8, 3 pages.

Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.

Heartsine Technology, samaritan™ Pad Accessories [online] [retrieved on Jun. 1, 2007] Retrieved from the Internet <URL: http://www.heartsine.com/aboutsam-accessories.htm>, 4 pages.

CliniSense Corporation, "Drug delivery devices A potentially harsh environment for drugs," Stability [online] [retrieved on Jun. 1, 2007] Retrieved from the Internet <URL: http://www.clinisense.com/devices.htm>, 2 pages.

CliniSense Corporation, "LifeTrack Technology A new method to detect improper storage." Stability [online] [retrieved on Jun. 1, 2007] Retrieved from the Internet <URL: http://www.clinisense.com/tech.htm>, 2 pages.

AED Professionals™ Brochure [online] [retrieved on Jun. 1, 2007] Retrieved from the Internet <URL: http://www.aedprofessionals.com>, 4 pages.

Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-.

Meridian Medical Technologies, Inc., "Pralidoxime Chloride Trainer," 2006. [retrieved on Feb. 16, 2007] Retrieved from the Internet <URL: http://www.meridianmeds.com/auto-injectors/2pamcl_trainer.html/>, 1 pages.

Gosbee, L. L., "Nuts! I Can't Figure Out How to Use My Life-Saving Epinephrine Auto-Injector," Joint Commision Journal on Quality and Safety, 30(4):220-223 (Apr. 2004).

Amgen, "Using Aranesp prefilled SureClick autoinjector is a simple 3-step process," 2006. [retrieved on Feb. 16, 2007] Retrieved from the Internet <URL: http://www.aranesp.com/patient/cia/sureclick/using_three_steps.jsp/>, 4 pages.

Apple, Inc., "Bluetooth Accessory Design Guidelines for Apple Products," Release R7, (Sep. 18, 2013), 40 pages.

Stuart, M., "Cellnovo's Mobile Health Approach to Diabetes Care," In Vivo: The Business & Medicine Report, (Dec. 2010), pp. 40-44.

Knapp, Louise. "A Easter Way to Call 911," Wired.com [online], [retrieved Jul. 26, 2017] Retrieved from the Internet <https://www.wired.com/2001/03/a-faster-way-to-call-911> (Mar. 10, 2001), 9 pages.

Libov, Charlotte. "EpiPen 101," Everyday Health [online], [retrieved Jul. 26, 2017] Retrieved from the Internet <http://www.everydayhealth.com/allergy/epipen-101.aspx> (Feb. 23, 2012), 2 pages.

Enable Injections. "Enable Connections: A Bluetooth-Connected Wearable, On-Body Injector," OnDrugDelivery Magazine, Retrieved from the Internet <http://www.ondrugdelivery.com> (Jun. 21, 2016), 4 pages.

International Search Report and Written Opinion for International Patent Application No. PCT/US2006/051612, dated Dec. 9, 2008, 7 pages.

Office Action for U.S. Appl. No. 13/550,999, dated Apr. 18, 2014, 17 pages.

International Search Report and Written Opinion for International Patent Application No. PCT/US2013/078071, dated May 6, 2014, 19 pages.

International Preliminary Report on Patentability for International Patent Application No. PCT/US2013/077996, dated Jun. 30, 2015.

Search Report for European Patent Application No. 13868849.4, dated Aug. 5, 2016.

Search Report for European Patent Application No. 13867489.0, dated Jan. 4, 2017.

Office Action for U.S. Appl. No. 14/142,287, dated Apr. 6, 2017.

Office Action for Australia Patent Application No. 2015249064, dated Aug. 25, 2017.

International Search Report and Written Opinion for International Application No. PCT/US2018/013855, dated Jul. 5, 2018.

* cited by examiner

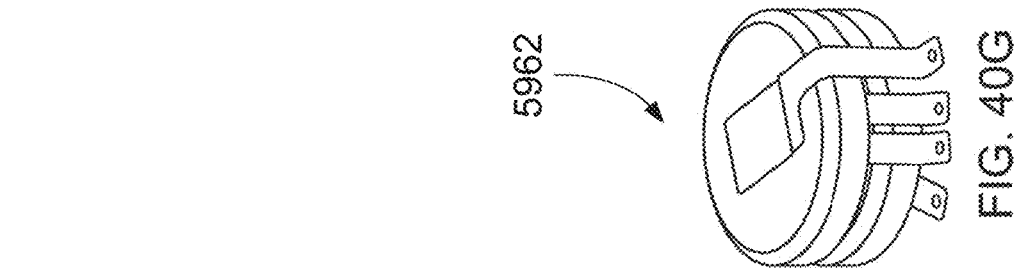
FIG. 40G
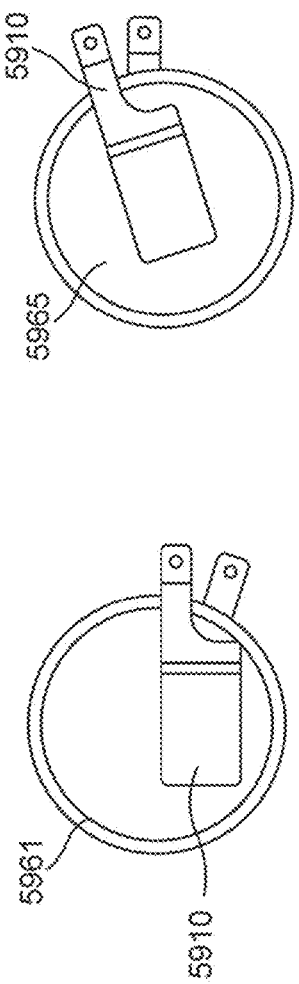
FIG. 40B
FIG. 40D
FIG. 40F
FIG. 40A
FIG. 40C
FIG. 40E

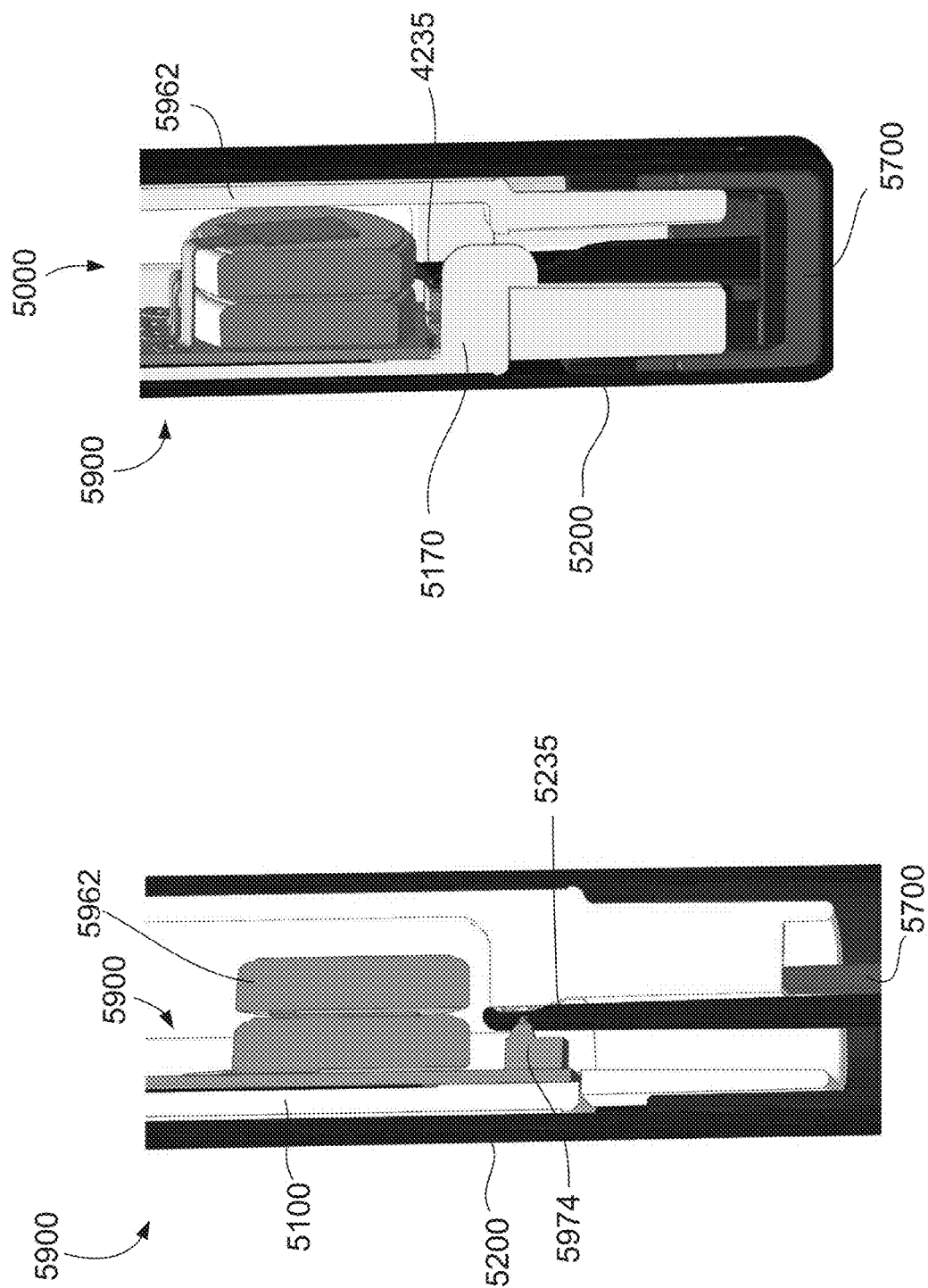

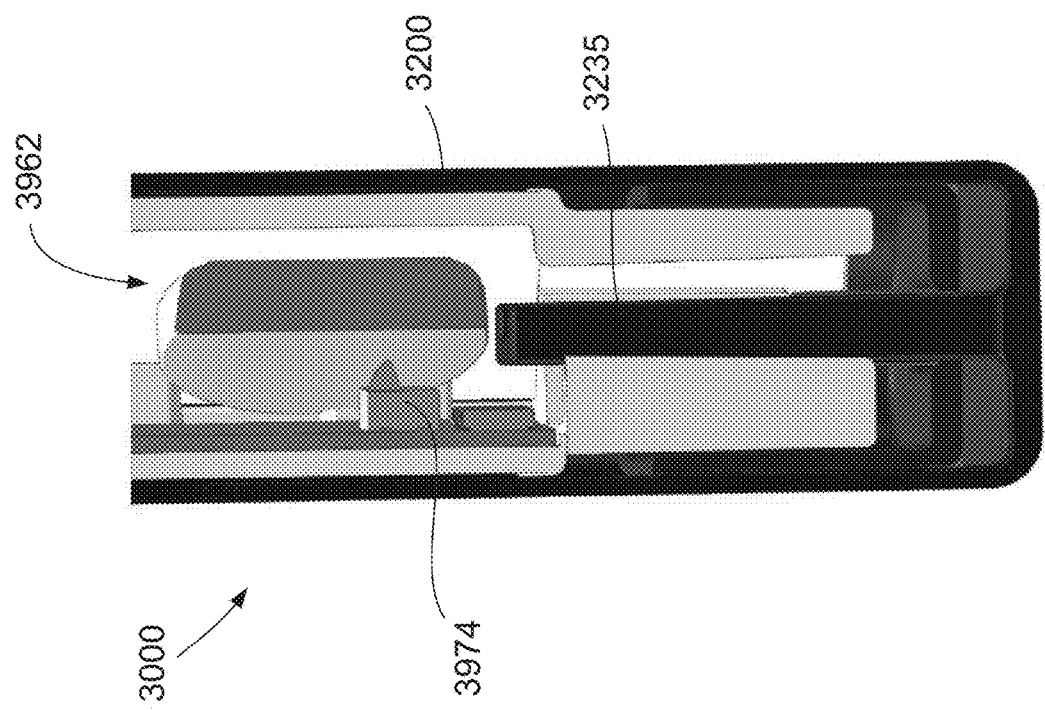
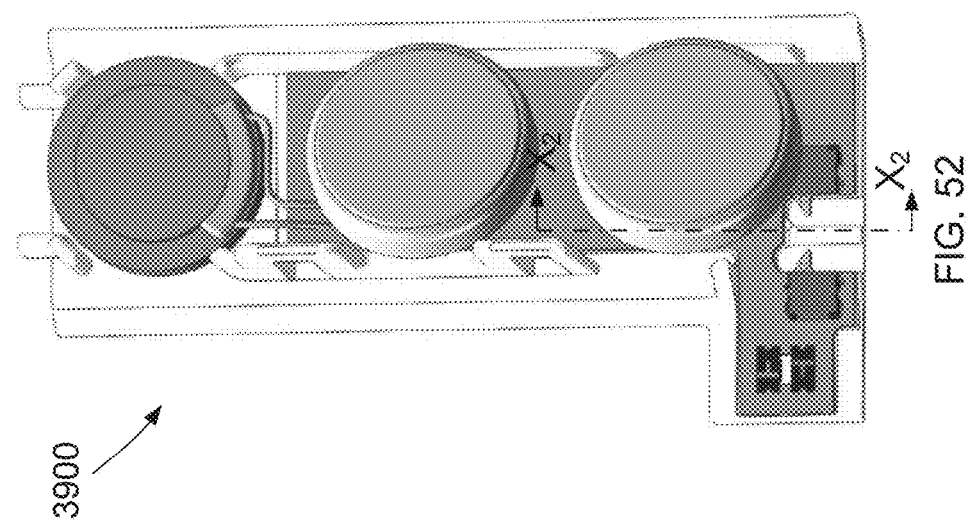

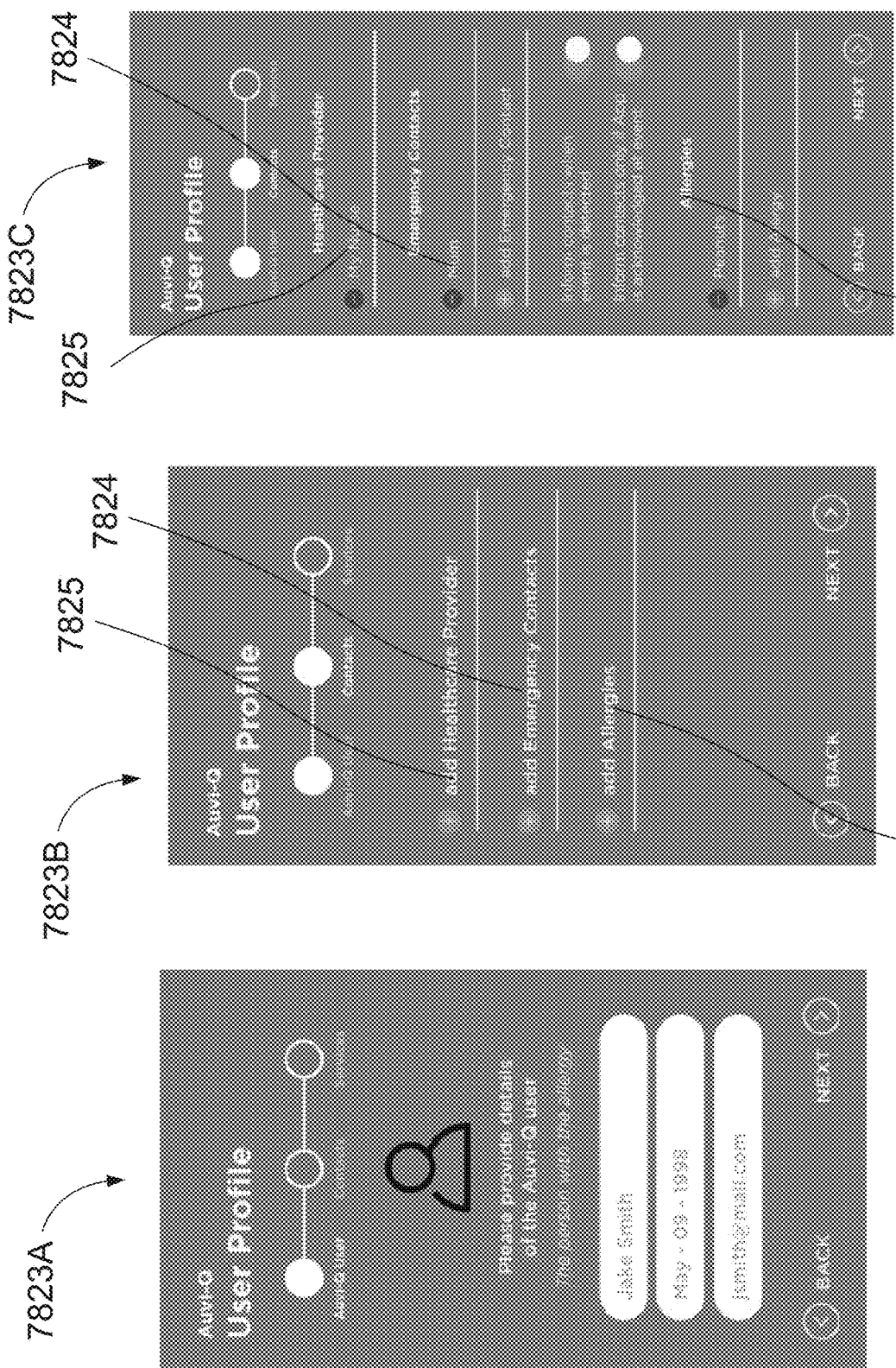

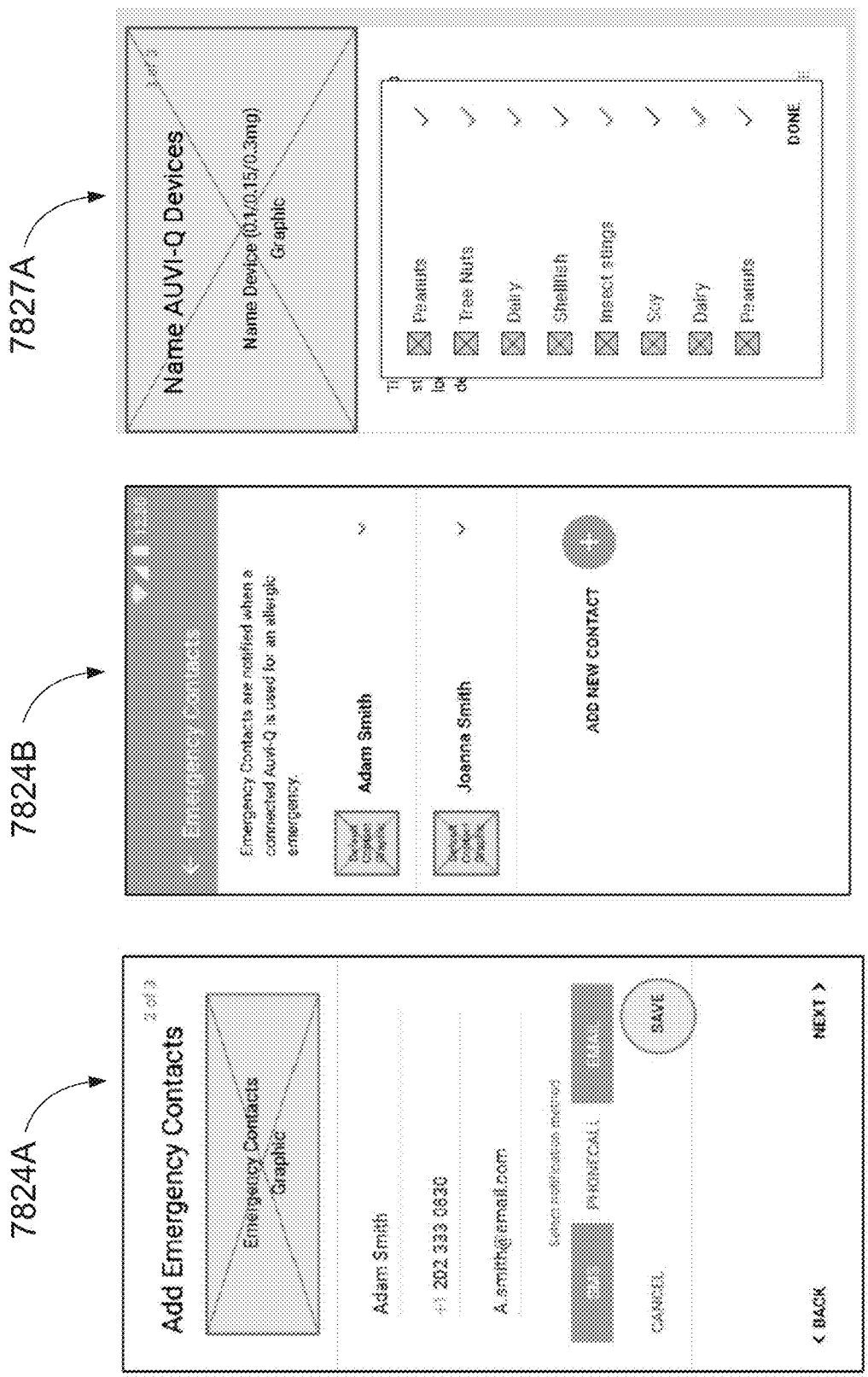

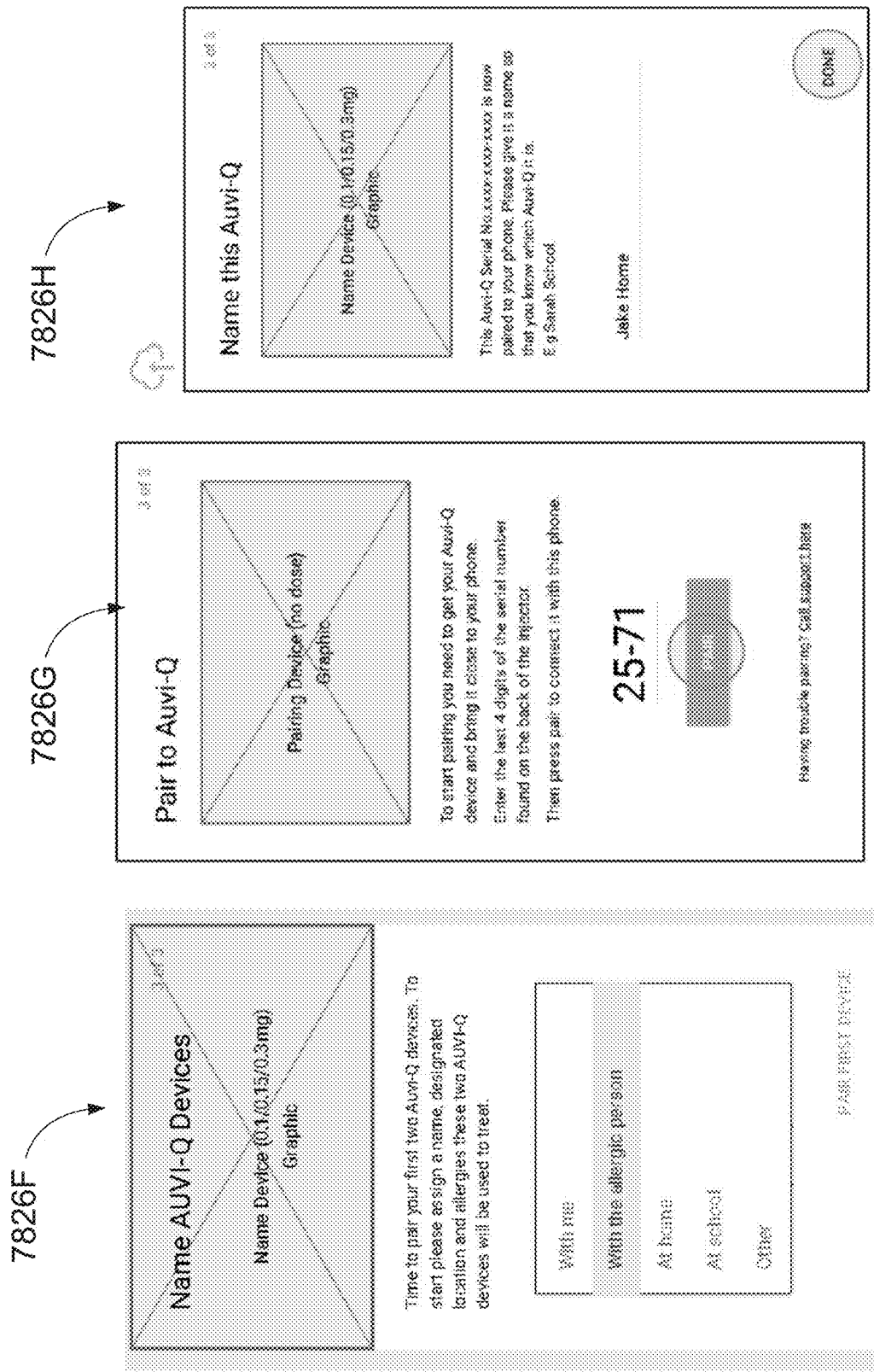

MEDICAMENT DELIVERY DEVICES WITH WIRELESS CONNECTIVITY AND EVENT DETECTION

CROSS-REFERENCE TO RELATED APPLICATIONS

This application claims benefit of priority to U.S. Provisional Application Ser. No. 62/447,351, entitled "Medicament Delivery Devices with Wireless Connectivity and Event Detection," filed Jan. 17, 2017, and U.S. Provisional Application Ser. No. 62/559,066, entitled "Medicament Delivery Devices with Wireless Connectivity and Event Detection," filed Sep. 15, 2017, each of which is incorporated herein by reference in its entirety.

BACKGROUND

The embodiments described herein relate generally to a medical device, and more particularly to a medicament delivery device, and/or a simulated medicament delivery device having wireless connectivity and/or the capability to detect a delivery event. The embodiments described herein also relate to devices for interacting with and/or monitoring (e.g., wirelessly) with such medicament delivery devices and/or simulated medicament delivery devices via a wireless communication module.

Exposure to certain substances, such as, for example, peanuts, shellfish, bee venom, certain drugs, toxins, and the like, can cause allergic reactions in some individuals. Such allergic reactions can, at times, lead to anaphylactic shock, which can cause a sharp drop in blood pressure, hives, and/or severe airway constriction. Accordingly, responding rapidly to mitigate the effects from such exposures can prevent injury and/or death. For example, in certain situations, an injection of epinephrine (i.e., adrenaline) can provide substantial and/or complete relief from the allergic reaction. In other situations, for example, an injection of an antidote to a toxin can greatly reduce and/or eliminate the harm potentially caused by the exposure. Because emergency medical facilities may not be available when an individual is suffering from an allergic reaction, some individuals carry a medicament delivery device, such as, for example, an auto-injector, to rapidly self-administer a medicament in response to an allergic reaction.

As another example, naloxone is a medicament that prevents and/or reverses the life-threatening breathing effects of opioids. Known formulations of naloxone can be used, for example, to treat respiratory depression and other indications that result from opioid toxicity. For example, known formulations for naloxone can be used to reverse and/or mitigate the effects of an overdose of a drug containing opioids, such as, for example, prescription opioids like oxycodone or illicit opiates like heroin. In such situations, it is desirable to deliver the naloxone formulation quickly and in a manner that will produce a rapid onset of action. Known methods for delivering naloxone intranasally or via injection, however, often involve completing a series of operations that, if not done properly, can limit the effectiveness of the naloxone formulation. Moreover, because naloxone is often administered during an emergency situation, even experienced and/or trained users may be subject to confusion and/or panic, thereby compromising the delivery of the naloxone formulation.

As yet another example, glucagon is a medicament that is administered to treat patients suffering from hypoglycemia. In certain situations, the onset of hypoglycemia can cause the patient to lose motor coordination and/or lose consciousness. Thus, glucagon is often administered by a care-giver during an emergency situation.

In the above-identified examples, the individual requiring the medicament may be inexperienced and/or may infrequently require medical intervention (e.g., in the case of a naloxone delivery device), and thus may be forget to carry the medicament delivery device and/or forget how to use the delivery device. For example, to actuate some known auto-injectors, the user may be required to execute a series of operations. For example, to actuate some known auto-injectors, the user must remove a protective cap, remove a locking device, place the auto-injector in a proper position against the body and then press a button to actuate the auto-injector. Failure to complete these operations properly can result in an incomplete injection and/or injection into an undesired location of the body. If the medicament delivery device is not available or if the individual is unable to properly operate the medicament delivery device, important medical aid may not be properly delivered.

The likelihood of improper use of known medicament delivery devices can be compounded by the nature of the user and/or the circumstances under which such devices are used. For example, many users are not trained medical professionals and may have never been trained in the operation of such devices. Moreover, in certain situations, the user may not be the patient, or primary care-giver, and may therefore have no experience with the medicament delivery device. Similarly, because some known medicament delivery devices are configured to be used relatively infrequently in response to an allergic reaction or other medical emergency, even those users familiar with a device and/or who have been trained may not be well practiced at operating the device. Finally, such devices are often used during an emergency situation, during which even experienced and/or trained users may be subject to confusion, panic, and/or the physiological effects of the condition requiring treatment.

Additionally, or alternatively, the individual requiring the medicament may be incapacitated and unable to inform bystanders of the nature of the medical emergency, that a medicament delivery device is available, and/or how to use the medicament delivery device. If bystanders remain unaware of the availability and location of the medicament delivery device, or are unable to administer the medicament, important medical aid may not be delivered. To enhance the likelihood of proper use, some known medicament delivery devices include printed instructions to inform the user of the steps required to properly deliver the medicament. Such printed instructions, however, can be inadequate for the class of users and/or the situations described above. Moreover, because some known medicament delivery devices, such as, for example, auto-injectors, pen injectors, nasal delivery systems, wearable injectors or bolus pumps, transdermal delivery systems, inhalers or the like, can be compact, such printed instructions may be too small to read and comprehend during a situation requiring the need for immediate and accurate administration.

Furthermore, some known medicament delivery devices, such as, for example, auto-injectors, pen injectors, inhalers, nasal delivery systems, and/or simulated medicament delivery devices are configured to be carried with the user. Although such devices may improve the likelihood of compliance, such portable devices can exacerbate the shortcomings described above (e.g., inadequate instructions for use). Additionally, because such portable devices are small, there is an increased likelihood that such devices will be forgotten and/or misplaced. Moreover, the cost and size constraints of known devices prevents the inclusion of more detailed features to address the shortcomings described herein. As one example, such portable medicament delivery devices may have limited space for electronics. For example, unlike stationary devices, such as infusion pumps and the like, compact medicament delivery devices may have insufficient space for full-scale computational devices, such as general purpose processors, large form-factor printed circuit boards, and the like.

In addition to the issues relating to improper use of medicament delivery devices, monitoring the patient's compliance with known medicament delivery devices can also be problematic. For example, many children carry an auto-injector to deliver epinephrine in the event of an allergic reaction. Known epinephrine auto-injectors, however, do not provide robust mechanisms (or communication systems) for alerting a parent or caregiver when the child has enabled and/or used the auto-injector. For example, some known systems produce a notification when an auto-injector is removed from a case. Although this information can be helpful, it does not provide any confirmation of actual use of the device (i.e., delivery of the medicament). Additionally, simply providing an alert upon opening a container and/or removing an auto-injector can result numerous "false positives" when a user simply opens the container and/or removes the device in a situation unrelated to an actual emergency.

Moreover, known auto-injectors do not provide a suitable mechanism (or communication systems) for alerting the parent or caregiver when the child is not carrying (or within a suitable range of) the auto-injector or provide associated information related to ensuring the device is kept on or with a user at all times. For example, although some known systems produce a notification when an auto-injector is not within a predetermined distance from the user's phone, such known systems do not accommodate different usage patterns for different devices that may be owned by the user. For example, know compliance tracking systems do not differentiate between a device that is typically carried with the user and a device that is stored at a predetermined location (e.g., an auto-injector maintained at school or work).

Some known treatment regimens include multiple doses of a medicament that must be administered in a timely fashion and/or in a particular order to ensure effectiveness, especially in more chronic diseases (e.g., insulin for diabetes, certain biologic therapies for inflammatory conditions or certain vaccination regimens). Thus, in addition to alerting a caregiver in an emergency situation, monitoring the patient's adherence to a medication regimen is an important aspect in ensuring that the treatment method will be both safe and effective. Some known medicament delivery systems include a medicament delivery device and an accompanying electronic system to assist the user in setting the proper dosage and/or maintaining a compliance log. Such known medicament delivery systems and the accompanying electronic systems can be large and therefore not conveniently carried by the user. Such known medicament delivery systems and the accompanying electronic systems can also be complicated to use and/or expensive to manufacture.

In addition, an extended shelf life may be desirable for some medicament delivery devices, such as devices intended to be carried by a user on a daily basis. For example, an auto-injector intended to be carried by a user on a daily basis may be expected to work after weeks, months, or years without user maintenance. As another example, known emergency-use auto-injectors are single-use devices that are expected to be carried for years before a potential use. The disposable nature and/or extended shelf-life of such devices can further exacerbate the shortcomings described above. For example, the electronics of known stationary devices, particularly known devices having electronic communication means (e.g., for compliance tracking), may not be efficient enough to provide sufficiently long battery life for use in a portable, extended shelf life device. Furthermore, efficient power management may be desirable to extend the useful life of a medicament delivery device, particularly for a device having limited battery capacity, limited or no user replaceable batteries, and/or limited or no charging capacity.

As another way to enhance the likelihood of proper use, some known medicament delivery devices are associated with simulated medicament delivery devices (e.g., "trainers") to provide a method for users to practice using the medicament delivery device without being exposed to the medicament and/or needles typically contained therein. Such simulated medicament delivery devices, however, can also include inadequate use instructions as described above.

Thus, a need exists for medicament delivery systems and/or devices that allow a medicament delivery device to be quickly identified and located, alert the user if the medicament delivery device is forgotten, and provide instructions that can be easily understood by a user in any type of situation. Additionally, a need exists for simulated medicament delivery systems and/or devices that can provide instructions and that can be reused multiple times. Moreover, a need exists for medicament delivery systems and/or devices that can provide compliance information associated with the use of the device and/or that can communicate electronically with other communications devices.

SUMMARY

System and methods to facilitate wireless communications with medicament delivery devices and simulated medicament delivery devices are described herein. In some embodiments, a method includes receiving a signal associated with a characteristic of an actuation event of a medicament delivery device. The method includes sending a wireless signal in response to the receiving of the signal.

In some embodiments, a computer-implemented method includes establishing a communications link, via a short-range wireless protocol, between a mobile computing device and a medicament delivery device. A user input selecting a motion profile of the medicament delivery device is then received in response to an input prompt. A wireless signal is received from the medicament delivery device, the wireless signal associated with an actual motion profile of the medicament delivery device. A notification is produced to indicate a motion difference between the actual motion profile and the target motion profile. In some embodiments, the method optionally includes modifying the target motion profile based on the motion profile over a time period of at least one week, the notification indicating a motion difference between the motion profile and the modified target motion profile.

BRIEF DESCRIPTION OF THE DRAWINGS

FIGS. 40A-40G shows various views of a battery assembly of the electronic circuit system shown in FIG. 36.

FIGS. 41 and 42 are cross-sectional views of the medical injector shown in FIG. 35 and taken along the line $X_1$-$X_1$ and the line $X_2$-$X_2$, respectively, showing portions of the electronic circuit system.

FIG. 52 is a top view of the electronic circuit system shown in FIG. 50.

FIG. 53 is a cross-sectional view of a portion of the electronic circuit system shown in FIG. 50 within a medicament delivery device, taken along line $X_2$-$X_2$ in FIG. 52.

FIGS. 63-67 depict graphical user interface elements produced in connection with a method of establishing a connected health medicament delivery system, according to an embodiment.

FIGS. 68-75 depict graphical user interface elements produced in connection with a method of establishing a connected health medicament delivery system, according to an embodiment.

FIGS. 76-84 depict graphical user interface elements produced in connection with a method of connecting a medicament delivery device to a connected health medicament delivery system, according to an embodiment.

DETAILED DESCRIPTION

Figure 1:
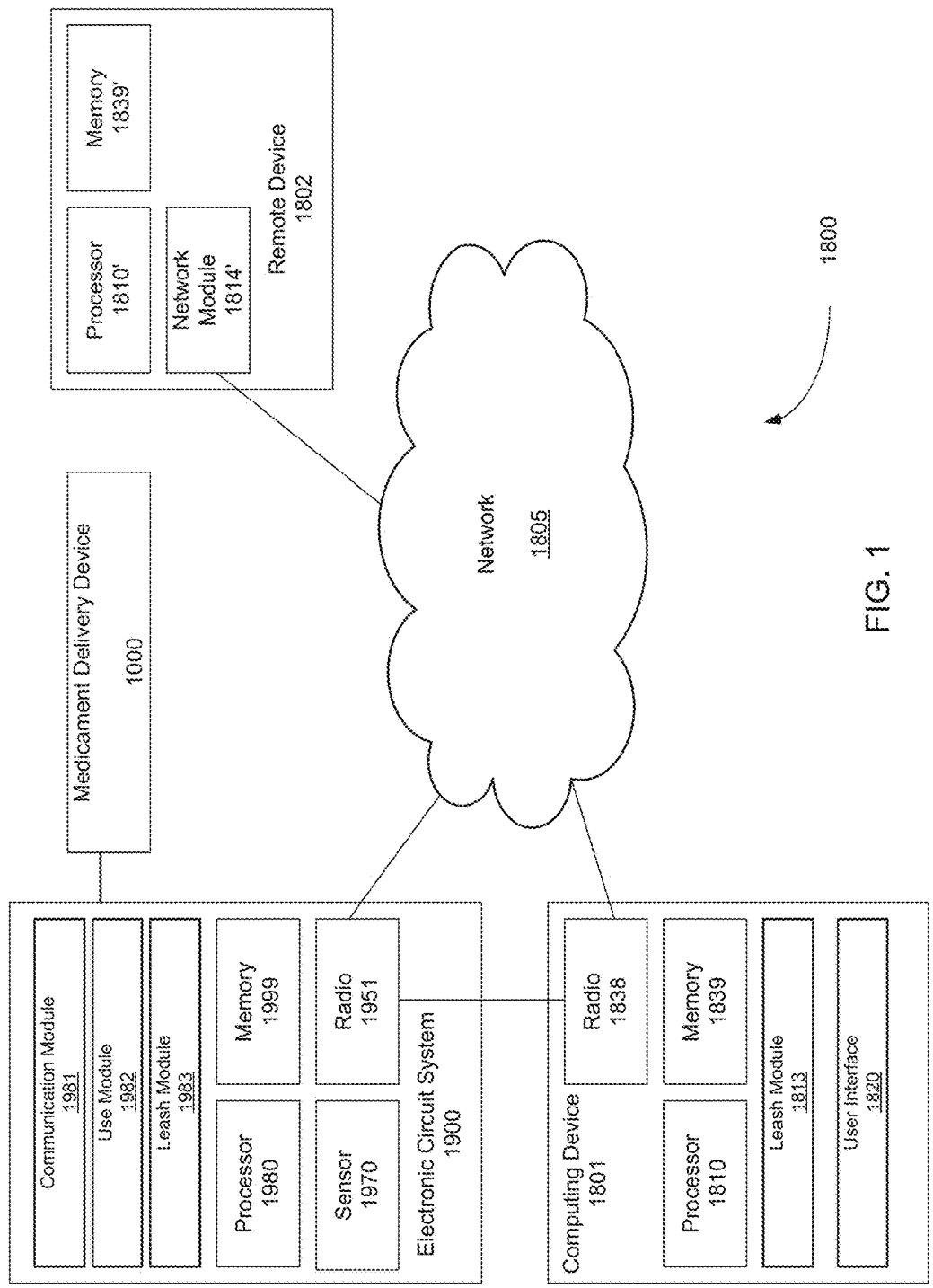
FIG. 1 is a schematic illustration of medicament delivery system according to an embodiment of the invention.

This application describes devices that are related to and/or can be used with the devices and systems described in U.S. Pat. No. 8,172,082, entitled "Devices Systems and Methods for Medicament Delivery," filed Feb. 5, 2007, U.S. Pat. No. 8,231,573, entitled "Medicament Delivery Device Having an Electronic Circuit System," filed May 12, 2008, and U.S. Pat. No. 8,361,026, entitled Apparatus and Methods for Self-Administration of Vaccines and Other Medicaments," filed Nov. 10, 2009, each of which is incorporated herein by reference in its entirety.

The medicament delivery systems shown and described herein, including any of the service delivery architectures described herein, can be used in conjunction with any suitable medicament delivery device and/or medicament container such that the medicament delivery device and/or medicament container can be easily accessed, identified, located and used, as described herein. In some embodiments, the medicament delivery device can be a medical injector (such as a pen injector, a prefilled syringe, or an auto-injector), an inhaler, a nasal delivery device or the like.

In some embodiments, an apparatus includes a medicament delivery device and an electronic circuit system. The electronic circuit system includes a radio such that the apparatus can be electronically linked to a computing device using a wireless protocol. The medicament delivery device can have a first configuration and a second configuration. The radio can send a signal characterized by a first communication interval when the medicament delivery device is in the first configuration. The radio can send a signal characterized by a second, different, communication interval when the medicament delivery device is in the second configuration.

In some embodiments, a computer-implemented method includes producing a first wireless signal characterized by a first communication interval when a medicament delivery device is in a first configuration. An indication can be received indicating that the medicament delivery device has transitioned from the first configuration to a second configuration. A second wireless signal, characterized by a second, different, communication interval can be sent in response to receiving the indication that the medicament delivery device has transitioned from the first configuration to a second configuration. In some embodiments, the first communication interval is associated with a first communication mode, and the second communication interval is associated with a second communication mode. The first communication mode and/or the second communication mode can be an advertising mode, a hold mode, a sniff mode or a park mode.

In some embodiments, a non-transitory processor-readable medium includes code to cause a processor of a device to produce a first wireless signal characterized by a first communication interval when a medicament delivery device is in a first configuration. The non-transitory processor-readable medium includes code to receive an indication that the medicament delivery device has transitioned from the first configuration to a second configuration. The code (executed on a processor) can cause the device to produce a second wireless signal, characterized by a second, different, communication interval in response to receiving the indication that the medicament delivery device has transitioned.

In some embodiments, an apparatus includes a radio, a memory and a communication module. The radio is configured to electronically communicate with a computing device via a wireless protocol (e.g., Bluetooth®). The radio is configured to send a first wireless signal associated with a first communication interval and a second wireless signal associated with a second communication interval. The memory is configured to store transition information associated with a transition of a medicament delivery device from a first configuration to a second configuration. The communication module, which is implemented in at least one of the memory or a processing device, is configured to receive the transition information and determine, based on the transition information, at least the second communication interval.

In some embodiments, an apparatus includes an adapter configured to receive at least a portion of a medicament delivery device or a simulated medicament delivery device. The apparatus also includes an electronic circuit system having a sensor and a radio. The sensor can detect when the adapter is removed from the medicament delivery device or the simulated medicament delivery device. The radio can electronically communicate with a computing device via a wireless protocol. The radio can send a first signal characterized by a first communication interval when the adapter is coupled to the medicament delivery device or the simulated medicament delivery device, and can send a second signal characterized by a second communication interval when the adapter is not coupled to the medicament delivery device or the simulated medicament delivery device. In some such embodiments, the medicament delivery device or the simulated medicament delivery can include a second electronic circuit system configured to produce an electronic output when the medicament delivery device or the simulated medicament delivery device is actuated. In such embodiments, the adapter can include a protrusion that can isolate the circuit of the medicament delivery device or the simulated medicament delivery device from a battery when the adapter is coupled to the medicament delivery device or a simulated medicament delivery device.

In some embodiments, an apparatus includes an adapter configured to receive at least a portion of a medicament delivery device or a simulated medicament delivery device. The medicament delivery device or the simulated medicament delivery device includes a first electronic circuit system configured to produce an electronic output when the device is actuated. The adapter has a protrusion configured to isolate at least a portion of the first electronic circuit system from a power source (or actuate a switch to electrically couple the first electronic circuit system to the power source) when the portion of the at least one of the medicament delivery device or the simulated medicament delivery device is disposed within the adapter. The apparatus further includes a second electronic circuit system coupled to the adapter. The second electronic circuit system includes a radio configured to electronically communicate with a computing device via a wireless protocol. The radio is configured to send a first signal when the portion of the medicament delivery device or the simulated medicament delivery device is within the adapter and a second signal when the portion of the medicament delivery device or the simulated medicament delivery device is spaced apart from the adapter, the second signal different from the first signal.

In some embodiments, a computer-implemented method includes producing, from an adapter, a first wireless signal characterized by a first communication mode with a computing device when a portion of at least one of a medicament delivery device or a simulated medicament delivery is disposed within the adapter. An indication is received when the portion of the medicament delivery device or the simulated medicament delivery device is removed from the adapter. A second wireless signal characterized by a second communication mode with the computing device is produced in response to the indication. The second communication mode is different from the first communication mode. The second communication mode can be, for example, a hold mode, a sniff mode or a park mode.

In some embodiments, a simulated medicament delivery device can produce an indication associated with an operation of the simulated medicament delivery device. In response, a recorded speech output can be generated and information associated with the operation can be stored in a memory. A training script can be updated based on the information stored in the memory.

In some embodiments, a computer-implemented method includes receiving an indication associated with an operation from a set of operations associated with a simulated medicament delivery device. The set of operations can be, for example, a series of operations to be taken when actuating an actual medicament delivery device that corresponds to the simulated device. In response to the indication, a recorded speech output associated with a first training script is produced. Additionally, in response to the indication, use information associated with the plurality of operations associated with a simulated medicament delivery device is updated. The method further includes producing, in response to the updated use information, a second training script.

In some embodiments, a method includes receiving at a first time a wireless signal associated with a slave device. A first location associated with a master device at the first time is determined. An alarm is produced when the wireless signal is not received within a time period after the first time and a second location associated with the master device at a second time is different from the first location by a distance.

In some embodiments, a computer-implemented method includes establishing a communications link, via a short-range wireless protocol, between a mobile computing device and a medicament delivery device. A user input selecting a motion profile of the medicament delivery device is then received in response to an input prompt. A wireless signal is received from the medicament delivery device, the wireless signal associated with an actual motion profile of the medicament delivery device. A notification is produced to indicate a motion difference between the actual motion profile and the target motion profile. In some embodiments, the method optionally includes modifying the target motion profile based on the motion profile over a time period of at least one week, the notification indicating a motion difference between the motion profile and the modified target motion profile.

In some embodiments, any of the medicament delivery devices (including the devices, housings, containers, or casings) described herein can track and transmit information associated with a motion profile of the medicament delivery device. For example, in some embodiments, a computer-implemented method includes transmitting, from a radio of an electronic circuit system associated with a medicament delivery device, a first wireless signal to establish a communications link between a mobile computing device and the medicament delivery device. A motion signal is received, from a sensor of the electronic circuit system. The motion signal is associated with at least one of a position, a velocity, an acceleration, or an orientation of the medicament delivery device. A motion profile of the medicament delivery device is stored in a memory of the electronic circuit system. The motion profile includes the motion signal received during a time period. A second wireless signal associated with the motion profile of the medicament delivery device is then transmitted from the radio.

In some embodiments, the computer-implemented method can include learning or predicting the expected motion of the medicament delivery device. For example, in some embodiments, in the method above the time period can be at least one week. The method can further include producing, via a predictive module implemented in at least one of the memory or a processing device of the electronic circuit system, a target motion profile based on the motion profile over the time period. A motion difference between the motion profile at a first time and the target motion profile is then stored in the memory. A third wireless signal associated with the motion difference is then transmitted from the radio.

In some embodiments, an apparatus includes a medicament delivery device and an electronic circuit system. The electronic circuit system is coupled to at least one of a housing of the medicament delivery device or a cover configured to receive a portion of the medicament delivery device. The electronic circuit system includes a sensor, a motion module, and a radio. The sensor is configured to produce a motion signal associated with at least one of a position, a velocity, an acceleration, or an orientation of at least one of the housing or the cover. The motion module is implemented in at least one of a memory or a processing device, and receives the motion signal. The motion module is configured to determine, based on the motion signal, a motion profile associated with the medicament delivery device. The radio is configured to electronically communicate with a computing device via a short-range wireless communication protocol. The radio sends a first wireless signal to establish a communications link between the computing device and the medicament delivery device. The radio sends a second wireless signal associated with the motion profile of the medicament delivery device.

In some embodiments, a computer-implemented method includes establishing a communications link, via a short-range wireless protocol, between a mobile computing device and a medicament delivery device. The medicament delivery device includes a medicament container, an actuator, and an electronic circuit system. The actuator is configured to initiate delivery of a medicament from the medicament container. The electronic circuit system includes a first sensor, and a second sensor. The first sensor is configured to produce a first actuation signal in response to movement of the actuator relative to the medicament container. The second sensor configured to produce a second actuation signal associated with a delivery characteristic of delivery of the medicament from the medicament container. A first wireless signal associated with the first actuation signal is received from the medicament delivery device. A second wireless signal associated with the second actuation signal is received from the medicament delivery device. An event detection notification based on the first wireless signal and the second wireless signal is then produced. The event detection notification can be produced by a user interface of the mobile computing device, and can include, for example, any of an audible alarm, a visual alarm, a text message (Short Message Service [SMS]), Simple Notification Service (SNS), an e-mail, or the like.

In some embodiments, a computer-implemented method includes establishing a communications link, via a short-range wireless protocol, between a mobile computing device and a medicament delivery device. The medicament delivery device includes a medicament container, an actuator, and an electronic circuit system. The actuator is configured to initiate delivery of a medicament from the medicament container. The electronic circuit system includes a radio, a first sensor, and a second sensor. A first actuation signal in response to movement of the actuator relative to the medicament container is received from the first sensor. A second actuation signal associated with a delivery characteristic of delivery of the medicament from the medicament container is received from the second sensor. An event detection notification based on the first actuation signal and the second actuation signal is produced. A wireless signal associated with the event detection notification is then transmitted from the radio of the electronic circuit system.

In some embodiments, an apparatus includes a medicament delivery device and an electronic circuit system. The medicament delivery device includes a housing, a medicament container at least partially within the housing, and an actuator. The actuator is configured to move relative to the housing to initiate delivery of a medicament from the medicament container. The electronic circuit system is coupled to at least one of the housing of the medicament delivery device or a cover configured to receive a portion of the medicament delivery device. The electronic circuit system includes a first sensor, a second sensor, a use module, and a radio. The first sensor is configured to produce a first actuation signal in response to movement of the actuator relative to the housing. The second sensor is configured to produce a second actuation signal associated with a delivery characteristic of delivery of the medicament from the medicament container. The use module is configured to produce an event detection notification based at least in part on the first actuation signal and the second actuation signal. The radio is configured to electronically communicate with a computing device via a short-range wireless communication protocol. The radio sends a first wireless signal to establish a communications link between the computing device and the medicament delivery device, and a second wireless signal associated with the event detection notification.

In some embodiments, an apparatus includes a medicament delivery device and an electronic circuit system. The medicament delivery device includes a housing, a medicament container at least partially within the housing, an actuator, and a safety member movably coupled to the housing. The safety member is configured to prevent movement of the actuator when the safety member is in a first position. The actuator is movable to actuate the medicament delivery device when the safety member is a second position. The electronic circuit system is coupled to at least one of the housing of the medicament delivery device or the safety member. The electronic circuit system includes a processing device, an output device, a first sensor, a second sensor, and a power management module. The electronic circuit system is configured to produce a first electronic output via the output device when the first sensor produces a safety signal. The safety member configured to actuate the first sensor when the safety member is moved from the first position to the second position. The electronic circuit system is configured to produce a second electronic output when the second sensor produces an actuation signal. The actuator is configured to actuate the second sensor when the actuator is moved. The power management module is implemented in at least one of a memory or the processing device, and is configured to modify the first electronic output when a number of times the safety member has actuated the first sensor exceeds a threshold safety member number.

In some embodiments, an apparatus includes a medicament delivery device and an electronic circuit system. The medicament delivery device includes a housing, a medicament container at least partially within the housing, and an actuator. The actuator is configured to move relative to the housing to initiate delivery of a medicament from the medicament container. The electronic circuit system is coupled to at least one of the housing or a cover configured to receive at least a portion of the medicament delivery device. The electronic circuit system includes a processing device, an output device, a set of sensors, a power source and a power management module. The electronic circuit system is configured to produce a set of electronic outputs via the output device in response to a set of signals produced by any of the sensors. The signals are associated with at least one of a use of the medicament delivery device, a movement of the medicament delivery device, or a position of the medicament delivery device. The power management module is implemented in at least one of a memory or the processing device, and is configured to modify at least one of the plurality of electronic outputs based on a power level of the power source. In some embodiments, for example, the power management module is configured to suppress at least one of the electronic outputs.

In some embodiments, an apparatus includes a medicament delivery device and an electronic circuit system. The medicament delivery device includes a housing, a medicament container at least partially within the housing, and an actuator. The actuator is configured to move relative to the housing to initiate delivery of a medicament from the medicament container. The electronic circuit system is coupled to at least one of the housing or a cover configured to receive at least a portion of the medicament delivery device. The electronic circuit system includes a processing device, an output device, a radio, a set of sensors, a power source and a power management module. The electronic circuit system is configured to produce a set of electronic outputs via the output device in response to a set of signals produced by any of the sensors. The signals are associated with at least one of a use of the medicament delivery device, a movement of the medicament delivery device, or a position of the medicament delivery device. The electronic circuit system is configured to produce a set of wireless communication signals via the radio in response to the set of signals produced by any of the sensors. The power management module is implemented in at least one of a memory or the processing device, and is configured to suppress at least one of the wireless communication signals while maintaining the electronic outputs based on a power level of the power source.

In some embodiments, a computer-implemented method includes establishing a communications link, via a short-range wireless protocol, between a mobile computing device and a medicament delivery device. The communications link established within a first application executed by a processor of the mobile computing device. A wireless signal associated with a characteristic of the medicament delivery device is received from the medicament delivery device. Information associated with the medicament delivery device is received from a second application executed by the processor of the mobile computing device. A notification based on the characteristic and the information is then produced via a user interface of the first application.

The term "about" when used in connection with a referenced numeric indication means the referenced numeric indication plus or minus up to 10% of that referenced numeric indication. For example, "about 100" means from 90 to 110.

As used herein, the term "medicament" includes any constituent of a therapeutic substance. A medicament can include such constituents regardless of their state of matter (e.g., solid, liquid or gas). Moreover, a medicament can include the multiple constituents that can be included in a therapeutic substance in a mixed state, in an unmixed state and/or in a partially mixed state. A medicament can include both the active constituents and inert constituents of a therapeutic substance. Accordingly, as used herein, a medicament can include non-active constituents such as, water, colorant or the like.

In a similar manner, term "substantially" when used in connection with, for example, a geometric relationship, a numerical value, and/or a range is intended to convey that the geometric relationship (or the structures described thereby), the number, and/or the range so defined is nominally the recited geometric relationship, number, and/or range. For example, two structures described herein as being "substantially parallel" is intended to convey that, although a parallel geometric relationship is desirable, some non-parallelism can occur in a "substantially parallel" arrangement. By way of another example, a structure defining a volume that is "substantially 0.50 milliliters (mL)" is intended to convey that, while the recited volume is desirable, some tolerances can occur when the volume is "substantially" the recited volume (e.g., 0.50 mL). Such tolerances can result from manufacturing tolerances, measurement tolerances, and/or other practical considerations (such as, for example, minute imperfections, age of a structure so defined, a pressure or a force exerted within a system, and/or the like). As described above, a suitable tolerance can be, for example, of ±10% of the stated geometric construction, numerical value, and/or range. Furthermore, although a numerical value modified by the term "substantially" can allow for and/or otherwise encompass a tolerance of the stated numerical value, it is not intended to exclude the exact numerical value stated.

As used herein, the term "set" can refer to multiple features or a singular feature with multiple parts. For example, when referring to set of walls, the set of walls can be considered as one wall with multiple portions, or the set of walls can be considered as multiple, distinct walls. Thus, a monolithically-constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used in this specification and the appended claims, the words "proximal" and "distal" refer to direction closer to and away from, respectively, an operator of the medical device. Thus, for example, the end of the medicament delivery device contacting the patient's body would be the distal end of the medicament delivery device, while the end opposite the distal end would be the proximal end of the medicament delivery device.

FIG. 1 is a schematic illustration of a medicament delivery system 1800 (also referred to herein simply as "the system 1800") according to an embodiment. The system 1800 includes a medicament delivery device 1000, an electronic circuit system 1900, a computing device 1801, and a remote device 1802.

The medicament delivery device 1000 can be any of the medicament delivery devices described herein. For example, the medicament delivery device 1000 can be an auto-injector similar to the auto-injector 4000 described below with reference to FIGS. 3-34 or the medicament delivery device 5000 described below with reference to FIGS. 35-46. In other embodiments, the medicament delivery device 1000 can be a pen injector, a syringe, a nasal delivery device (such a nasal spray device), an inhaler, a device for delivering drugs to the buccal cavity, a body-worn drug delivery device, etc. In yet other embodiments, the device 1000 can be a simulated medicament delivery device (i.e., a device that is devoid of a medicament and/or that can simulate the use of a corresponding actual medicament delivery device).

The electronic circuit system 1900 can be coupled to and/or within a housing, cover, case, and/or any other portion of the medicament delivery device. For example, in some embodiments, the electronic circuit system 1900 can be coupled to any of the covers, housings, kits and/or containers described in further detail herein. In other embodiments, the electronic circuit system 1900 can be integrated within the medicament delivery device 1000. For example, the electronic circuit system 1900 can be integrated within the auto-injector 4000 or the auto-injector 5000 (e.g., by being coupled to the housing 4170 and/or included within the electronic circuit system 4900). The electronic circuit system 1900 includes a processor 1980, a memory 1999, a sensor 1970, and a radio 1951. The electronic circuit system 1900 also includes a communication module 1981, a use (or history) module 1982, and a leash module 1983. Although shown as including each of the communication module 1981, the use (or history) module 1982 and the leash module 1983, in other embodiments an electronic circuit system need not include all (or any) of these modules, and can include any other modules described herein, such as a motion module, (e.g., the motion module 7983), a power management module (e.g., the power management module 7987), a predictive module (e.g., the predictive module 7986), and/or the temperature history module (e.g., the temperature history module 7985). For example, in some embodiments, an electronic circuit system includes only a leash module 1983, and is configured to perform the leash methods associated therewith, and need not include the use module 1982 or the communication module 1981. Alternatively, in other embodiments an electronic circuit system includes only the use module 1982 and the communication module 1983. In such embodiments, the use module 1982 can detect a medicament delivery event and the communication module 1983 can produce a wireless signal associated with the actuation of the medicament delivery device 1000.

Figure 2A:
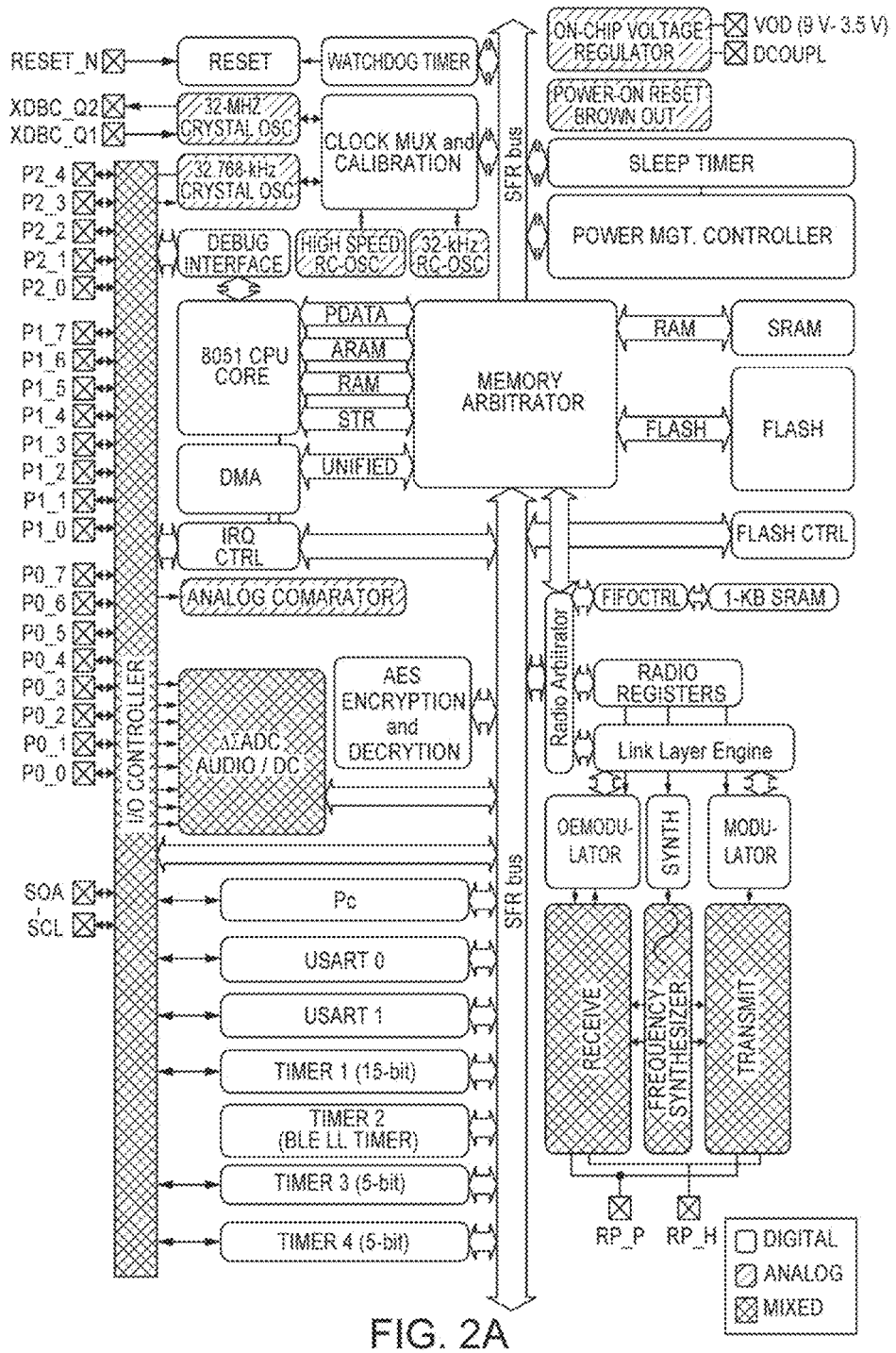
FIGS. 2A and 2B are schematic illustrations of processors used to perform the methods described, according to various embodiments.
Figure 2B:
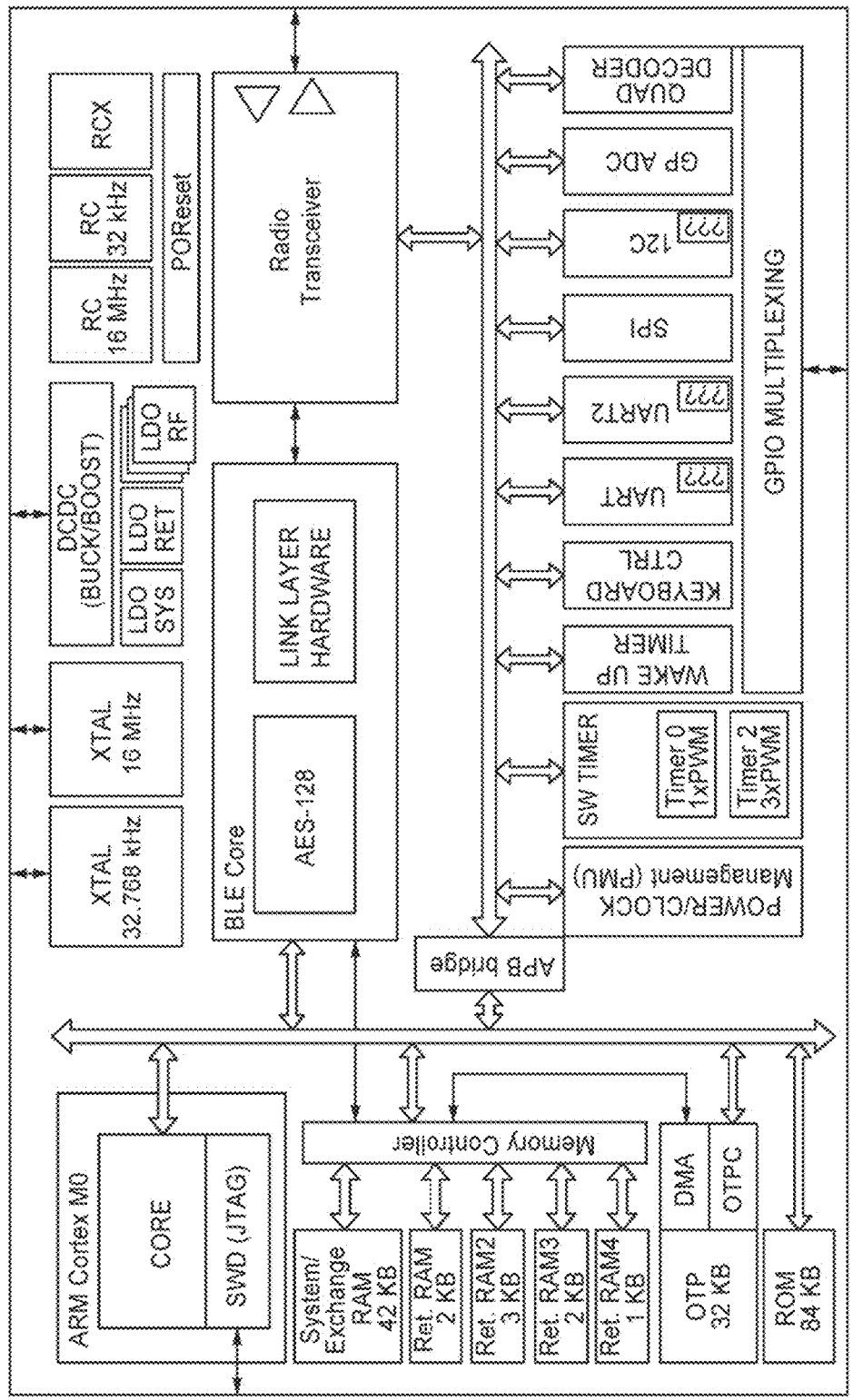

The processor 1980, and any of the processors described herein (including the processor 5980 described below), can be any suitable processor for performing the methods described herein. In some embodiments, processor 1980 can be configured to run and/or execute application modules, processes and/or functions associated with such a medicament delivery system 1800. For example, the processor 1980 can be configured to run and/or execute the communication module 1981, the use (also referred to as an event detection or history) module 1982, the leash module 1983, and/or any of the other modules described herein, and perform the methods associated therewith. The processor 1980 can be, for example, a Field Programmable Gate Array (FPGA), an Application Specific Integrated Circuit (ASIC), a Digital Signal Processor (DSP), and/or the like. The processor 1980 can be configured to retrieve data from and/or write data to memory, e.g., the memory 1999. As described herein, in some embodiments, the processor 1980 can cooperatively function with the radio 1951 and/or execute instructions from code to provide signals to communicatively couple the electronic circuit system 1900 to the computing device 1801 (e.g., via wireless communication) and/or any other computing entity via a network 1805. In some embodiments, the processor 1980 is a Bluetooth® low energy (BLE) processor, such as The Texas Instruments® CC2540 series of processors, the Broadcom® BCM43341 processor, and/or any other processor suitable or configured specifically to execute the Bluetooth® v4.0 low energy stack. In other embodiments, the processor 1980 is a Bluetooth® low energy (BLE) processor, such as DA14581 processor, produced by Dialog Semiconductor. Schematic illustrations of suitable Bluetooth® processors are shown in FIGS. 2A and 2B.

In some embodiments, the processor 1980 can be operable to facilitate any suitable communication mode with the computing device 1801 and/or any other computing entity (e.g., by executing the communication module 1981). Such modes can include, for example, an active mode, hold mode, sniff mode, and/or park mode in accordance with the Bluetooth® wireless protocol. Moreover, the processor 1980 can also be operable to engage in any suitable type of data transfer, such as asynchronous connection-less logical transport (ACL), synchronous connection-oriented link (SCO), and/or any other suitable means.

The memory 1999 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 1999 stores instructions to cause the processor 1980 to execute modules, processes and/or functions associated with such medicament delivery system 1800 and/or the medicament delivery device 1000. For example, the memory 1999 can store instructions to cause the processor 1980 to execute one or more of the communication module 1981, the use module 1982 and/or the leash module 1983, and perform the methods associated therewith.

The sensor 1970 can be a switch, an audible input sensor (e.g., a microphone), optical sensor, accelerometer, temperature sensor, contact sensor, and/or any other suitable input device. In some embodiments, the sensor 1970 can be operable to monitor and/or measure the configuration and/or status of the medicament delivery device 1000. The sensor 1970 can be operable to detect if the medicament delivery device 1000 is removed from a case (such as an outer cover 4200), if a safety lock is removed to "arm" the medicament delivery device 1000, if the medicament delivery device 1000 is actuated (i.e., to provide "delivery event" detection), whether a temperature of the medicament has exceeded a threshold value, and so forth. For example, the sensor 1970 can include an electrical contact or switch operable to detect (e.g., in conjunction with the processor 1980) when the medicament delivery device 1000 is physically separated from a cover. As another example, the sensor 1970 can include a microphone operable to detect (e.g., in conjunction with the processor 1980) a mechanical and/or electronic sound associated with the actuation of the medicament delivery device, such as a characteristic hiss of a compressed gas container being discharged and/or a sound emitted from a speaker of the medicament delivery device 1000 (not shown). As yet another example, the sensor 1970 can include an optical sensor operable to detect the configuration of a status window of the medicament delivery device 1000, or the presence of light versus the absence of light (e.g., to detect whether component is blocking a beam). For example, the sensor 1970 can be operable to detect when a status window of the medicament delivery device 1000 turns color or opaque, which may be associated with use of the medicament delivery device 1000. As yet another example, the sensor 1970 can include an accelerometer operable to detect a characteristic movement or vibration signature of the medicament delivery device 1000 when the device is actuated.

The radio 1951 (also referred to as a receiver, transmitter and/or transceiver) can be operable to send signals to, and/or receive radio signals, such as Bluetooth®, ZigBee, Wi-Fi, cellular telephone signals, etc. In some embodiments, such as embodiments where the processor 1980 is Bluetooth® processor, the radio 1951 can be integral with the processor 1980. In other embodiments, the radio 1951 can include a processor distinct from the processor 1980. In some embodiments, the radio 1951 can be operable to communicatively couple (also referred to herein as "linking" or "pairing") the electronic circuit system 1900 to the computing device 1801 and/or any other computing entity via a network 1805. The radio 1951 can include or be coupled to a ceramic chip antenna, a stamped antenna, a sintered antenna, a PCB conductive trace antenna, and/or any other suitable antenna.

The communication module 1981 can be a hardware and/or software module (stored in memory 1999 and/or executed in the processor 1980). As described in more detail herein, the communication module 1981 is configured to receive an indication (e.g., from the sensor 1970) and/or transition information associated with a change in status of the medicament delivery device 1000 and determine, based on the indication or the transition information, a connection and/or communications characteristic. Such communication characteristics can include, for example, a communication interval and/or connection interval (e.g., a time period between successive signals or portions of a signal, such an "advertising interval," also referred to herein as a "connection interval"), a communication mode (e.g., a park mode, sniff mode or the like), etc.

The use module 1982 can be a hardware and/or software module (stored in memory 1999 and/or executed in the processor 1980). As described in more detail herein, the use module 1982 is configured to receive an indication (e.g., from the sensor 1970) and/or use information associated with a use or history of the medicament delivery device 1000 and produce a script (e.g., a recorded speech instruction, signal for wireless transmission, or the like) based thereupon. In this manner, the use module 1982 can facilitate the electronic circuit system 1900 and/or the medicament delivery device 1000 (or simulated medicament delivery device) being a "smart" device that can produce updated instructions and/or guidance based on the past history of usage. The use module 1982 can also process signals and/or information from the sensor 1970 to determine whether an actual use of the device 1000 has occurred.

The leash module 1983 can be a hardware and/or software module (stored in memory 1999 and/or executed in the processor 1980). As described in more detail herein, the leash module 1983 is configured to receive information associated with the connection (or pairing) between the electronic circuit system 1900 and the computing device 1801 and produce an alarm based thereupon. In some embodiments, the leash module 1983 can base the alarms on the position and/or location of the electronic circuit system 1900 and/or the computing device 1801 or a combination of both.

The network 1805 can be a piconet, the Internet, an intranet, a local area network (LAN), a wide area network (WAN), a virtual network, a telecommunications network, any other suitable communication system and/or combination of such networks. The network 1805 can be implemented as a wired and/or wireless network.

The computing device 1801 (or other "remote" computing devices, such as the device 5801 described below) can be a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), or a computer (e.g., a laptop, desktop, smart TV, etc.), and/or any other suitable computing entity. The computing device 1801 includes a processor 1810, a memory 1839, a user interface 1820, and a radio 1838.

The processor 1810 can be, for example, a FPGA, an ASIC, a DSP, and/or the like. The processor 1810 can be configured to retrieve data from and/or write data to memory, e.g., the memory 1839, which can be, for example, RAM, memory buffers, hard drives, databases, EPROMs, EEPROMs, ROM, flash memory, hard disks, floppy disks, cloud storage, and/or so forth. In some embodiments, processor 1810 can be configured to run and/or execute application modules, processes and/or functions associated with the medicament delivery system 1800 (or any of the medicament delivery systems described herein). For example, in some embodiments, the processor 1810 can be configured to run and/or execute a communication module (see, e.g., the communication module 7811, a use (or event detection) module (e.g., the event detection module, 7812), a motion module (also referred to as a leash or soft leash module, see the motion module 7813), a temperature history module (e.g., the temperature history module 7815), a predictive module (e.g., the predictive module 7816), a notification module (e.g., the notification module 7817), an application interface module (e.g., the application interface module 7818), an onboarding module (e.g., the onboarding module 7819), and/or any of the other modules described herein, and perform the methods associated therewith.

The user interface 1820 can be, for example, a monitor or screen that displays visual elements to a user. The user interface 1820 can be a touch screen (of a smart mobile phone) upon which a series of graphical user interface elements (e.g., windows, icons, input prompts, graphical buttons, data displays, notification, or the like) can be displayed. In some embodiments, the graphical user interface elements (not shown) are produced by a user interface module.

The radio 1838 can be structurally and/or functionally similar to the radio 1951. In some embodiments, the radio 1838 can include a processor (e.g., a Bluetooth® processor) distinct from the processor 1810. In some embodiments, a short-range radio link can be established between the computing device 1801 and the electronic circuit system 1900. For example, the computing device 1801 and the electronic circuit system 1900 can be paired via the Bluetooth® wireless protocol. Similarly stated, the computing device 1801 and the electronic circuit system 1900 can be paired via a wireless protocol that facilitates the transmission of signals within a range of approximately 100 meters or less (i.e., a Class 3 radio) and/or having a frequency within the range of 2400 MHz and 2480 MHz. In such an embodiment, as described in further detail herein, the computing device 1801 can be operable to send and/or receive data from the electronic circuit system 1900 related to the medicament delivery device 1000, such as data associated with use, preparation for use, status, and so forth. Furthermore, the electronic circuit system 1900 and/or the computing device 1801 can be operable to determine when a short-range communication link is broken (e.g., when the electronic circuit system 1900 is out of range of the computing device 1801).

The leash module 1983 can be a hardware and/or software module (stored in memory 1999 and/or executed in the processor 1980). As described in more detail herein, the leash module 1983 is configured to receive information associated with the connection (or pairing) between the electronic circuit system 1900 and the computing device 1801 and produce an alarm based thereupon. In some embodiments, the leash module 1983 can base the alarms on the position and/or location of the electronic circuit system 1900 and/or the computing device 1801. In other embodiments, the leash module 1983 (and any other leash modules or motion modules described herein) can base the alarms on a difference between a target motion profile and an actual motion profile of the medicament delivery device 1000.

In some embodiments, such as an embodiment where the computing device 1801 is a Bluetooth® enabled mobile phone, the radio 1838 can be suitable to establish a short-range radio link with the electronic circuit system 1900 and establish a long-range with another computing device (e.g., the remote device 1802) via the network. For example, the radio 1838 can be a dual-function radio and/or the computing device 1801 can include multiple radios to relay information associated with the electronic circuit system 1900 (which may be equipped with only a short-range radio) to the remote device 1802 using, for example, a cellular data network and/or a Wi-Fi link to the Internet. In other embodiments, the electronic circuit system 1900 may be equipped with a radio operable to communicate with the remote device 1802 via the network 1805.

The computing device 1801 can be operable to store (e.g., in the memory 1999) information associated with the electronic circuit system 1900, such as connection time, a medicament device 1000 use record, details of a medicament delivery event (e.g., date, time, duration, and any other characteristics of the use) and so forth. In some embodiments, the computing device 1801 can be operable to determine its location (e.g., via a global positioning system (GPS) sensor (not shown)). In such an embodiment, the computing device 1801 can be operable to associate location data with information associated with the electronic circuit system 1900, such as use data.

The remote device 1802 can be any suitable computing entity, such as a server or personal computer. The remote device 1802 includes a processor 1810', which can be, for example, a FPGA, an ASIC, a DSP, and/or the like. The processor 1810' can be configured to retrieve data from and/or write data to memory, e.g., the memory 1839', which can be, for example, RAM, memory buffers, hard drives, databases, EPROMs, EEPROMs, ROM, flash memory, hard disks, floppy disks, cloud storage, and/or so forth. The network module 1814' can be any suitable module operable to communicatively couple the remote device 1802 to the network 1805. For example, the network module 1814' can be a network interface controller (NIC). In some embodiments, the remote device 1802 can be a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), and/or any other suitable computing entity. For example, in some embodiments, the remote device 1802 can be another user's mobile phone that is not paired or otherwise communicating with the electronic circuit system 1900 via short-range communication protocol (e.g., the Bluetooth® wireless protocol).

In some embodiments, the remote device 1802 can be operable to receive reports associated with the medicament delivery device 1000 from the electronic circuit system 1900 and/or the computing device 1801 via the network 1805. For example, the remote device 1802 can be associated with a health-care provider and/or emergency contact and used to monitor medicament delivery device 1000 use and/or compliance.

In some embodiments, the processor 1980 of the electronic circuit system 1900 and/or the processor 1810 of the computing device 1801 (and any of the processors described herein) can be operable to execute code to implement a wireless communications protocol. For example, the processor 1980 and/or the processor 1810 can execute a Bluetooth® stack (which may be stored in memory 1999, 1839) having service, profile, and/or application layers operable to control and/or improve connectivity, power management, and/or any other suitable feature associated with the Bluetooth® protocol. For example, as described in further detail herein, the processor(s) 1980, 1810, can be operable to alter mode (e.g., from park to sniff, from sniff to active, or any other suitable change), alter communication type (e.g., from ACL communication to SCO communication), alter advertising interval, and/or any other suitable communication parameter. In this manner, in accordance with the methods described herein, the processor 1980 and/or the processor 1810 can alter and/or implement a characteristic of the wireless communication in response to a change associated with the medicament delivery device 1000 (or simulated medicament delivery device). As one example, the processor(s) 1980, 1810 can be operable to alter a communication mode from advertising a connectable status on a first channel (or set of channels) to sending and/or receiving communication packets on a second channel (or set of channels).

As described in further detail herein, in some embodiments, the computing device 1801 can be operable to track the location and/or status of the electronic circuit system 1900. For example, by recording when the computing device 1801 is communicatively coupled to the electronic circuit system 1900, which may be associated with location information, the computing device 1801 can provide an indication of the last location at which it was linked to the electronic circuit system 1900. Furthermore, the computing device 1801 can be operable to use triangulation, homing, and/or any other suitable technique to locate the electronic circuit system 1900 when the electronic circuit system 1900 is within radio range. In addition, or alternatively, the computing device 1801 can send a signal to the electronic circuit system 1900 operable to cause the adapter to emit a noise or other signal to aid the user in locating the electronic circuit system 1900 (and the medicament delivery device 1000).

In some embodiments, as described in further detail herein, the computing device 1801 and/or the electronic circuit system 1900 can include a leash functionality (e.g., implemented in the leash module 1983 and/or the leash module 1813) such that when the communications between the computing device 1801 and the electronic circuit system 1900 is disrupted (e.g., the communication device 1801 moves out of range and/or vice versa), the electronic circuit system 1900 and/or the communication device 1801 can generate an alert to notify a user that a link has been lost. For example, an individual may be advised to carry a medicament delivery device, such as an epinephrine auto-injector, but may rarely use the medicament delivery device. As a result, the user may occasionally forget to carry the medicament delivery device, which can have serious consequences in the event of a medical emergency. If the user additionally carries the computing device 1801, and is less likely to forget the computing device 1801 (for example, where the computing device 1801 is a mobile phone that the user uses on a regular basis), a leash function can alert the user if the medicament delivery device 1000 is forgotten. In some embodiments, the computing device 1801 and/or the electronic circuit system 1900 can generate an alert any time the computing device 1801 is moved out of range of the electronic circuit system 1900 (i.e., indicating that the electronic circuit system 1900 is not being carried together with the computing device 1801). In another embodiment, the computing device 1801 can be operable to verify its location (e.g. via GPS) and alert if the computing device 1801 is out of range of the electronic circuit system 1900 and the computing device 1801 has moved a distance from the position where it was last coupled to the electronic circuit system 1900. Such an embodiment can reduce false alarms, which may be caused by radio interference, traveling only a short distance from the medicament delivery device 1100, and so forth. For example, the computing device 1801 can be configured to produce an alert when it loses connectivity with the medicament delivery device 1100 and is more than ⅛ of a mile from the last location at which the computing device 1801 was linked to the electronic circuit system 1900. Any other suitable threshold, such as 200 feet, ½ mile, 5 miles, etc. is possible. In addition, or alternatively, an alert can be generated if the communication link is lost and the computing device 1801 is moving at more than a threshold velocity, such as 10 mph, 20 mph, 50 mph, etc. which may be associated with traveling by automobile. In this manner, the leash feature may reduce false alarms that can occur where the user is within walking distance of the medicament delivery device 1000 (e.g., the user may be walking within a large building and the communications between the computing device 1801 and the electronic circuit system 1900 may be temporarily disrupted).

In some embodiments, as described in further detail herein, the computing device 1801 and/or the electronic circuit system 1900 can include a status tracking functionality such that when the medicament delivery device 1000

(and/or a simulated medicament delivery device) changes status, the electronic circuit system 1900 can adjust the communications protocol and/or characteristics. For example, in some embodiments, the electronic circuit system 1900 can enhance the electronic communications with the computing device 1801 by changing a signaling rate, signal power and/or the information contained in a signal sent via the radio 1951 in response to the actuation of the medicament delivery device 1000 (and/or a simulated medicament delivery device).

In some embodiments, for example, the electronic circuit system 1900 can be operable to switch between several connection and/or communication modes (each of which may be associated with different broadcast intervals, power consumption levels, battery power levels, or the like). For example, the electronic circuit system 1900 can have an off mode, where there is substantially no electrical activity (e.g., no power draw) associated with the processor 1980 and/or the radio 1951. When the electronic circuit system 1900 is in the off mode, there is no communications between the electronic circuit system 1900 and the computing device 1801 and/or the remote device 1802. In some embodiments, an electrical connection between a power source (e.g., a battery) and the processor 1980 and/or the radio 1951 may be mechanically isolated when the electronic circuit system 1900 is in the off mode. In other embodiments, the power source can remain electrically coupled to the processor 1980 and/or the radio 1951, but communications activity can be otherwise curtailed to limit power consumption. The low- or no-power draw mode can be entered, for example, when the available power from the battery drops below a threshold value. In such instances, this allows certain "critical functions" of the medicament delivery device 1000 to be supported for an extended period of time. For example, in some embodiments, when the battery power drops below a threshold value (e.g., 20 percent), the communication can be switched to the OFF mode, thereby preserving the remaining battery power to produce audible instructions for the use of the device 1000.

As another example, the electronic circuit system 1900 can be operable in a connectable mode where the electronic circuit system 1900 is available to link with and/or is soliciting a link with the computing device 1801. For example, when in the connectable mode, the electronic circuit system 1900 can repeatedly send a signal to advertise its availability to establish a communication link (or "pair with") the computing device 1801 via the radio 1951. In some embodiments, the advertising signal can be sent in a non-periodic advertising interval, which can avoid synchronization with the computing device 1801 (e.g., avoid the electronic circuit system 1900 advertising on a cycle that does not overlap with a computing device 1801 "listening" cycle). In some embodiments, the advertising interval can be based, at least in part, on the status of the medicament delivery device 1000. In this manner, the electronic circuit system 1900 can control the electronic communications with the computing device 1801 to limit the power consumption during periods when such communications are less likely. For example, if the medicament delivery device 1000 is disposed within a case (e.g., similar to the cover 4200) or is otherwise not "armed" for immediate use, a relatively long advertising interval (such as about 7 ms, about 10 ms, about 20 ms, about 152.5 ms, about 211.25 ms, about 500 ms, about 760 ms, about 1 s, about 5 s, 5 min, and/or any other suitable interval therebetween) can be chosen. If, on the other hand, the medicament delivery device 1000 has been removed from its case, or a safety guard has been removed from the device 1000, a relatively short advertising interval (such as about 1 ms, about 3, ms, about 10 ms, about 20 ms and/or any other suitable interval) can be chosen and/or power can be increased to the radio 1951. In this way, the electronic circuit system 1900 can conserve power when the medicament delivery device 1000 is not configured to deliver a medicament, while prioritizing connectivity and/or reducing latency when the medicament delivery device 1000 is poised to deliver a medicament.

As another example, the electronic circuit system 1900 can have a connected mode, for example, where the electronic circuit system 1900 is linked with the computing device 1801 (i.e., the electronic circuit system 1900 and the computing device 1801 form a piconet). When the electronic circuit system 1900 is in the connected mode, the electronic circuit system 1900 can periodically exchange messages with the computing device 1801 to maintain the connection. In some embodiments, the communication interval (i.e., the time interval between successive signals and/or portions of a signal, also referred to herein as a "connection interval") can be selected in accordance with a status of the electronic circuit system 1900 and/or medicament delivery device 1000 to minimize power consumption. For example, the communication interval can be 0.5 s, 1 s, 2 s, and/or any other suitable interval. In some embodiments, the electronic circuit system 1900 can selectively enter a particular "mode" of communications when connected with the computing device 1801. For example, the Bluetooth® Low Energy protocol employs a sleep mode, a sniff mode and park mode to facilitate conservation of power of the slave device (i.e., the electronic circuit system 1900, in this example). In some embodiments, the electronic circuit system 1900 can selectively enter the sleep, sniff, and/or park mode once connected, in response to a change in status of the medicament delivery device 1000 (e.g., removed, armed, actuated) and/or if the data associated with the medicament delivery device 1000 is not transferred for a period of time.

In some embodiments, for example, the electronic circuit system 1900 can be configured such that the radio 1951 is configured to send a first signal characterized by a first communication interval and/or mode when the medicament delivery device 1000 is in a first configuration. The first signal can be, for example, an advertising signal characterized by a first advertising interval. In other embodiments, the first signal can be a signal to maintain an already-exiting pairing between the electronic circuit system 1900 and the computing device 1801. The first configuration of the medicament delivery device 1000 can be, for example, a "standby" configuration (when the device is within and/or coupled to the electronic circuit system 1900). Alternatively, the first configuration can be any other suitable configuration (e.g., an armed configuration, a "power off" configuration or the like). The radio is configured to send a second signal characterized by a second communication interval and/or mode when the medicament delivery device is in a second configuration. The second communication interval can be different from the first communication interval.

In some embodiments, the computing device 1801 can send a signal to the electronic circuit system 1900 to cause the adapter to emit an audible output. In some embodiments, there may be limited space in the memory 1999 of the electronic circuit system 1900 to store voice prompts and/or customized voice prompts, and/or the memory 1999 may be ROM memory or another type of memory that is not writeable and/or requires significant time, computational resources, and/or power to alter. In such an embodiment, sending a signal from the computing device 1801, which may have more memory and/or computational power, to cause the electronic circuit system 1900 to generate an output, can extend the battery life of the electronic circuit system 1900 and/or can allow the electronic circuit system 1900 to be more flexible and/or customizable than the processor 1980, the memory 1999. Such methods can further address the power constraints of the electronic circuit system 1900 by using less power than if the output were generated entirely by the electronic circuit system 1900.

In other embodiments, the electronic configuration of the electronic circuit system 1900 can facilitate methods of updating an instruction script and/or voice prompt stored in the memory 1999 of the electronic circuit system 1900. For example, in some embodiments, the electronic circuit system 1900 can receive signals from the computing device 1801 via the radio 1951 that include information associated with an instruction script and/or voice prompt of the types described herein. This information can then be written to the memory 1999, thus allowing the voice prompts to be updated using the wireless communications capabilities described herein. These methods avoid the need to have the voice prompts contained in a ROM mask, which can be difficult to update. Moreover, these methods allow for the user to customize their voice prompts (e.g., with a specific user's voice, with customized content or the like).

In some embodiments, the electronic circuit system 1900 can be associated with a unique identifier and/or part number. In such an embodiment, when the computing device 1801 pairs with the electronic circuit system 1900, the computing device 1801 (e.g., by communicating with the remote device 1802, which may include a database of electronic circuit systems or devices) can retrieve information associated with the medicament delivery device 1000, such as type of medicament, expiration date, particular use instructions, and so forth.

Although described as facilitating a user-implemented update to a voice prompt, in other embodiments, the electronic circuit system 1900 (and any of the system described herein) can be configured to update the voice prompts based on the user's past history (e.g., via the use module 1982). In this manner, the systems and methods described herein can be used to produce a "smart" or "trainable" device. In some embodiments, the medicament delivery device 1000 can be a simulated medicament delivery device intended for use training a user in the operation of an actual medicament delivery device. In such an embodiment, the electronic circuit system 1900 (and/or the simulated medicament delivery device 1000 itself) can be operable to detect whether the simulated medicament delivery device was used properly. For example, via input received from the sensor 1970 (and/or a series of sensors), the electronic circuit system 1900 can be operable to detect whether the simulated medicament delivery device was properly armed, whether it was properly positioned to simulate delivery of medicament, whether sufficient force was applied to actuate the simulated medicament delivery device, whether the medicament delivery device was held in position for a sufficient period of time, and so forth. The electronic circuit system 1900 can send a signal to the computing device 1801 such that personalized instructions can be provided to the user by the computing device 1801 and/or the electronic circuit system 1900. For example, if the user applies insufficient force to actuate the simulated medicament delivery device, this information can be stored within the memory 1999 and the electronic circuit system 1900, the simulated device 1000, and/or the computing device 1801 can be operable to instruct the user to apply additional force and/or to remind the user that insufficient force was applied in previous instances. Furthermore, in some embodiments, a record of simulated medicament delivery device use can be stored by the electronic circuit system 1900, the computing device 1801, and/or the remote device 1802, such that personalized instructions in the event the user attempts to use an actual medicament delivery device 1000. For example, the computing device 1801 can remind the user of mistakes made with a simulated medicament delivery device, for example, to remind the user that he or she has a history of applying insufficient force when practicing with the simulated medicament delivery device. Similarly stated, the computing device and/or the remote device 1802 can be operable to provide information to the user of the medicament delivery device 1000 based on data associated with a simulated medicament delivery device.

In some embodiments, an application (executing on the processor 1810 of the computing device 1801) can be operable to detect and/or pair with multiple medicament delivery devices and/or electronic circuit systems associated therewith. For example, the communication device 1801 can be operable to detect one or more medicament delivery devices (or adapters, covers, tags, or the like that are coupled to such devices) at a retail location, such as a pharmacy. In such an embodiment, the computing device 1801 can send a signal to and/or receive a signal from the remote device 1802 indicating the location of the devices. The remote device 1802, in turn, can provide information to users (e.g., via the Internet) of the location of the adapters. Thus, the remote device 1802 can be operable to provide, for example, to a user, sales rep, health-care professional, etc. information about the availability of a particular medicament delivery device or particular type of medicament delivery device. Furthermore, in the event of a medicament recall or expiration, the remote device 1802 can have a database of locations having the recalled or expired medicament.

Figure 3:
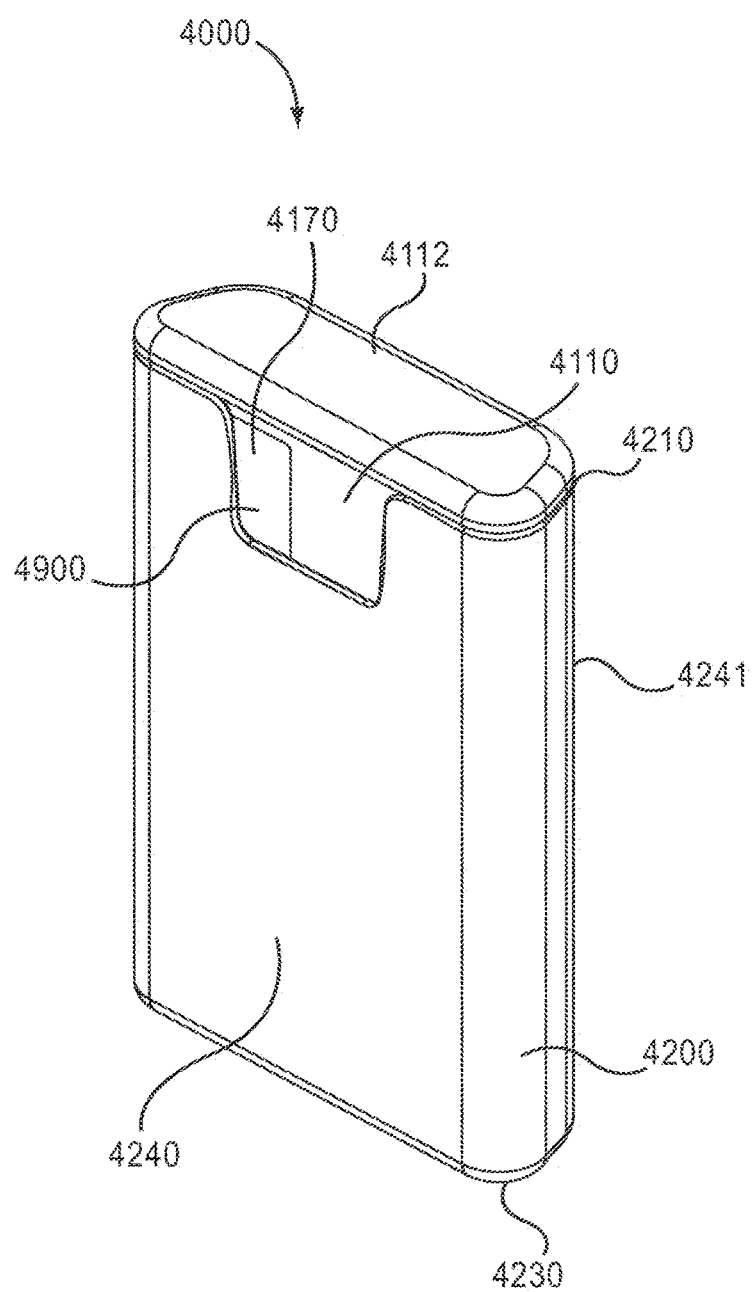
FIGS. 3 and 4 are perspective views of a medical injector according to an embodiment of the invention, in a first configuration.
Figure 4:
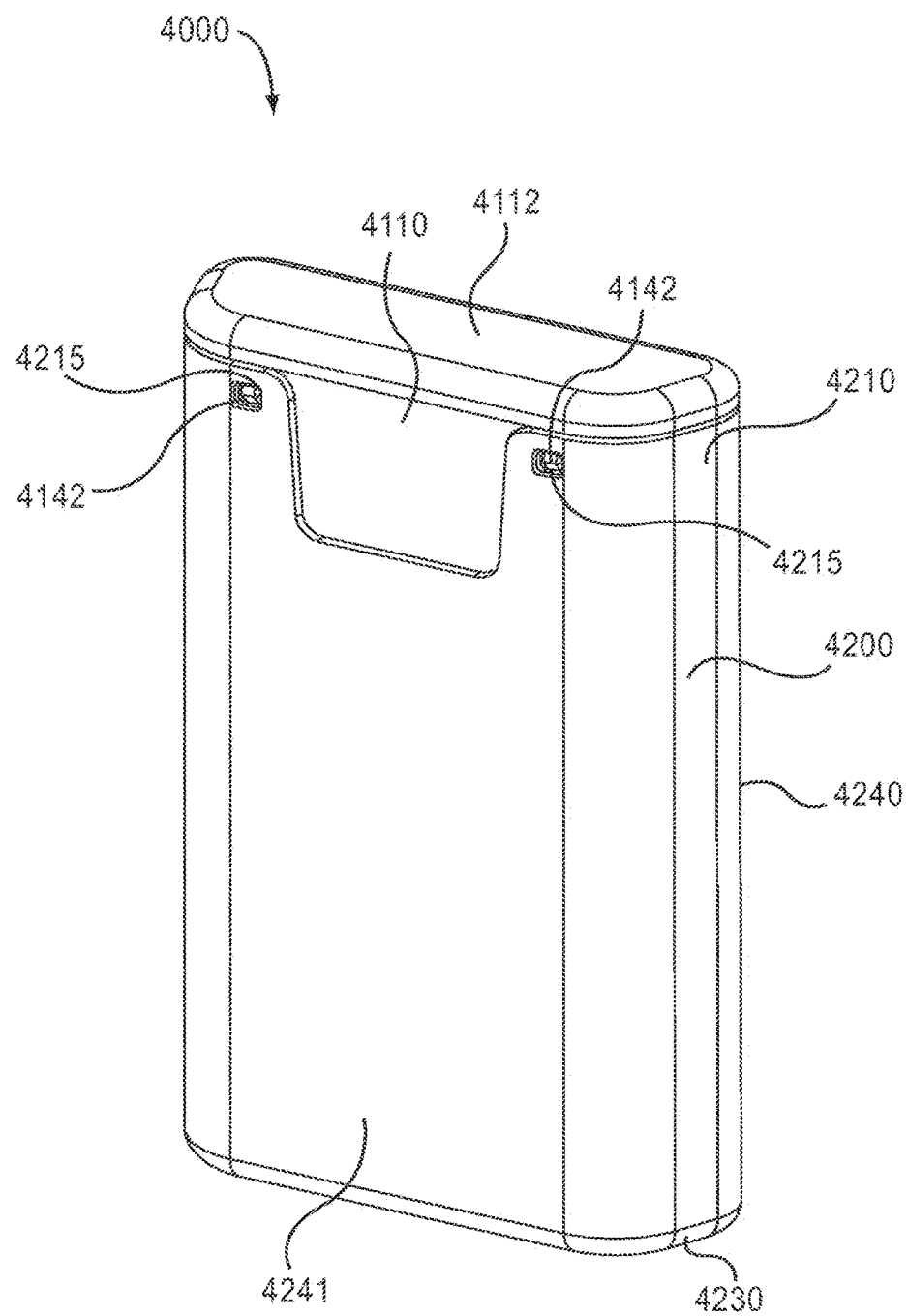
Figure 5:
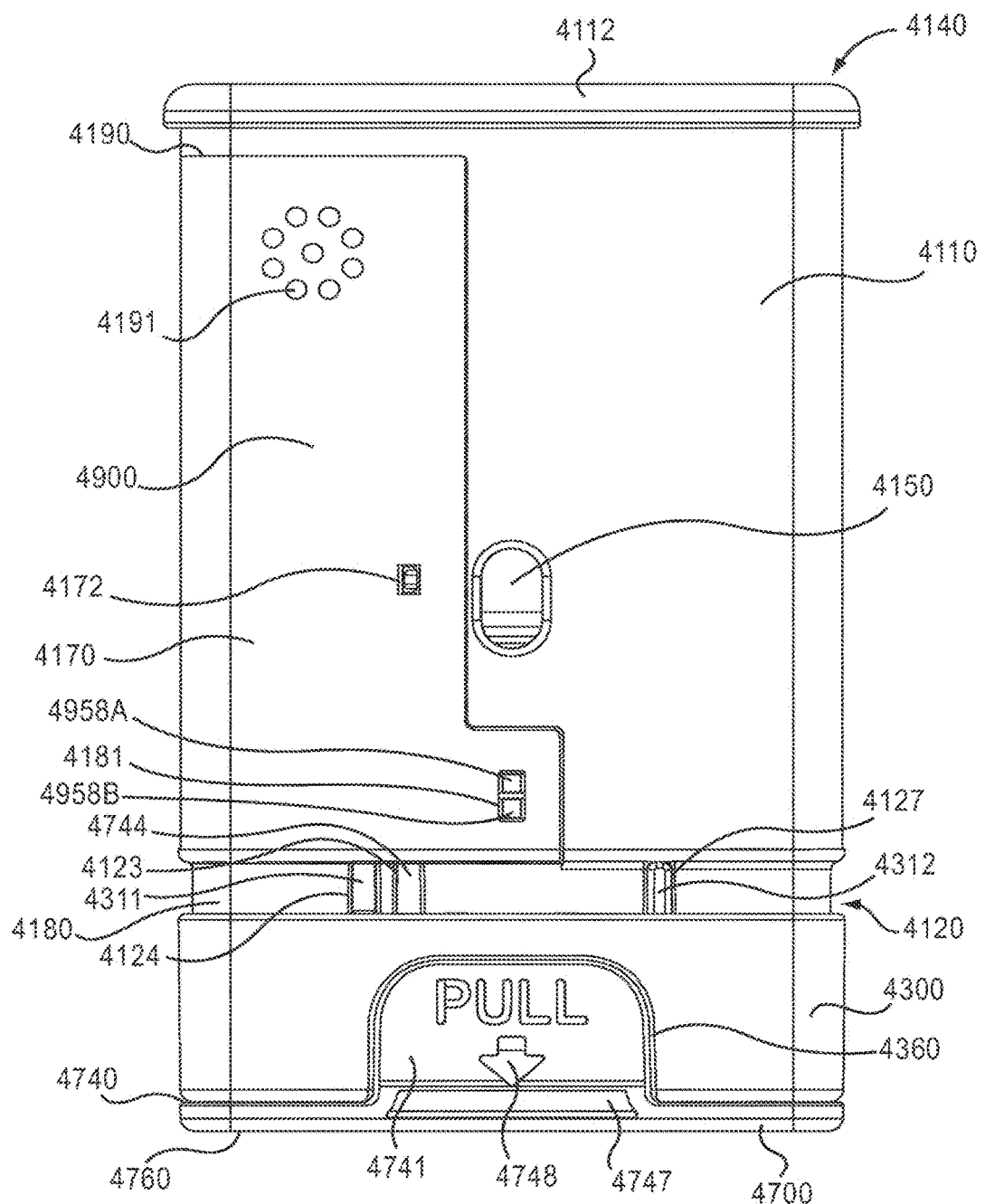
FIGS. 5 and 6 are a front view and a back view, respectively, of the medical injector illustrated in FIG. 3 with the cover removed.

The methods and systems described herein can be used in conjunction with any suitable medicament delivery device, including any of the delivery devices (or drug products) described herein. For example, FIGS. 3-34 show a medical injector 4000 as another example of a delivery device that can be used in conjunction with and/or as a part of the delivery systems and methods described herein. FIGS. 3-4 are perspective views of the medical injector 4000 in a first configuration (i.e., prior to use). The medical injector 4000 includes a housing 4110, a delivery mechanism 4500 (see e.g., FIG. 12), an electronic circuit system 4900 (see e.g., FIGS. 13-23), a cover 4200 (see e.g., FIGS. 24-25), a safety lock 4700 (see e.g., FIGS. 26-29) and a base 4300 (see e.g., FIGS. 30-31). A discussion of the components of the medical injector 4000 will be followed by a discussion of the operation of the medical injector 4000.

As shown in FIGS. 5-11, the housing 4110 has a proximal end portion 4140 and a distal end portion 4120. The housing 4110 defines a first status indicator aperture 4150 and a second status indicator aperture 4151. The first status indicator aperture 4150 defined by the housing 4110 is located on a first side of the housing 4110, and the second status indicator aperture 4151 of the housing 4110 is located on a second side of the housing 4110. The status indicator apertures 4150, 4151 can allow a patient to monitor the status and/or contents of a medicament container 4560. For example, by visually inspecting the status indicator apertures 4150, 4151, a patient can determine whether the medicament container 4560 contains a medicament and/or whether a medicament has been dispensed.

Figure 9:
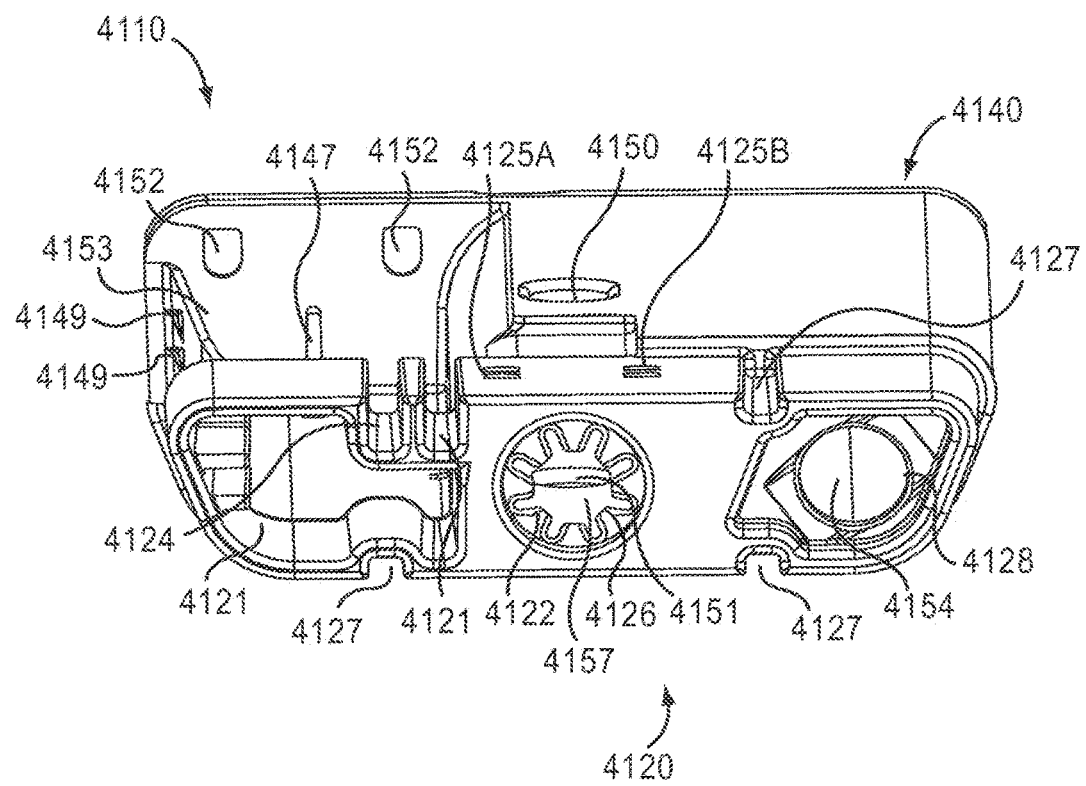
FIG. 9 is a bottom perspective view of a housing of the medical injector illustrated in FIG. 3.
Figure 10:
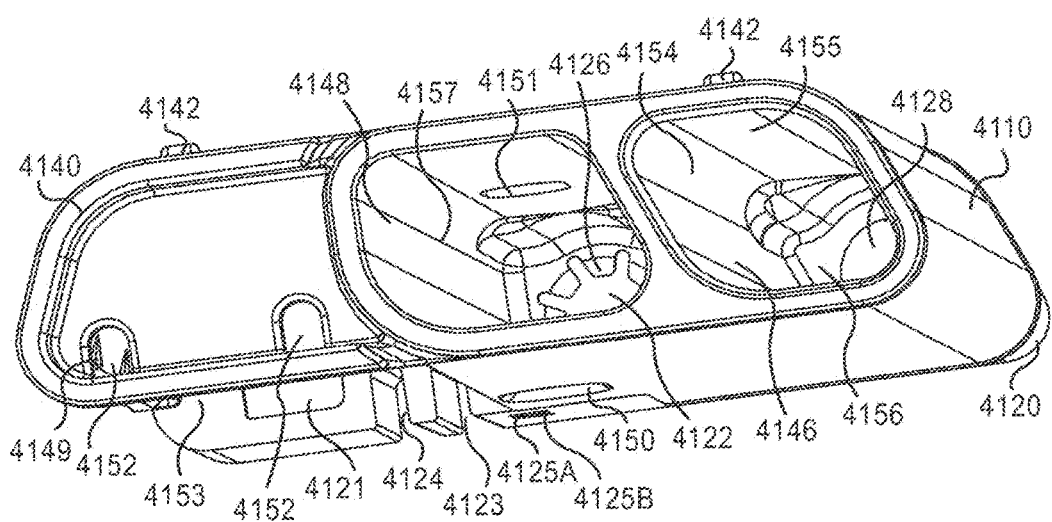
FIGS. 10 and 11 are perspective views of a housing and a proximal cap of the housing, respectively, of the medical injector illustrated in FIG. 3.

As shown in FIGS. 9 and 10, the housing 4110 defines a gas cavity 4154, a medicament cavity 4157 and an electronic circuit system cavity 4153. The gas cavity 4154 has a proximal end portion 4155 and a distal end portion 4156. The gas cavity 4154 is configured to receive the gas container 4570 and the release member 4540 of the medicament delivery mechanism 4500 (see e.g., FIG. 12) as described in further detail herein. The proximal end portion 4155 of the gas cavity 4154 is configured to receive the gas container retention member 4580 of the proximal cap 4112 of the housing 4110, as described in further detail herein. The gas cavity 4154 is in fluid communication with the medicament cavity 4157 via a gas passageway 4144, as described in further detail herein, and the gas cavity 4154 is in fluid communication with a region outside the housing 4110 via a safety lock aperture 4128.

The medicament cavity 4157 is configured to receive a portion of the delivery mechanism 4500. In particular, the carrier 4520, the moveable member 4530 and the needle 4512 of the medicament delivery mechanism 4500 are movably disposed in the medicament cavity 4157. The medicament cavity 4157 is in fluid communication with a region outside the housing 4110 via a needle aperture 4122.

The electronic circuit system cavity 4153 is configured to receive the electronic circuit system 4900. The housing 4110 has protrusions 4149 (see e.g., FIG. 8) configured to stabilize the electronic circuit system 4900 when the electronic circuit system 4900 is disposed within the electronic circuit system cavity 4153. The housing 4110 also defines connection apertures 4152 configured to receive connection protrusions 4171 of the electronic circuit system 4900, and aperture 4145 (see e.g., FIG. 6) configured to receive a portion of a protrusion 4174 of the electronic circuit system 4900. In this manner, the electronic circuit system 4900 can be coupled to the housing 4110 within the electronic circuit system cavity 4153. In other embodiments, the electronic circuit system 4900 can be coupled within the electronic circuit system cavity 4153 by other suitable means such as an adhesive, a clip and/or the like.

The electronic circuit system cavity 4153 is fluidically and/or physically isolated from the gas cavity 4154 and/or the medicament cavity 4157 by a sidewall 4148. The sidewall 4148 can be any suitable structure to isolate the electronic circuit system cavity 4153 within the housing 4110 from the gas cavity 4154 and/or the medicament cavity 4157 within the housing 4110. Similarly, the gas cavity 4154 and the medicament cavity 4157 are separated by a sidewall 4146. In some embodiments, sidewall 4146 can be similar to the sidewall 4148, which isolates the gas cavity 4154 and the medicament cavity 4157 from the electronic circuit system cavity 4153. In other embodiments the gas cavity 4154 can be fluidically and/or physically isolated from the medicament cavity 4157.

Figure 6:
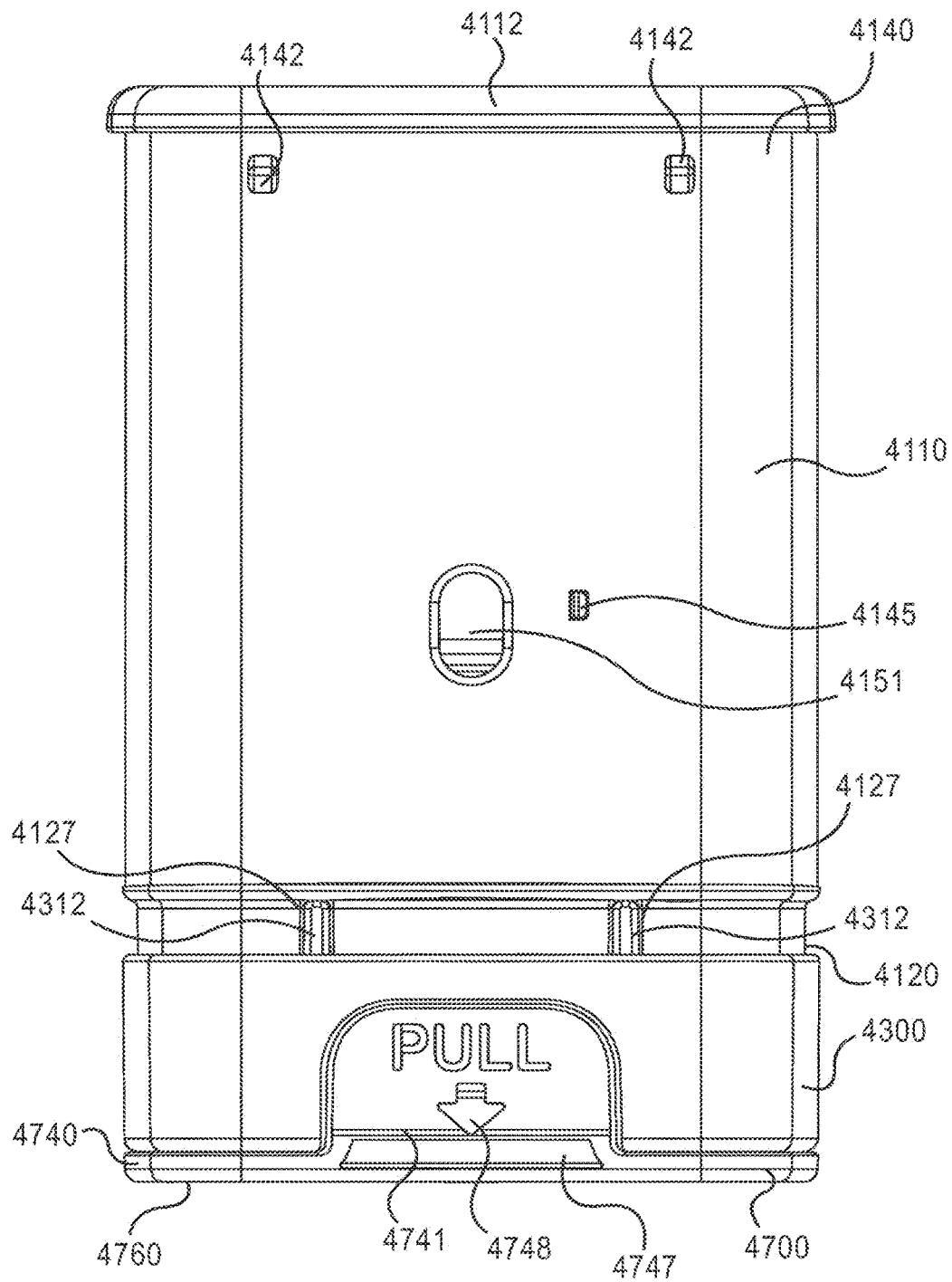

The proximal end portion 4140 of the housing 4110 includes a proximal cap 4112, a speaker protrusion 4147 (see e.g., FIGS. 8 and 9), and cover retention protrusions 4142 (see e.g., FIGS. 4 and 6). The speaker protrusion 4147 is configured to maintain a position of an audio output device 4956 of the electronic circuit system 4900 relative to the housing 4110 when the electronic circuit system 4900 is attached to the housing 4110, as described herein. Cover retention protrusions 4142 are configured to be received within corresponding openings 4215 on the cover 4200. In this manner, as described in more detail herein, the cover 4200 can be removably coupled to and disposed about at least a portion of the housing 4110.

Figure 11:
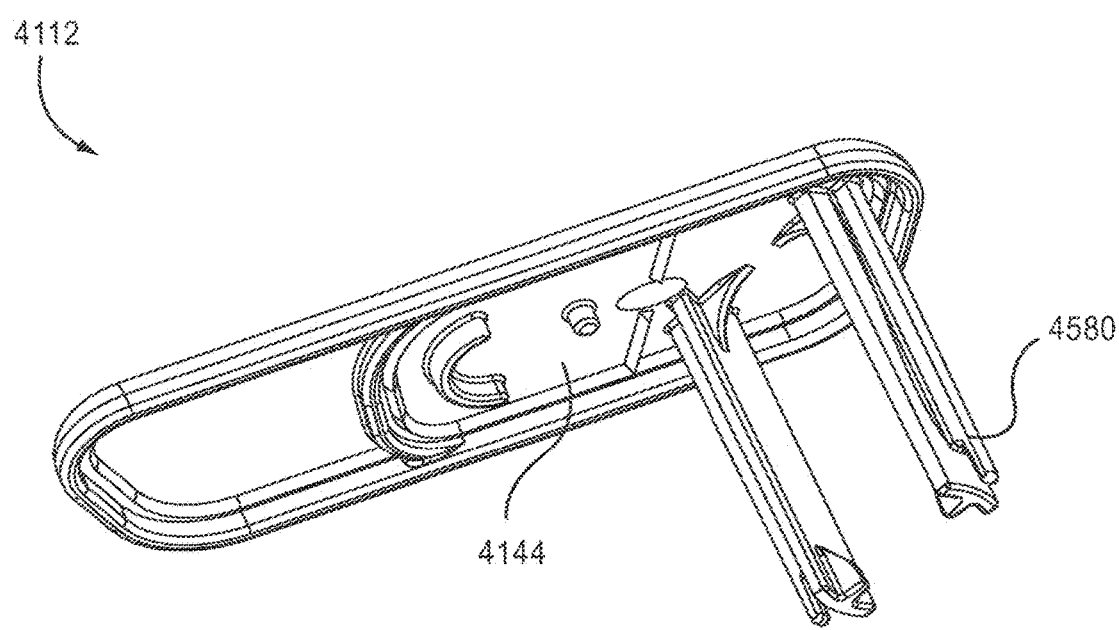

As shown in FIG. 11, the proximal cap 4112 includes a gas container retention member 4580 and defines a gas passageway 4144. The gas container retention member 4580 is configured to receive and/or retain a gas container 4570 that can contain a pressurized gas. The gas passageway 4144 is configured to allow for the passage of gas contained in the gas container 4570 from the gas cavity 4154 to the medicament cavity 4157, as further described herein. Said another way, the gas passageway 4144 places the gas cavity 4154 in fluid communication with the medicament cavity 4157.

Figure 7:
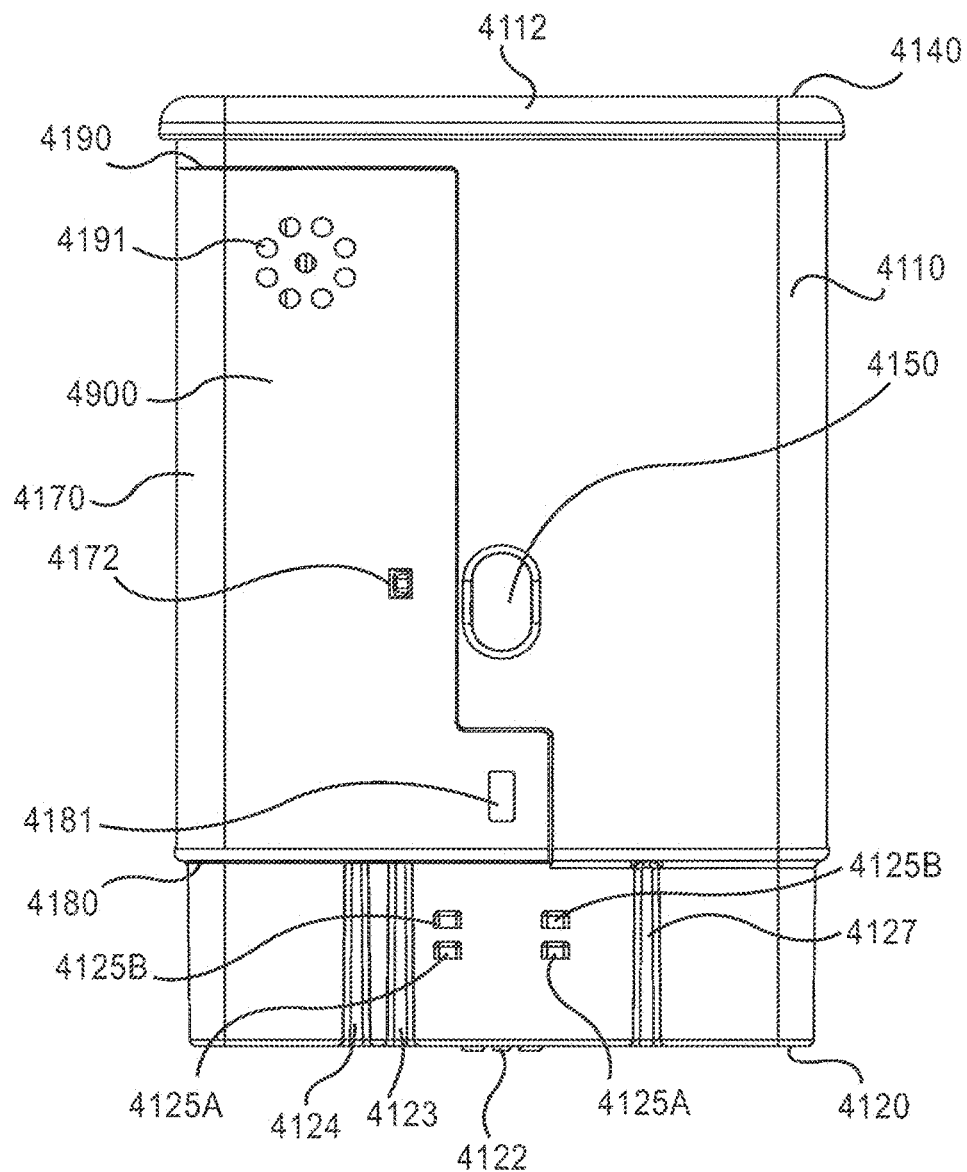
FIG. 7 is a front view of a portion of the medical injector illustrated in FIG. 3.
Figure 8:
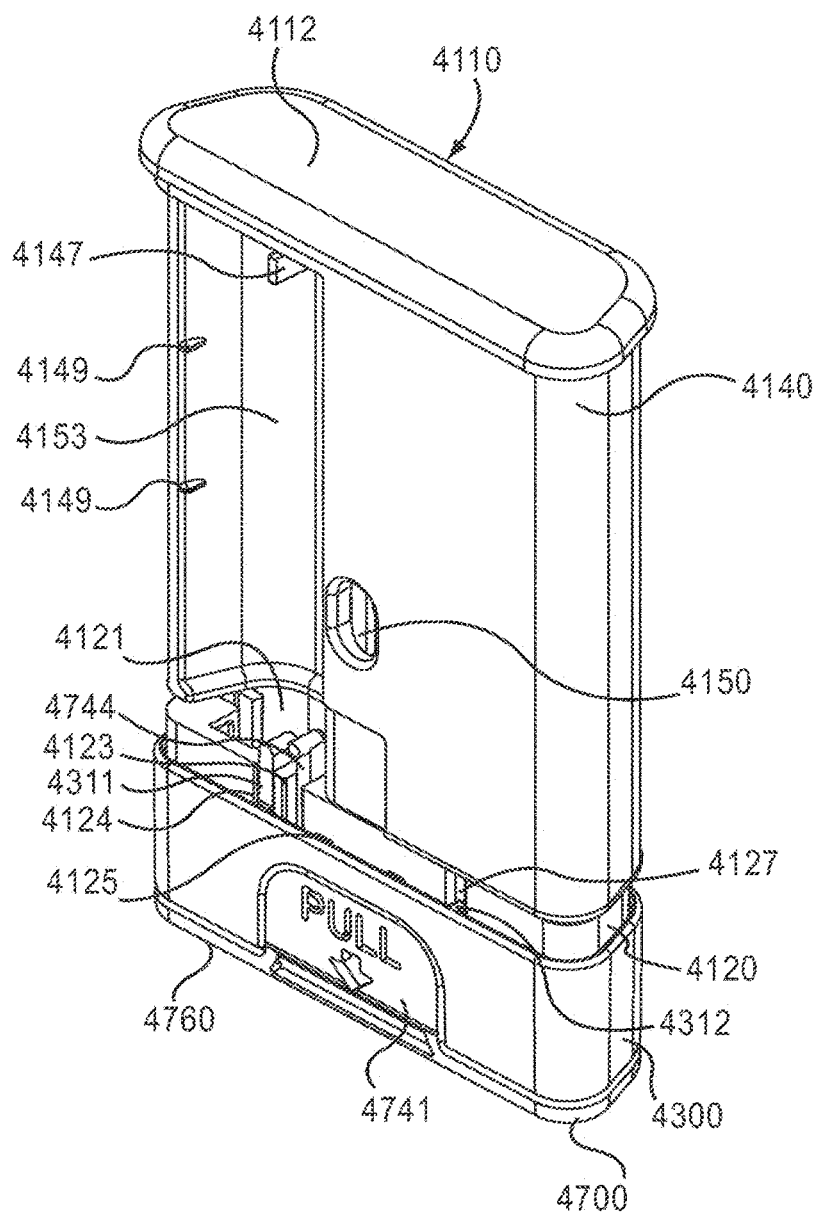
FIG. 8 is a perspective view of a portion of the medical injector illustrated in FIG. 3.

As shown in FIGS. 7 and 9, the distal end portion 4120 of the housing 4110 defines a battery isolation protrusion aperture 4121, a needle aperture 4122, a safety lock actuator groove 4123, a safety lock aperture 4128, a base actuator groove 4124, base retention recesses 4125A, 4125B, and base rail grooves 4127. The battery isolation protrusion aperture 4121 is configured to receive the battery isolation protrusion 4235 of the cover 4200 (see e.g., FIG. 25), as described in further detail herein.

The needle aperture 4122 is configured to allow the needle 4512 (see e.g., FIG. 12) to exit the housing 4110 when the medical injector 4000 is actuated. The portion of the sidewall of the housing 4110 that defines the needle aperture 4122 includes multiple sheath retention protrusions 4126. In some embodiments, the sheath retention protrusions can interact with a plurality of ribs 4728 of the needle sheath 4720 (see e.g. FIG. 29) to maintain a position of the needle sheath 4720 relative to the safety lock 4700 when the safety lock 4700 is coupled to the housing 4110 and/or when the safety lock 4700 is being removed from the housing 4110.

The safety lock actuator groove 4123 is configured to receive an actuator 4744 of the safety lock 4700. As described in more detail herein, the actuator 4744 is configured to engage and/or activate the electronic circuit system 4900 when the safety lock 4700 is moved with respect to the housing 4110. The safety lock aperture 4128 is configured to receive a safety lock protrusion 4742 (see e.g., FIGS. 25 and 26). As described in more detail below, the safety lock protrusion 4742 is received within an opening 4554 between extensions 4552 of a release member 4540 such that activation of the medical injector 4000 is prevented when the safety lock 4700 is in place. The safety lock 4700, its components and functions are further described herein.

The distal base retention recesses 4125A are configured to receive the base connection knobs 4358 of the base 4300 (see e.g., FIG. 30) when the base 4300 is in a first position relative to the housing 4110. The proximal base retention recesses 4125B are configured to receive the base connection knobs 4358 of the base 4300 when the base 4300 is in a second position relative to the housing 4110. The base retention recesses 4125A, 4125B have a tapered proximal sidewall and a non-tapered distal sidewall. This allows the base retention recesses 4125A, 4125B to receive the base connection knobs 4358 such that the base 4300 can move proximally relative to the housing 4110, but cannot move distally relative to the housing 4110. Said another way, the distal base retention recesses 4125A are configured to prevent the base 4300 from moving distally when the base 4300 is in a first position and the proximal base retention recesses 4125B are configured to prevent the base 4300 from moving distally when the base 4300 is in a second position. Similarly stated, the proximal base retention recesses 4125B and the base connection knobs 4358 cooperatively prevent "kickback" after the medical injector 4000 is actuated.

The base actuator groove 4124 is configured to receive an actuator 4311 of the base 4300. As described in more detail herein, the actuator 4311 of the base 4300 is configured to engage the electronic circuit system 4900 when the base 4100 is moved with respect to the housing 4110. The base rail grooves 4127 are configured to receive the guide members 4312 of the base 4300. The guide members 4312 of the base 4300 and the base rail grooves 4127 of the housing 4110 engage each other in a way that allows the guide members 4312 of the base 4300 to slide in a proximal and/or distal direction within the base rail grooves 4127 while limiting lateral movement of the guide members 4312. This arrangement allows the base 4300 to move in a proximal and/or distal direction with respect to the housing 4110 but prevents the base 4300 from moving in a lateral direction with respect to the housing 4110.

Figure 12:
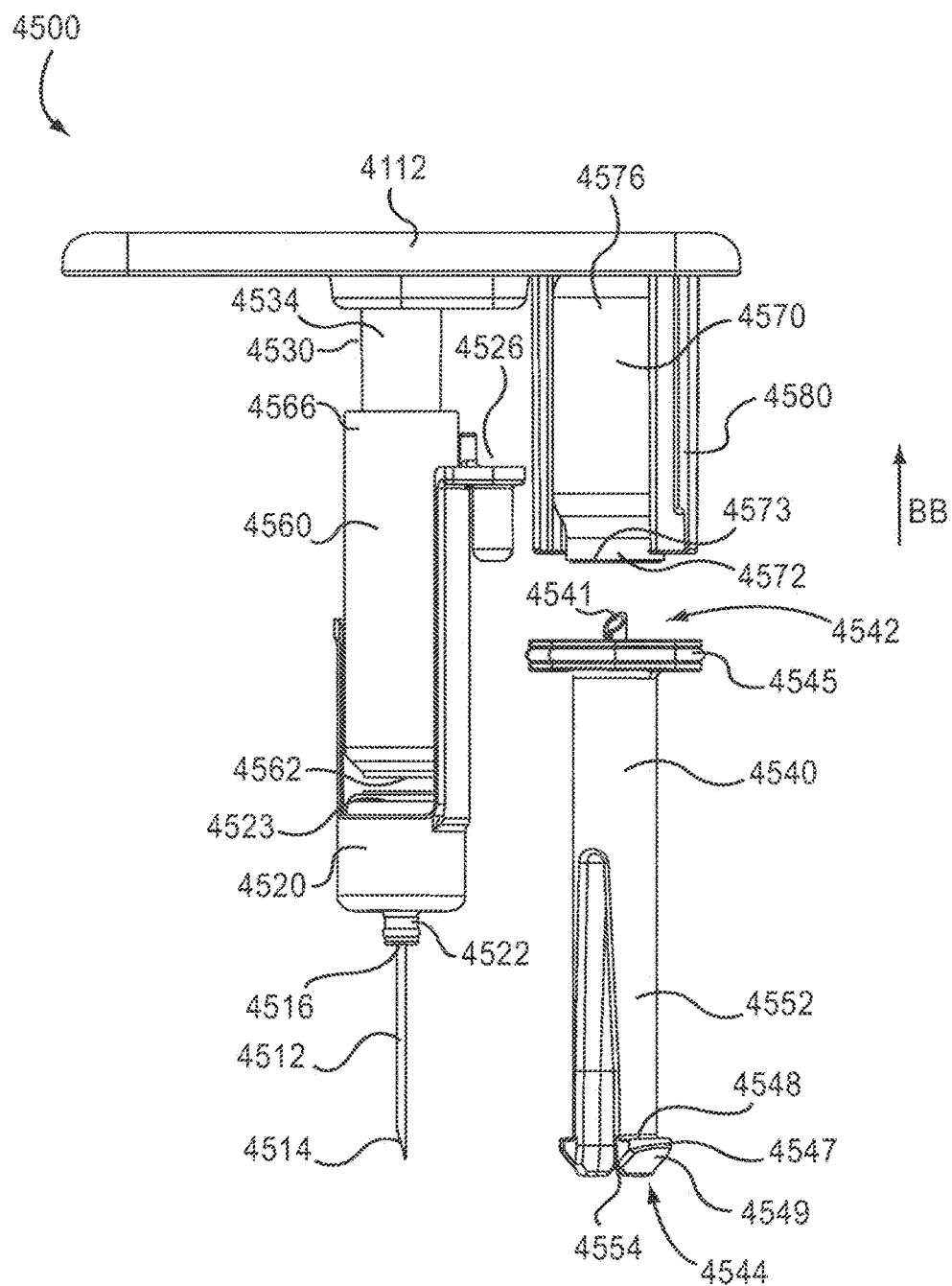
FIG. 12 is a front view of a medicament delivery mechanism of the medical injector illustrated in FIG. 3.
Figure 13:
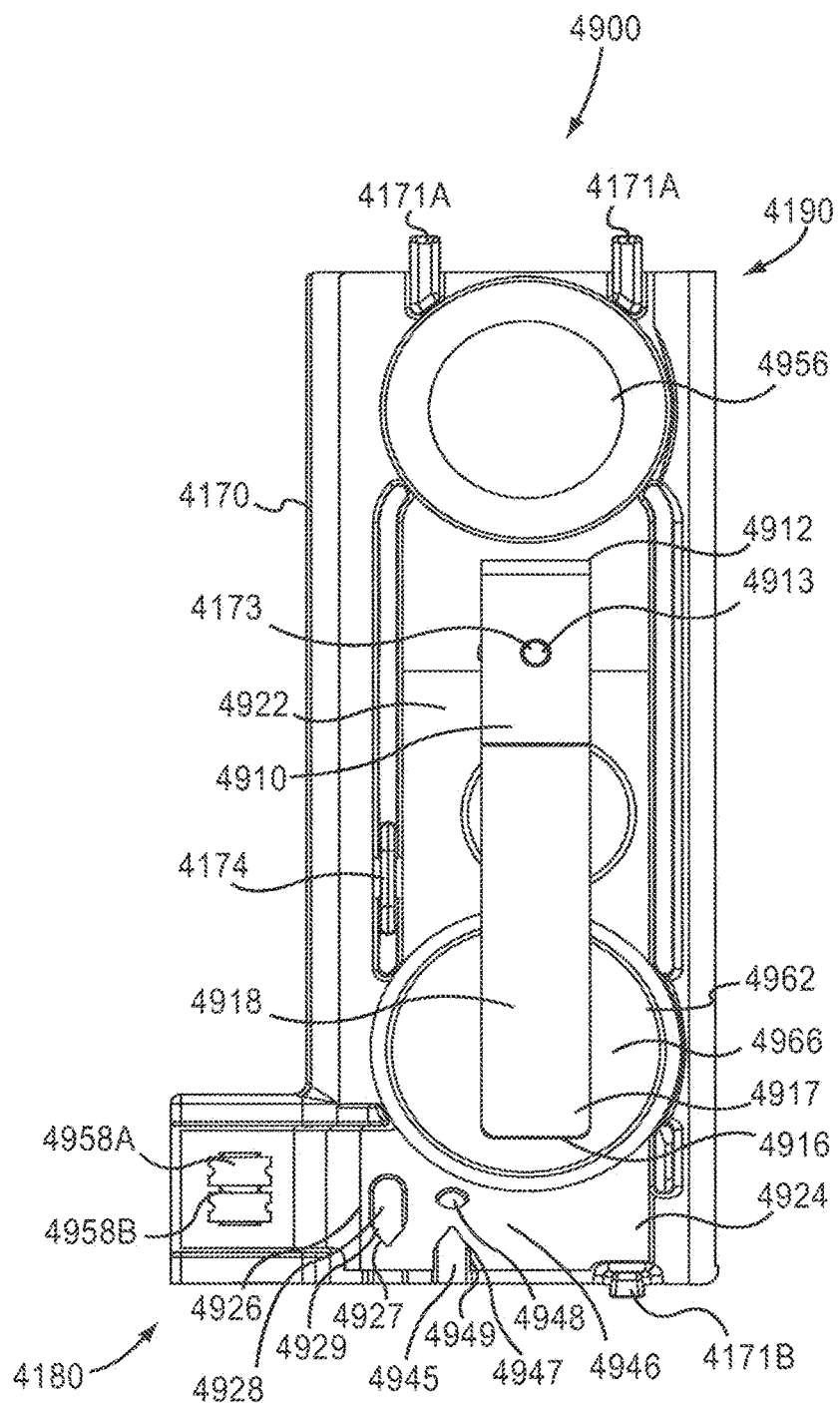
FIGS. 13 and 14 are a back view and a front view, respectively, of an electronic circuit system of the medical injector illustrated in FIG. 3.
Figure 14:
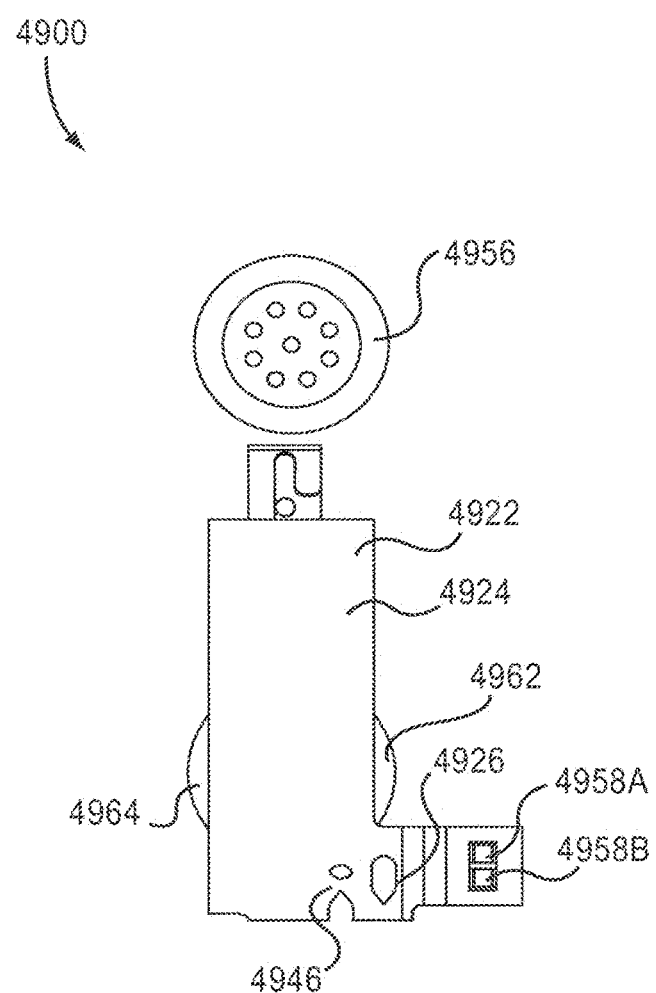
Figure 15:
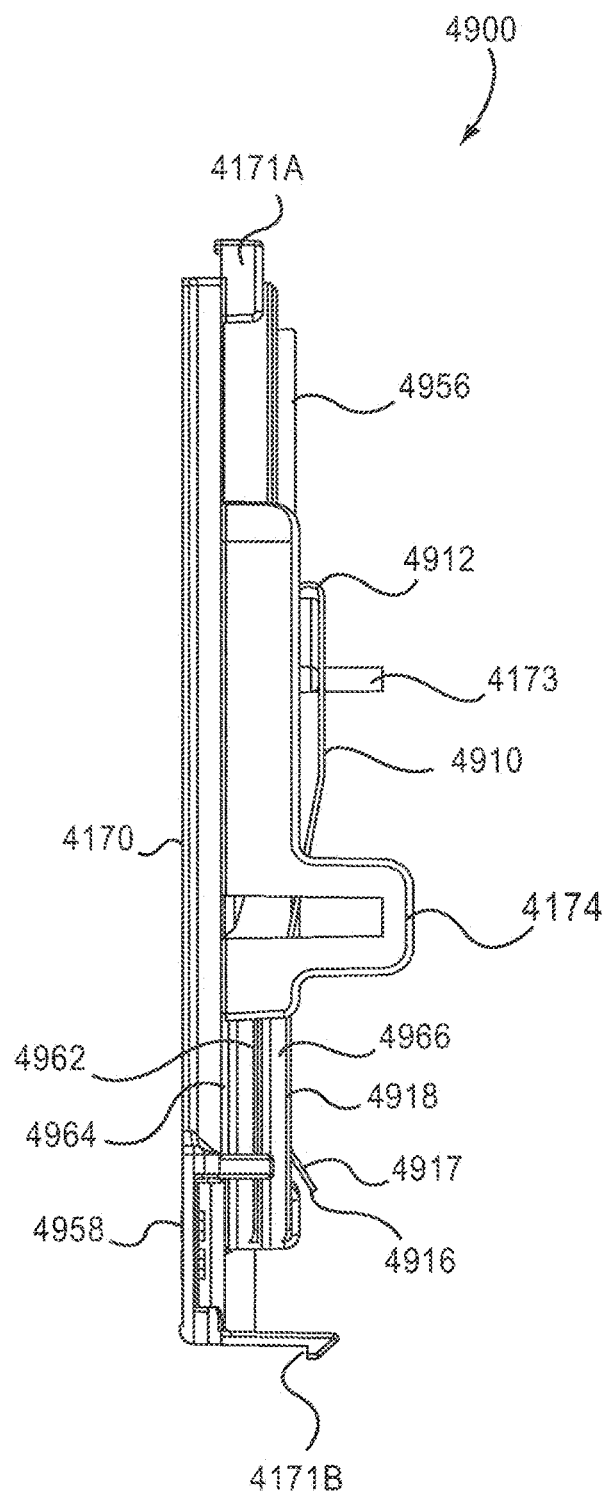
FIG. 15 is a side view of the electronic circuit system of the medical injector illustrated in FIG. 13.

FIG. 12 shows the medicament delivery mechanism 4500 of the medical injector 4000. The medical injector 4000 is similar to the auto-injectors described in U.S. Pat. No. 7,648,482, entitled "Devices, Systems and Methods for Medicament Delivery," filed Nov. 21, 2006, which is incorporated herein by reference in its entirety. Accordingly, only an overview of the medicament delivery mechanism 4500 and related operation of the medical injector 4000 is included below.

The medicament delivery mechanism 4500 includes a needle 4512, a carrier 4520, a movable member 4530, a medicament container 4560, a gas container 4570, and a release member 4540. As described above, the needle 4512, carrier 4520, movable member 4530 and medicament container 4560 are disposed within the medicament cavity 4157 of the housing 4110. The gas container 4570 and the release member 4540 are disposed within the gas cavity 4154 of the housing 4110.

The release member 4540 has a proximal end portion 4542 and a distal end portion 4544, and is movably disposed within the distal end portion 4156 of the gas cavity 4154. The proximal end portion 4542 of the release member 4540 includes a sealing member 4545 and a puncturer 4541. The sealing member 4545 is configured to engage the sidewall of the housing 4110 defining the gas cavity 4154 such that the proximal end portion 4155 of the gas cavity 4154 is fluidically isolated from the distal end portion 4156 of the gas cavity 4154. In this manner, when gas is released from the gas container 4570, the gas contained in the proximal end portion 4155 of the gas cavity 4154 is unable to enter the distal end portion 4156 of the gas cavity 4154. The puncturer 4541 of the proximal end portion 4542 of the release member 4540 is configured to contact and puncture a frangible seal 4573 on the gas container 4570 when the release member 4540 moves proximally within the gas cavity 4154, as shown by the arrow BB in FIG. 12.

The distal end portion 4544 of the release member 4540 includes extensions 4552. The extensions 4552 include projections 4547 that include tapered surfaces 4549 and engagement surfaces 4548. Further, the extensions 4552 define an opening 4554 between the extensions 4552. The tapered surfaces 4549 of the projections 4547 are configured to contact protrusions 4313 on a proximal surface 4310 of the base 4300 (see e.g., FIG. 30). The engagement surfaces 4548 of the projections 4547 are configured to extend through the safety lock aperture 4128 of the housing 4110 and contact a distal surface of the housing 4110. In this manner, the engagement surfaces 4548 of the projections 4547 limit proximal movement of the release member 4540 when the engagement surfaces 4548 are in contact with the distal surface of the housing 4110.

Figure 27:
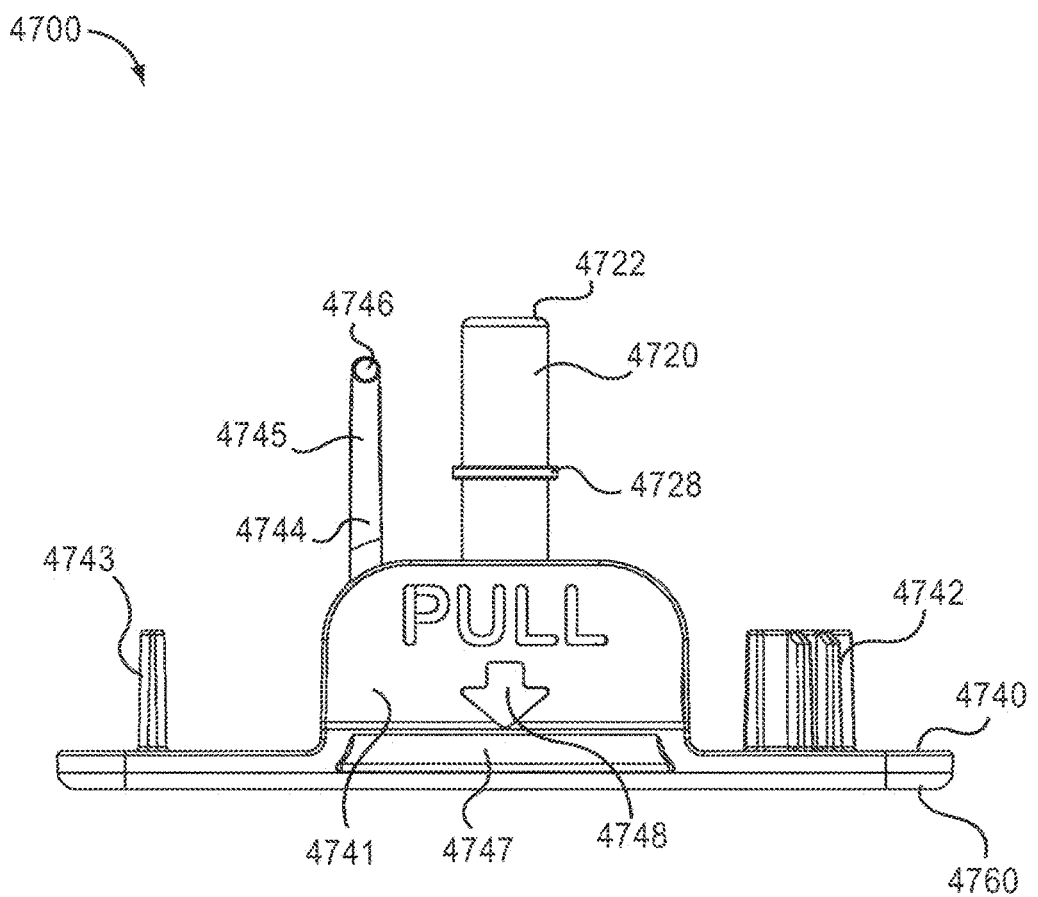

The opening 4554 defined by the extensions 4552 is configured to receive the safety lock protrusion 4742 of the safety lock 4700 (see e.g., FIG. 27). The safety lock protrusion 4742 is configured to prevent the extensions 4552 from moving closer to each other. Said another way, the safety lock protrusion 4742 is configured to ensure that the extensions 4552 remain apart and the engagement surfaces 4548 of the projections 4547 remain in contact with the distal end portion 4120 of the housing 4110. In some embodiments, for example, the release member 4540 and/or the extensions 4552 can be constructed from any suitable material configured to withstand deformation that may occur when exposed to a load over an extended period of time. In some embodiments, for example, the release member 4540 and/or the extensions 4552 can be constructed from brass.

The gas container 4570 includes a distal end portion 4572 and a proximal end portion 4576, and is configured to contain a pressurized gas. The distal end portion 4572 of the gas container 4570 contains a frangible seal 4573 configured to break when the puncturer 4541 of the proximal end portion 4542 of the release member 4540 contacts the frangible seal 4573. The gas container retention member 4580 of the proximal cap 4112 of the housing 4110 is configured to receive and/or retain the proximal end portion 4576 of the gas container 4570. Said another way, the position of the gas container 4570 within the gas cavity 4154 is maintained by the gas container retention member 4580.

The medicament container 4560 of the medicament delivery mechanism 4500 has a distal end portion 4562 and a proximal end portion 4566, and is configured to contain a medicament. The distal end portion 4562 of the medicament container 4560 contains a seal 4523. The seal 4523 is configured to burst when punctured by the proximal end 4516 of the needle 4512, as described below. The proximal end portion 4566 of the medicament container 4560 is configured to receive a piston portion 4534 of the movable member 4530.

The movable member 4530 of the medicament delivery mechanism 4500 is movably disposed within the medicament cavity 4157. The movable member 4530 includes a piston portion 4534 having a plunger at the distal end portion of the piston portion 4534. The piston portion 4534 is configured to move within the medicament container 4560. In this manner, the piston portion 4534 of the movable member 4530 can apply pressure to a medicament contained in the medicament container 4560. The piston portion 4534 can be constructed of a resilient, durable, and/or sealing material, such as a rubber.

The carrier 4520 of the medicament delivery mechanism 4500 includes a distal end portion 4522 and a proximal end portion 4526. The medicament container 4560 is coupled to the carrier 4520 via a "snap-fit" connection (not shown) such that the medicament container 4560 can move relative to the carrier 4520 between a first configuration and a second configuration during an injection event. In the first configuration, the carrier 4520 is configured to move within the medicament cavity 4157 such that movement of the carrier 4520 within the medicament cavity 4157 causes contemporaneous movement of the medicament container 4560 within the medicament cavity 4157. The proximal end portion 4516 of the needle 4512 is spaced apart from the seal 4523 of the medicament container 4560 when the carrier 4520 is in the first configuration. In the second configuration, the medicament container 4560 releases from the "snap-fit" causing the medicament container 4560 to move distally with respect to the carrier 4520, causing the proximal end portion 4516 of the needle 4512 to pierce the seal 4523. In this manner, the needle 4512 can be selectively placed in fluid communication with the medicament container 4560 to define a medicament delivery path (not shown).

Figure 20:
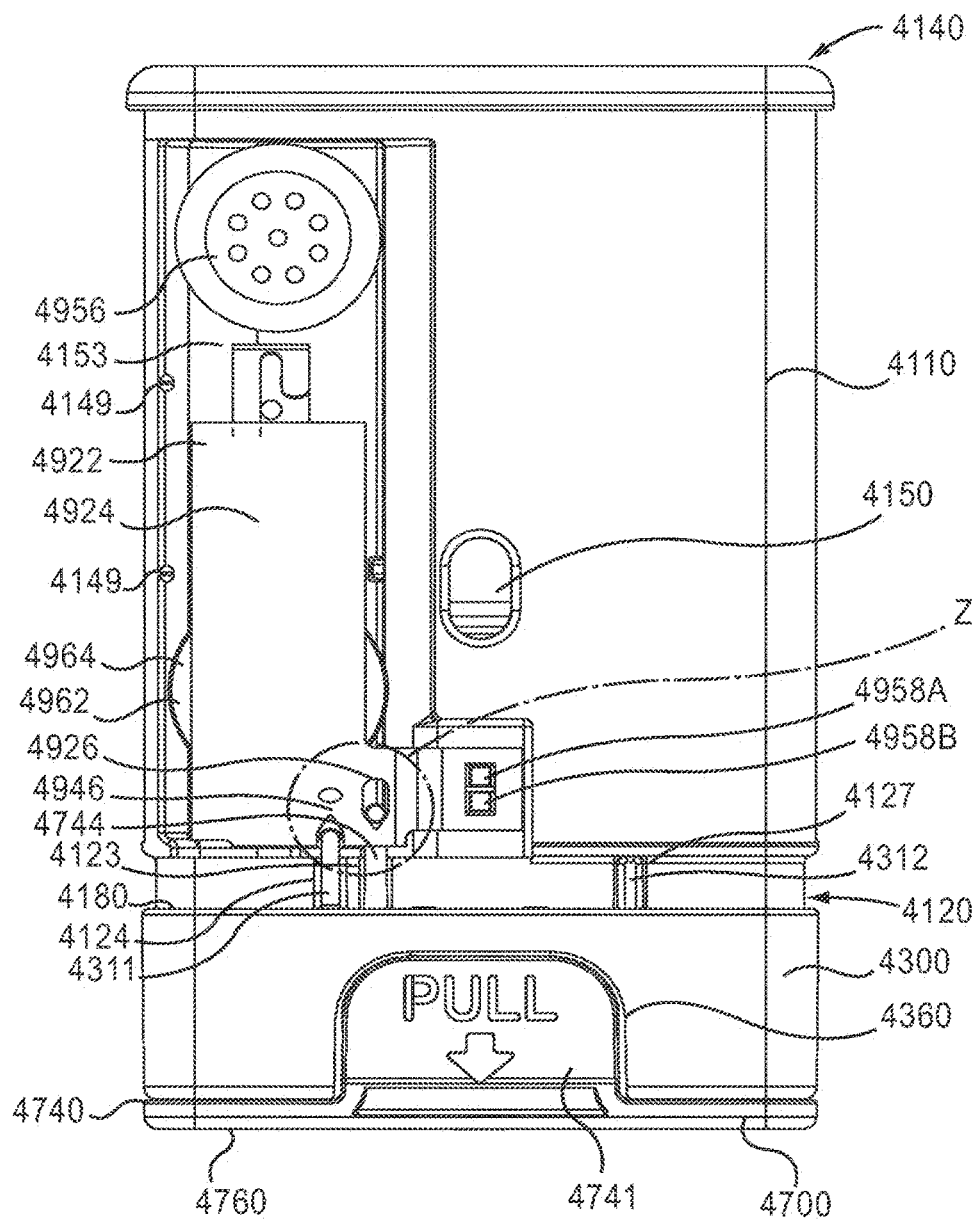
FIG. 20 is a front view of the medical injector illustrated in FIG. 3 in a first configuration showing the electronic circuit system.

FIGS. 13-22 show the electronic circuit system 4900. The electronic circuit system 4900 of the medical injector 4000 includes an electronic circuit system housing 4170, a printed circuit board 4922, a battery assembly 4962, an audio output device 4956, two light emitting diodes (LEDs) 4958A, 4958B and a battery clip 4910. As shown in FIG. 20, the electronic circuit system 4900 is configured to fit within the electronic circuit system cavity 4153 of the housing 4110. Accordingly, as described above, the electronic circuit system 4900 is physically and/or fluidically isolated from the medicament cavity 4157, the gas cavity 4154 and/or the medicament delivery device 4500. As described herein, the electronic circuit system 4900 is configured to output an electronic output associated with the use of the medical injector 4000.

The electronic circuit system housing 4170 of the electronic circuit system 4900 includes a distal end portion 4180 and a proximal end portion 4190. The proximal end portion 4190 includes connection protrusions 4171A and a battery clip protrusion 4173. The connection protrusions 4171A extend from the proximal end portion 4190 of the electronic circuit system housing 4170, and are configured to be disposed within the connection apertures 4152 of the housing 4110, as described above. In this manner, the electronic circuit system 4900 can be coupled to the housing 4110 within the electronic circuit system cavity 4153. In other embodiments, the electronic circuit system 4900 can be coupled to the housing 4110 by other suitable means such as an adhesive, a clip and/or the like. As described in more detail herein, the battery clip protrusion 4173 is configured to hold the battery clip 4910 in place.

The proximal end portion 4190 of the electronic circuit system housing 4170 defines multiple sound apertures 4191. The audible output device 4956 is disposed against the proximal end portion 4190 of the electronic circuit system housing 4170 such that the front face of the audible output device 4956 is disposed adjacent the sound apertures 4191. In this manner, the sound apertures 4191 are configured to allow sound from an audio output device 4956 to pass from the audio output device 4956 to a region outside of the housing 4110.

Figure 16:
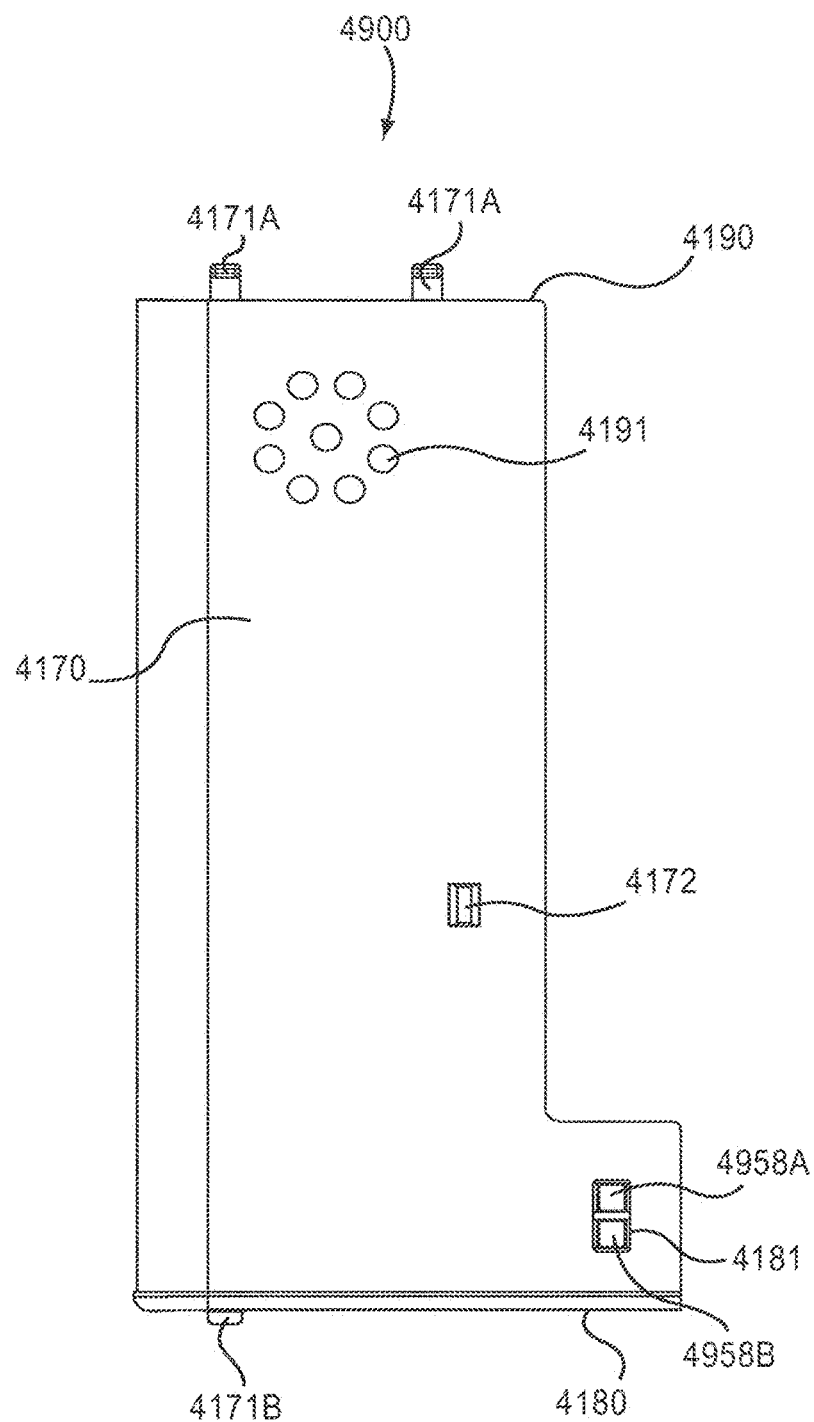
FIGS. 16 and 17 are a front view and a perspective view, respectively, of an electronic circuit system housing of the medical injector illustrated in FIG. 13.
Figure 17:
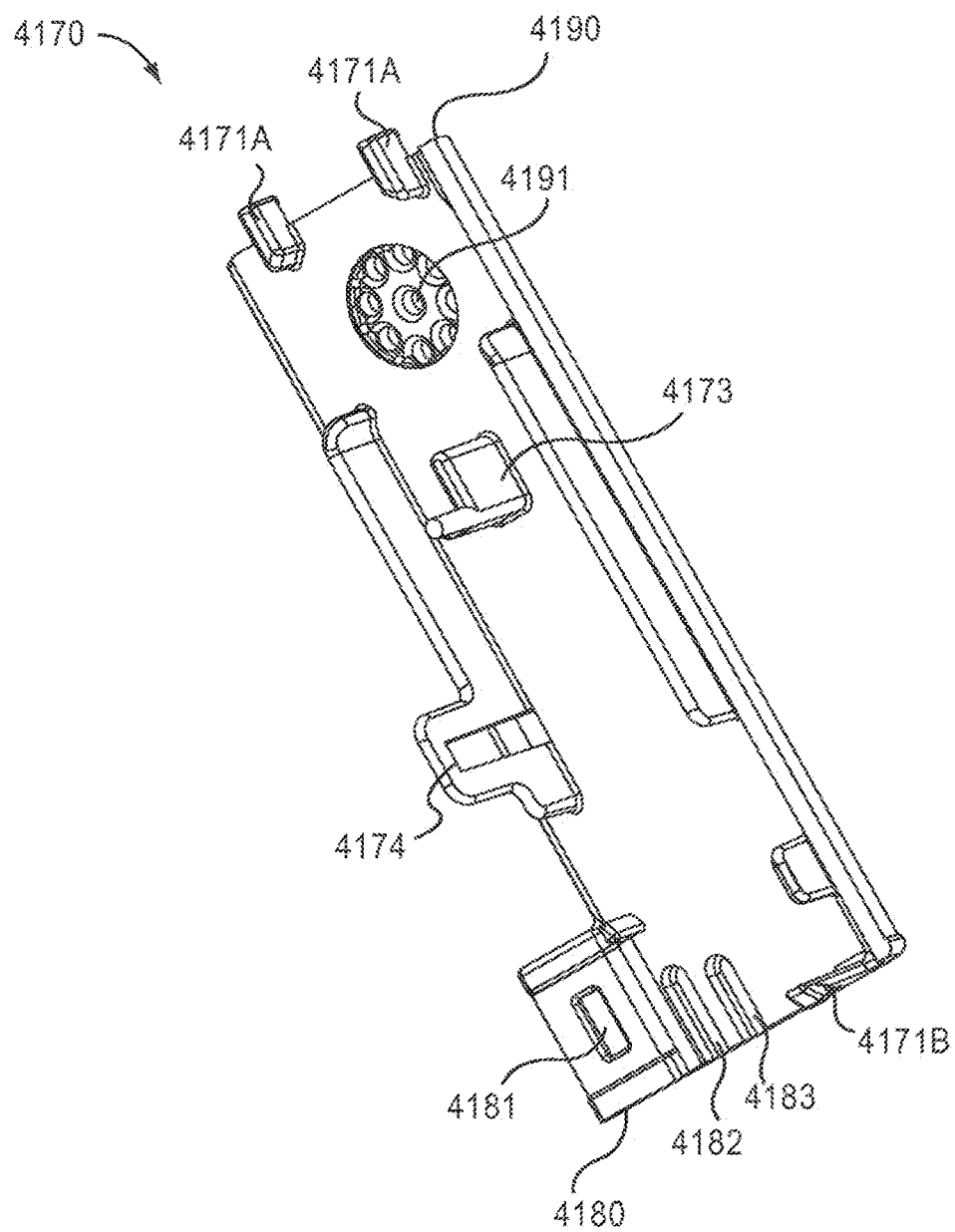
Figure 18:
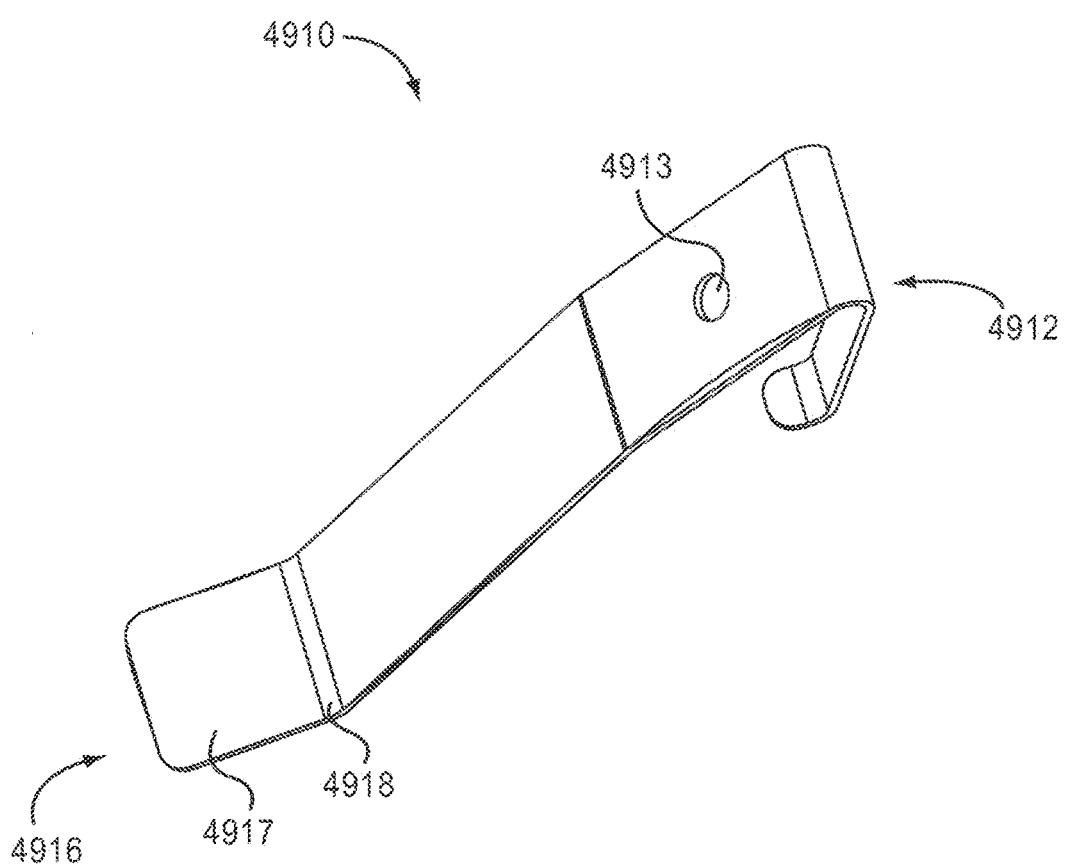
FIG. 18 is a perspective view of a battery clip of the medical injector illustrated in FIG. 13.
Figure 19:
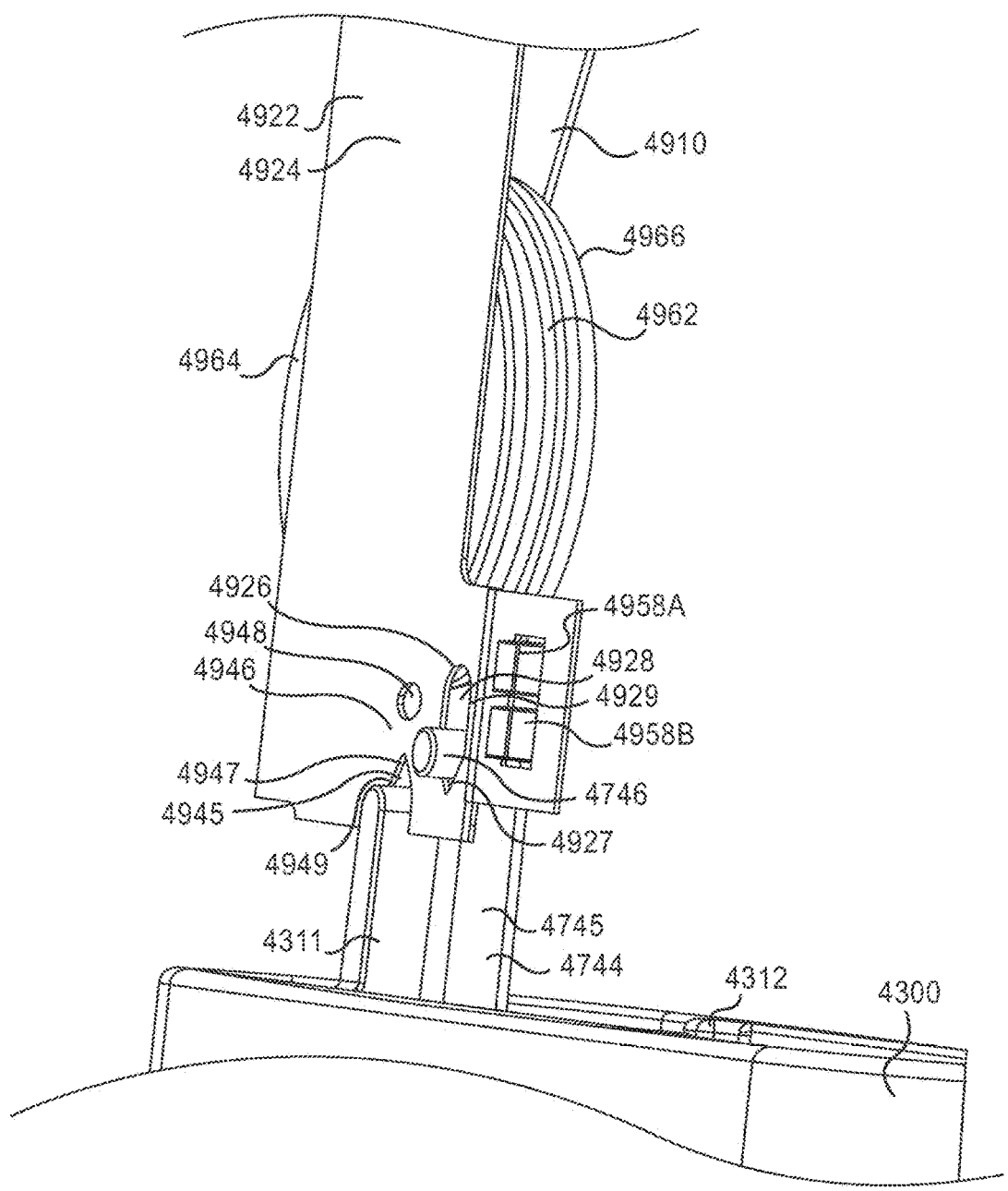
FIG. 19 is a perspective view of a portion of an electronic circuit system of the medical injector illustrated in FIG. 3, in a first configuration.

As shown in FIGS. 16 and 17, the distal end portion 4180 of the electronic circuit system housing 4170 includes a connection protrusion 4171B, a stiffening protrusion 4174, and defines an LED aperture 4181, an aperture 4172, a safety lock actuator groove 4182, and a base actuator groove 4183. The LED aperture 4181 is configured to receive the LEDs 4958A, 4958B such that a user can view the LEDs 4958A, 4958B, which are described in more detail herein.

The connection protrusion 4171B extends from the distal end portion 4180 of the electronic circuit system housing 4170, and is configured to attach the electronic circuit system 4900 to the housing 4110, as described above. The stiffening protrusion 4174 is configured to have at least a portion received within and/or accessible via the aperture 4145 in the housing 4110 (see e.g., FIG. 6). The stiffening protrusion 4174 is configured to limit the bending (e.g., buckling) of the electronic circuit system housing 4170 when the electronic circuit system housing 4170 is coupled to the housing 4110. Moreover, a user can access the stiffening protrusion 4174 via the aperture 4172. In this manner, for example, the user can disengage the stiffening protrusion 4174 from the aperture 4145.

The safety lock actuator groove 4182 of the electronic circuit system housing 4170 is configured to be disposed adjacent the safety lock actuator groove 4123 of the distal end portion 4120 of the housing 4110. In this manner, the safety lock actuator groove 4182 of the electronic circuit system housing 4170 and the safety lock actuator groove 4123 of the distal end portion 4120 of the housing 4110 collectively receive the actuator 4744 of the safety lock 4700, which is described in more detail herein. Similarly, the base actuator groove 4183 of the electronic circuit system housing 4170 is configured to be disposed about the base actuator groove 4124 of the distal end portion 4120 of the housing 4110. The base actuator groove 4183 of the electronic circuit system housing 4170 and the base actuator groove 4124 of the distal end portion 4120 of the housing 4110 collectively receive the actuator 4311 of the base 4300, which is described in more detail herein.

The printed circuit board 4922 of the electronic circuit system 4900 includes a substrate 4924, a first actuation portion 4926 and a second actuation portion 4946. The substrate 4924 of the printed circuit board 4922 includes the electrical components necessary for the electronic circuit system 4900 to operate as desired. For example, the electrical components can be resistors, capacitors, inductors, switches, microcontrollers, microprocessors and/or the like.

Figure 21:
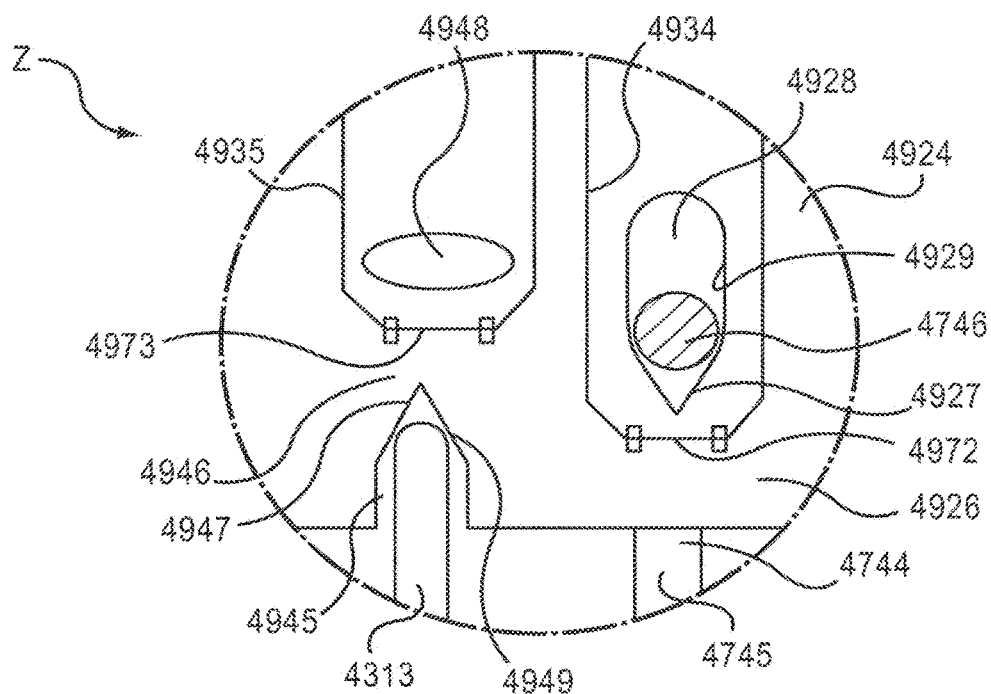
FIGS. 21, 22, and 23 are front views of a portion of the electronic circuit system of the medical injector labeled as Region Z in FIG. 20 in a first configuration, a second configuration, and a third configuration, respectively.
Figure 22:
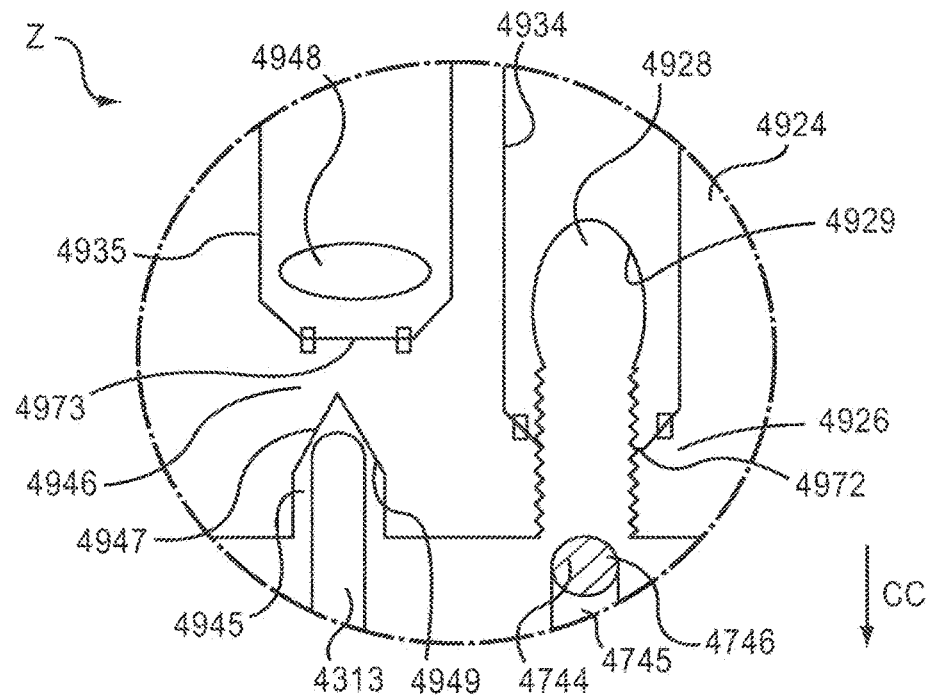
Figure 23:
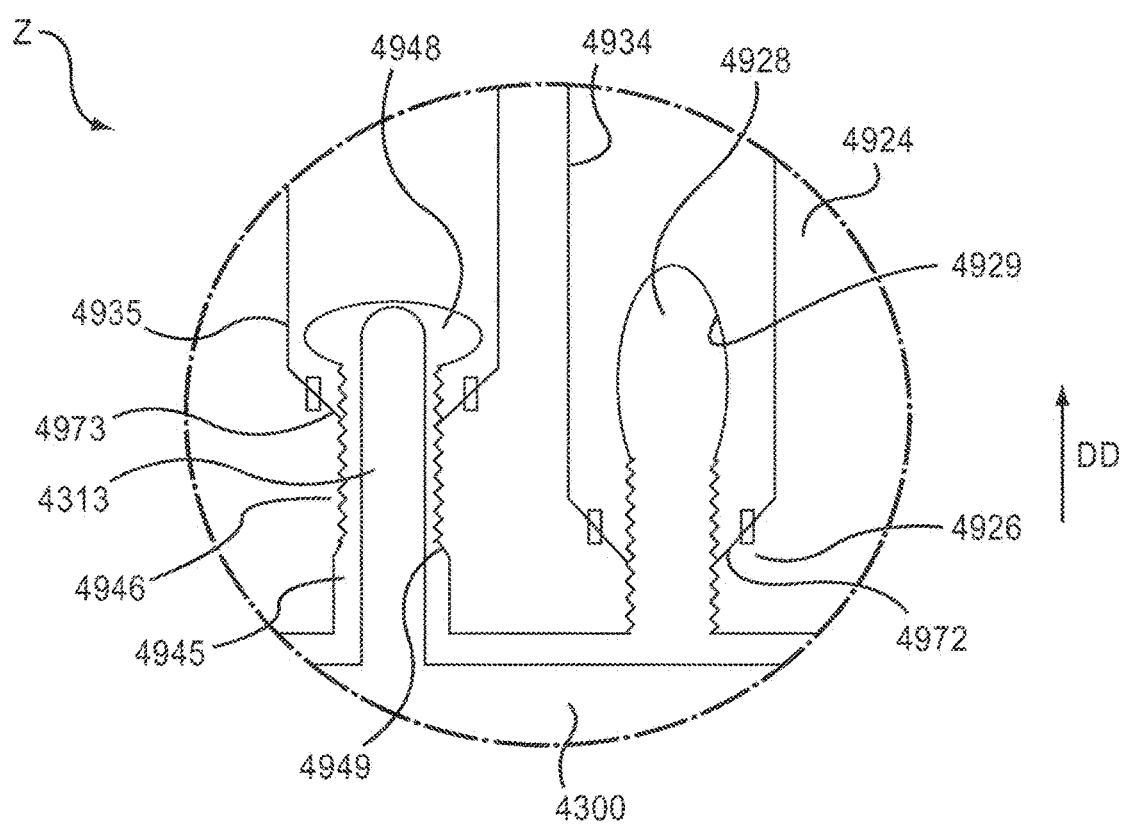

As shown in FIGS. 21-23, the first actuation portion 4926 includes a first electrical conductor 4934 and defines an opening 4928 having a boundary 4929. The opening 4928 of the first actuation portion 4926 is configured to receive a protrusion 4746 of the actuator 4744 of the safety lock 4700. The boundary 4929 of the first opening 4928 has a discontinuous shape, such as, for example, a teardrop shape, that includes a stress concentration riser 4927. The discontinuity and/or the stress concentration riser 4927 of the boundary 4929 can be of any suitable shape to cause the substrate 4924 to deform in a predetermined direction when the protrusion 4746 of the actuator 4744 of the safety lock 4700 is moved relative to the opening 4928, as shown by the arrow CC in FIG. 22.

The opening 4928 is defined adjacent the first electrical conductor 4934 that electronically couples the components included in the electronic circuit system 4900. The first electrical conductor 4934 includes a first switch 4972, which can be, for example a frangible portion of the first electrical conductor 4934. In use, when the safety lock 4700 is moved from a first position (see e.g., FIG. 21) to a second position (see e.g., FIG. 22), the actuator 4744 moves in a direction substantially parallel to a plane defined by a surface of the first actuation portion 4926 of the substrate 4924. The movement of the actuator 4744 causes the protrusion 4746 to move within the first opening 4928, as indicated by the arrow CC in FIG. 22. The movement of the protrusion 4746 tears the first actuation portion 4926 of the substrate 4924, thereby separating the portion of the first electrical conductor 4934 including the first switch 4972. Said another way, when the safety lock 4700 is moved from its first position to its second position (see e.g., FIG. 33), the actuator 4744 moves irreversibly the first switch 4972 from a first state (e.g., a state of electrical continuity) to a second state (e.g., a state of electrical discontinuity). Said yet another way, when the safety lock 4700 is moved from its first position to its second position, the actuator 4744 disrupts the first electrical conductor 4934.

The second actuation portion 4946 includes a second electrical conductor 4935 and defines an opening 4945, having a boundary 4949 and a tear propagation limit aperture 4948. As shown in FIGS. 20-23, the opening 4945 of the second actuation portion 4946 is configured to receive a portion of an actuator 4311 of the base 4300. The boundary 4949 of the opening 4945 has a discontinuous shape that includes a stress concentration riser 4947. The discontinuity and/or the stress concentration riser 4947 of the boundary 4949 can be of any suitable shape to cause the substrate 4924 to deform in a predetermined direction when the actuator 4311 of the base 4300 is moved in a proximal direction relative to the opening 4945, as shown by the arrow DD in FIG. 23.

The second electrical conductor 4935 includes a second switch 4973 disposed between the opening 4945 and the tear propagation limit aperture 4948, which can be, for example, a frangible portion of the second electrical conductor 4935. In use, when the base 4300 is moved from its first position to its second position (see e.g., FIG. 34), the actuator 4311 moves in a proximal direction, substantially parallel to a plane defined by a surface of the second actuation portion 4946 of the substrate 4924. The proximal movement of the actuator 4311 tears the second actuation portion 4946 of the substrate 4924, thereby separating the portion of the second electrical conductor 4935 including the second switch 4973. Said another way, when the base 4300 is moved from its first position to its second position, the actuator 4311 moves irreversibly the second switch 4973 from a first state (e.g., a state of electrical continuity) to a second state (e.g., a state of electrical discontinuity). The tear propagation limit aperture 4948 is configured to limit the propagation of the tear in the substrate 4924 in the proximal direction. Said another way, the tear propagation limit aperture 4948 is configured to ensure that the tear in the substrate 4924 does not extend beyond the tear propagation limit aperture 4948. The tear propagation limit aperture 4948 can be any shape configured to stop the propagation of a tear and/or disruption of the substrate 4924. For example, the tear propagation limit aperture 4948 can be oval shaped. In other embodiments, the proximal boundary of the tear propagation limit aperture 4948 can be reinforced to ensure that the tear in the substrate 4924 does not extend beyond the tear propagation limit aperture 4948.

The battery assembly 4962 of the electronic circuit system 4900 comprises two batteries stacked on top of one another. The battery assembly 4962 has a first surface 4964 and a second surface 4966. The first surface 4964 of the battery assembly 4962 can contact an electrical contact (not shown) disposed on the substrate 4924. The second surface 4966 of the battery assembly 4962 is configured to contact a contact portion 4918 of a distal end portion 4916 of a battery clip 4910. When both the electrical contact of the substrate 4924 and the contact portion 4918 of the distal end portion 4916 of the battery clip 4910 contact the battery assembly 4962, the batteries of the battery assembly 4962 are placed in electrical communication with the electronic circuit system 4900. Said another way, when the electrical contact of the substrate 4924 and the contact portion 4918 of the distal end portion 4916 of the battery clip 4910 contact the battery assembly 4962, the battery assembly 4962 is configured to supply power to the electronic circuit system 4900.

The battery clip 4910 (shown in FIG. 18) includes a proximal end portion 4912 and a distal end portion 4916. The proximal end portion 4912 defines a retention aperture 4913. The retention aperture 4913 is configured to receive the battery clip protrusion 4173 of the electronic circuit system housing 4170. In this manner, the battery clip protrusion 4173 maintains the position of the battery clip 4910 with respect to the electronic circuit system housing 4170 and/or the battery assembly 4962.

The distal end portion 4916 of the battery clip 4910 includes a contact portion 4918 and an angled portion 4917. As described above, the contact portion 4918 is configured to contact the second surface 4916 of the battery assembly 4962 to place the battery assembly 4962 in electrical communication with the electronic circuit system 4900. The angled portion 4917 of the distal end portion 4916 of the battery clip 4910 is configured to allow a proximal end portion 4236 of a battery isolation protrusion 4235 (see e.g., FIG. 25) to be disposed between the second surface 4966 of the battery assembly 4962 and the contact portion 4918 of the distal end portion 4916 of the battery clip 4910. When the battery isolation protrusion 4235 is disposed between the second surface 4966 of the battery assembly 4962 and the contact portion 4918 of the distal end portion 4916 of the battery clip 4910, the electrical path between the battery assembly 4962 and the remainder of the electrical circuit system 4900 is severed, thereby removing power from the electronic circuit system 4900. The contact portion 4918 of the distal end portion 4916 of the battery clip 4910 is biased such that when the battery isolation protrusion 4235 is removed, the contact portion 4918 will move into contact the second surface 4916 of the battery assembly 4962, thereby restoring electrical communication between the battery assembly 4962 and the electronic circuit system 4900. In some embodiments, the battery isolation protrusion 4235 can be repeatedly removed from between the second surface 4966 of the battery assembly 4962 and the contact portion 4918 of the distal end portion 4916 of the battery clip 4910 and reinserted. Said another way, the battery isolation protrusion 4235 and the battery clip 4910 collectively form a reversible on/off switch.

The audio output device 4956 of the electronic circuit system 4900 is configured to output audible sound to a user in response to a use of the medical injector 4000. In some embodiments, the audible output device 4956 can be a speaker. In some embodiments, the audible sound can be, for example, associated with a recorded message and/or a recorded speech. In other embodiments, the audible instructions can be an audible beep, a series of tones and/or or the like.

In other embodiments, the medical injector 4000 can have a network interface device (not shown) configured to operatively connect the electronic circuit system 4900 to a remote device (not shown, but which can be similar to the computing device 1801 shown above) and/or a communications network (not shown, but which can be a short-range network or the network 1805 shown above). In some embodiments, the electronic circuit system can be configured to establish a short-range radio link with a remote computing device (not shown, e.g., a user's smart phone). For example, the electronic circuit system 4900 can be paired to a remote computing device via the Bluetooth® wireless protocol. Similarly stated, the electronic circuit system 4900 can include a processor and/or radio configured to be paired to a remote computing device (not shown) via a wireless protocol that facilitates the transmission of signals within a range of approximately 100 meters or less (i.e., a Class 3 radio) and/or having a frequency within the range of 2400 MHz and 2480 MHz. In this manner, the electronic circuit system 4900 can send information to and/or receive information from the remote device. The remote device can be similar to the device 1801, for example, a remote communications network, a computer, a compliance monitoring device, a cell phone, a personal digital assistant (PDA) or the like. Such an arrangement can be used, for example, to download replacement processor-readable code from a central network to the electronic circuit system 4900. In some embodiments, for example, the electronic circuit system 4900 can download information associated with a medical injector 4000, such as an expiration date, a recall notice, updated use instructions or the like. Similarly, in some embodiments, the electronic circuit system 4900 can upload compliance information associated with the use of the medical injector 4000 via the network interface device.

The electronic circuit system 4900 (and any of the electronic circuit systems described herein) can include any of the structure and can be configured to perform any of the functions of any of the electronic circuit systems described herein, such as, for example, the electronic circuit system 1900 or the electronic circuit system 5900. For example, in some embodiments, the electronic circuit system 4900 can include a Bluetooth® low energy (BLE) processor (not shown), such as DA14581 processor, produced by Dialog Semiconductor. In other embodiments, the electronic circuit system 4900 can include a Bluetooth® low energy (BLE) processor, such any of the processors or chipsets produced by Cambridge Silicon Radio Limited (CSR Ltd), including those in the CSR101x Product family. In yet other embodiments, the electronic circuit system 4900 can include any of the Bluetooth® low energy (BLE) system on chip (SoC) produced by Nordic Semiconductor, including the nRF52840, the nRF52832, the nRF52810 chips. In some embodiments, the electronic circuit system 4900 (and any of the electronic circuit systems described herein) can include a use (or event detection) module, similar to the use module 1982 described herein.

Figure 24:
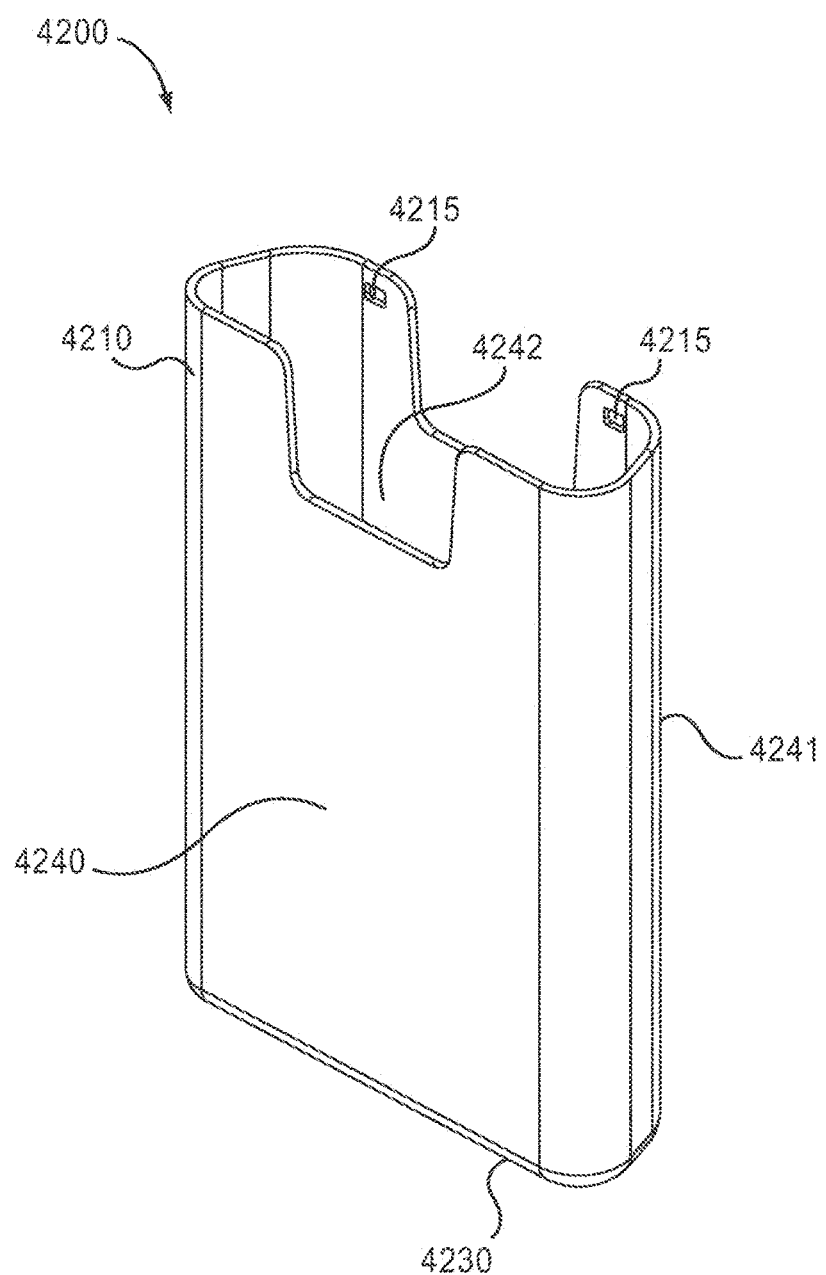
FIGS. 24 and 25 are perspective views of a cover of the medical injector illustrated in FIG. 3.
Figure 25:
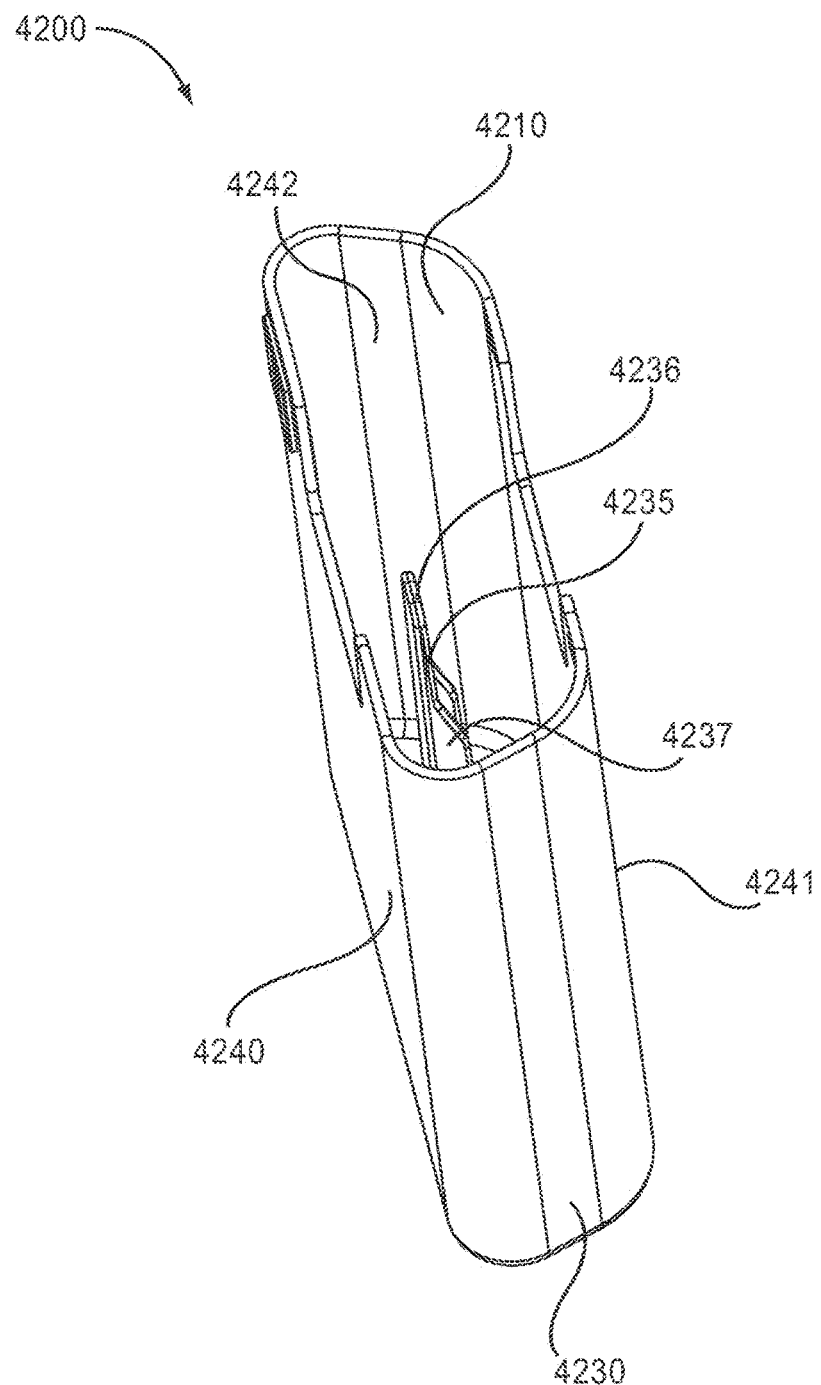
Figure 26:
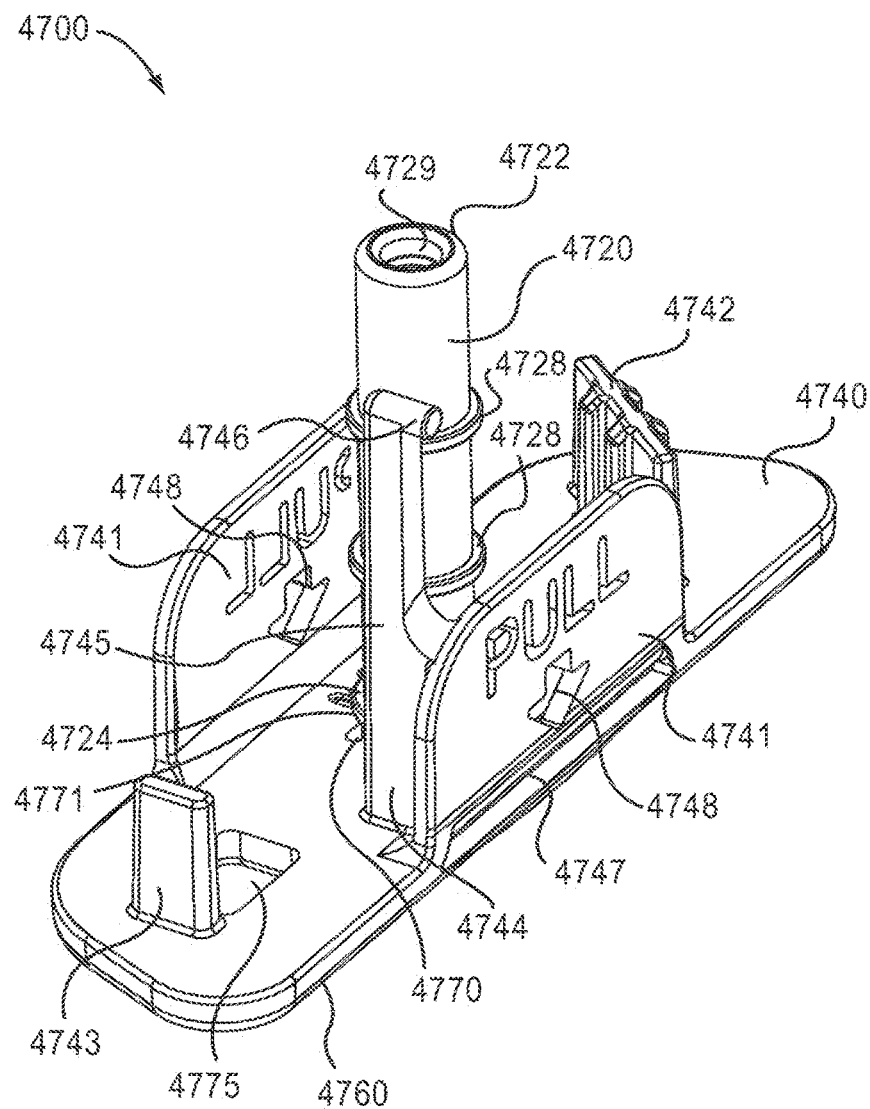
FIGS. 26-28 are a perspective view, a front view, and a bottom view, respectively, of a safety lock of the medical injector illustrated in FIG. 3.

FIGS. 24 and 25 show the cover 4200 of the medical injector 4000. The cover 4200 includes a proximal end portion 4210 and a distal end portion 4230, and defines a cavity 4242. The cavity 4242 of the cover 4200 is configured to receive at least a portion of the housing 4110. The proximal end portion 4210 defines apertures 4215 configured to receive the cover retention protrusions 4142 of the housing 4110 (shown in FIGS. 4 and 6). In this manner, the apertures 4215 and the cover retention protrusions 4142 of the housing 4110 removably retain the cover 4200 about at least a portion of the housing 4110. Said another way, the apertures 4215 and the cover retention protrusions 4142 of the housing 4110 are configured such that the cover 4200 can be removed from a portion of the housing 4110 and then replaced about the portion of the housing 4110.

The distal end portion 4230 of the cover 4200 includes a battery isolation protrusion 4235. The battery isolation protrusion 4235 includes a proximal end portion 4236 and a tapered portion 4237. The proximal end portion 4236 of the battery isolation protrusion 4235 is configured to be removably disposed between the second surface 4966 of the battery assembly 4962 and the contact portion 4918 of the distal end portion 4916 of the battery clip 4910, as described above.

FIGS. 26-29 show the safety lock 4700 of the medical injector 4000. The safety lock 4700 of the medical injector 4000 includes a proximal surface 4740, a distal surface 4760 opposite the proximal surface 4740 and a needle sheath 4720. The safety lock 4700 defines a needle sheath aperture 4770 and a battery isolation protrusion aperture 4775. The battery isolation protrusion aperture 4775 is configured to receive the battery isolation protrusion 4235 of the cover 4200 such that the battery isolation protrusion 4235 can be disposed within the electronic circuit system cavity 4153 or the electronic circuit system 4900, as described above. Similarly stated, the battery isolation protrusion aperture 4775 of the safety lock 4700 is aligned with the battery isolation protrusion aperture 4121 of the housing 4110, such that the battery isolation protrusion 4235 can be disposed within the electronic circuit system cavity 4153 when the cover 4200 is disposed about a portion of the housing 4110.

The proximal surface 4740 of the safety lock 4700 includes a safety lock protrusion 4742, a stopper 4743, an actuator 4744 and two opposing pull tabs 4741. As described above, when the safety lock 4700 is in a first (locked) position, the safety lock protrusion 4742 is configured to be disposed in the opening 4554 defined by the extensions 4552 of the distal end portion 4544 of the release member 4540. Accordingly, the safety lock protrusion 4742 is configured to prevent the extensions 4552 from moving closer to each other, thereby preventing proximal movement of the release member 4540 of the medicament delivery mechanism 4500 and/or delivery of a medicament. The stopper 4743 of the safety lock 4700 is a protrusion extending from the proximal surface 4740 of the safety lock 4700. The stopper 4743 is configured to contact a portion of the housing 4110 to limit the proximal movement of the safety lock 4700 relative to the housing 4110. In other embodiments, the stopper 4743 can be any structure configured to limit the proximal movement of the safety lock 4700.

The actuator 4744 of the safety lock 4700 has an elongated portion 4745 and a protrusion 4746. The elongated portion 4745 extends in a proximal direction from the proximal surface 4740. In this manner, the elongated portion 4745 can extend through a safety lock actuator opening 4356 of the base 4300 (see e.g., FIG. 30) and within the safety lock actuator groove 4123 of the housing 4110 and the safety lock actuator groove 4182 of the electronic circuit system housing 4170. The protrusion 4746 extends in a direction substantially transverse to the elongated portion 4745 and/or substantially parallel to the proximal surface 4740 of the safety lock 4700. As described above, the opening 4928 of the first actuation portion 4926 is configured to receive the protrusion 4746 of the actuator 4744 of the safety lock 4700.

The pull tabs 4741 of the safety lock 4700 include a grip portion 4747 and indicia 4748. The grip portion 4747 of the pull tabs 4741 provides an area for the user to grip and/or remove the safety lock 4700 from the rest of the medicament delivery system 4700. The indicia 4748 provides instruction on how to remove the safety lock 4700. In some embodiments, for example, the indicia 4748 can indicate the direction the user should pull the safety lock 4700 to remove the safety lock 4700.

Figure 28:
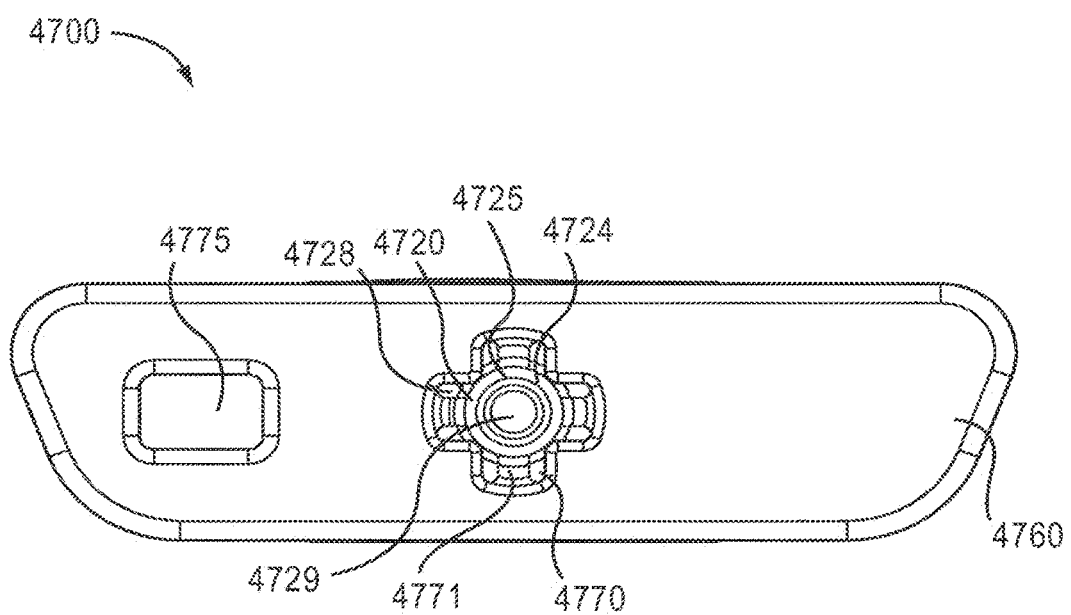
Figure 29:
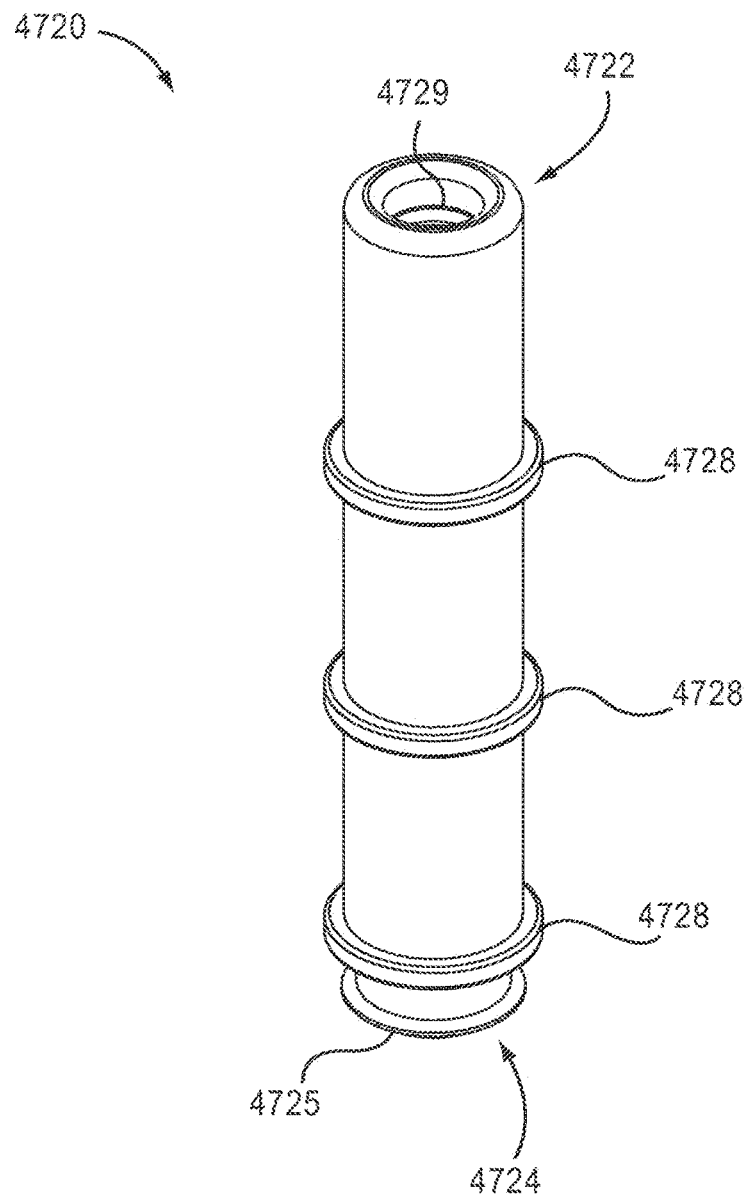
FIG. 29 is a perspective view of a needle sheath of the safety lock of the medical injector illustrated in FIG. 26.

As shown in FIG. 28, the needle sheath 4720 of the safety lock 4700 includes a distal end portion 4724, a proximal end portion 4722 and a plurality of ribs 4728. The needle sheath 4720 can also define a lumen 4729. The lumen 4729 of the safety lock 4700 is configured to receive the needle 4512. In this manner, the needle sheath 4720 can protect the user from the needle 4512 and/or can keep the needle 4512 sterile before the user uses the medical injector 4000. The proximal end portion 4722 of the needle sheath is configured to contact the distal end portion 4522 of the carrier 4520 of the medicament delivery mechanism 4500.

Figure 33:
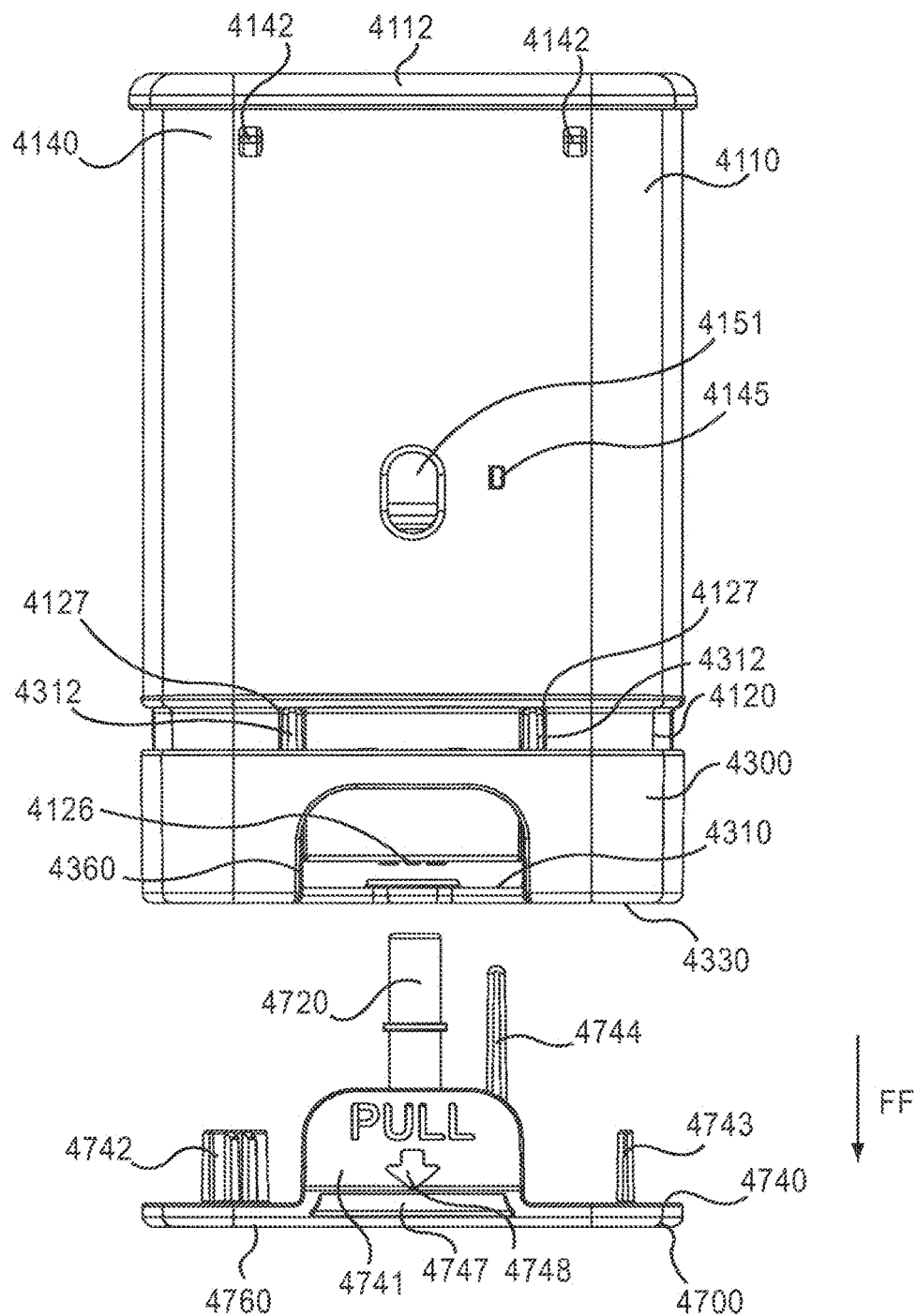
Figure 34:
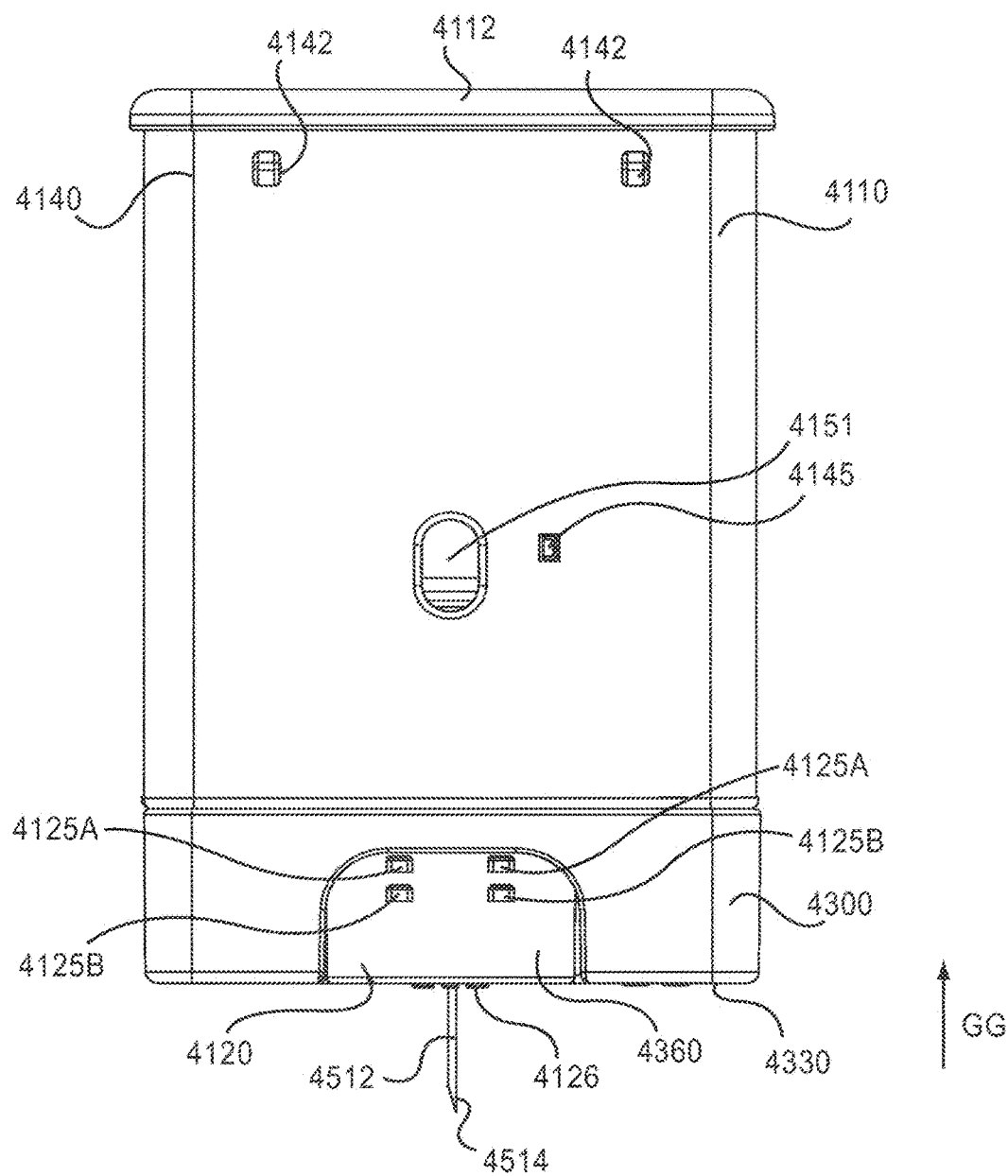

The distal end portion 4724 of the needle sheath 4720 has an angled ridge 4725. The angled ridge 4725 is configured to allow the proximal end portion 4722 of the needle sheath 4720 to irreversibly move through the needle sheath aperture 4770 of the safety lock 4700 in a distal direction. Said another way, the angled ridge 4725 can be configured in such a way as to allow the proximal end portion 4722 of the needle sheath 4720 to move through the needle sheath aperture 4770 in a distal direction, but not in a proximal direction. The needle sheath aperture 4770 has retaining tabs 4771 configured to engage the proximal end of the angled ridge 4725 when the needle sheath 4720 is moved in a proximal direction. In this manner, the retaining tabs 4771 prevent the proximal movement of the needle sheath with respect to the safety lock 4700. Further, the retaining tabs 4771 are configured to engage the proximal end of the angled ridge 4725 when the safety lock 4700 is moved in a distal direction. Said another way, as shown in FIG. 33, the needle sheath 4720 is removed from the needle 4512 when the safety lock 4700 is moved in a distal direction with respect to the housing 4110.

Figure 30:
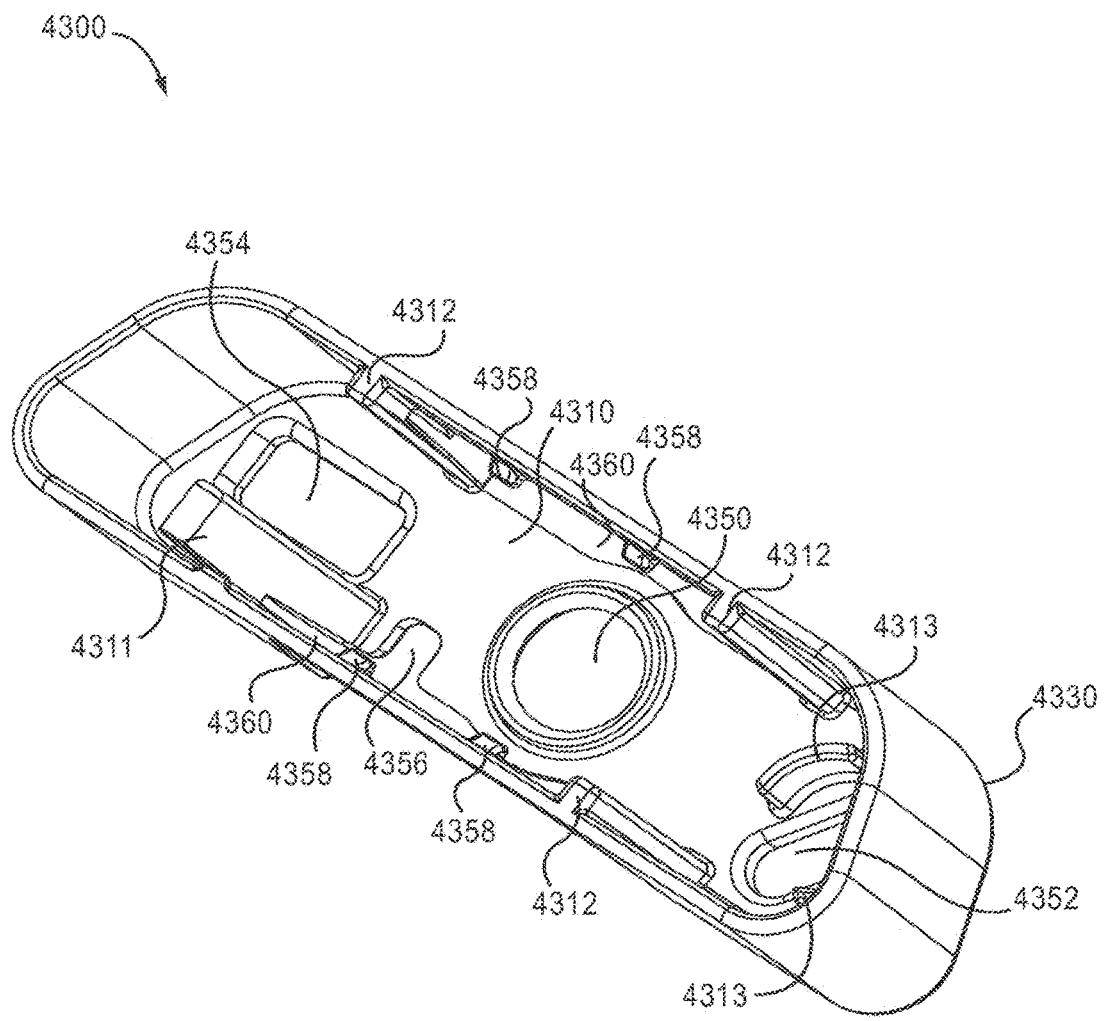
FIGS. 30 and 31 are a perspective view and a front view, respectively, of a base of the medical injector illustrated in FIG. 3.
Figure 31:
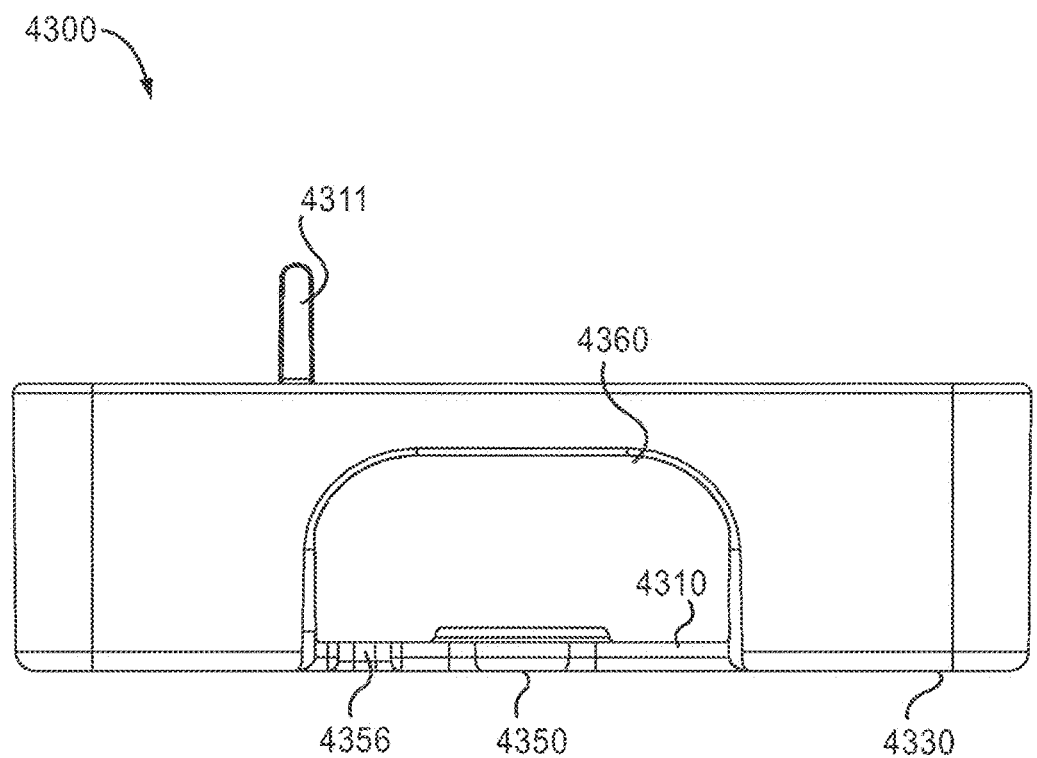

FIGS. 30-31 show the base 4300 of the medical injector 4000. The base 4300 includes a proximal surface 4310, a distal surface 4330 and base connection knobs 4358. The base 4300 defines a needle aperture 4350, a safety lock protrusion aperture 4352, a battery isolation protrusion aperture 4354, a safety lock actuator opening 4356, and pull tab openings 4360. The needle aperture 4350 is configured to receive the needle 4512 when the medical injector 4000 is actuated. The safety lock protrusion aperture 4352 of the base 4300 receives the safety lock protrusion 4742 of the safety lock 4700. The battery isolation protrusion aperture 4354 of the base 4300 receives the battery isolation protrusion 4235 of the cover 4200 and the stopper 4743 of the safety lock 4700. The safety lock actuator opening 4356 receives the safety lock actuator 4744 of the safety lock 4700. The pull tab openings 4360 are configured to receive the pull tabs 4741 of the safety lock 4700.

The proximal surface 4310 of the base 4300 includes an actuator 4311, guide members 4312, and protrusions 4313. The actuator 4311 is an elongate member configured to engage the substrate 4924 of the electronic circuit system 4900. As described above, the opening 4945 of the second actuation portion 4946 is configured to receive the actuator 4311 of the base 4300. The guide members 4312 of the base 4300 are configured to engage and/or slide within the base rail grooves 4127 of the housing 4110, as described above. The protrusions 4313 of the base 4300 are configured to engage the tapered surfaces 4549 of the extensions 4552 of the release member 4540. As described in further detail herein, when the safety lock 4700 is removed and the base 4300 is moved in a proximal direction with respect to the housing 4110, the protrusion 4313 of the base 4300 are configured to move the extensions 4552 of the release member 4540 closer to each other, actuating the medicament delivery mechanism 4500. As described above, the base connection knobs 4358 are configured to engage the base retention recesses 4125A, 4125B in a way that allows proximal movement of the base 4300 but limits distal movement of the base 4300.

Figure 32:
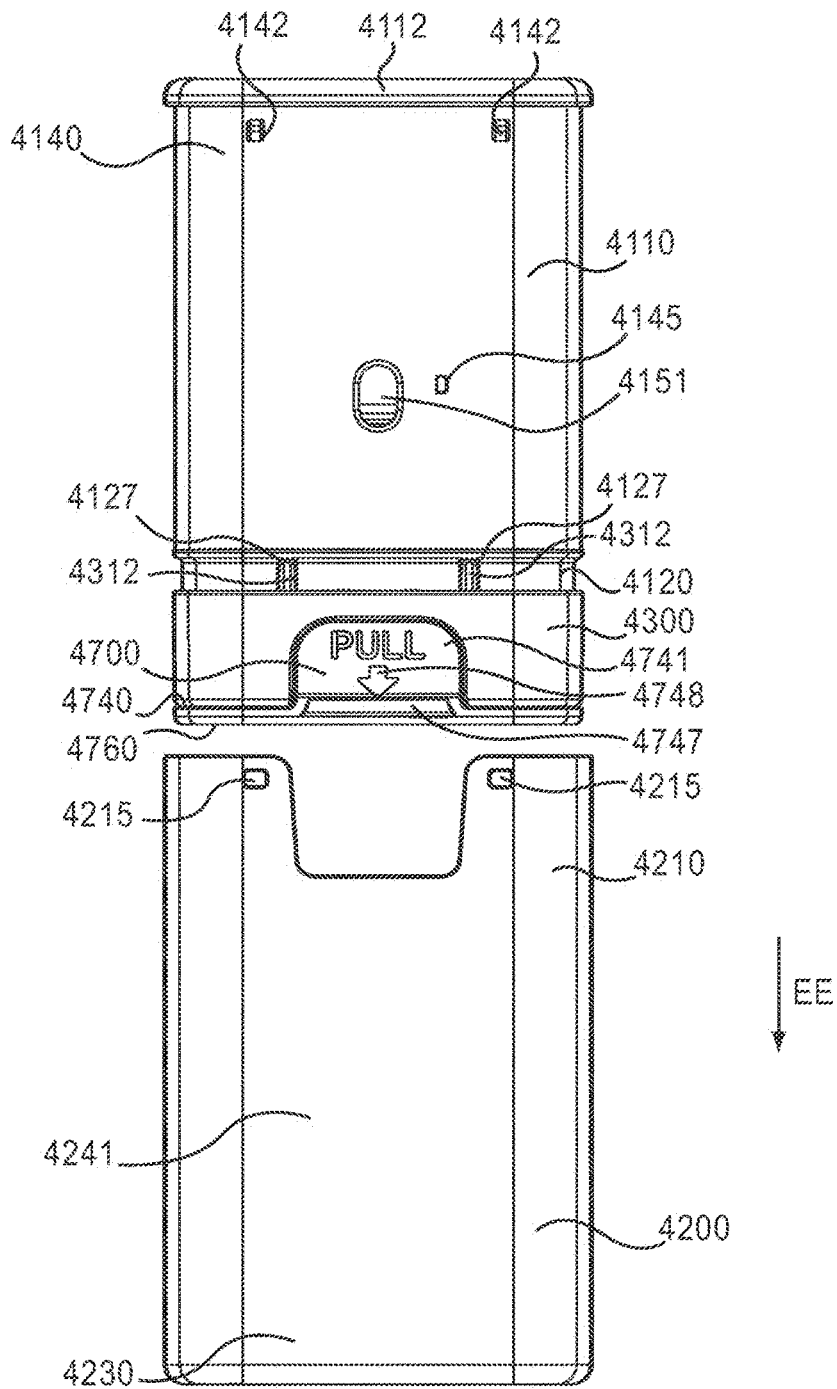
FIGS. 32-34 are a back view of the medical injector illustrated in FIG. 3 in a second configuration, a third configuration, and a fourth configuration, respectively.

As shown in FIG. 32, the medical injector 4000 is first enabled by moving the medicament delivery device from a first configuration to a second configuration by moving the cover 4200 from a first position to a second position. The cover 4200 is moved from the first position to the second position by moving it with respect to the housing 4110 in the direction shown by the arrow EE in FIG. 32. When the cover 4200 is moved with respect to the housing 4110 in the direction EE, the battery isolation protrusion 4235 is removed from the area between the battery clip 4910 and the second surface 4966 of the battery assembly 4962. In this manner, the battery assembly 4962 can be operatively coupled to the electronic circuit system 4900 when the cover 4200 is removed, thereby providing power to the electronic circuit system 4900. In other embodiments, the battery assembly 4962 can be electrically and/or operatively coupled to the electronic circuit system 4900 when the cover 4200 is in its first position. For example, in some embodiments, removal of the cover 4200 actuates a switch to produce an electronic output, similar to that described below with reference to the medical injector 5000.

When power is provided, as described above, the electronic circuit system 4900 can output one or more predetermined electronic outputs. For example, in some embodiments, the electronic circuit system 4900 can output an electronic signal associated with recorded speech to the audible output device 4956. Such an electronic signal can be, for example, associated with a .WAV file that contains a recorded instruction instructing the user in the operation of the medical injector 4000. Such an instruction can state, for example, "remove the safety tab near the base of the auto-injector." The electronic circuit system 4900 can simultaneously output an electronic signal to one and/or both of the LEDs 4958A, 4958B thereby causing one and/or both of the LEDs 4958A, 4958B to flash a particular color. In this manner, the electronic circuit system 4900 can provide both audible and visual instructions to assist the user in the initial operation of the medical injector 4000.

In other embodiments, the electronic circuit system 4900 can output an electronic output associated with a description and/or status of the medical injector 4000 and/or the medicament contained therein. For example, in some embodiments, the electronic circuit system 4900 can output an audible message indicating the type of medicament contained in the medical injector 4000, the expiration date of the medicament, the dosage of the medicament or the like.

In yet other embodiments, the electronic circuit system 4900 can output a wireless electronic output that is received by a computing device (e.g., a user's mobile phone, such as the computing device 1801 described herein). Such wireless outputs can be any wireless outputs of the types shown and described herein.

In yet other embodiments, the removal of the cover 4200 can result in a signal being transmitted to the processor (not shown, but similar to the processor 1980 or the processor 5980 described herein) of the electronic circuit system 4900. Such signals can be received, manipulated and/or used by any of the modules described herein (e.g., an event detection module, a power management module, or the like) to perform any of the methods described herein.

As described above, the medical injector 4000 can be repeatedly moved between the first configuration and the second configuration when the cover 4200 is moved repeatedly between the first position and the second position respectively. Said another way, the cover 4200 can be removed and replaced about the housing 4110 any number of times. When the cover 4200 is moved from the second position to the first position, the battery isolation protrusion 4235 is inserted between the battery clip 4910 and the second surface 4966 of the battery assembly 4962, deactivating the electronic circuit system 4900. When the cover is moved from the first position to the second position a second time, the electronic circuit system 4900 is once again activated. In this manner, the cover 4200 can be removed and the electronic circuit system 4900 can output an electronic output without compromising the sterility of the needle 4512.

In some embodiments, the electronic circuit system 4900 (or any of the electronic circuit system described herein) can include a voltage monitor that monitors the voltage (and/or the capacity) of the battery assembly 4962. In this manner, as the power is depleted, which can occur, for example, due to numerous removals of the cover 4200, the electronic circuit system 4900 can produce an output and/or change its operating configuration. For example, in some embodiments, when the capacity of the battery assembly 4962 drops below a threshold level, the electronic circuit system 4900 can produce an audible warning to the user. In some embodiments, when the capacity of the battery assembly 4962 drops below a threshold level, the electronic circuit system 4900 can produce a wireless output that is received by the user's computing device (not shown, but similar to the computing device 1801), a caregiver's computing device (not shown, but similar to the computing device 1802), or the like. In this manner, a person associated with the user can be apprised of the low power state of the device. In some embodiments, when the capacity of the battery assembly 4962 drops below a threshold level, the electronic circuit system 4900 can change a wireless communication mode to limit or eliminate communications with a computing device (e.g., the device 1801). In this manner, the power can be saved for critical operations, such as providing audible instructions during actual use.

After the cover 4200 is removed from the housing 4110, the medical injector 4000 can be moved from the second configuration to a third configuration by moving the safety lock 4700 from a first position to a second position. The safety lock 4700 is moved from a first position to a second position by moving the safety lock 4700 with respect to the housing 4110 in the direction shown by the arrow FF in FIG. 33. When the safety lock 4700 is moved from the first position to the second position, the safety lock protrusion 4742 is removed from between the extensions 4552 of the release member 4540, thereby enabling the medicament delivery member 4500. Moreover, as shown in FIGS. 21 and 22, when the safety lock 4700 is moved from the housing 4110, the actuator 4744 of the safety lock 4700 moves in the direction CC as shown in FIG. 22, irreversibly moving the first switch 4972 from a first state (e.g., a state of electrical continuity) to a second state (e.g., a state of electrical discontinuity). When the actuator 4744 of the safety lock 4700 moves irreversibly the first switch 4972 of the electronic circuit system 4900 to the second state, the electronic circuit system 4900 can output one or more predetermined electronic outputs. For example, in some embodiments, a processor (not shown) can output an electronic signal associated with recorded speech to the audible output device 4956. Such an electronic signal can be, for example, associated with a recorded message notifying the user of the status of the medical injector 4000. Such a status message can state, for example, "The medical injector is now enabled." The electronic circuit system 4900 can also simultaneously output an electronic signal to one and/or both of the LEDs 4958A, 4958B, thereby causing one and/or both of the LEDs 4958A, 4958B to stop flashing, change color or the like. In some embodiments, the electronic circuit system 4900 can produce a wireless output, of any of the types shown and described herein.

In some embodiments, the first actuation portion 4926 and the actuator 4744 can be configured such that the actuator 4744 must move a predetermined distance before the actuator 4744 engages the boundary 4929 of the opening 4928. For example, in some embodiments, the actuator 4744 must move approximately 0.200 inches before the actuator 4744 engages the boundary 4929 of the opening 4928. In this manner, the safety lock 4700 can be moved slightly without irreversibly moving the first switch 4972 of the electronic circuit system 4900 to the second state. Accordingly, this arrangement will permit the user to inadvertently and/or accidentally move the safety lock 4700 without actuating the electronic circuit system 4900.

In some embodiments, the electronic circuit system 4900 can be configured to output the status message for a predetermined time period, such as, for example, five seconds. After the predetermined time period has elapsed, the electronic circuit system 4900 can output an audible message further instructing the user in the operation of the medical injector 4000. Such an instruction can state, for example, "Place the base of the auto-injector against the patient's thigh. To complete the injection, press the base firmly against the patient's thigh." In some embodiments, the electronic circuit system 4900 can simultaneously output an electronic signal to one and/or both of the LEDs 4958A, 4958B, thereby causing one and/or both of the LEDs 4958A, 4958B to flash a particular color. In this manner, the electronic circuit system 4900 can provide both audible and/or visual instructions to assist the user in the placement and actuation of the medical injector 4000. In some embodiments, the electronic circuit system 4900 can be configured to repeat the instructions after a predetermined time period has elapsed.

As described above, in other embodiments, the medical injector 4000 can have a network interface device or radio (not shown, but similar to that shown for the electronic circuit system 1900) configured to operatively connect the electronic circuit system 4900 to a remote device (not shown, but similar to the device 1801) and/or a communications network (not shown, but similar to the network 1805). In this manner, the electronic circuit system 4900 can send a wireless signal notifying a remote device that the safety lock 4700 of the medical injector 4000 has been removed and that the medical injector 4000 has been armed.

In yet other embodiments, the removal of the safety lock 4700 can result in a signal being transmitted to the processor (not shown, but similar to the processor 1980 or the processor 5980 described herein) of the electronic circuit system 4900. Such signals can be received, manipulated and/or used by any of the modules described herein (e.g., an event detection module, a motion module, or the like) to perform any of the methods described herein.

After the safety lock 4700 is moved from the first position to the second position, the medical injector 4000 can be moved from the third configuration to a fourth configuration by moving the base 4300 from a first position to a second position. The base 4300 is moved from its first position to its second position by placing the medical injector 4000 against the body of the patient and moving the base 4300 with respect to the housing 4110 in the direction shown by the arrow GG in FIG. 34. Moving the base 4300 from the first position to the second position causes the protrusions 4313 on the proximal surface 4310 of the base 4300 to engage the tapered surfaces 4549 of the extensions 4552 of the release member 4540, causing the release member 4540 to actuate the medicament delivery mechanism 4500 and deliver a medicament to a body of a patient.

When the base 4300 is moved from the first position to the second position, the medicament delivery mechanism 4500 is actuated such that the puncturer 4541 of the release member 4540 is brought in contact with and/or punctures the frangible seal 4573 of the gas container 4570. In some embodiments, the movement of the release member 4540 can be caused by a spring (not shown in FIG. 12). After the frangible seal 4573 has been punctured, an actuating portion of a compressed gas can escape from the gas container 4570 and flow via the gas passageway 4144 into the medicament cavity 4157. The gas applies gas pressure to the movable member 4530 causing the movable member 4530 and the carrier 4520 to move in a distal direction within the medicament cavity 4157. When the carrier 4520 moves distally within the medicament cavity 4157, the carrier 4520 and the medicament container 4560 are in a first configuration. Accordingly, as described above, the medicament container 4560 is connected to the carrier 4520 by a "snap fit" connection. In this manner, the medicament container 4560 and the needle 4512 contemporaneously move with movable member 4530 and/or the carrier 4520 in a distal direction. As described above, the proximal end portion 4516 of the needle 4512 is connected to the distal end portion 4522 of the carrier 4520 and is spaced from the seal 4523 of the medicament container 4560 when the carrier 4520 is in its first configuration. Said another way, the medicament container 4560 and the needle 4512 do not define a medicament delivery path when the carrier 4520 is in the first configuration. The movement of the needle 4512 in a distal direction causes the proximal end portion 4516 of the needle 4512 to exit the housing 4110 and enter the body of a patient prior to administering a medicament.

After the carrier 4520 and/or the needle 4512 have moved within the medicament cavity 4157 a predetermined distance, the carrier 4520 and the medicament container 4560 are moved from the first configuration to a second configuration. In the second configuration of the carrier 4520, the medicament container 4560 is released from the "snap-fit" allowing the medicament container 4560 and the movable member 4530 to continue to move in a distal direction relative to the carrier 4520. Said another way, the medicament container 4560 is configured to slidably move within the carrier 4520 when the carrier is moved from the first configuration to the second configuration. As the medicament container 4560 continues to move within the carrier 4520, the proximal end portion 4516 of the needle 4512 contacts and punctures the seal 4523 of the medicament container 4560. This allows the medicament contained in the medicament container 4560 to flow into the lumen (not shown) defined by the needle 4512, thereby defining a medicament delivery path.

As the medicament container 4560 contacts the distal end of the carrier 4520, the medicament container 4560 stops moving within the carrier 4520 while the movable member 4530 continues to move in a distal direction. This causes the piston portion 4534 of the movable member 4530 to sealingly slide and/or move within the medicament container 4560 containing a liquid medicament. As the piston portion 4534 of the movable member 4530 sealingly slides and/or moves within the medicament container 4560, the piston portion 4534 generates a pressure upon the medicament contained within the medicament container 4560, thereby allowing at least a portion of the medicament to flow out of the medicament container 4560 and into the lumen defined by the needle 4512. The medicament is delivered to a body of a user via the medicament delivery path defined by the medicament container 4560 and the needle 4512.

As described above, the actuator 4538 of the base 4300 actuates the electronic circuit 4900 to trigger a predetermined output or sequence of outputs when the base 4520 is moved from its first position to its second position (see, e.g., FIGS. 19-23). When the actuator 4538 is moved in a proximal direction relative to the opening 4945, as shown by the arrow DD in FIG. 23, the electronic circuit system 4900 is actuated to output one or more predetermined electronic outputs. For example, in some embodiments, the electronic circuit system 4900 can output an electronic signal associated with recorded speech to the audible output device 4956. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 4000 in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 4900 can also simultaneously output an electronic signal to one and/or both LEDs 4958A, 4958B, thereby causing one and/or both LEDs 4958A, 4958B to stop flashing, change color or the like, to provide a visual indication that the injection is complete. In other embodiments, the electronic circuit system 4900 can send a wireless signal notifying a remote device that the injection is complete. In this manner, a patient's compliance can be monitored.

In some embodiments, the second actuation portion 4946 and the actuator 4538 can be configured such that the base 4500 and/or the actuator 4538 must move a predetermined distance before the actuator 4538 engages the boundary 4949 of the opening 4945. For example, in some embodiments, the actuator 4538 must move approximately 0.200 inches before the actuator 4538 engages the boundary 4949 of the opening 4945. In this manner, the base 4700 can be moved slightly without irreversibly moving the second switch 4973 of the electronic circuit system 4900 to the second state. Accordingly, this arrangement will permit the user to inadvertently and/or accidentally move the base 4500 without actuating the electronic circuit system 4900.

As described above, in other embodiments, the medical injector 4000 can have a network interface device or radio (not shown, but similar to that shown for the electronic circuit system 1900) configured to operatively connect the electronic circuit system 4900 to a remote device (not shown, but similar to the device 1801) and/or a communications network (not shown, but similar to the network 1805). In this manner, the electronic circuit system 4900 can send a wireless signal notifying a remote device that the base 4300 of the medical injector 4000 has been moved and that the medical injector 4000 has been actuated. In some embodiments, the electronic circuit system 4900 can include a sensor (e.g., of the types described above with reference to the sensor 1970) that produces provides "event detection" capability for the medical injector 4000. For example, in some embodiments, the electronic circuit system 4900 can include an accelerometer that detects a characteristic movement or vibration signature of the medical injector 4000 when the device is actuated.

Although the electronic circuit system 4900 is shown and described as being configured to receive the battery isolation protrusion 4235 of the cover 4200 to electrically isolate the battery assembly 4956, in other embodiments, a power source can remain coupled to other portions of an electronic circuit system (such as a processor) when device is in a "storage state." Specifically, in some embodiments, a medicament delivery device (or drug product) can include an electronic circuit system that remains powered even when within a sleeve or cover (such as the cover 4200). In this manner, certain portions of the electronic circuit system can continue to function to facilitate the methods associated with the alerts, the connected health delivery systems (e.g., the systems 5800, 6800), or the like. Such functions can include, for example, continued operation of an internal processor clock, continued operation of wireless communication functions (e.g., to be paired with, communicate with, or search for a remote computing device, such as the user's mobile phone).

Although the electronic circuit system 4900 is shown and described as including single-use or "tear through" switches 4972, 4973 that provide feedback to the electronic circuit system 4900 (and processor) regarding the status of the device 4000, in other embodiments, any suitable switches can be included in any of the electronic circuit system 4900 (or any other electronic circuit systems) described herein. For example, in some embodiments, an electronic circuit system can include re-usable toggle switches, optical switches, or the like.

For example, FIGS. 35-46 show a medicament delivery device (also referred to as a medical injector an auto-injector) 5000 having an electronic circuit system 5900 that has wireless connectivity. The medicament delivery device 5000 can be included in any of the connected health medicament delivery systems shown and described herein, such as the connected health medicament delivery systems 5800, 6800, and 7800 described herein. The medicament delivery device 5000 can include any of the features of any of the devices shown and described herein, including the features shown and described above with reference to the device 4000. For example, the medicament delivery device 5000 can include a gas container, similar to the gas container 4570 shown and described above, that produces a force to deliver a medicament (e.g., by first inserting a needle, and then delivering the medicament therethrough). As another example, the medicament delivery device 5000 can include a carrier, similar to the carrier 4520, that holds and/or moves a medicament container during use.

Figure 35:
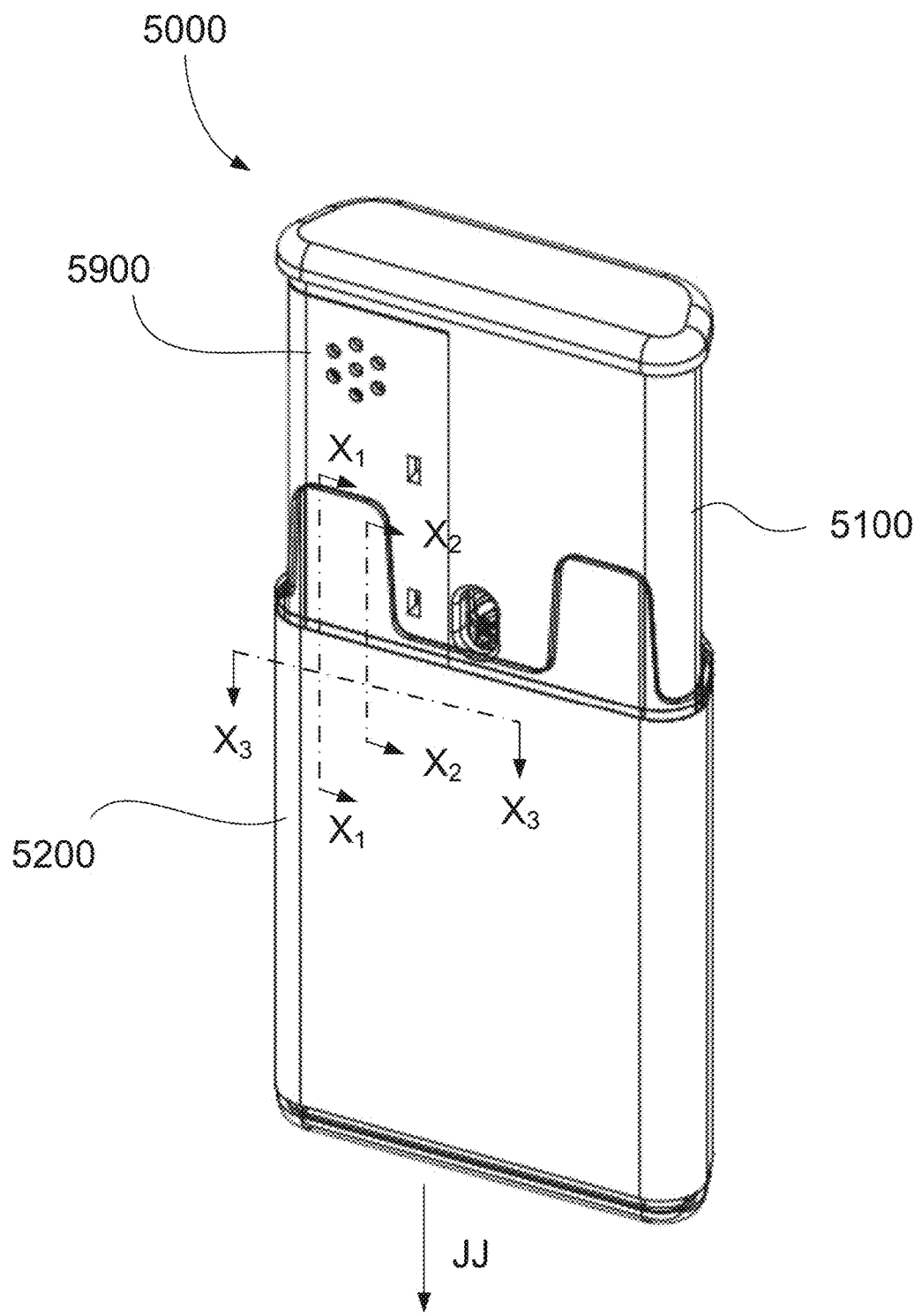
FIG. 35 is a perspective view of a medical injector according to an embodiment.
Figure 36:
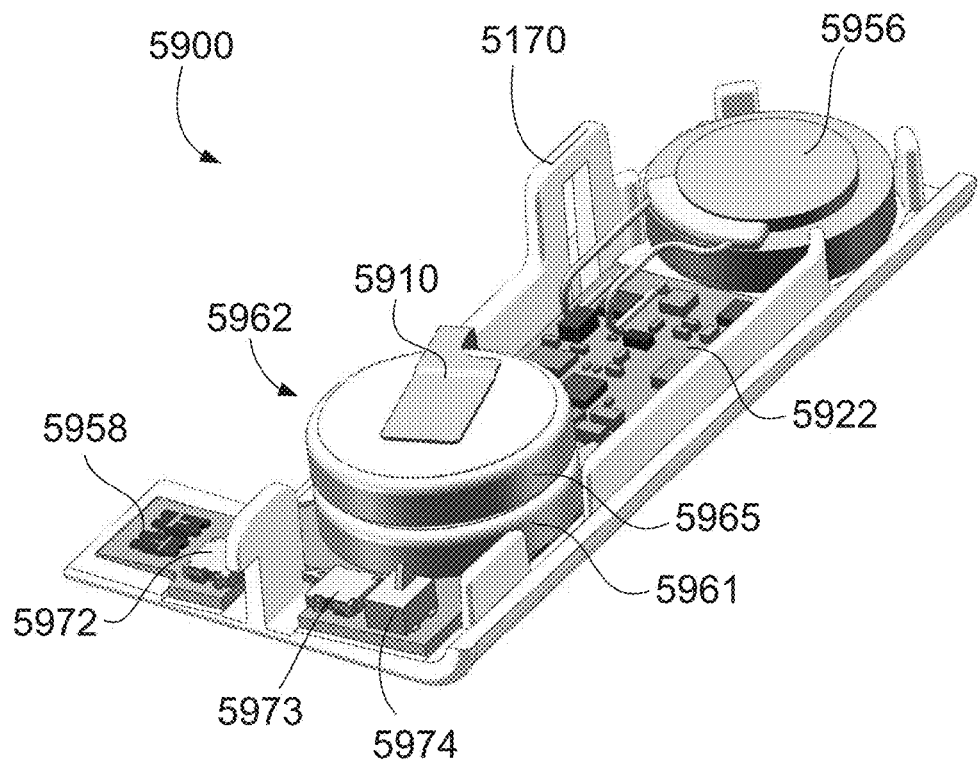
FIGS. 36 and 38 are perspective views of an electronic circuit system of the medical injector shown in FIG. 35.

As shown in FIG. 35, the medicament delivery device 5000 includes, among other components, a housing 5100, a cover 5200 (see also FIG. 43), a safety lock 5700 (see FIG. 46), and an electronic circuit system 5900. The housing 5100 contains the components of the medicament delivery device 5000, and is similar in structure and function to the housing 4110 described above. Similar to the cover 4200 described above, the cover 5200 can be removably coupled to and disposed about at least a portion of the housing 5100. In some embodiments, the cover 5200 can define one or more apertures or can include one or more protrusions that matingly engage corresponding portions of the housing 5100 to removably retain the cover 5200 about at least a portion of the housing 5100. In this manner, the cover 5200 is configured to be repeatedly removed from and replaced about a portion of the housing 5100, but in a manner that requires a minimum threshold force to remove the cover 5200. In this manner, the cover cannot easily "fall from" or be inadvertently removed from about the housing 5100.

Figure 43:
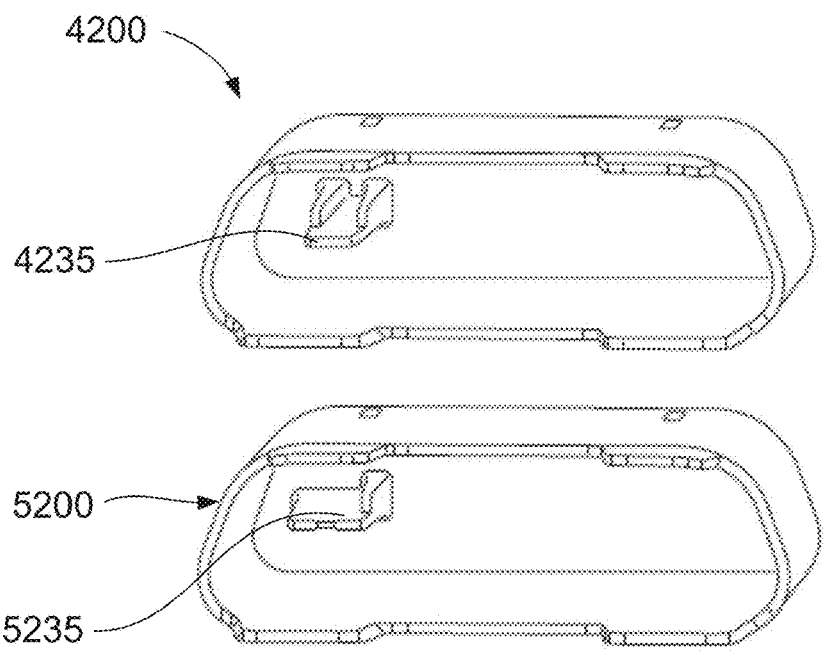
FIG. 43 shows various covers of a medicament delivery device, according to an embodiment.

Referring to FIG. 43, the distal end portion of the cover 5200 includes a switch protrusion 5235. In contrast to the cover 4200, which includes a battery isolation protrusion 4235, the switch protrusion 5235 is configured to engage and/or actuate the switch 5974 (see FIG. 41) to actuate the electronic circuit system 5900 when the cover 5200 is removed from about the housing 5100.

The electronic circuit system 5900 can include any suitable components to perform any of the functions described herein, including functions associated with the electronic circuit system 1900 and 4900 described herein. Specifically, the electronic circuit system 5900 of the medical injector 5000 includes an electronic circuit system housing 5170, a printed circuit board 5922, a battery assembly 5962, an audio output device 5956, two light emitting diodes (LEDs) 5958, a series of sensors and switches, and a processor that includes wireless communication functionality. The electronic circuit system 5900 is configured to fit within an electronic circuit system cavity of the housing 5100. Accordingly, the electronic circuit system 5900 is physically and/or fluidically isolated from the medicament cavity or any medicament delivery path of the device 5000. As described herein, the electronic circuit system 5900 is configured to output one or more electronic outputs, including wireless signals, associated with the use of the medical injector 5000. The electronic circuit system 5900 can therefore communicate with (either directly or indirectly via a network) other devices within any of the connected health medicament delivery systems shown and described herein, such as the connected health medicament delivery systems 1800, 5800, 6800, and 7800 described herein.

The electronic circuit system housing 5170 includes connection protrusions, ribs, and tabs (defining connection apertures) that are configured to be disposed within or otherwise matingly engage the connection portions of the housing 5100. In this manner, the electronic circuit system 5900 can be coupled to the housing 5110 within an electronic circuit system cavity. In other embodiments, the electronic circuit system 5900 can be coupled to the housing 5100 by other suitable means such as an adhesive, a clip and/or the like. Although shown as being coupled to the housing 5100, in other embodiments, an electronic circuit system can be coupled to the cover 5200, and can thus be removably coupled to the housing 5100 and/or the medicament delivery device 5000.

Figure 37:
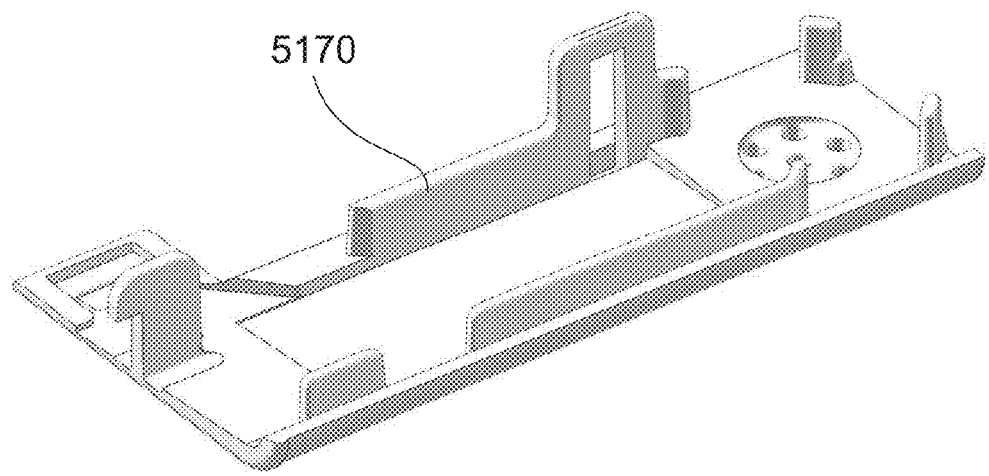
FIG. 37 is a perspective view of a housing of the electronic circuit system shown in FIG. 36.
Figure 38:
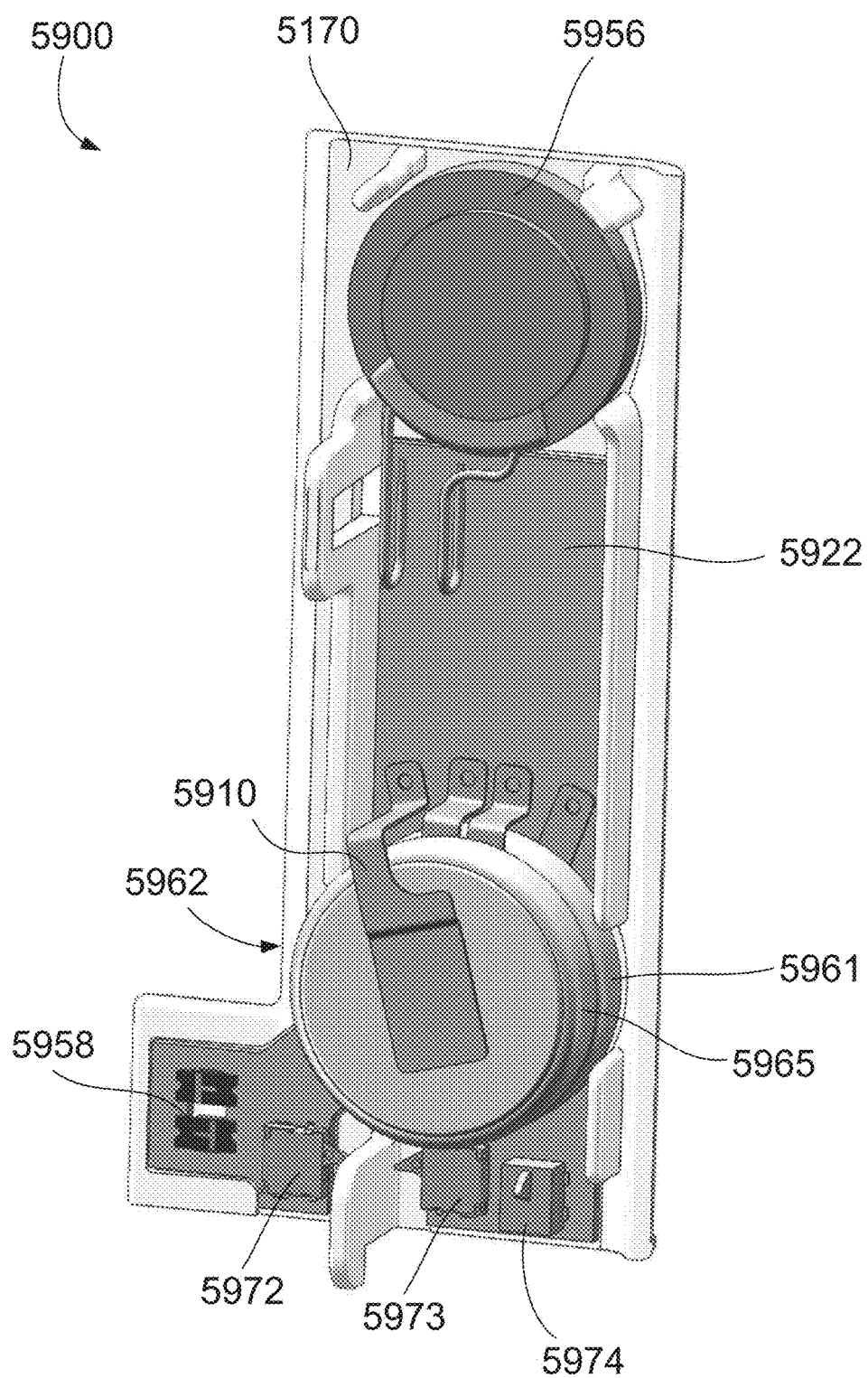

As shown in FIG. 37, the proximal end portion of the electronic circuit system housing 5170 defines multiple sound apertures. The audible output device 5956 is disposed against the proximal end portion of the electronic circuit system housing 5170 such that the front face of the audible output device 5956 is disposed adjacent the sound apertures. In this manner, the sound apertures are configured to allow sound from an audio output device 5956 to pass from the audio output device 5956 to a region outside of the housing 5100.

The printed circuit board 5922 of the electronic circuit system 5900 includes a substrate upon (or to) which the electrical components necessary for the electronic circuit system 5900 to operate as desired. For example, the electrical components can be resistors, capacitors, inductors, sensors, accelerometers, switches, memory, microcontrollers, microprocessors, drivers, antennas, and/or the like.

Figure 39:
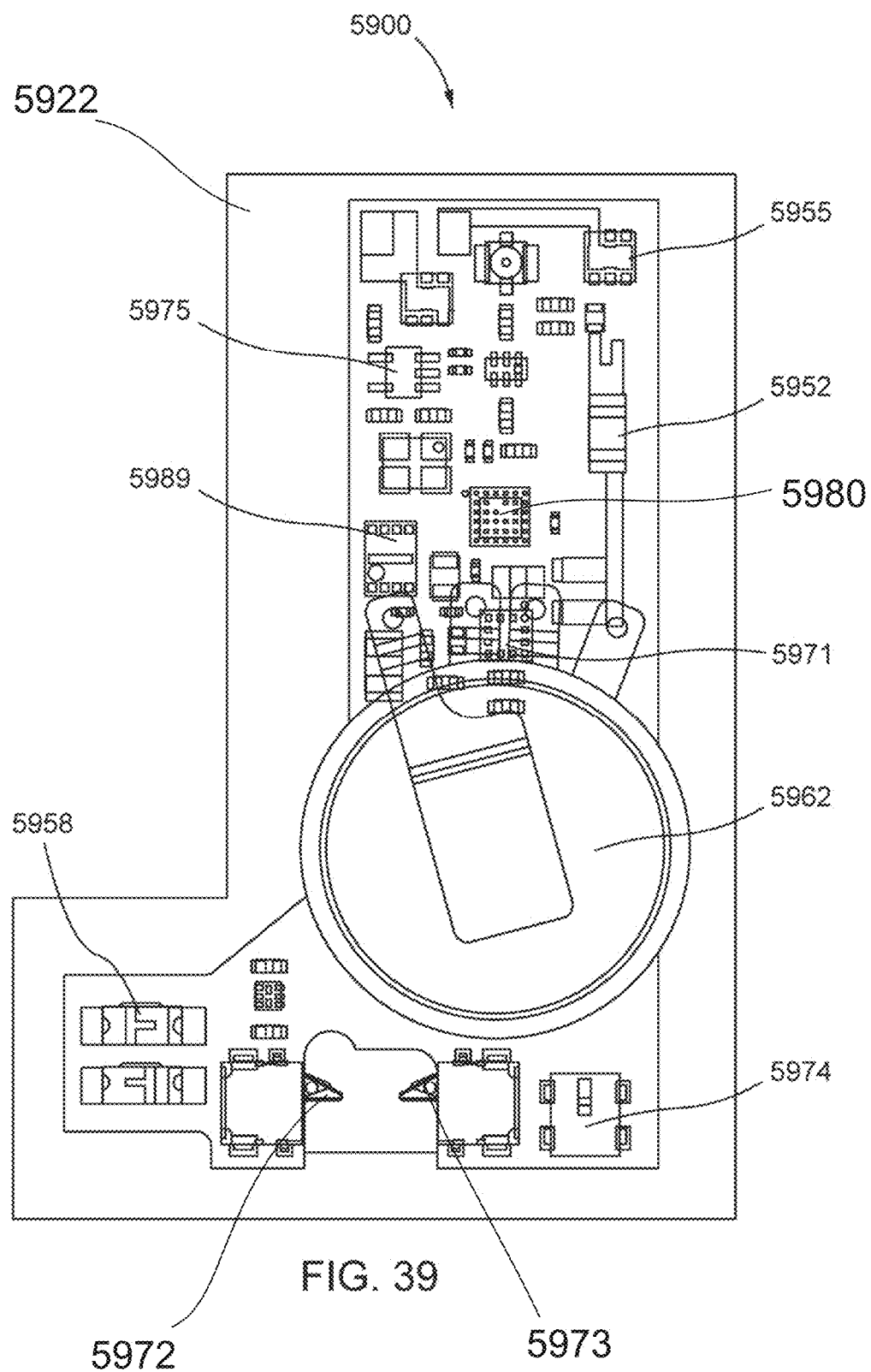
FIG. 39 is a front view of a portion of the electronic circuit system shown in FIG. 36.

Referring to FIG. 39, the electronic circuit system 5900 includes a Bluetooth® low energy (BLE) processor 5980. The processor 5980, and any of the processors described herein, can be any suitable processor for performing the methods described herein. In some embodiments, processor 5980 can be configured to run and/or execute application modules, processes and/or functions associated with such a medicament delivery system 5800. For example, the processor 5980 can be configured to run and/or execute any or all of the computer-implemented modules described herein. Such modules include, for example, the communication module 1981, described above, a power management module (e.g., the power management module 7987), a use (or event detection) module (e.g., the event detection module 7982), an expiration/reordering module (e.g., the notification module 7988), a temperature history module (e.g., the temperature history module 7985), a motion module, (e.g., the motion module 7983), a predictive module (e.g., the predictive module 7986), and/or the leash module (e.g., the leash module 1983), and perform the methods associated therewith.

The processor 5980 can be configured to retrieve data from and/or write data to memory, e.g., the memory 5989. As described herein, in some embodiments, the processor 5980 can cooperatively function with a radio (including the antenna 5952) and/or execute instructions from code to provide signals to communicatively couple the electronic circuit system 5900 to the computing device 5801 (e.g., via wireless communication) and/or any other computing entity via a network (similar to the network 1805 shown herein). In some embodiments, the processor 5980 can cooperatively function with an audio driver 5955 to produce signals that are converted by the audible output device 5656 into instructions. In some embodiments, the processor 5980 is a Bluetooth® low energy (BLE) processor, such as The Texas Instruments® CC2540 series of processors, the Broadcom® BCM43341 processor, and/or any other processor suitable or configured specifically to execute the Bluetooth® v4.0 low energy stack. In other embodiments, the processor 5980 is a Bluetooth® low energy (BLE) processor, such as DA14581 processor, produced by Dialog Semiconductor. Schematic illustrations of suitable Bluetooth® processors are shown in FIGS. 2A and 2B. In yet other embodiments, the electronic circuit system 4900 can include a Bluetooth® low energy (BLE) processor, such any of the processors or chipsets produced by Cambridge Silicon Radio Limited (CSR Ltd), including those in the CSR101x Product family. In yet other embodiments, the processor 5980 can include any of the Bluetooth® low energy (BLE) system on chip (SoC) produced by Nordic Semiconductor, including the nRF52840, the nRF52832, the nRF52810 chips.

In some embodiments, the processor 5980 can be operable to facilitate any suitable communication mode with the computing device 5801 and/or any other computing entity (e.g., by executing a communication module, such as the communication module 1981). Such modes can include, for example, an active mode, hold mode, sniff mode, and/or park mode in accordance with the Bluetooth® wireless protocol. Moreover, the processor 5980 can also be operable to engage in any suitable type of data transfer, such as asynchronous connection-less logical transport (ACL), synchronous connection-oriented link (SCO), and/or any other suitable means.

The electronic circuit system includes a radio and/or a network interface device (not shown) configured to operatively connect the electronic circuit system 5900 to a remote device (not shown, but which can be similar to the computing device 1801 shown above or the remote device 5801 shown below) and/or a communications network (not shown, but which can be a short-range network or the network 1805 shown above). In some embodiments, the electronic circuit system 5900 can be configured to establish a short-range radio link with a remote computing device (e.g., a user's smart phone, such as the device 5801 shown in FIG. 54, or the device 7801 shown in FIG. 56). For example, the electronic circuit system 5900 can be paired to a remote computing device via the Bluetooth® wireless protocol. Similarly stated, the electronic circuit system 5900 can include a processor and/or radio configured to be paired to a remote computing device (not shown) via a wireless protocol that facilitates the transmission of signals within a range of approximately 100 meters or less (i.e., a Class 3 radio) and/or having a frequency within the range of 2400 MHz and 2480 MHz. In this manner, the electronic circuit system 5900 can send information to and/or receive information from the remote device. The remote device can be similar to the device 1801, for example, a remote communications network, a computer, a compliance monitoring device, a cell phone, a personal digital assistant (PDA) or the like. Such an arrangement can be used, for example, to download replacement processor-readable code from a central network to the electronic circuit system 5900. In some embodiments, for example, the electronic circuit system 5900 can download information associated with a medical injector 5000, such as an expiration date, a recall notice, updated use instructions or the like. Similarly, in some embodiments, the electronic circuit system 5900 can upload compliance information associated with the use of the medical injector 5000 via the network interface device.

The memory 5989 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 5989 stores instructions to cause the processor 5980 to execute modules, processes and/or functions associated with such medicament delivery system 5800 and/or the medicament delivery device 5000. For example, the memory 5989 can store instructions to cause the processor 5980 to execute one or more of the modules described herein.

The battery assembly 5962 of the electronic circuit system 5900 includes two batteries stacked on top of one another. The battery assembly 5962 includes a first battery 5961 and a second battery 5965. The battery assembly 5962 is configured to contact a contact portion a battery clip assembly 5910 to maintain the battery assembly in connection with (and electrically coupled to) the printed circuit board 5922 and the remainder of the electronic circuit system 5900. Referring to FIGS. 40A-40G, the battery clip assembly 5910 includes a series of solder tabs, metallic member, and contacts that maintain the position of the battery clip assembly 5910 and the battery assembly 5962 with respect to the printed circuit board 5922. In some embodiments, the battery clip assembly 5910 can include multiple components that are separately assembled to the battery assembly 5962. In other embodiments, the battery clip assembly 5910 can include a monolithically-constructed member. In yet other embodiments, the electronic circuit system can include one or more batteries having an integrated solder tab.

The battery assembly 5962 can include any suitable number and type of batteries. The batteries can be, for example CR1632 batteries.

The electronic circuit system 5900 includes a series of sensors that provide feedback to (and/or produce a signal received by) the processor 5980, thus allowing the processor to produce electronic outputs based on the state of the medicament delivery device 5000. In particular, the electronic circuit system 5900 includes a first (or safety) switch 5972, a second (or actuation) switch 5973, and a third (or cover) switch 5974. As described above, in contrast to the electronic circuit system 4900, the electronic circuit system 5900 is not isolated from the battery assembly 5962 when the cover 5200 is disposed about the housing 5100. Rather, power is continuously supplied to the processor 5980. When the cover 5200 is removed (see FIGS. 41 and 42), the switch protrusion 5235 actuates the cover switch 5974 to actuate the electronic circuit system 5900. Upon actuation of the cover switch 5974, the processor 5980 and/or any of the modules described herein can produce any of the electronic outputs described herein (e.g., audible, visual, wireless, or the like), can change the communication mode of the radio, and/or otherwise interact with a connected health medicament delivery system (e.g., the system 5800 or any of the other connected health system described herein). For example, in some embodiments, upon removal of the cover 5200, the electronic circuit system 5900 can exit a "low power" mode and increase the speed of communication with any surrounding computing devices (e.g., a mobile phone). In other embodiments, upon removal of the safety lock 5700, the electronic circuit system 5900 can activate and/or increase the sample rate for any of the sensors (e.g., the accelerometer) to improve the likelihood of receiving data associated with an injection event. Similarly stated, in some embodiments, the removal of the safety lock 5700 (i.e., the signal produced by the cover switch 5974) causes other portions and/or modules of the electronic circuit system 5900 to exit a dormant or "sleep" mode.

Figure 44:
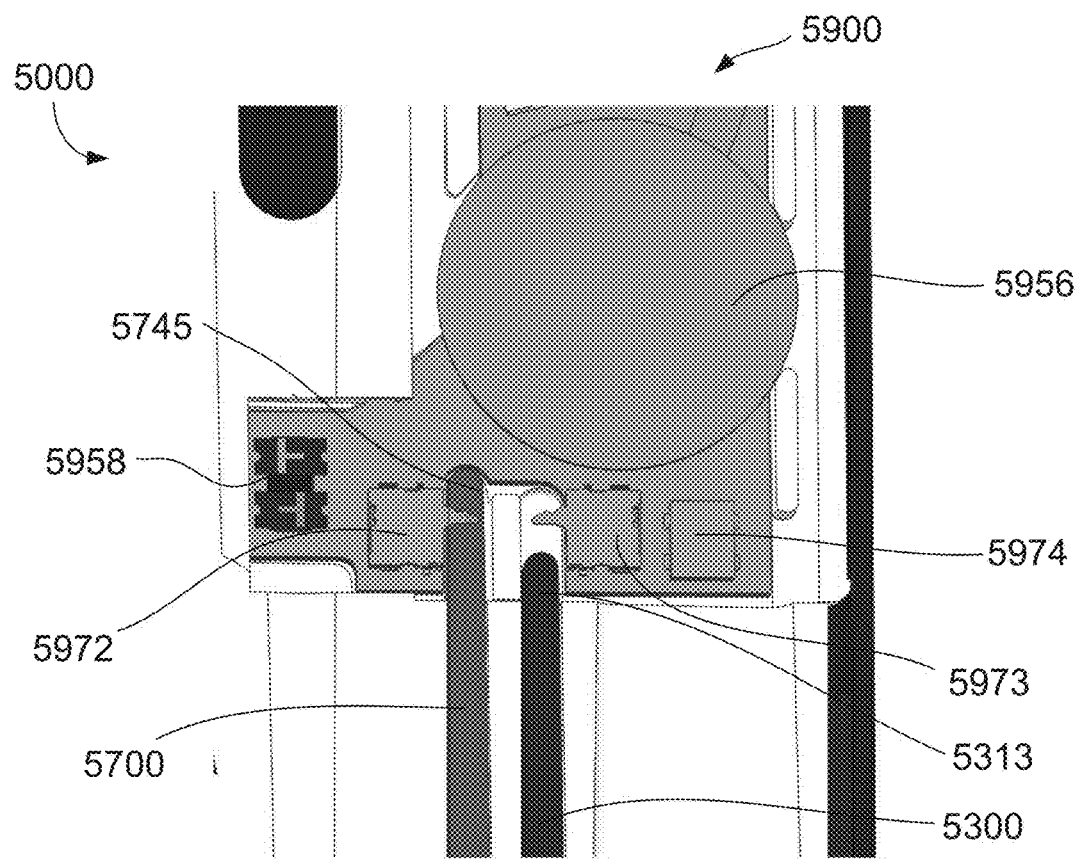
FIG. 44 shows a front view of a portion of the electronic circuit system shown in FIG. 36.
Figure 45:
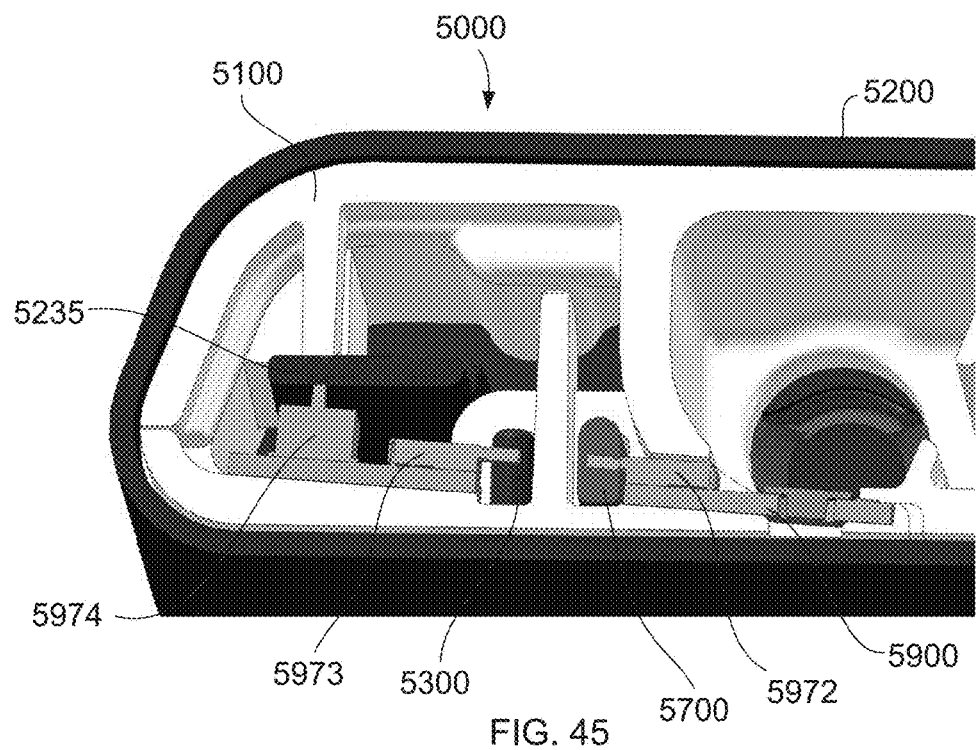
FIG. 45 shows a perspective cross-sectional view of a portion of the electronic circuit system shown in FIG. 36 and the medical injector shown in FIG. 35, taken along the line $X_3$-$X_3$ in FIG. 35.
Figure 46:
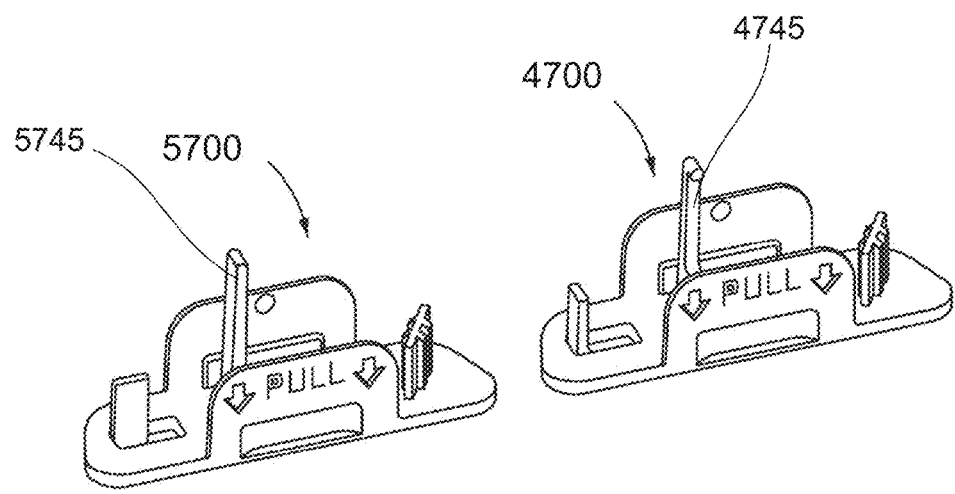
FIG. 46 shows various safety locks of a medicament delivery device, according to an embodiment.

The first (or safety) switch 5972 is actuated when the safety lock 5700 is moved from a first position to a second position (see e.g., FIG. 44). Specifically, when the safety lock 5700 is removed, a protrusion 5745 of the safety lock 4700 engages and/or actuates the first switch 5972. Upon actuation of the safety switch 5972, the processor 5980 and/or any of the modules described herein can produce any of the electronic outputs described herein (e.g., audible, visual, wireless, or the like), can change the communication mode of the radio, and/or otherwise interact with a connected health medicament delivery system. For example, in some embodiments, upon removal of the safety lock 5700, the electronic circuit system 5900 can increase the broadcasting interval to improve the likelihood of pairing with any surrounding computing devices (e.g., a mobile phone).

The second (or actuation) switch 5973 is actuated when the base 5300 is moved from its first position to its second position (see e.g., FIG. 44). Specifically, the proximal movement of the actuator 5300 causes a protrusion 5313 of the base to engage and/or actuate the second switch 5973. Upon actuation of the actuation switch 5973, the processor 5980 and/or any of the modules described herein can produce any of the electronic outputs described herein (e.g., audible, visual, wireless, or the like), can change the communication mode of the radio, and/or otherwise interact with a connected health medicament delivery system (e.g., the system 5800). For example, in some embodiments, upon movement of the base (or actuator) 5300, the electronic circuit system 5900 can increase the speed of communication with any surrounding computing devices (e.g., a mobile phone), can send a signal confirming actuation of the device 5000, or the like. In other embodiments, upon movement of the base 5300, the electronic circuit system 5900 can activate a use module (also referred to as an event detection module, see e.g., the event detection or "use" module 7982). As described herein, the use module 7982 is configured to multiple signals (from at least two different sensors of the electronic circuit system 5900) to verify than an actual injection even occurred and produce a notification associated with the actual injection.

The audio output device 5956 of the electronic circuit system 5900 is configured to output audible sound to a user in response to a use of the medical injector 5000. In some embodiments, the audible output device 5956 can be a speaker. In some embodiments, the audible sound can be, for example, associated with a recorded message and/or a recorded speech. In other embodiments, the audible instructions can be an audible beep, a series of tones and/or or the like.

The light emitting diodes (LEDs) 5958 can be similar to the LEDs shown and described herein, and can produce visual outputs in response to a use of the medicament delivery device 5000.

Figure 109:
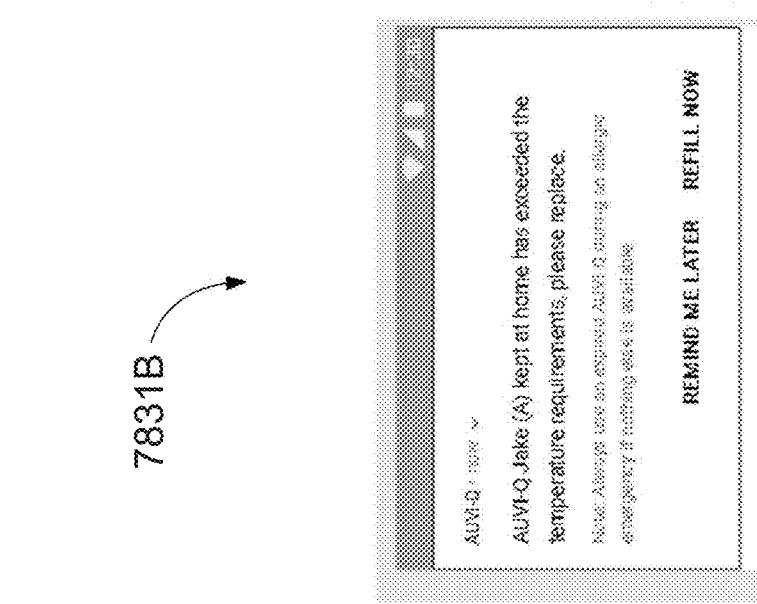
FIGS. 108-109 depict graphical user interface elements produced in connection with a method of producing a temperature notification, according to an embodiment.
Figure 108:
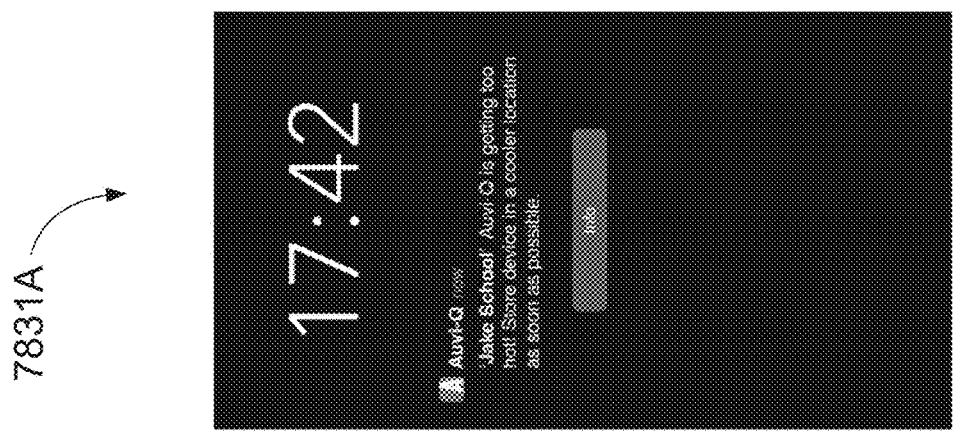

As shown in FIG. 39, in addition to the switches, the electronic circuit system 5900 also includes a temperature sensor 5975 and an accelerometer 5971. The temperature sensor 5975 can be any suitable temperature sensing device, and can provide input to the processor 5980 regarding the current temperature of the medicament delivery device 5000, the temperature history of the device or the like. Based on the temperature input the processor 5980 can execute any of the modules and/or execute any of the methods described herein, such as for example, the temperature alerts described with reference to FIGS. 108 and 109.

The accelerometer 5971 can be any suitable accelerometer, and can provide input to the processor 5980 regarding the movement and/or vibration of the medicament delivery device 5000. Based on the movement/vibration input the processor 5980 can execute any of the modules and/or execute any of the methods described herein, such as for example, the motion (or leash) module to implement "soft leashing" methods as described herein or the "event detection" methods described herein. In this manner, the electronic circuit system 5900 can produce a signal (audible, wireless, visual, or the like) that confirms the actual actuation of the device.

Although the series of sensors described herein includes switches, a temperature sensor, and an accelerometer, in other embodiments, the electronic circuit system 5900 (and any of the electronic circuit systems described herein) can include any suitable sensor. Specifically, any of the sensors described herein can be any suitable electronic device that receives a physical input (e.g., a change in position, temperature, or pressure) and produces an electronic output in response. For example, although one of the sensors described above is an actuation switch 5973, in other embodiments, the movement of the base 5300 can be measured by any other suitable sensor, such as, for example, a linear position sensor (e.g., an LVDT or the like).

Moreover, in some embodiments power management techniques, such as time multiplexing can be executed by the processor 5980 (or any of the processors described herein). Such power management methods can be performed, for example, by a power management module (see, e.g., the power management module 7987). For example, the processor 5980 can be operable to manage power draw such that high-draw and/or processor intensive operations, such as voice processing and operating the radio are not executed simultaneously. For example, in some embodiments, a method can include delaying and/or extending a communication interval during a time period when operations involving a recorded speech output via the speaker 5956 and/or a light output device 5958 are performed. In other embodiments, a method can include changing a communication mode during a time period when operations involving a recorded speech output via the speaker 5956 and/or a light output device (not shown) are performed. For example, in some embodiments, a method can include transitioning the device to a sniff or park mode upon activation of the device to conserve power draw from the instruction features of the device.

In yet other embodiments, the processor 5980 and/or the power management module can disable wireless communications when the power level of the battery assembly 5962 drops below a threshold value, as described herein.

Figure 48:
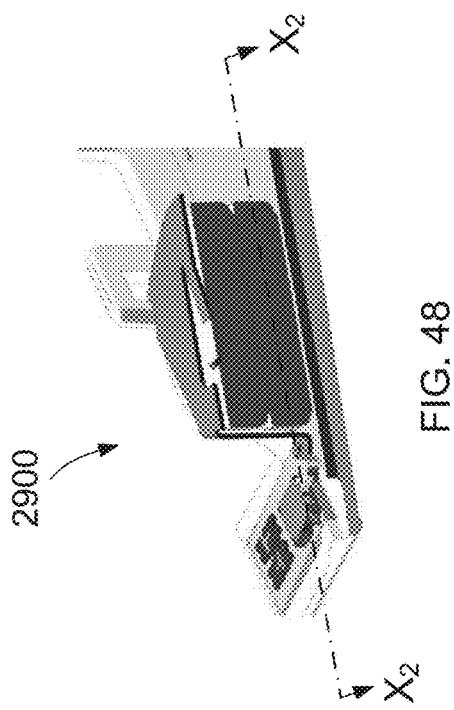
FIG. 48 is a cross-sectional view of a portion of the electronic circuit system shown in FIG. 47 taken along line $X_1$-$X_1$ in FIG. 47.
Figure 49:
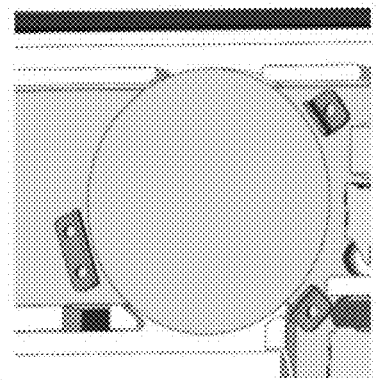
FIG. 49 is a cross-sectional view of a portion of the electronic circuit system shown in FIG. 47 taken along line $X_2$-$X_2$ in FIG. 48.
Figure 47:
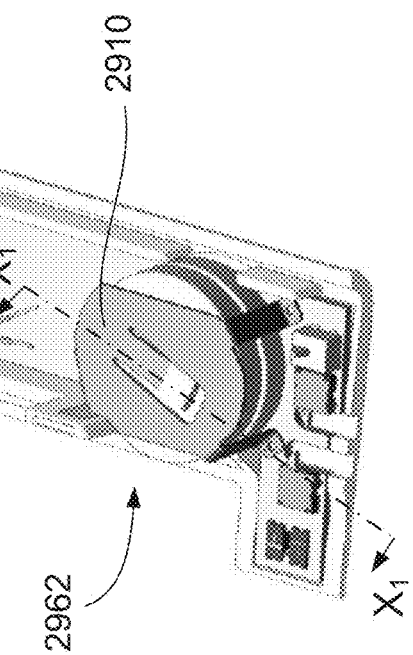
FIG. 47 is a perspective view of an electronic circuit system of a medicament delivery device, according to an embodiment.
Figure 50:
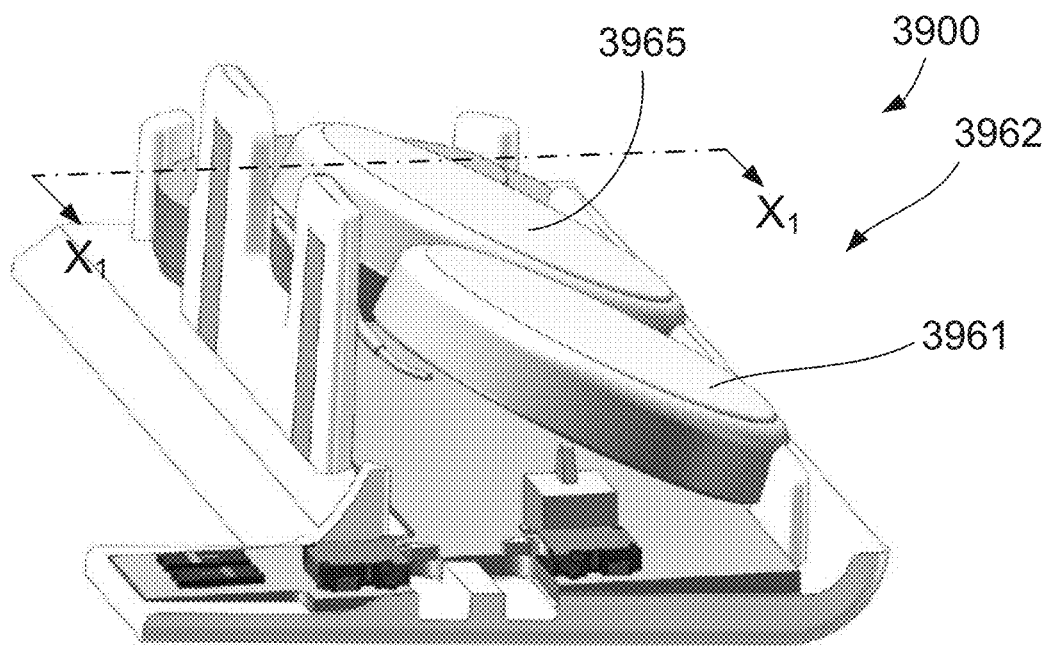
FIG. 50 is a perspective view of an electronic circuit system of a medicament delivery device, according to an embodiment.
Figure 51:
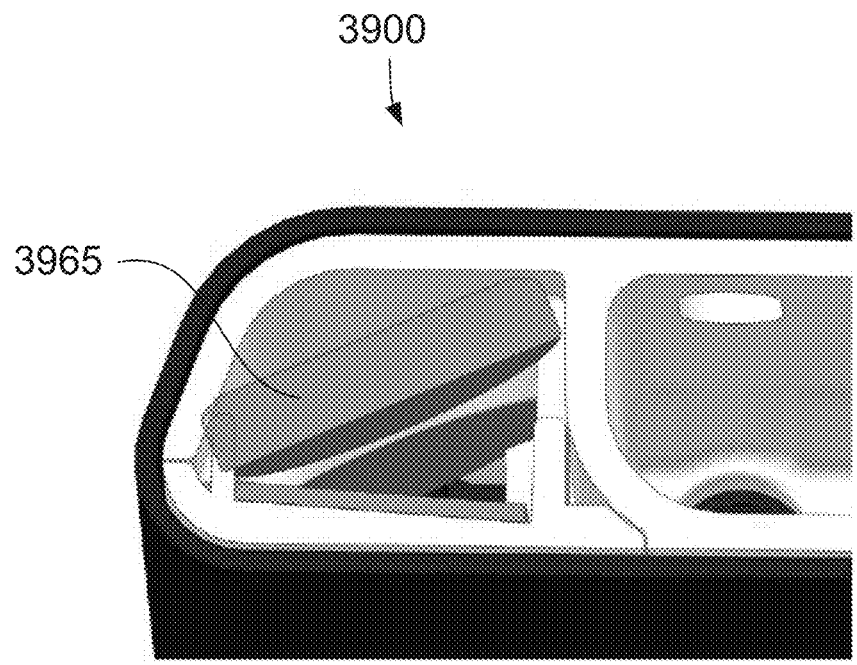
FIG. 51 is a cross-sectional view of a portion of the electronic circuit system shown in FIG. 50 within a medicament delivery device, taken along line $X_1$-$X_1$ in FIG. 50.

FIGS. 47-49 show various views of an electronic circuit system 2900 according to an embodiment. The electronic circuit system 2900 is similar to the electronic circuit system 5900 shown and described above. The electronic circuit system 2900 differs from the electronic circuit system 5900, however, in the battery clip arrangement. Specifically, the electronic circuit system 2900 includes a battery assembly 2962 and a battery clip assembly 2910. The battery clip assembly 2910 is a monolithically constructed clip.

FIGS. 50-53 are various views of an electronic circuit system 3900 of a medicament delivery device 3000, according to an embodiment. The medicament delivery device 3000 and the electronic circuit system 3900 are similar to the medicament delivery device 5000 and the electronic circuit system 5900, respectively, shown and described above. The electronic circuit system 3900 differs from the electronic circuit system 5900, however, in that the battery assembly 8962 is positioned at an angle within device. Specifically, the electronic circuit system 3900 includes a battery assembly 3962 including a first battery 3961 and a second battery 3965. The batteries are disposed within the housing of the device 3000 at an angle to provide more room and/or to meet space constraints. Specifically, the angled orientation of the battery assembly 3962 allows room for the switch protrusion 3235 of the cover 3200 to engage and/or actuate the switch 3974. The switch 3974 is similar to the switch 5974 described above, and actuates the electronic circuit system 3900 when the cover 3200 is removed from about the housing of the device 3000.

Figure 54:
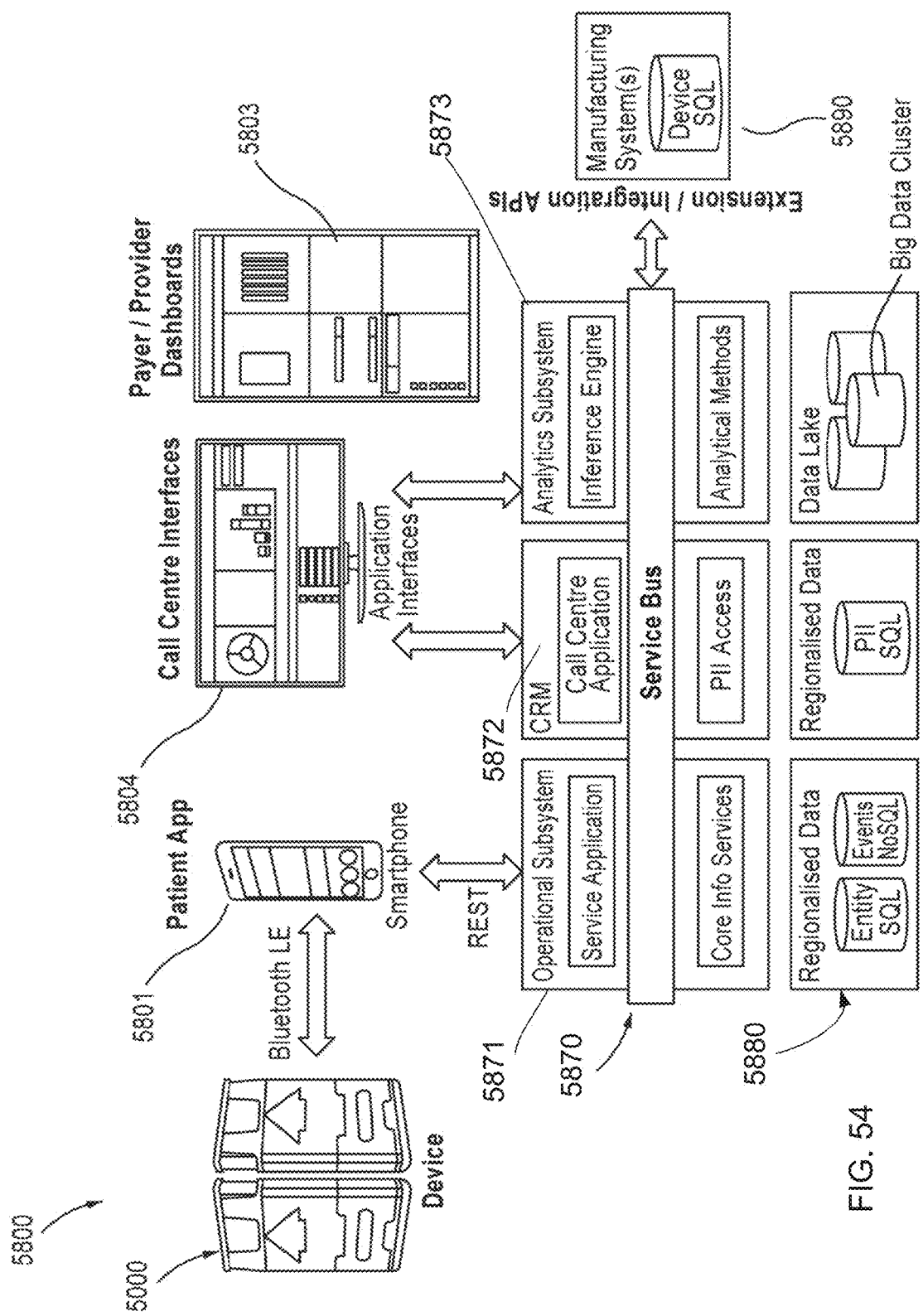
FIG. 54 is a schematic illustration of a connected health medicament delivery system, according to an embodiment.

In some embodiments, the medicament delivery device 5000 and any of the devices or drug products described herein can be included as a part of a connected health medicament delivery system. For example, FIG. 54 is a schematic illustration of a connected health medicament delivery system (also referred to as a connected health system) 5800, according to an embodiment. The connected health medicament delivery system 5800 includes at least one medicament delivery device 5000 (or any other medicament delivery device of the types described herein), an external (or remote) computing device 5801, a remote (or call center) interface 5804, a remote (or payer/provider) interface 5803, a service platform 5870, and a database platform 5880. The components, modules, and/or functions described in connection with the connected health system 5800 can be included within any of the connected health systems described herein. For example, any of the connected health systems described herein (such as the connected health systems 1800, 6800, and 7800) can include the payer/provider interface 5803, the database platform 5880 and/or the service platform 5870. Moreover, although the connected health system 5800 is shown and described as including at least one medicament delivery device 5000, in other embodiments, the connected health system 5800 (and any of the connected health systems described herein) can include any of the medicament delivery devices (or drug products) shown and described herein. Similarly, the connected health system 5800 (and any of the connected health systems described herein) can include any of the remote computing devices described herein, such as, for example, the remote computing devices 7801, 7802 described below. The connected health system 5800 and any components therein (including any of the functional modules) can perform any of the methods described herein, including methods related to "leashing" the device 5000 to the user, power management methods, and/or event detection methods.

As described herein, the external (or remote) computing device 5801 (e.g., either the user's mobile computing device or the patient's mobile computing device) can be configured to transmit and/or receive a signal (indicated by the arrow "Bluetooth LE" in FIG. 54) to and/or from the medicament delivery device 5000. The signal can be transmitted and/or received by any of the methods described herein. For example, in some embodiments, the signal is received after the computing device 5801 is used to scan a label, tag or other machine-readable code on (or associated with) the medicament delivery device 5000. For example, as described below, in some embodiments, the computing device 5801 can be used to photograph a container or packaging within which the medicament delivery device 5000 is stored. In this manner, a signal is received (via the photograph) that provides information related to the specific medicament delivery device (e.g., the serial number, the manufacturing lot number, etc.). In some embodiments, the signal (and/or information) can be received from the photograph by an optical character recognition (OCR) algorithm. In other embodiments, the signal can be received automatically (e.g., without the need to scan a code). For example, in some embodiments, the electronic circuit system 5900 of the medicament delivery device 5000 can transmit a signal to the computing device 5801 in response to the manipulation of the medicament delivery device 5000 (removal of the case 5200, removal of the safety lock 5700, movement of the base 5300). Specifically, the radio and/or wireless communication module of the electronic circuit system 5900 produces a wireless signal in response to actuation of the switches therein (e.g., switches 5972, 5973, and 5974). Upon receiving the signal, the computing device 5801 can then transmit visual and/or audible instructions for using the medicament delivery device 5000. The computing device 5801 can produce the audible and visual instructions according to any of the methods described herein. Specifically, the computing device 5801 (and any of the remote computing devices described herein) can include any of the modules described herein, including, for example, the network module 7814, the notification module 7817, and/or the event detection module 7812 described below. In this manner, the computing device 5801 can produce notifications using sounds and/or any of the graphical user interface elements, as described herein. Moreover, as described below with reference to the user interface 7820, the computing device 5801 can also receive input (e.g., via a touchscreen, a microphone or the like). This input can be used to send additional instructions and/or signals (to the service platform 5870, the medicament delivery device 5000, or other devices within the system). This arrangement allows the computing and/or communication resources of the communication device to be used to enhance the instructions, locating capabilities and/or the like of the systems described herein.

The external (or remote) computing device 5801 can also be operable to display e.g., via a visual output device, or emit, e.g., via an audible output device, information and/or instructions regarding the patient's medical history and/or the administration of medicament using the medicament delivery device 5000. For example, in some embodiments, the computing device 5801 (and any of the remote computing devices described herein) can include an on-boarding module (e.g., the on-boarding module 7819) through which the patient can "opt in" to allow sharing of medical history, patient-specific data, and the like.

The external (or remote) computing device 5801 can also automatically contact emergency personnel and/or prompt the patient and/or the user to contact emergency personnel. For example, in some embodiments, the external (or remote) computing device 5801 can execute an application (of the types described herein) that can unlock and/or otherwise configure the cell phone to be used by the patient and/or the user to facilitate the methods of the connected health medicament delivery system 5800. In some embodiments, the external (or remote) computing device 5801 can automatically display a prompt and/or instruction (see, e.g., the graphical user interface elements described herein) upon detecting a specified condition (e.g., a delivery event, as detected by an event detection module). Thus, in those embodiments in which the external (or remote) computing device 5801 is a cell phone, the cell phone can be configured to be useable and/or provide information to the user in the event of a medical emergency without requiring a password or unlock sequence. For example, in some embodiments, the touch screen of the cell phone can display a button in response to the detection of a specified condition that prompts a user (e.g., a third party) to enter the application. In other embodiments, the cell phone can display a message prompting the user to "swipe," scan or read a particular code thereby unlocking the cell phone for subsequent use as described herein. For example, in some embodiments, the user can be prompted to swipe, scan or read an identification card, another device, a medicament container or the like. For example, in some embodiments, the user can be prompted to take a photograph of an identification card, and information can be from the photograph by an optical character recognition (OCR) algorithm.

In some embodiments, the computing device 5801 can be used to transmit a signal to the medicament delivery device 5000. For example, in some embodiments, the computing device 5801 can transmit a short-range wireless signal to establish and/or maintain a communication link with the medicament delivery device 5000. For example, the computing device 5801 and the electronic circuit system 5900 can be paired via the Bluetooth® wireless protocol. Similarly stated, the computing device 5801 and the electronic circuit system 5900 can be paired via a wireless protocol that facilitates the transmission of signals within a range of approximately 100 meters or less (i.e., a Class 3 radio) and/or having a frequency within the range of 2400 MHz and 2480 MHz.

Although the external communication (or computing) device 5801 is described primarily as being a mobile phone, in other embodiments, the external computing device 5801 can be any suitable device configured to communicate with the electronic circuit system 5900 and/or the medicament delivery device. For example, in some embodiments, the external computing device 5801 (or any of the computing/communication devices that receive signals from the medicament delivery device 5000) can be any suitable monitoring device or locator, such as the monitoring device 150 shown and described in U.S. Patent Publication No. 2014/0243749, entitled "Devices, Systems and Methods for Interacting with Medicament Delivery Systems" filed on Dec. 27, 2013, the disclosure of which is incorporated herein by reference in its entirety. For example, in some embodiments, the external computing device 5801 can be a bracelet, a necklace, a keychain fob, a watch, a ring, an adhesive patch, or other personal electronic device, and/or any other suitable object. The external computing device 5801 can be a piece of jewelry and/or integrated into a piece of jewelry, such as a necklace or bracelet. In some embodiments, however, the external computing device 5801 can be inconspicuous, so as to not draw attention to the user. For example, in some embodiments, the external computing device 5801 can be similar to and/or incorporated within an article that is inconspicuous. For example, in some embodiments, the external computing device 5801 can be located on an inner layer of clothing, incorporated or manufactured as a part of the clothing, incorporated into a common accessory, fabricated to resemble a standard key fob, or the like. Such devices can, for example, retain the data and/or information transmitted by the medicament delivery device 5000 until such time as the user is within range of a mobile phone or other more sophisticated computing device.

In some embodiments, the external computing device 5801 (or any of the computing/communication devices that receive signals from the medicament delivery device 5000) can be a docking station (e.g., within the user's home). The docket station can also function to be physically coupled to the medicament delivery device 5000, for example, to recharge the device. In some embodiments, the external computing device 5801 (or any of the computing/communication devices that receive signals from the medicament delivery device 5000) can be a network hub for a community of users, a link to the network (or cloud), or any other suitable communication device.

Although the connected health system 5800 is shown as including only one remote computing device 5801, in other embodiments, the connected health system 5800 (and any of the connected health systems described herein) can include any number of remote computing devices 5801. For example, in some embodiments, the connected health system 5800 includes a first remote computing device 5801 that belongs to the patient and that can be wirelessly coupled to the medicament delivery device(s) 5000 via a short-range protocol, as shown in FIG. 54. The connected health system 5800 can include a second remote computing device (not shown) that belongs to an emergency contact associated with the patient (e.g., the patient's parent), and/or a third remote computing device (not shown) that belongs to a caregiver associated with the patient (e.g., a school nurse, a doctor, or the like). Such additional devices can either establish and/or maintain a communication link with the medicament delivery device 5000 (similar to the first device 5801 described above) or receive information associated with the medicament delivery device 5000 via the service platform 5870, which can be communicatively coupled to any of the remote computing devices or interfaces by a network (e.g., the network 1805 described herein).

In addition to the remote computing device 5801, the connected health system 5800 also includes the remote (or call center) interface 5804. The call center interface 5804 can be any suitable computer-implemented interface and/or computing entity, such as a server or personal computer, that transmits and/or receives information to and/or from the service platform 5870. The call center interface 5804 can include any suitable hardware and/or software modules. The call center interface 5804 can be communicatively coupled to the service platform 5870 and/or a customer relationship management (CRM) module 5872 within the service platform 5870 by a network (e.g., the network 1805 described herein).

The connected health system 5800 also includes the remote (or payer/provider) interface 5803. The payer/provider interface 5803 can be any suitable computer-implemented interface and/or computing entity, such as a server or personal computer, that transmits and/or receives information to and/or from the service platform 5870. The payer/provider interface 5803 can include any suitable hardware and/or software modules. For example, in some embodiments, the payer/provider interface 5803 can include one or more analytics modules configured to receive and/or process data stored by the payer (e.g., an insurance company) that is specific to the patient. The payer/provider interface 5803 can be communicatively coupled to the service platform 5870 and/or an analytics system 5873 within the service platform 5870 by a network (e.g., the network 1805 described herein).

The service platform 5870 can be any suitable computer-implemented interface and/or computing entity, such as a server or personal computer, that is configured to communicate with the remote computing device(s) 5801, the call center interface 5804, the payer/provider interface 5803, the manufacturing system 5890, and/or any other portions of the connected health system 5800. More specifically, the service platform 5870 can receive information from devices within the connected health system 5800, manipulate the information, and produce information to any of the devices within the connected health system 5800. For example, in some embodiments, expiration information associated with the medicament delivery 5000 can be transmitted from the device 5000 to the patient's remote computing device 5801. The remote computing device 5801 can transmit the expiration information (e.g., via a network similar to the network 1805) to the service platform 5870. Based on the expiration information, the service platform 5870 (e.g., the operation subsystem 5871) can transmit notifications back to the patient's remote computing device 5801 to warn the user of an upcoming expiration date. In this manner, the service platform 5870 can control and/or manage certain notifications and/or features. Similarly stated, in this manner the service platform 5870 can function as the "back end" for the connected health system 5800. As shown, the service platform 5870 can be coupled to and/or access a database system 5880.

Figure 55:
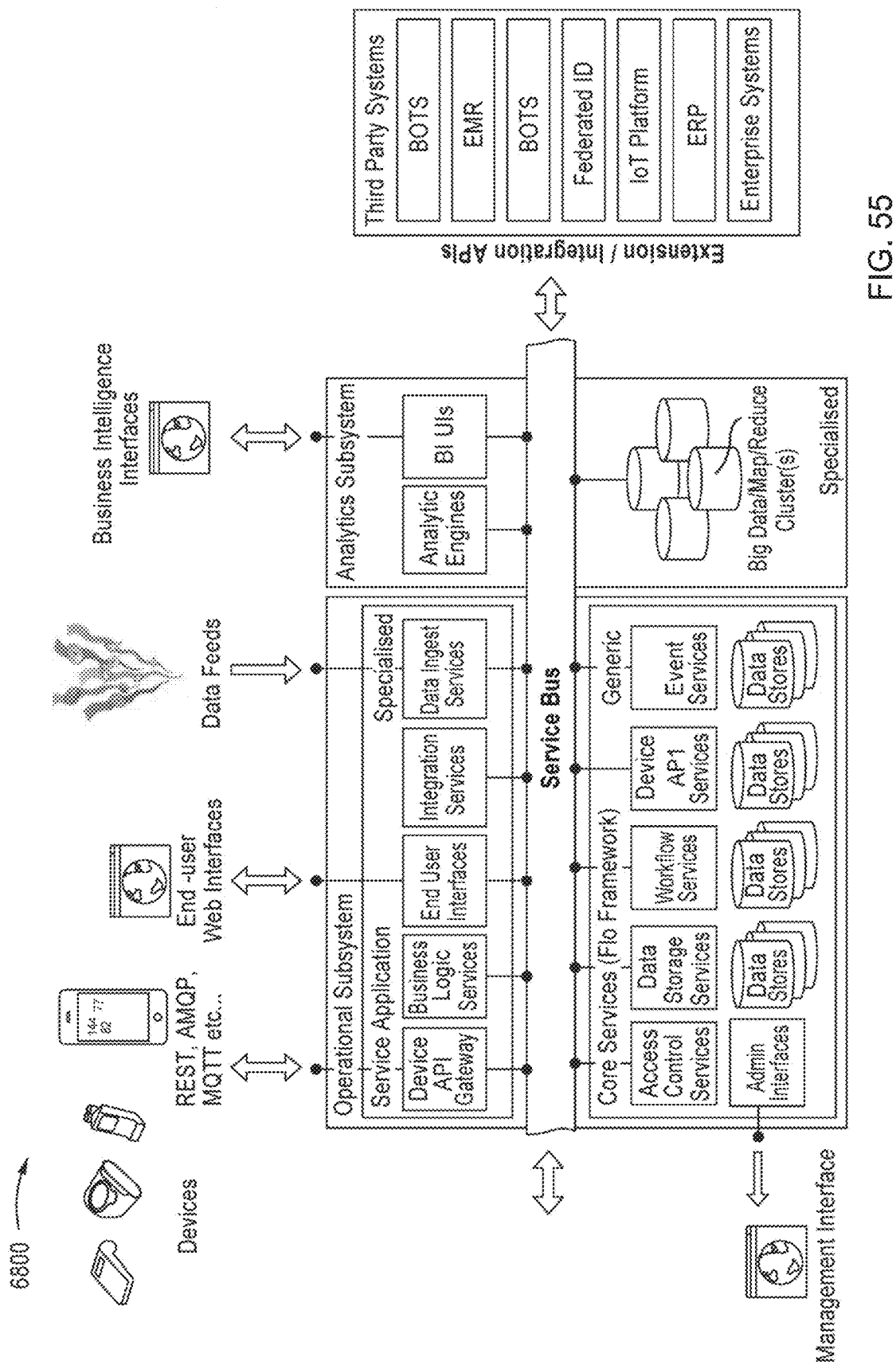
FIG. 55 is a schematic illustration of a connected health medicament delivery system, according to an embodiment.

FIG. 55 is a schematic illustration of a connected health medicament delivery system 6800, according to an embodiment. The connected health medicament delivery system 6800 includes at least one medicament delivery device (e.g., any medicament delivery device of the types described herein), at least one external (or remote) computing device (e.g., similar to the remote computing device 5801), and a series of interfaces. The remote computing devices and interfaces are coupled via a network (e.g., the network 1805) to a service platform and database system. The connected health system 6800 is similar to the connected health system 5800 described above, and is therefore not described in detail.

Figure 56:
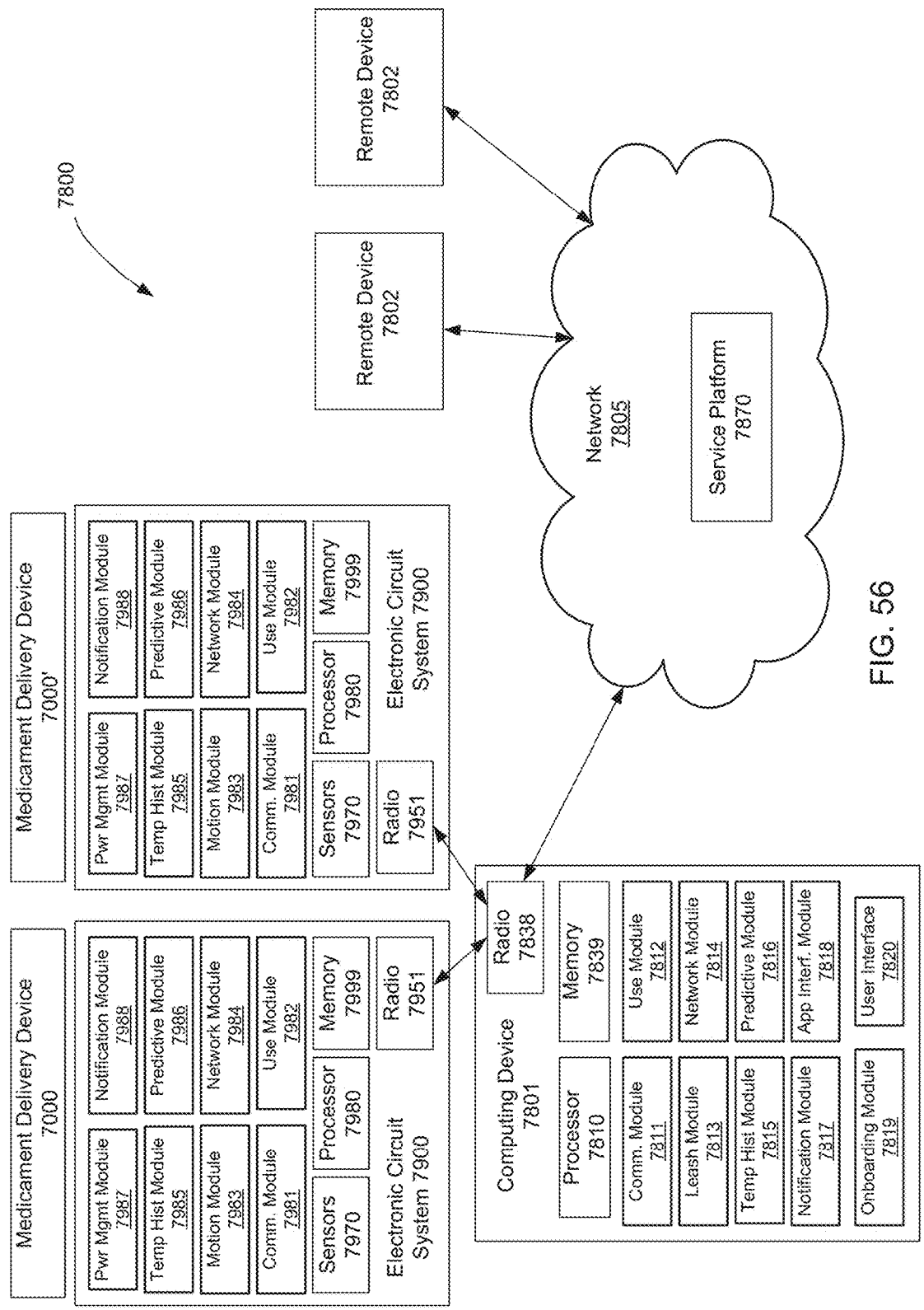
FIG. 56 is a schematic illustration of a connected health medicament delivery system, according to an embodiment.

FIG. 56 is a schematic illustration of a medicament delivery system 7800 (also referred to herein simply as "the system 7800" or "the connected health system 7800") according to an embodiment. The system 7800 includes a first medicament delivery device 7000, a second medicament delivery device 7000', an electronic circuit system 7900, a first remote computing device 7801, one or more second remote computing devices 7802, and a service platform 7870. Although not shown in FIG. 56, the service platform 7870. The components, modules, and/or functions described in connection with the connected health system 7800 can be included within any of the connected health systems described herein. Similarly, the components, modules and/or functions described in the other connected health systems described herein can be included in the connected health system 7800. For example, although not shown, the connected health system 7800 can include the payer/provider interface 5803 and the database platform 5880. Moreover, although the connected health system 7800 is shown and described as including two medicament delivery devices 7000 and 7000', in other embodiments, the connected health system 7800 (and any of the connected health systems described herein) can include any number of any of the medicament delivery devices (or drug products) shown and described herein. Similarly, the connected health system 5800 (and any of the connected health systems described herein) can include any number and any type of the remote computing devices described herein, such as, for example, the remote computing devices 5801, 5802 described below. The connected health system 7800 and any components therein (including any of the functional modules) can perform any of the methods described herein, including methods related to the soft leash (or motion detection) feature, the event (use) detection feature, and/or the computer application interface features described herein.

The service platform 7870 can be any suitable computer-implemented interface and/or computing entity, such as a server or personal computer, that is configured to communicate via the network 7805 with the remote computing device 7801, the remote computing devices 7802, and/or any other portions of the connected health system 7800 (e.g., a call center interface, a payer/provider interface, or the like). More specifically, the service platform 7870 can receive information from devices within the connected health system 7800, manipulate the information, and produce information to any of the devices within the connected health system 7800. For example, in some embodiments, expiration information associated with the medicament delivery 7000 can be transmitted from the device 7000 to the patient's remote computing device 7801. The remote computing device 7801 can transmit the expiration information (e.g., via the network 7805) to the service platform 7870. Based on the expiration information, the service platform 7870 can transmit notifications back to the patient's remote computing device 7801 and/or the remote computing devices 7802 (e.g., the parent's devices, an emergency contact's device, etc.) to warn the user of an upcoming expiration date. In this manner, the service platform 7870 can control and/or manage certain notifications and/or features. Similarly stated, in this manner the service platform 7870 can function as the "back end" for the connected health system 7800.

The network 7805 can be a piconet, the Internet, an intranet, a local area network (LAN), a wide area network (WAN), a virtual network, a telecommunications network, any other suitable communication system and/or combination of such networks. The network 7805 can be implemented as a wired and/or wireless network. Although FIG. 56 shows the medicament delivery device 7000 and the medicament delivery device 7000' being coupled to the network 7805 via the computing device 7801, in other embodiments, the medicament delivery device 7000 and the medicament delivery device 7000' can be coupled to (or connected with) the network via any suitable mechanism and/or by any protocol. For example, in some embodiments, the medicament delivery device 7000 and the medicament delivery device 7000' can be in direct communication with the network 7805, the remote devices 7802 and/or the service platform 7870 via the LTE Direct protocol or any other suitable protocol (e.g., the 5G mobile wireless standard based on the IEEE 802.11ac standard for broadband technology).

The medicament delivery device 7000 and the medicament delivery device 7000' can be any of the medicament delivery devices described herein. In the following description, the medicament delivery device 7000' is considered to be the same as the medicament delivery device 7000 (i.e., two identical devices), and is therefore not described separately. In other embodiments, however, the connected health system 7800 can include multiple different medicament delivery devices (e.g., an epinephrine auto-injector, a rescue inhaler for asthma, a naloxone delivery device, or the like). The medicament delivery device 7000 can be an auto-injector similar to the auto-injector 4000 described below with reference to FIGS. 3-34 or the medicament delivery device 5000 described below with reference to FIGS. 35-46. In other embodiments, the medicament delivery device 7000 can be a pen injector, a syringe, a nasal delivery device (such a nasal spray device), an inhaler, a device for delivering drugs to the buccal cavity, a body-worn drug delivery device, etc. In yet other embodiments, the device 7000 can be a simulated medicament delivery device (i.e., a device that is devoid of a medicament and/or that can simulate the use of a corresponding actual medicament delivery device).

The medicament delivery device includes or is attached to an electronic circuit system 7900. For example, in some embodiments, the electronic circuit system 7900 can be coupled to and/or within a housing, cover, case, and/or any other portion of the medicament delivery device. In other embodiments, the electronic circuit system 7900 can be integrated within the medicament delivery device 7000. For example, the electronic circuit system 7900 can be integrated within the auto-injector 4000 or the auto-injector 5000 (e.g., by being coupled to the housing 4170 and/or included within the housing 5100). The electronic circuit system 7900 includes a processor 7980, a memory 7999, one or more sensors (collectively identified as a sensor 7970), and a radio 7951. The electronic circuit system 7900 also includes a communication module 7981, a use (or history) module 7982, a leash (or motion tracking) module 7983, a network module 7984, a temperature history module 7985, a predictive module 7986, a power management module 7987, and a notification module 7988. Although shown as including each of these application modules, in other embodiments, an electronic circuit system need not include all (or any) of these modules, and can include any other modules described herein. For example, in some embodiments, an electronic circuit system includes only a motion tracking module 7983, and is configured to perform the soft leash methods associated therewith, and need not include the use module 7982 or the communication module 7981. Alternatively, in other embodiments, an electronic circuit system includes only the use module 7982 and the communication module 7983. In such embodiments, the use module 7982 can detect a medicament delivery event and the communication module 7983 can produce a wireless signal associated with the actuation of the medicament delivery device 7000.

The processor 7980, and any of the processors described herein can be any suitable processor for performing the methods described herein. In some embodiments, processor 7980 can be configured to run and/or execute application modules, processes and/or functions associated with the medicament delivery system 7800. For example, the processor 7980 can be configured to run and/or execute the communication module 7981, the use (also referred to as an event detection) module 7982, the leash module 7983, and/or any of the other modules described herein, and perform the methods associated therewith. The processor 7980 can be, for example, a Field Programmable Gate Array (FPGA), an Application Specific Integrated Circuit (ASIC), a Digital Signal Processor (DSP), and/or the like. The processor 7980 can be configured to retrieve data from and/or write data to memory, e.g., the memory 7999. As described herein, in some embodiments, the processor 7980 can cooperatively function with the radio 7951 and/or execute instructions from code to provide signals to communicatively couple the electronic circuit system 7900 to the computing device 7801 (e.g., via wireless communication) and/or any other computing entity via a network 7805. In some embodiments, the processor 7980 is a Bluetooth® low energy (BLE) processor, such as The Texas Instruments® CC2540 series of processors, the Broadcom® BCM43341 processor, and/or any other processor suitable or configured specifically to execute the Bluetooth® v4.0 low energy stack. In other embodiments, the processor 7980 is a Bluetooth® low energy (BLE) processor, such as DA14581 processor, produced by Dialog Semiconductor. In other embodiments, the processor 7980 can include any of the processors or chipsets produced by Cambridge Silicon Radio Limited (CSR Ltd), including those in the CSR101x Product family. In yet other embodiments, the processor 7980 can include any of the Bluetooth® low energy (BLE) system on chip (SoC) produced by Nordic Semiconductor, including the nRF52840, the nRF52832, the nRF52810 chips. Schematic illustrations of suitable Bluetooth® processors are shown in FIGS. 2A and 2B.

In some embodiments, the processor 7980 (via the communication module 7981) can be operable to facilitate any suitable communication mode with the computing device 7801 and/or any other computing entity (e.g., by executing the communication module 7981). Such modes can include, for example, an active mode, hold mode, sniff mode, and/or park mode in accordance with the Bluetooth® wireless protocol. Moreover, the processor 7980 can also be operable to engage in any suitable type of data transfer, such as asynchronous connection-less logical transport (ACL), synchronous connection-oriented link (SCO), and/or any other suitable means.

The memory 7999 can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 7999 stores instructions to cause the processor 7980 to execute modules, processes and/or functions associated with such medicament delivery system 7800 and/or the medicament delivery device 7000. For example, the memory 7999 can store instructions to cause the processor 7980 to execute any of the application modules described herein, and perform the methods associated therewith. In some embodiments, the memory 7999 stores information, such as one or more short-term or long-term security keys received from and/or exchanged with the remote computing device 7801 as a part of the pairing and/or bonding process described herein.

The sensor(s) 7970 included within the electronic circuit system 7900 can include any number of switches, audible input sensors (e.g., a microphone), optical sensors, accelerometers, temperature sensors, contact sensors, and/or any other suitable input device. In some embodiments, the sensor(s) 7970 can include any of the sensors described above with reference to the electronic circuit system 4900 and/or the electronic circuit system 5900. For example, in some embodiments, the sensor(s) 7970 can include a sensor operable to monitor and/or measure the configuration and/or status of the medicament delivery device 7000. The sensor 7970 can be operable to detect if the medicament delivery device 7000 is removed from a case (such as the switch 5974 which detects removal of the outer cover 5200), if a safety lock is removed to "arm" the medicament delivery device 7000 (e.g., such as the switch 5972), if the medicament delivery device 7000 is actuated (i.e., to provide "delivery event" detection, such as that provided by the switch 5973), whether a temperature of the medicament has exceeded a threshold value (such as via the temperature sensor 5975), and so forth. For example, in some embodiments, the sensor 7970 can include a microphone operable to detect (e.g., in conjunction with the processor 7980) a mechanical and/or electronic sound associated with the actuation of the medicament delivery device, such as a characteristic hiss of a compressed gas container being discharged and/or a sound emitted from a speaker of the medicament delivery device 7000 (not shown). As yet another example, the sensor 7970 can include an optical sensor operable to detect the configuration of a status window of the medicament delivery device 7000, or the presence of light versus the absence of light (e.g., to detect whether component is blocking a beam). For example, the sensor 7970 can be operable to detect when a status window of the medicament delivery device 7000 turns color or opaque, which may be associated with use of the medicament delivery device 7000. As yet another example, the sensor 7970 can include an accelerometer (such as the accelerometer 5971) operable to detect a characteristic movement or vibration signature of the medicament delivery device 7000 when the device is actuated. As described herein, in some embodiments, the sensor 7970 can detect any of a position, a velocity, an acceleration, or an orientation of the medicament delivery device 7000 over a time period (e.g., 24 hours, 3 days, or the like). Based on the amount of motion, the leash or motion module 7983 can produce a motion profile that can be compared to a target motion profile unique to the medicament delivery device 7000 to determine whether the device is being carried as intended.

The radio 7951 (also referred to as a receiver, transmitter and/or transceiver) can be operable to send signals to, and/or receive radio signals, such as Bluetooth®, ZigBee, Wi-Fi, cellular telephone signals, etc. In some embodiments, such as embodiments where the processor 7980 is Bluetooth® processor, the radio 7951 can be integral with the processor 7980. In other embodiments, the radio 7951 can include a processor distinct from the processor 7980. In some embodiments, the radio 7951 can be operable to communicatively couple (also referred to herein as "linking," "pairing," or "bonding") the electronic circuit system 7900 to the computing device 7801 and/or any other computing entity via a network 7805. The radio 7951 can include or be coupled to a ceramic chip antenna, a stamped antenna, a sintered antenna, a PCB conductive trace antenna, and/or any other suitable antenna.

The communication module 7981 can be a hardware and/or software module (stored in memory 7999 and/or executed in the processor 7980). As described in more detail herein, the communication module 7981 is configured to receive an indication (e.g., from the sensor(s) 7970) and/or transition information associated with a change in status of the medicament delivery device 7000 and determine, based on the indication or the transition information, a connection and/or communications characteristic. Such communication characteristics can include, for example, a communication interval and/or connection interval (e.g., a time period between successive signals or portions of a signal, such an "advertising interval," also referred to herein as a "connection interval"), a communication mode (e.g., a park mode, sniff mode or the like), etc. In some embodiments, the communication module 7981 can function cooperatively with the power management module 7987 to reduce the power consumption of the electronic circuit system 7900 by modifying communication characteristics, suppressing certain communication signals produced by the electronic circuit system 7900, and/or disabling wireless communication.

The use (or event detection) module 7982 can be a hardware and/or software module (stored in memory 7999 and/or executed in the processor 7980). As described in more detail herein, in some embodiments, the use module 7982 is configured to receive multiple different actuation signals associated with the delivery of a medicament from the medicament delivery device 7000, and produce a notification confirming an "actual" delivery event. For example, in some embodiments, the use (or event detection) module 7982 can receive a first actuation signal in response to movement of an actuator (e.g., a signal from a switch similar to the switch 5973) and a second actuator signal from an accelerometer (e.g., similar to the accelerometer 5971) that is indicative of a vibration profile consistent with medicament delivery. The use module 7982 can then produce an event detection notification, which can be transmitted via the radio 7951 for receipt by the remote computing device 7801. In other embodiments, the use module can receive an indication (e.g., from the sensor 7970) and/or use information associated with a use or history of the medicament delivery device 7000 other than simply the device actuation, and produce a notification (e.g., a recorded speech instruction, signal for wireless transmission, or the like) based thereupon. In this manner, the use module 7982 can facilitate the electronic circuit system 7900 and/or the medicament delivery device 7000 (or simulated medicament delivery device) being a "smart" device that can produce updated instructions and/or guidance based on the history of usage. For example, in some embodiments, the use module 7982 can receive a cover removal signal in response to removal of the device 7000 from a cover (e.g., a signal from a switch similar to the switch 5974). When the number of instances of cover removal within a time period exceeds a threshold number, the use module can produce a notification (or script), which can be transmitted via the radio 7951 (i.e., a wireless communication signal) or transmitted via an audible output device. Such notification can, for example, remind the user to limit the number of cover removal instances to preserve battery power.

The leash (or motion) module 7983 can be a hardware and/or software module (stored in memory 7999 and/or executed in the processor 7980). As described in more detail herein, in some embodiments, the leash module 7983 is configured to receive information associated with the connection (or pairing) between the electronic circuit system 7900 and the computing device 7801 and produce an alarm based thereupon. In some embodiments, the leash module 7983 can base the alarms on the position and/or location of the electronic circuit system 7900 and/or the computing device 7801 or a combination of both. In other embodiments, the leash module 7983 can receive a motion signal (e.g. from a sensor, such as an accelerometer like the accelerometer 5971) and determine a motion profile associated with the medicament delivery device 7000. The motion profile can include, for example, an amount of the change over a period of time for any of a position, a velocity, an acceleration, or an orientation of the medicament delivery device 7000 (i.e., a housing the device, a cover within which the device is stored, or the like). In some embodiments, the motion module 7983 can compare the measured motion profile to a target (or intended) motion profile. When the motion profile differs from the target motion profile, a notification or alert can be transmitted via the radio 7951 for receipt by the remote computing device 7801. Such a notification can indicate, for example, that a device 7000 designated as being carried by a patient has not been moving in a manner that indicates it is actually being carried. In other embodiments, the motion profile can be transmitted via the radio 7951 for receipt by the remote computing device 7801. The leash module 7813 (described below) can then perform the comparison to a target motion profile and/or produce any desired notifications. By performing a "soft leashing" method, which is based on motion and is unique to each device within the connected health system 7800, as opposed to simply generating reminders based on the presence of or absence of a communication signal, the leash module 7983 can limit instances of false alarms. For example, if a device (e.g., the device 7000') is designated as being intended for storage at the user's school, the target motion profile for that device 7000' will be low, and thus lack of motion and/or lack of a wireless connection will not trigger the production of a notification for the device 7000'.

In some embodiments, the leash module 7983 and/or the predictive module 7986 can learn or predict the user's behavior, and then adapt the leash notifications in response to conditions that deviate from the predicted behavior. Specifically, the predictive module 7986 can be a hardware and/or software module (stored in memory 7999 and/or executed in the processor 7980). In some embodiments, the predictive module 7986 can determine and/or change the target motion profile based on the motion profile received over a time period. For example, if the motion profile for a medicament delivery device 7000 that is designated as being carried by a patient consistently has a magnitude, amount and/or characteristic of motion at a certain level (e.g., a level consistent with being carried from the user's home to school over a certain distance, a certain number of times per day and/or at certain times of the day), then the predictive module 7986 can update a baseline target (or intended) motion profile to reflect an intended motion profile that is specific or unique to the user. In this manner, the predictive module 7986 can learn the user's behavior and modify the notifications produced based on the learned behavior.

The network module 7984 can be a hardware and/or software module (stored in memory 7999 and/or executed in the processor 7980). As described in more detail herein, the network module 7984 is configured to exchange information associated with the medicament delivery device 7000 and the remote computing device 7801 to facilitate the paring and/or bonding process. For example, the network module 7984 of the medicament delivery device 7000 can cause the remote computing device 7801 and the medicament delivery device 7000 to exchange short term and/or long term security keys to complete the pairing and bonding process.

The temperature history module 7985 can be a hardware and/or software module (stored in memory 7999 and/or executed in the processor 7980). As described in more detail herein, the temperature history module 7985 is configured to receive a temperature signal (e.g., from a temperature sensor similar to the sensor 5975) and produce a notification when the temperature history indicates that the medicament may be outside (or nearing the limits of) an acceptable temperature threshold. For example, in some embodiments, the temperature history module 7985 can calculate a mean kinetic temperature based on the temperature signal. The temperature history module 7985 can then produce a temperature notification, which can be transmitted via the radio 7951 for receipt by the remote computing device 7801.

The power management module 7987 can be a hardware and/or software module (stored in memory 7999 and/or executed in the processor 7980). As described in more detail herein, the power management module 7987 is configured to receive one or more signals from any of the sensors described herein and, based on the received signals, modify an electronic function (or output) of the electronic circuit system 7900 to preserve power. For example, in some embodiments, the power management module 7987 can receive a safety signal when a safety member of the medicament delivery device 7000 is moved. Specifically, the medicament delivery device can include a cover (e.g., similar to the covers 4200 and 5200 described above) that actuates a sensor (e.g., similar to the switch 5974). As described above with reference to the electronic circuit systems 4900 and 5900, when the cover is removed, the electronic circuit system 7900 can produce an electronic output (e.g., an audible output) providing instructions to the user. The power management module 7987 can receive a signal from the sensor (e.g., the switch 5974) each time the cover is removed and modify the electronic output when a number of times the cover has been removed exceeds a threshold number. Thus, if the user repeatedly removes and replaces the cover, the power consumption from the power source (not shown in FIG. 56, but which can be similar to the battery assemblies 4962 and 5962 shown above) will be limited after a threshold number of cover removals has been detected.

For example, in some embodiments, the power management module 7987 can modify an audible output to include a warning to the user that such repeated uses are causing a power drain, and advise the user to limit any unnecessary cover removals. In other embodiments, the power management module can either A) modify an output to produce a warning after a first threshold has been crossed, and/or B) truncate and/or disable the default audible output when a second threshold has been crossed. For example, if the default audible output provides extensive use instructions upon removal of the cover, the power management module 7987 can modify the default audible output to provide critical information only (e.g., the location of the safety tab, the location of the actuator or the like). Similarly stated, the power management module 7987 can modify a default recorded speech output to include an updated content when the number of times the cover has been removed exceeds the threshold number, wherein the updated content is less than the default content. In yet other embodiments, the power management module 7987 can suppress and/or disable the audible output feature. Although described as modifying an audible output, in other embodiments, the power management module 7987 can modify any of the electronic outputs described herein, such as, for example, the wireless communication signals produced by the radio 7951, any of the visual outputs described herein, a haptic output or the like.

In some embodiments, the power management module 7987 can receive a signal associated with the voltage of the power source (e.g., the battery assembly) and modify an electronic output based on an available power level of the power source. In this manner, the power management module 7987 can limit, truncate, suppress and/or disable features as a function of the remaining power and/or expected life of the medicament delivery device 7000. For example, in some embodiments, the power source (not shown, but similar to the battery assembly 5962) can be continuously electrically coupled to the processor 7980. Thus, the processor 7980 and/or the electronic circuit system 7900 will be drawing (or using) power throughout the life of the device 7000. To preserve the life and/or critical functions of the device 7000 (such as the use instructions after removal of the safety lock, e.g., the safety lock 5700), the power management module 7987 can determine the threshold number of cover removal events based on at least one of a power level of the power source, a temperature of the medicament delivery device 7000, or an expiration date of the medicament delivery device 7000.

In some embodiments, the power management module 7987 can determine and expected battery life based on any of the power level of the power source, a rate of power usage from the power source over a time period, or an expiration date of the medicament delivery device 7000. In this manner, the power management module 7987 can modify an electronic output based on the expected life, and not necessarily a number of cover removals, etc. For example, in some embodiments, the power management module 7987 is configured to suppress at least one of the electronic outputs based on both: A) an expected life of the power source and B) a priority factor of the plurality of electronic outputs. The priority factor can be based, for example, on the criticality of the outputs as they relate to the safety of the patient.

The notification module 7988 can be a hardware and/or software module (stored in memory 7999 and/or executed in the processor 7980). As described in more detail herein, the notification module 7988 is configured to produce notifications associated with any of the methods and/or application modules described herein. For example, in some embodiments, the notification module 7988 can produce a notification that is transmitted via the radio 7951 and is for receipt by the notification module 7817 of the remote computing device 7801. In this manner, the notification module 7988 and/or the notification module 7817 can produce outputs (e.g., wireless communication signals, GUI elements, audible outputs, visual outputs, or the like) to notify the user, patient, or account administrator of events.

The computing device 7801 (or other "remote" computing devices, such as the device 5801 described below) can be a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), or a computer (e.g., a laptop, desktop, smart TV, etc.), and/or any other suitable computing entity. The computing device 7801 includes a processor 7810, a memory 7839, a user interface 7820, and a radio 7838.

The computing device 7801 also includes a communication module 7811, a use (or history) module 7812, a leash (or motion tracking) module 7813, a network module 7814, a temperature history module 7815, a predictive module 7816, a notification module 7817, an application interface module 7818, and an onboarding module 7819. Although shown as including each of these application modules, in other embodiments, a computing device need not include all (or any) of these modules, and can include any other modules described herein. For example, in some embodiments, the computing device 7801 includes only a motion tracking module 7813, and is configured to perform the soft leash methods associated therewith, and need not include the use module 7812 or the other application modules listed above. Alternatively, in other embodiments, the computing device 7801 includes only the use module 7812 and the notification module 7817. In such embodiments, the use module 7812 can detect a medicament delivery event (e.g., via a wireless signal from the electronic circuit system 7900 of the device 7000) and the notification module 7817 can produce an instruction, a GUI element, or the like associated with the actuation of the medicament delivery device 7000.

The processor 7810 can be, for example, a FPGA, an ASIC, a DSP, and/or the like. The processor 7810 can be configured to retrieve data from and/or write data to memory, e.g., the memory 7839, which can be, for example, RAM, memory buffers, hard drives, databases, EPROMs, EEPROMs, ROM, flash memory, hard disks, floppy disks, cloud storage, and/or so forth. In some embodiments, processor 7810 can be configured to run and/or execute application modules, processes and/or functions associated with the medicament delivery system 7800 (or any of the medicament delivery systems described herein). For example, in some embodiments, the processor 7810 can be configured to run and/or execute the communication module 7811, the use (or history) module 7812, the leash (or motion tracking) module 7813, the network module 7814, the temperature history module 7815, the predictive module 7816, the notification module 7817, the application interface module 7818, and the onboarding module 7819, and/or any of the other modules described herein, and perform the methods associated therewith.

The user interface 7820 can be, for example, a monitor or screen that displays visual elements to a user. The user interface 7820 can be a touch screen (of a smart mobile phone) upon which a series of graphical user interface (GUI) elements (e.g., windows, icons, input prompts, graphical buttons, data displays, notification, or the like) can be displayed. In some embodiments, the graphical user interface elements (see e.g., the GUI elements described with reference to FIGS. 57-89, 92, 93, and 96-110) are produced by the notification module 7817, the onboarding module 7819, the network module 7814 or any of the other application modules. The user interface 7820 can also include an audible output device through which a series of audible outputs can be produced. Moreover, the user interface 7820 can also receive input from the user, such as, for example, input via a touch screen, input via a microphone, or the like.

The radio 7838 can be any suitable communication device and can be a part of the overall processor architecture, (e.g., a part of the Bluetooth® processor). In other embodiments, the radio 7838 can be distinct from the processor 7810. In some embodiments, a short-range radio link can be established between the computing device 7801 and the electronic circuit system 7900. For example, the computing device 7801 and the electronic circuit system 7900 can be paired via the Bluetooth® wireless protocol. Similarly stated, the computing device 7801 and the electronic circuit system 7900 can be paired via a wireless protocol that facilitates the transmission of signals within a range of approximately 700 meters or less (i.e., a Class 3 radio) and/or having a frequency within the range of 2400 MHz and 2480 MHz. In such an embodiment, as described in further detail herein, the computing device 7801 can be operable to send and/or receive data from the electronic circuit system 7900 related to the medicament delivery device 7000, such as data associated with use, preparation for use, status, and so forth. Furthermore, the electronic circuit system 7900 and/or the computing device 7801 can be operable to determine when a short-range communication link is broken (e.g., when the electronic circuit system 7900 is out of range of the computing device 7801).

In some embodiments, such as an embodiment where the computing device 7801 is a Bluetooth® enabled mobile phone, the radio 7838 can be suitable to establish a short-range radio link with the electronic circuit system 7900 and establish a long-range with another computing device (e.g., the remote device 7802) via the network. For example, the radio 7838 can be a dual-function radio and/or the computing device 7801 can include multiple radios to relay information associated with the electronic circuit system 7900 (which may be equipped with only a short-range radio) to the remote device 7802 using, for example, a cellular data network and/or a Wi-Fi link to the Internet. In other embodiments, the electronic circuit system 7900 may be equipped with a radio operable to communicate with the remote device 7802 via the network 7805.

The computing device 7801 can be operable to store (e.g., in the memory 7839) information associated with the electronic circuit system 7900, such as connection time, a medicament device 7000 use record, details of a medicament delivery event (e.g., date, time, duration, and any other characteristics of the use) and so forth. In some embodiments, the computing device 7801 can be operable to determine its location (e.g., via a global positioning system (GPS) sensor (not shown)). In such an embodiment, the computing device 7801 can be operable to associate location data with information associated with the electronic circuit system 7900, such as use data.

The communication module 7811 can be a hardware and/or software module (stored in memory 7839 and/or executed in the processor 7810). In some embodiments, the communication module 7811 is configured to receive an indication and/or transition information associated with a change in status of the medicament delivery device 7000 (e.g., via a wireless signal from the electronic circuit system 7900) and determine, based on the indication or the transition information, a connection and/or communications characteristic. Such communication characteristics can include, for example, a communication interval and/or connection interval (e.g., a time period between successive signals or portions of a signal, such an "advertising interval," also referred to herein as a "connection interval"), a communication mode (e.g., a park mode, sniff mode or the like), etc. In some embodiments, the communication module 7811 can suppress sending wireless communication signals to the electronic circuit system 7900, send a signal prompting the electronic circuit system 7900 (or the communication module 7981) to change communication modes, or the like. For example, in some embodiments, the processor 7980 and/or the processor 7810 can execute, via the communication module 7981 and the communication module 7811, respectively, a Bluetooth® stack (which may be stored in memory 7999, 7839) having service, profile, and/or application layers operable to control and/or improve connectivity, power management, and/or any other suitable feature associated with the Bluetooth® protocol. For example, the processor(s) 7980, 7810, can be operable to alter mode (e.g., from park to sniff, from sniff to active, or any other suitable change), alter communication type (e.g., from ACL communication to SCO communication), alter advertising interval, and/or any other suitable communication parameter. In this manner, in accordance with the methods described herein, the processor 7980 and/or the processor 7810 can alter and/or implement a characteristic of the wireless communication in response to a change associated with the medicament delivery device 7000 (or a simulated medicament delivery device). As one example, the processor(s) 7980, 7810 can be operable to alter a communication mode from advertising a connectable status on a first channel (or set of channels) to sending and/or receiving communication packets on a second channel (or set of channels).

The use (or event detection) module 7812 can be a hardware and/or software module (stored in memory 7839 and/or executed in the processor 7810). As described in more detail herein, in some embodiments, the determination of whether an actual delivery event has occurred is performed solely by the use (or event detection) module 7982 of the device 7000. In other embodiments, certain event detection methods can be performed by the use module 7812 of the remote computing device 7801. For example, in situations where the medicament delivery device 7000 is within range and/or communicatively coupled to the remote computing device 7801, the electronic circuit system 7900 can transmit one or more wireless signals to the remote computing device 7801, and the use module 7812 can determine, based on the received signals, whether an actual medicament delivery event has occurred. For example, in some embodiments, the use (or event detection) module 7812 can receive a first wireless signal (from the electronic circuit system 7900) in response to movement of an actuator (e.g., a signal from a switch similar to the switch 5973) and a second wireless signal (from the electronic circuit system 7900, produced based on a signal from an accelerometer) that is indicative of a vibration profile consistent with medicament delivery. The use module 7812 can then produce an event detection notification. In other embodiments, the use module 7812 can receive a wireless signal from the electronic circuit system 7900 that is in response to removal of the device 7000 from a cover (e.g., a signal from a switch similar to the switch 5974). When the number of instances of cover removal within a time period exceeds a threshold number, the use module 7812 can produce a notification (or script) via the notification module 7817 to produce a GUI element via the user interface 7820. Such notification can, for example, remind the user to limit the number of cover removal instances to preserve battery power.

Although the motion tracking or leash methods are described as being performed by the leash (or motion) module 7983, which is a part of the electronic circuit system 7900, in other embodiments, all or a portion of the leash (or motion tracking) methods can be performed by the leash module 7813, which is included within the remote computing device 7801. The leash module 7813 can be a hardware and/or software module (stored in memory 7839 and/or executed in the processor 7810). In some embodiments, the leash module 7813 is configured to receive information associated with the connection (or pairing) between the electronic circuit system 7900 and the computing device 7801 and produce an alarm or notification based thereupon. In some embodiments, the leash module 7813 can base the alarms on the position and/or location of the electronic circuit system 7900 and/or the computing device 7801. In other embodiments, the leash module 7813 (and any other leash modules or motion modules described herein) can base the alarms on a difference between a target motion profile and an actual motion profile of the medicament delivery device 7000.

In some embodiments, when the communications between the computing device 7801 and the electronic circuit system 7900 is disrupted (e.g., the communication device 7801 moves out of range and/or vice versa), the electronic circuit system 7900 (via the leash module 7983) and/or the communication device 7801 (via the leash module 7813) can generate an alert to notify a user that a link has been lost. For example, an individual may be advised to carry a medicament delivery device, such as an epinephrine auto-injector, but may rarely use the medicament delivery device. As a result, the user may occasionally forget to carry the medicament delivery device. If the user additionally carries the computing device 7801, and is less likely to forget the computing device 7801 (for example, where the computing device 7801 is a mobile phone that the user uses on a regular basis), a leash function can alert the user if the medicament delivery device 7000 is not within communication range of the remote computing device 7801. In some embodiments, the computing device 7801 and/or the electronic circuit system 7900 can generate an alert any time the computing device 7801 is moved out of range of the electronic circuit system 7900 (i.e., indicating that the electronic circuit system 7900 is not being carried together with the computing device 7801). In another embodiment, the computing device 7801 can be operable to verify its location (e.g. via GPS) and alert if the computing device 7801 is out of range of the electronic circuit system 7900 and the computing device 7801 has moved a distance from the position where it was last coupled to the electronic circuit system 7900. Such an embodiment can reduce false alarms, which may be caused by radio interference, traveling only a short distance from the medicament delivery device 7000, and so forth. For example, the computing device 7801 can be configured to produce an alert when it loses connectivity with the medicament delivery device 7000 and is more than ⅞ of a mile from the last location at which the computing device 7801 was linked to the electronic circuit system 7900. Any other suitable threshold, such as 200 feet, 7/2 mile, 5 miles, etc. is possible. In addition, or alternatively, an alert can be generated if the communication link is lost and the computing device 7801 is moving at more than a threshold velocity, such as 70 mph, 20 mph, 50 mph, etc. which may be associated with traveling by automobile. In this manner, the leash feature may reduce false alarms that can occur where the user is within walking distance of the medicament delivery device 7000 (e.g., the user may be walking within a large building and the communications between the computing device 7801 and the electronic circuit system 7900 may be temporarily disrupted).

In some embodiments, the leash module 7813 and/or the predictive module 7816 can learn or predict the user's behavior, and then adapt the leash notifications in response to conditions that deviate from the predicted behavior. Specifically, the predictive module 7816 can be a hardware and/or software module (stored in memory 7839 and/or executed in the processor 7810). In some embodiments, the predictive module 7816 can determine and/or change the target motion profile based on the motion profile received over a time period. For example, if the motion profile for a medicament delivery device 7000 that is designated as being carried by a patient consistently has a magnitude, amount and/or characteristic of motion at a certain level (e.g., a level consistent with being carried from the user's home to school over a certain distance, a certain number of times per day and/or at certain times of the day), then the predictive module 7816 can receive such information (e.g., via wireless signals from the medicament delivery device 7000) and update a baseline target (or intended) motion profile to reflect an intended motion profile that is specific or unique to the user. In this manner, the predictive module 7816 can learn the user's behavior and modify the notifications produced based on the learned behavior.

The network module 7814 can be a hardware and/or software module (stored in memory 7839 and/or executed in the processor 7810). As described in more detail herein, the network module 7814 is configured to exchange information associated with the medicament delivery device 7000 and the remote computing device 7801 to facilitate the paring and/or bonding process.

Although the temperature history methods are described as being performed by the temperature history module 7985, which is a part of the electronic circuit system 7900, in other embodiments, all or a portion of the temperature history methods can be performed by the temperature history module 7815, which is included within the remote computing device 7801. The temperature history module 7815 can be a hardware and/or software module (stored in memory 7839 and/or executed in the processor 7810). As described in more detail herein, the temperature history module 7815 is configured to receive a temperature signal (e.g., via wireless signal associated with an output from a temperature sensor similar to the sensor 5975) and produce a notification when the temperature history indicates that the medicament may be outside (or nearing the limits of) an acceptable temperature threshold. For example, in some embodiments, the temperature history module 7815 can calculate a mean kinetic temperature based on the temperature signal.

The application interface module 7818 can be a hardware and/or software module (stored in memory 7839 and/or executed in the processor 7810). As described in more detail herein, the application interface module 7818 is configured to exchange information with other applications external to the connected health system 7800. In this manner, the connected health system 7800 can utilize information from other computer-based applications or systems to enhance the performance of the connected health system 7800. For example, in some embodiments, the remote computing device 7801 can execute a first application (e.g., that includes any of the application modules described herein, such as the leash module 7813, the network module 7814, the temperature history module 7815, and/or the onboarding module 7819) and a second application (not shown in FIG. 56) that is different from the first application. The first application and/or the second application can be configured to run on any suitable platform or operating system, such as Apple iOS, Android (used by certain phones produced by Samsung), Symbian OS (used by certain phones produced by Nokia), Blackberry OS, or Windows OS. The first application is a part of the connected health system 7800, and can communicate with the medicament delivery device 7000, present information to, and receive information from the user via the remote computing device 7801 (e.g., via any of the graphical user interface elements described herein). The second application can be any other application that is executed by the processor 7810 and/or stored within the memory 7839 of the remote computing device 7801. For example, in some embodiments, the second application can be a non-browser application (i.e., the main purpose of the second application is something other than to contact sites on the internet on request).

In some embodiments, the second application is an application associated with allergy information (e.g., an application that rates restaurants within a specific geographic location based on their ability to accommodate patrons with certain allergies). In other embodiments, the second application is an application associated with the local weather. In yet other embodiments, the second application can be a mapping application (e.g., an application that presents map information, selects routes and the like). In yet other embodiments, the second application is an application associated with a health care system associated with the patient's health-care provider (e.g., a patient application of a medical group, an application of a pharmacy, or a patient application of an insurance provider). As described below, in use the application interface module 7818 can receive information from the second application executed by the processor 7810, including sending the requests (e.g., which may include transmitting credentials or other information to the second application) and/or filtering the received information. The application interface module 7818 can then utilize the received information to enhance the operation of the connected health system 7800. For example, in some embodiments, the application interface module 7818 can receive information from a mapping application (i.e., the second application) to enhance the display of the user's last known location in connection with the leash features executed by the leash module 7813. In other embodiments, the application interface module 7818 can receive information from a weather application (i.e., the second application) to enhance the temperature alarms produced by the temperature history module 7815. For example, if the local outside temperature is 95° F., notification produced by the temperature history module 7815 indicating a potentially unacceptable increase in the temperature of the medicament delivery device (e.g., "device left in car" notifications) can be produced more quickly (i.e., after less of a temperature increase has been noted) than if the local outside temperature is 95° F. In other embodiments, the application interface module 7818 can receive information from an allergy support application (i.e., the second application) to enhance information presented to the user within the first application. In other embodiments, the application interface module 7818 can receive information from a pharmacy application (i.e., the second application) to allow the onboarding module 7819 to present information about the nearest pharmacy that has replacement medicament delivery devices 7000 in stock.

Although the application interface module 7818 is described as requesting or receiving information from a second application, in other embodiments, the application interface module 7818 can send information to a second application. For example, the application interface module 7818 (either directly or via the service platform 7870) can send information to any of the second applications described above. In some embodiments, the application interface module 7818 can send allergy information about the patient that is entered into the connected health system 7800 to a second application that tracks and/or manages the user's allergies.

The remote computing devices 7802 can be devices within the connected health system 7800 that are operated by or in possession of an entity other than the user and/or patient. For example, the remote computing devices 7802 can be operated by or in possession of the patient's parents, emergency contacts, a health care provider, or the like. The remote computing devices 7802 can each be a mobile computing entity, such as a smart mobile phone (e.g., an iPhone®, an Android® device, a Windows® phone, a Blackberry® phone, etc.), a tablet computer (e.g., an Apple iPad®, a Samsung Nexus® device, a Microsoft Surface® device, etc.), or a computer (e.g., a laptop, desktop, smart TV, etc.), and/or any other suitable computing entity. Although not shown in FIG. 56, the computing devices 7802 include a processor, a memory, a user interface, and a radio, similar to the structure describe above for the remote computing device 7801. Moreover, the remote computing devices 7802 can include and/or execute any of the application modules described above with reference to the remote computing device 7801. For example, although the remote computing devices 7802 are not shown as being in direct communication (e.g., via a short-range wireless communication protocol) with the medicament delivery devices 7000, 7000', in other embodiments, any of the remote computing devices 7802 can be placed in wireless communication with the medicament delivery devices 7000, 7000'. The remote computing devices 7802 can produce notification and alerts (via any of the application modules described herein) to alert others (non-patient personnel) about the status of the medicament delivery devices 7000, 7000'. For example, the remote computing device 7802 can be a "parent device" and can present notification produced by a leash module.

Initial Onboarding and Establishing an Account

In some embodiments, the connected health system 7800 includes a medicament delivery kit that includes two medicament delivery devices, a trainer (not shown), and a set of instructions (not shown in FIG. 56). The two medicament delivery devices can be the device 7000 and the device 7000', as shown in FIG. 56, or any of the medicament delivery devices described herein (including, for example the medicament delivery device 4000 or 5000). Although not shown in FIG. 56, the trainer can be any of the simulated medicament delivery devices (or trainers) described herein. The instructions can include any suitable instructions, such as, for example, leaflets, stickers, or instruction cards. In some embodiments, the instructions can include an interactive device, such as an audible output instruction, or the like. As described herein, in some embodiments, the medicament delivery kit can be a refill kit that is automatically packaged and sent to the patient (e.g., upon the use or expiration of the preceding kit). In other embodiments, the medicament delivery kit can be a new kit delivered to a first-time patient.

In instances where an account is not already established, the instructions can prompt the user to download one or more computer applications to the mobile computing device 7801. The application(s) can reside in and/or be executed in the processor 7810 and/or the memory 7839 of the mobile computing device 7801, and can include any of the application modules described herein. For example, in some embodiments, the computer application can include any of the following application modules, shown and described with reference to FIG. 56: the communication module 7811, the use (or event detection) module 7812, the leash (or motion detection) module 7813, the network module 7814, the temperature history module 7815, the predictive module 7816, the notification module 7817, the application interface module 7818, and the onboarding module 7819.

The onboarding module 7819 is configured to cause the remote computing device 7801 to produce a series of prompts and information (e.g., via the user interface 7820) to facilitate the creation of a user account within the connected health system 7800. Specifically, onboarding module 7819 can cause the remote computing device 7801 to produce a graphical user interface (GUI) element 7821A that includes a prompt to enter an e-mail address and a button to initiate sending a setup e-mail to the specified address. The service platform 7870 can automatically generate and send the setup e-mail, which can be received by the remote computing device 7801 or any other computing device (e.g., a laptop). Through the setup e-mail, the account holder can access a link or password with which the account can be established, as shown in the GUI element 7821B.

Figures 57, 58, 59:
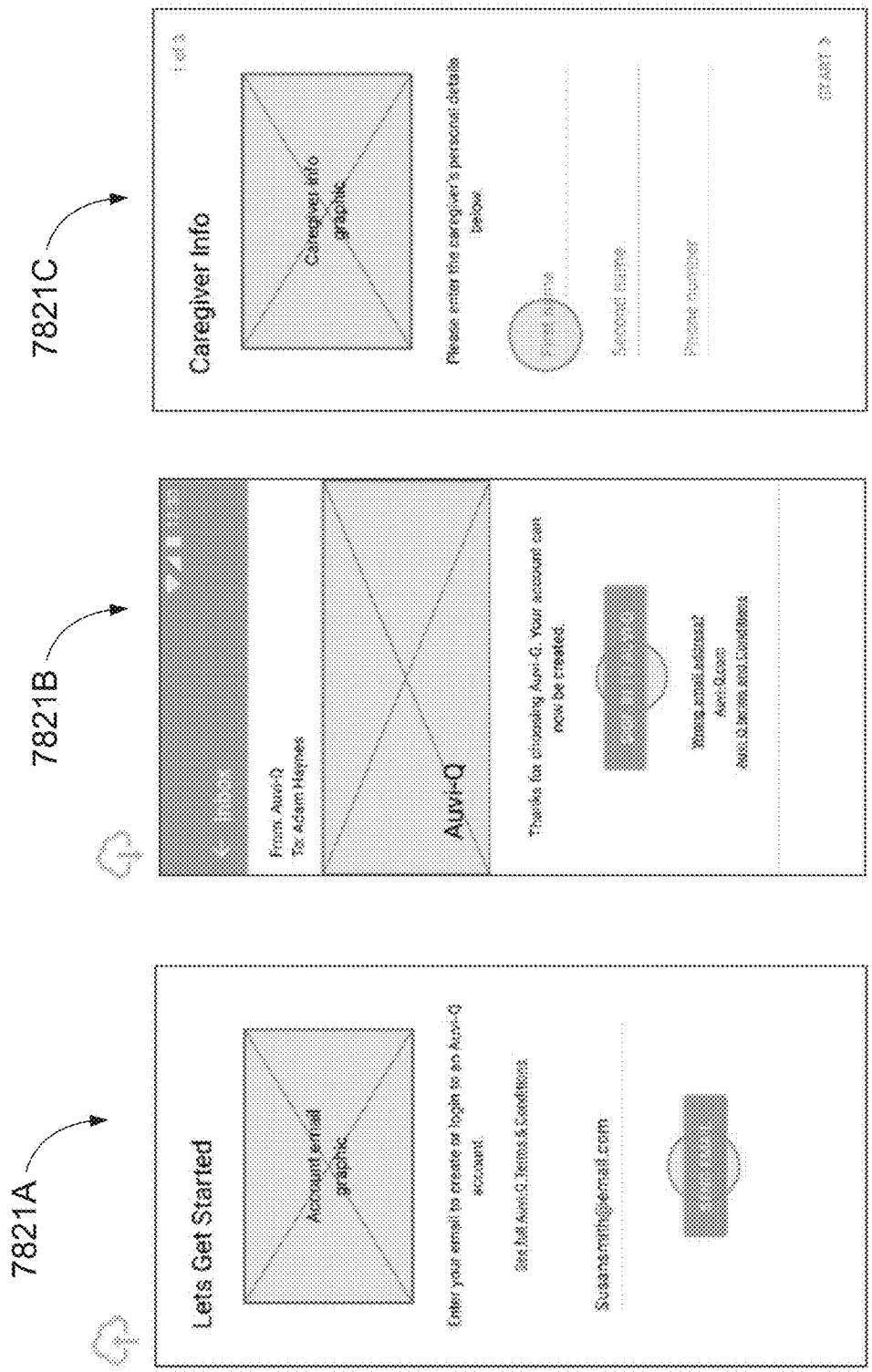
FIGS. 57-60 depict graphical user interface elements produced in connection with a method of establishing a connected health medicament delivery system, according to an embodiment.
Figure 62:
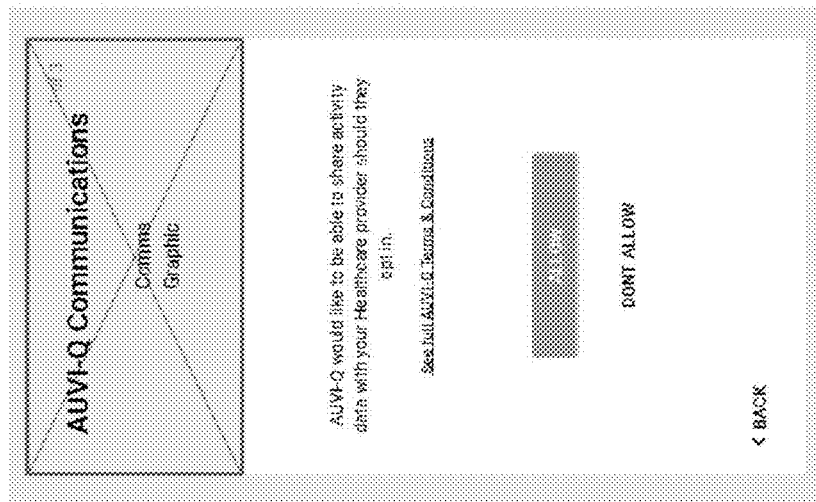
FIGS. 61 and 62 depict graphical user interface elements produced in connection with a method of ensuring regulatory compliance within a connected health medicament system, according to an embodiment.
Figure 61:
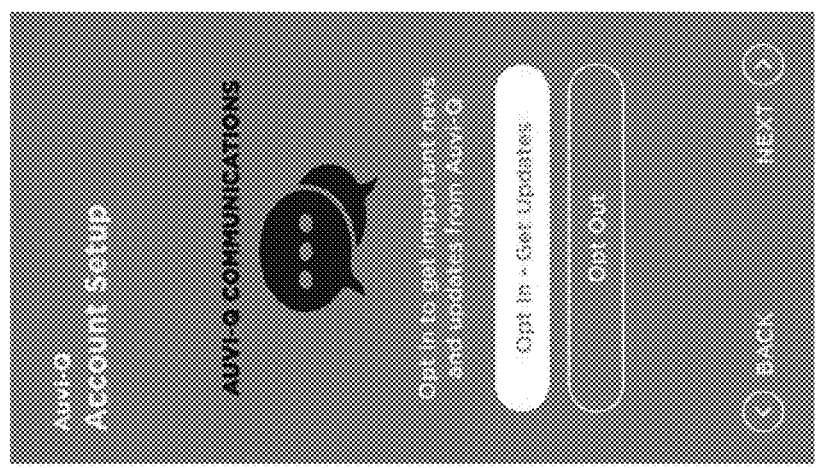
Figure 60:
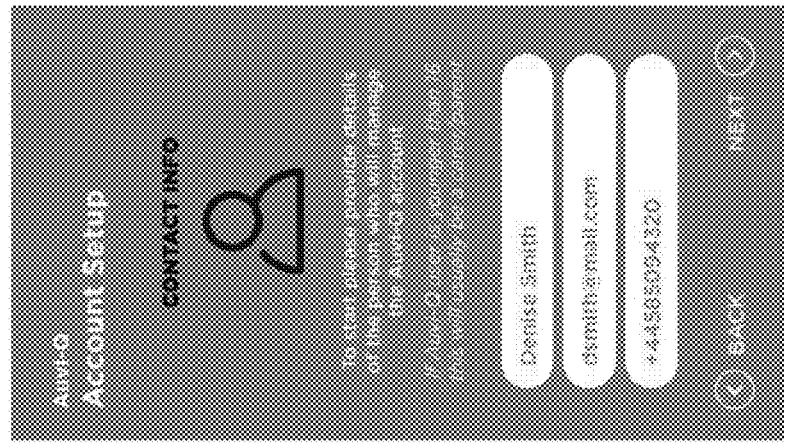
Figure 71:
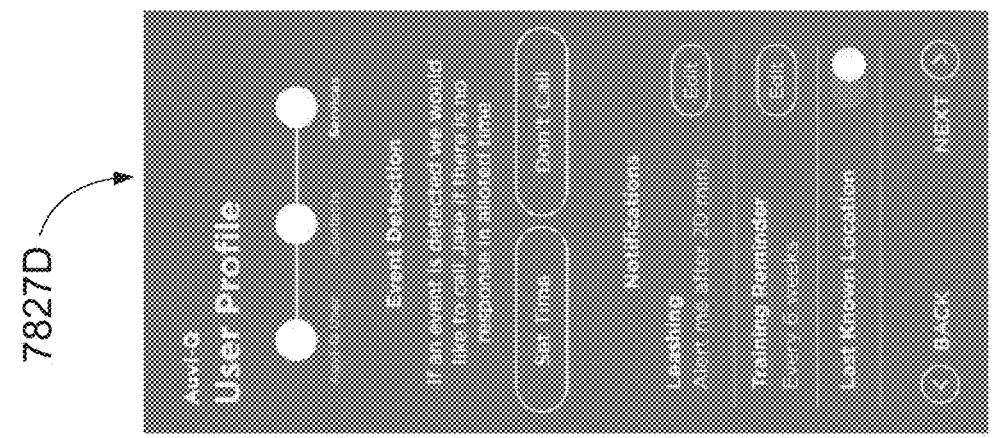
Figure 70:
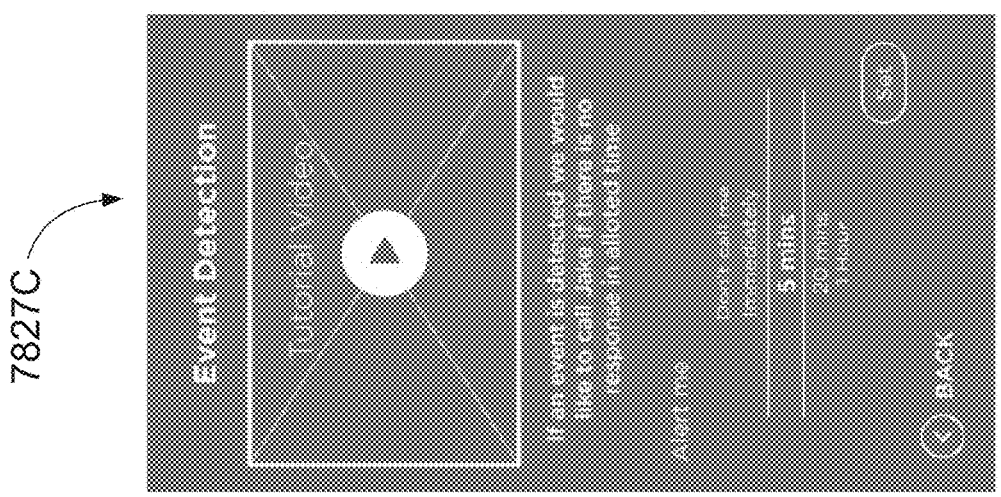

As shown in FIGS. 59 and 60, upon accessing the computer-implemented system 7800 via the remote computing device 7801 (or other computing device), the user is prompted (see, e.g., GUI elements 7821C, 7821D) to enter information associated with the patient or an account administrator (e.g., the parent). The information can be stored within the service platform 7870 (e.g., within an operation subsystem, such as operation subsystem 5871, a database system, such as the database system 5880, or any suitable portion, component or module of the service platform 7870). In some embodiments, information associated with the selected pharmacy, insurance company (i.e., the payer), and/or the health care provider can be exchanged and entered. In some embodiments, the onboarding process can be guided via a "setup wizard" application executed by the onboarding module 7819.

The onboarding module 7819 and the associated modules within the service platform 7870 can function to ensure and/or promote compliance with the Health Insurance Portability and Accountability Act of 1996 (HIPAA). For example, in some embodiments, the onboarding module 7819 can cause the remote computing device 7801 (or any other computing device) to display GUI elements 7822A and 7822B. These GUI elements prompt the user, patient and/or account administrator to enter information relating to their consent to "opt in" to receive further information (GUI element 7822A) and to provide consent to allow their information, including personal health information as defined by HIPAA, to be shared with third parties. Such third parties can include, for example, the patient's health care provider or the payer. In response to the user prompt, one or more signals can be sent, via the remote computing device 7801 to the service platform 7870. Through these signals, instructions can be executed within the service platform 7870 to enable sharing of personalized heath records in compliance with HIPAA. In some embodiments, the service platform 7870 can include one or more compliance modules (not shown) configured to manipulate information and otherwise ensure compliance with HIPAA. For example, in some embodiments, the service platform 7870 and/or the onboarding module 7819 can present education information to the patient or user to ensure that any consent for sharing of information is provided on an informed basis.

In some embodiments, the service platform 7870 can prevent any information associated with the use of any portion of the medicament delivery kit (e.g., the removal of the medicament delivery device from the outer case, the actuation of the medicament delivery device, the use of the trainer, or the like) and that is also associated with the identity of the user or patient from being sent to certain contacts, certain health care providers, and/or certain payers.

During the onboarding or setup process, the onboarding module 7819 can cause the remote computing device 7801 to produce a series of graphical user interface elements to prompt entry of data and/or information to complete the account setup (e.g., for the patient or account administrator). For example, in some embodiments, the onboarding module 7819 can cause the remote computing device 7801 to produce the GUI element 7823A that prompts the user to enter their name, date of birth, and contact e-mail (and/or phone number or identification of the remote computing device 7801). As shown in FIGS. 64 and 65, the information entry GUI element 7823A can include a prompt 7824 to add information associated with emergency contacts, a prompt 7825 to add information associated with health care providers, and a prompt 7827 to add information associated with the "user profile," including allergies of the user.

For example, in some embodiments, the onboarding module 7819 can cause the remote computing device 7801 to produce the GUI element 7824A (FIG. 66) and/or the GUI element 7824B. In response to the GUI element 7824A, the user, patient, or account administrator can input the name and contact information for one or more emergency contacts. For example, in some embodiments, the emergency contacts can be associated with any of the remote devices 7802, which are connected to the system 7800 via the network 7805. Moreover, in response to the GUI element 7824A, the user, patient, or account administrator can select one or more methods for contacting the emergency contact (e.g., via SMS, a phone call, or an e-mail). The emergency contact information can be stored within the service platform 7870 (e.g., within an operation subsystem, such as operation subsystem 5871, a database system, such as the database system 5880, or any suitable portion, component or module of the service platform 7870).

In some embodiments, the onboarding module 7819 can cause the remote computing device 7801 to produce a series of GUI elements that can allow the user, patient, or account administrator to receive additional information regarding features or services of the connected health system 7800 and set preferences (or enable) various features or services as described herein. For example, through the onboarding (or account setup) process and via the GUI elements described herein, one or more of the application modules (e.g., the leash module 7813, the predictive module 7814, or any other application modules described herein) can be enabled. For example, as shown in FIG. 68, the onboarding module 7819 can cause the remote computing device 7801 to produce the GUI element 7827A, which relates to the allergies associated with the user or patient. The allergy information can be stored within the service platform 7870 (e.g., within an operation subsystem, such as operation subsystem 5871, a database system, such as the database system 5880, or any suitable portion, component or module of the service platform 7870). In some embodiments, the GUI element 7827A can be displayed within a first application executed by the processor 7810, and the application interface module 7818 can receive information from a second application executed by the processor 7810 that relates to or is associated with the allergy information. For example, as described herein, in some embodiments, the application interface module 7818 can receive information from a second application that rates restaurants within a specific geographic location based on their ability to accommodate patrons with certain allergies. The application interface module 7818 can request or filter such information based on the allergy information specific to the user that is input in results to the GUI element 7827A. In this manner, the application interface module 7818 can automatically produce information (e.g., a restaurant or food listing) specific to the user from one or more other applications. In other embodiments, the application interface module 7818 can request information associated with a user's allergy profile from a second application (e.g., an application that monitors a user's allergy condition, treatment, and information). In this manner, the application interface module 7818 can populate the allergy information without the need for the user to enter all of the information requested in the GUI element 7827A.

In other embodiments, the application interface module 7818 can send information to a second application executed by the processor 7810 that relates to or is associated with the allergy information. For example, in some embodiments, the application interface module 7818 can submit information based on the allergy information (or any other within the system 7800) that is used by second application (e.g., the Belay application), for example, to pre-populate a user profile, etc.

Figure 69:
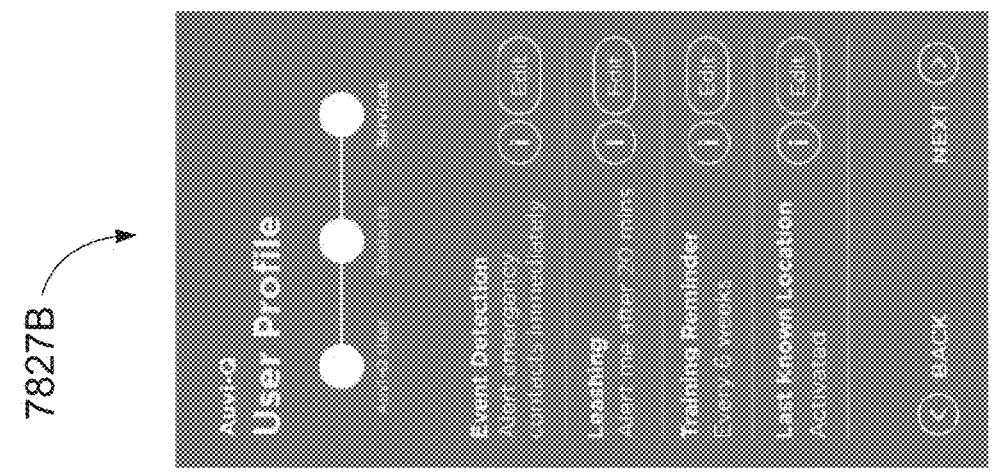

As shown in FIG. 69, the onboarding module 7819 can cause the remote computing device 7801 to produce the GUI element 7827B, which displays a menu of options and/or services within the system 7800. For example, in response to the prompts within the GUI element 7827B, the user, patient, or account administrator can enable the use or event detection features. The event detection features can be performed by the use module 7812 executed in the processor 7810, the use module 7982 executed in the processor 7980 of the medicament delivery device, or any other suitable application modules as described herein). Moreover, in response to the prompts within the GUI element 7827C (FIG. 70) and/or the GUI element 7827D (FIG. 71), the user, patient, or account administrator can receive instructions and/or information about the event detection feature, and set specified time periods for follow-up notifications. The instructions can be, for example, video instructions, audible instructions, or instructions in any other format.

In response to the prompts within the GUI element 7827B, the user, patient, or account administrator can also enable the leash (or "motion detection") feature. The leash features can enhance compliance by sending notifications and/or reminders for the user to carry their medicament delivery device 7000. As described below, the leash features can be enabled separately for each medicament delivery device (the device 7000 and the device 7000'). In this manner, the system 7800 can send one series of notifications specific to a first device (e.g., a device designated to be carried with the user) and a second series of notifications specific to a second device (e.g., a device designated to be maintained in a single location, e.g., at school). The leash features can be performed by the leash module 7813 and/or the predictive module 4816 executed in the processor 7810, the leash module 7983 and/or the predictive module 4986 executed in the processor 7980 of the medicament delivery device, or any other suitable application modules as described herein). Moreover, in response to the prompts within the GUI element 7827E (FIG. 72), the user, patient, or account administrator can receive instructions and/or information about the event detection feature, and set specified time periods for leash-related notifications. The instructions can be, for example, video instructions, audible instructions, or instructions in any other format.

Figure 74:
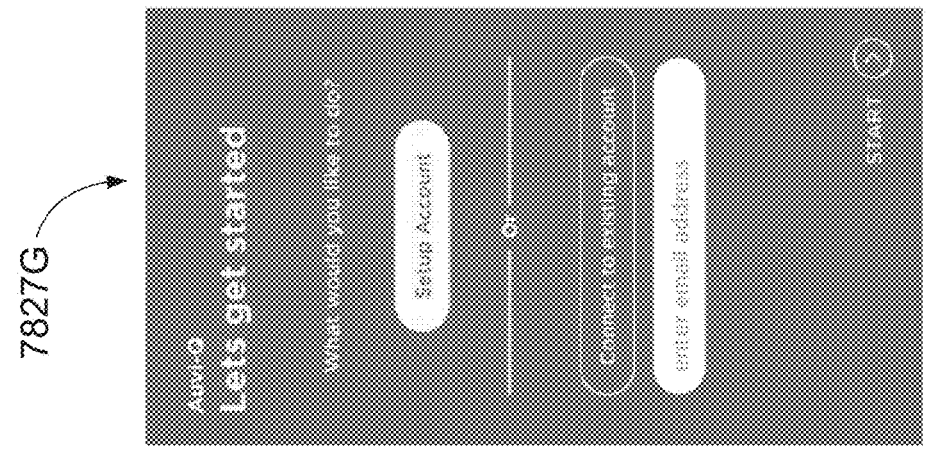
Figure 73:
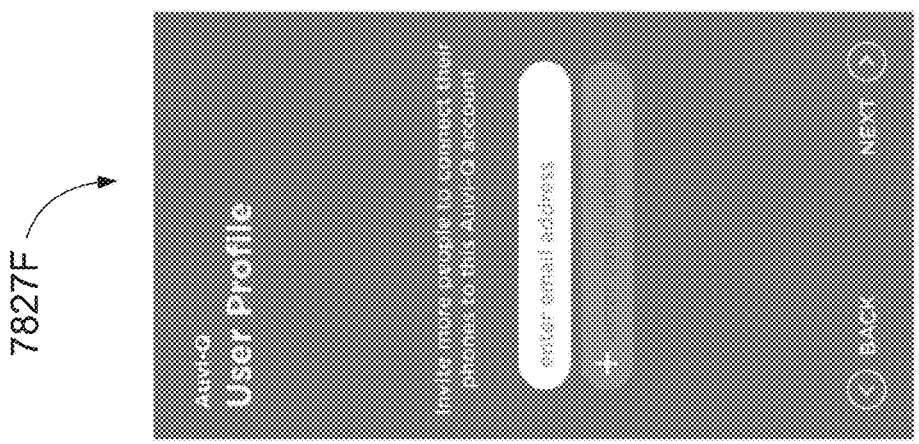
Figure 72:
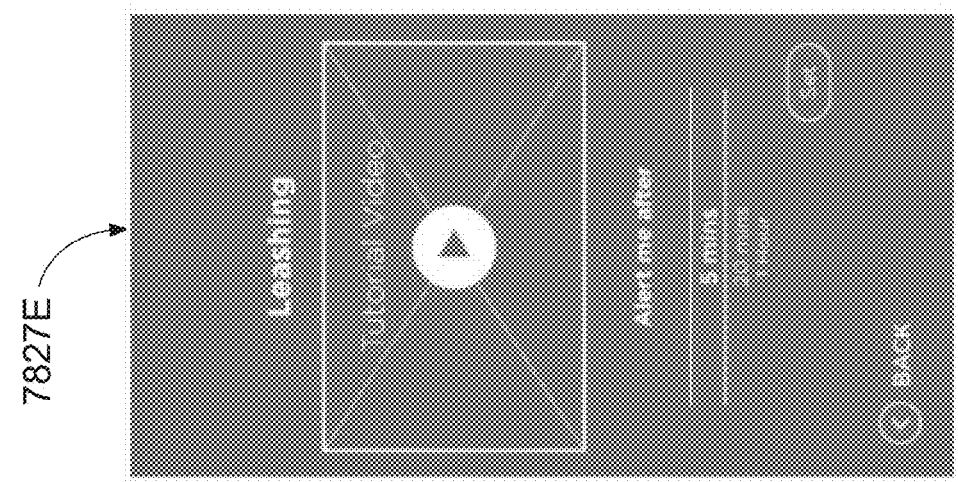
Figure 75:
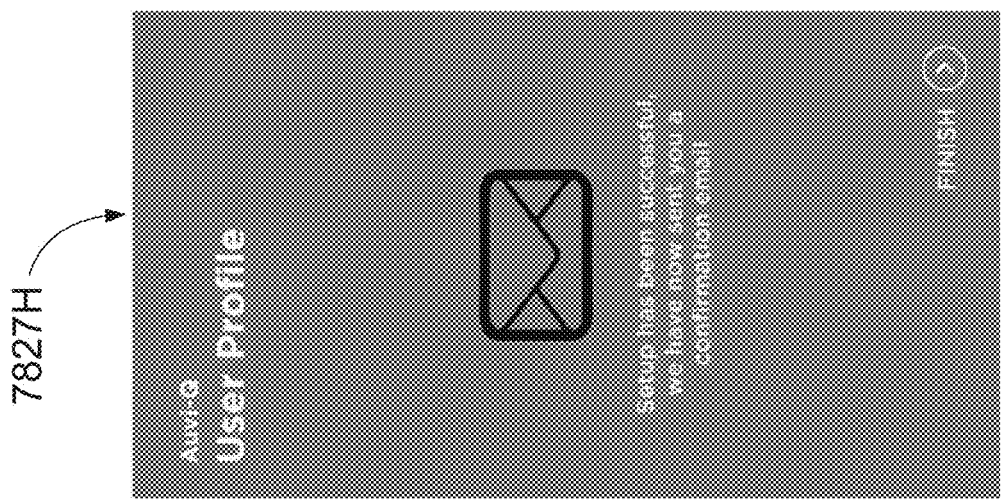

The onboarding module 7819 can cause the remote computing device 7801 to produce the GUI element 7827F prompting the user, patient, or account administrator to add additional users that can be connected or associated with the account. Referring to FIGS. 74 and 75, the onboarding module 7819 can cause the remote computing device 7801 to produce the GUI elements 7827G and 7827H, respectively, related to the account setup and initial onboarding methods.

Pairing and Bonding a Medicament Delivery Device

As a part of the onboarding process, the onboarding module 7819 and/or the network module 7814 can cause the remote computing device 7801 to produce a series of GUI elements (see FIGS. 76-84) to guide the user through the pairing process. Based on input received in response to the GUI elements and information within the processor 7980 and/or the memory 7999 (of the first medicament delivery device 7000 or the second medicament delivery device 7000'), the onboarding module 7819 and/or the network module 7814 of the remote computing device 7801, and the network module 7984 of the medicament delivery device can cause the remote computing device 7801 and the medicament delivery device 7000 (or 7000') to exchange information (e.g., short term and/or long term keys) to complete the pairing and bonding process. Specifically, the pairing process includes the exchange of security features and/or one or more short-term security keys between the remote computing device 7801 and the medicament delivery device 7000 (specifically, the electronic circuit system 7900). Through this process, an encrypted connection between the remote computing device 7801 and the medicament delivery device 7000 can be established, and one or more long-term security keys can be exchanged and stored (e.g., within the processor 7980, the processor 7810, the memory 7999 and/or the memory 7839) to bond the remote computing device 7801 and the medicament delivery device 7000. After being bonded, the devices can then exchange information, including secured information (e.g., personal health information or the like) via any suitable communication channel (e.g., an encrypted connection).

Figure 77:
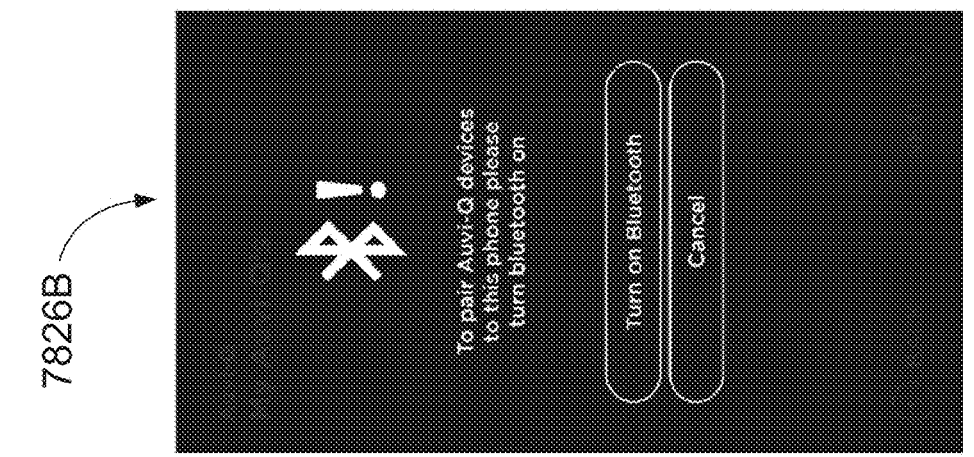
Figure 76:
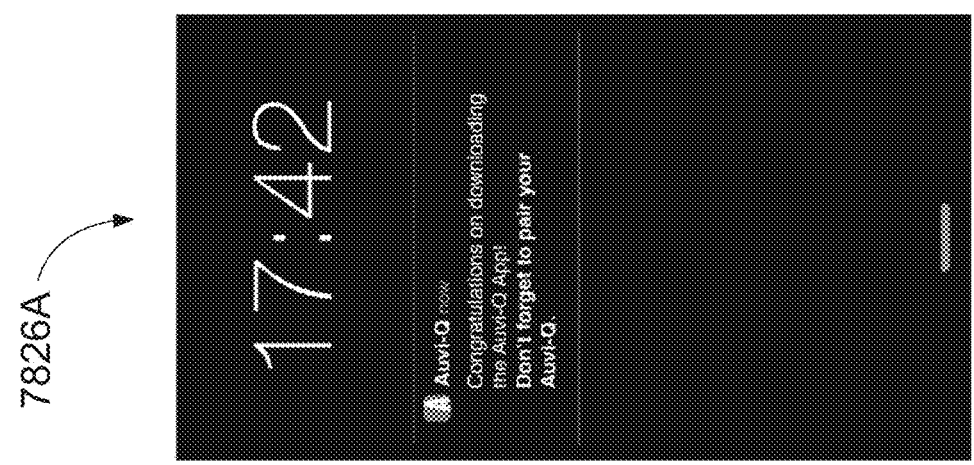

Referring to FIGS. 76 and 77, the onboarding module 7819 and/or the network module 7814 can cause the remote computing device 7801 to produce the GUI elements 7826A and 7826B, respectively. The GUI element 7826A provides a reminder to the user, patient, or account administrator to complete the pairing operation to ensure that the medicament delivery devices 7000, 7000' are paired with the remote computing device 7801. Through this connection, the medicament delivery devices 7000, 7000' can be communicatively coupled to the service platform 7870 and the remote computing devices 7802 (e.g., an emergency contact's phone) via the network 7805. The GUI element 7826B provides a reminder that the settings within the remote computing device 7801 must be enabled to establish a connection (e.g., via the Bluetooth® protocol) with the medicament delivery device 7000.

Figure 78:
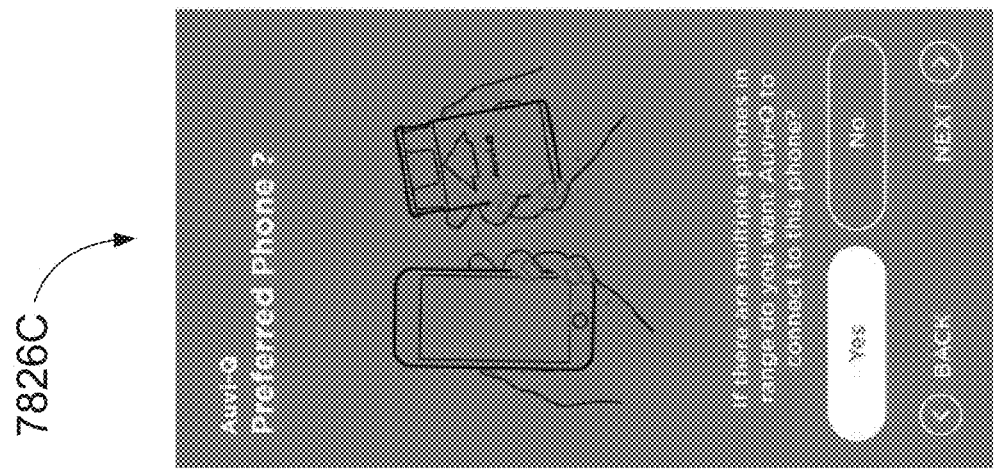
Figure 79:
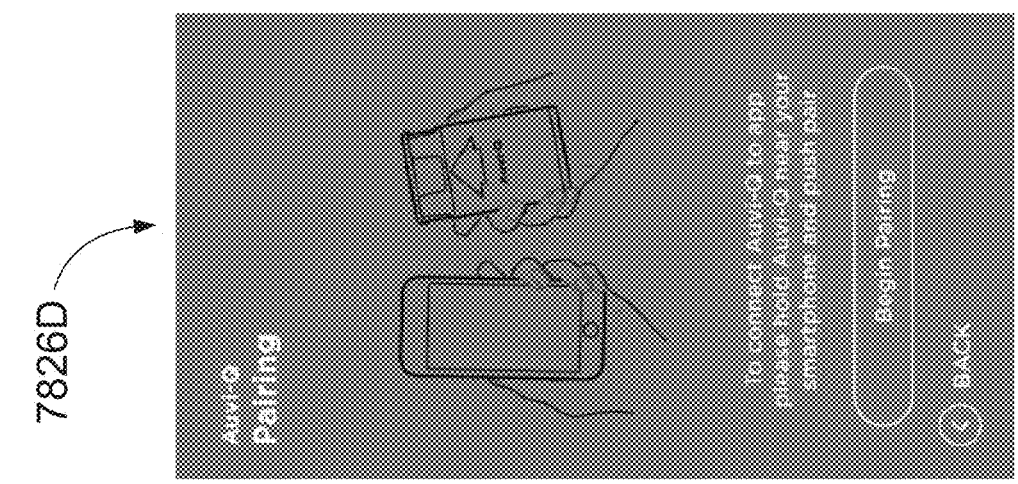
Figure 80:
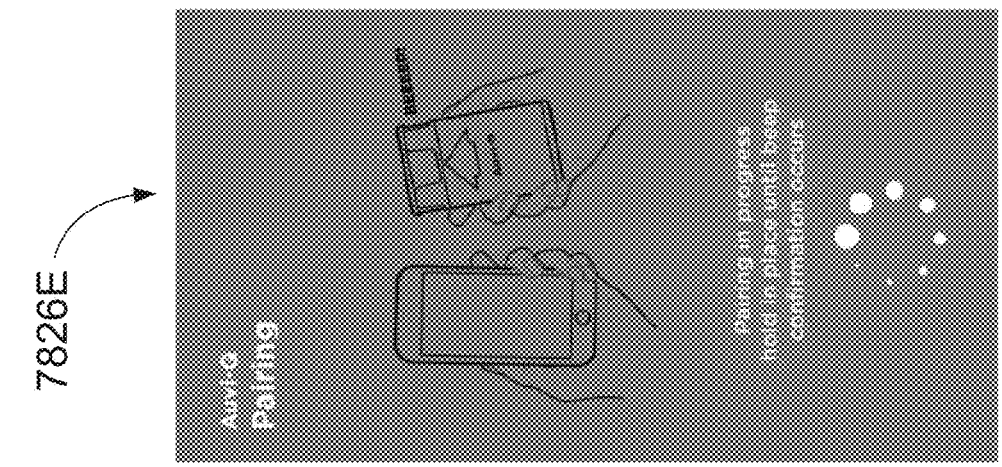

The pairing of the remote computing device 7801 and the medicament delivery device 7000 (or 7000') can be accomplished by any suitable method. For example, in some embodiments, the medicament delivery device 7000 can be paired with the remote computing device 7801 by simply bringing the medicament delivery device into proximity with the remote computing device 7801. For example, as shown in FIGS. 78-80, pairing can be completed by first confirming the identity of the remote computing device 7801 to which the medicament delivery device 7000 is being paired, as prompted by the GUI element 7826C. In this manner, if there are multiple remote computing devices (e.g., the remote computing device 7801 and any of the remote computing devices 7802) communication range of the medicament delivery device 7000, the user can confirm the identity of the remote computing device to be paired with the medicament delivery device. The pairing can then be initiated by moving the medicament delivery device 7000 into proximity with the remote computing device 7801, and entering a response to initiate pairing. as prompted by the GUI element 7826D. Pairing (and/or bonding) can then be completed by any of the application modules described herein, as shown by the GUI element 7826E. In some embodiments, the medicament delivery device 7000 (specifically, the electronic circuit system 7900) can produce an output, such as a flashing light, an audible output, or the like, when the pairing and/or bonding is completed.

In some embodiments, the pairing operation includes manipulating the medicament delivery device 7000 to send one or more signals to initiate pairing. For example, in some embodiments, a GUI element (not shown) can prompt the user to remove the case (e.g., the case 4200 or the case 5200) to initiate pairing between the medicament delivery device 7000 and the remote computing device 7801. As described herein, removing the case can actuate the electronic circuit system 7900 (e.g., via a switch, similar to the switch 5974 described above), to cause the network module 7984 to produce a signal transmitted via the radio 7951. In some embodiments, removal of the case can cause the advertising interval to be changed to a much faster interval to facilitate rapid pairing. In some embodiments, a GUI element (not shown) can prompt the user to remove the case in a specific sequence or manner (e.g., remove and reinstall three times within a 30 second period).

In some embodiments, the pairing operation includes entering information unique to the medicament delivery device 7000 within the remote computing device 7801 to facilitate establishing an appropriate communication channel. For example, in some embodiments, the onboarding module 7819 and/or the network module 7814 can cause the remote computing device 7801 to produce the GUI element 7826F and/or GUI element 7826H, each of which prompts the user, patient, or account administrator to enter information about the expected use of the medicament delivery device 7000. Such information can include, for example, a unique "name" (or identification) of the medicament delivery device, the expected location or use patterns of the medicament delivery device, or the like. Such information can be used by other application modules, such as for example, the leash (or motion) module 7813 or the predictive module 7816 to produce customized reminders and/or notifications, as described herein. In some embodiments, the onboarding module 7819 and/or the network module 7814 can cause the remote computing device 7801 to produce the GUI element 7826G, which prompts the user, patient, or account administrator to enter information unique to the physical medicament delivery device 7000. Such information can include, for example, a unique device identifier (UDI) associated with the medicament delivery device being paired, all or a portion of a serial number of the medicament delivery device being paired, a manufacturing lot number, or the like. Although the GUI element 7826G is shown as including a prompt in response to which the user can enter a series of numbers, in other embodiments, the onboarding module 7819 and/or the network module 7814 can receive the unique identification information in any suitable manner. For example, in some embodiments, a GUI element can prompt the user to scan a portion of the medicament delivery device 7000, take a photograph of a portion of the medicament delivery device 7000, or the like.

In some embodiments, the pairing operation includes moving the medicament delivery device 7000 into proximity with the remote computing device 7801 until a radio frequency identification (RFID) tag included in the medicament delivery device 7000 is detected by the remote computing device 7801. Upon establishing an RFID connection and/or signal, pairing can proceed according to any of the methods described herein.

In some embodiments, the onboarding module 7819 and/or the network module 7814 can cause the remote computing device 7801 to prompt the user, patient, or account administrator to enter information that is unique to both the individual user and that is unique to the physical medicament delivery device 7000. For example, in some embodiments, a method includes taking a photograph of the packaging or container of the medicament delivery kit using the remote computing device 7801. Through the photograph, the onboarding module 7819 and/or the network module 7814 can extract information, such as, the patient's name, prescription number, the pharmacy associated with the prescription, the patient's health care provider, the unique device identifier (or serial number) of the medicament delivery device 7000, or the like. In some embodiments, the information can be received from the photograph by an optical character recognition (OCR) algorithm. Such information can be used to facilitate the pairing and/or bonding operation. For example, in some embodiments, such information can be used to authenticate the patient, user, or account administrator.

Figure 84:
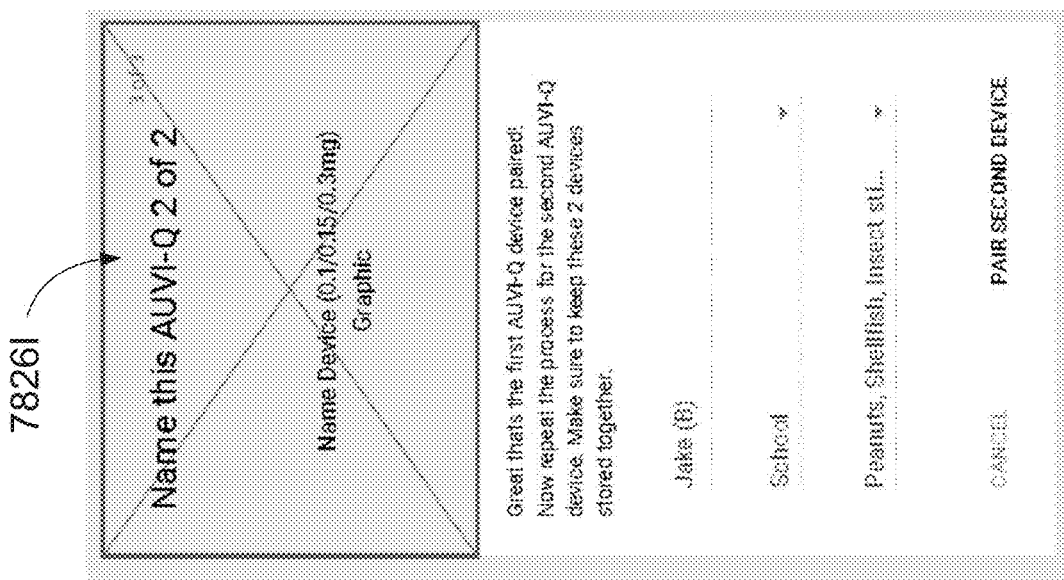

The remote computing device 7801 can be paired and/or bonded with multiple different medicament delivery devices (e.g., the device 7000 and the device 7000'). Accordingly, as shown in FIG. 84, in some embodiments, the onboarding module 7819 and/or the network module 7814 can cause the remote computing device 7801 to produce the GUI element 7826I, which prompts the user, patient, or account administrator to complete the pairing process for a second medicament delivery device 7000'.

In some embodiments, a remote computing device 7801 can be pre-bonded with multiple different medicament delivery devices. Similarly stated, in some embodiments, either or both of the short-term security keys or the long-term security keys associated with each of a set of medicament delivery devices can be stored within a remote computing device 7801 (referred to as a "master computing device") and the short-term security keys or the long-term security keys associated with the remote computing device 7801 can be stored within each of the set of medicament delivery devices. Moreover, this information can be stored and/or downloaded in a manufacturing environment, thus obviating the need to pair each medicament delivery device to the master computing device, as described above. In this manner, the master computing device can access information within and/or communicate with each of the set of medicament delivery devices immediately upon becoming within communication range of the devices. The master computing device can be used, for example, by a system administrator, company (or sales) representative, representative from a health care provider, or the like to easily extract information from a set of medicament delivery devices.

Managing an Account with Multiple Medicament Delivery Devices

Figure 85:
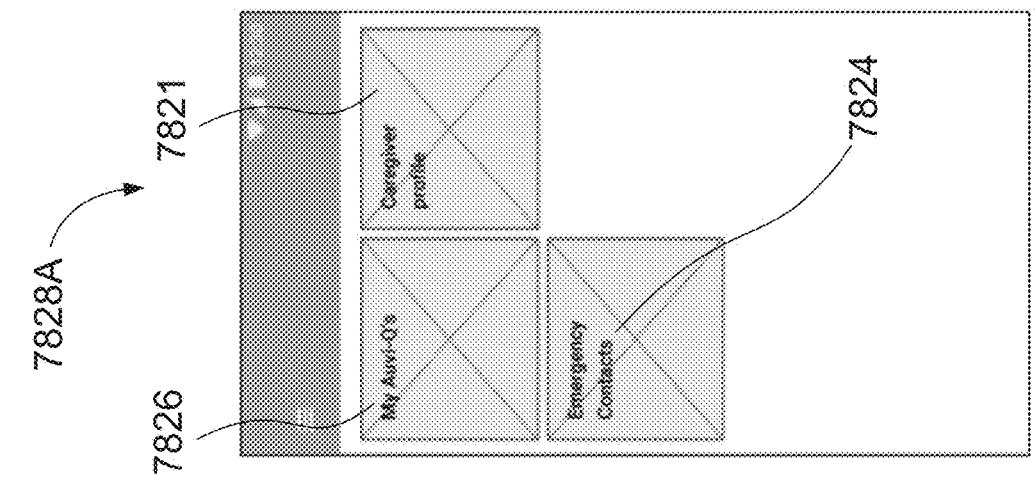

The connected health system 7800 (and any of the connected health systems described herein) can produce a series of notifications, GUI elements, or the like to assist the user, patient, and/or account administrator in managing the account, updating services and/or features, or the like. For example, the connected health system 7800 (and any of the connected health systems described herein) can allow a patient or user (e.g., via the remote computing device 7801) to review, update and/or edit certain preferences or information associated with a connected medicament delivery device. Referring to FIG. 85, the onboarding module 7819 or any other application module can cause the remote computing device 7801 to produce the GUI element 7828A that is a menu-drive "dashboard" screen. The GUI element 7828A can include a prompt 7826 through which the user can review settings associated with the connected medicament delivery devices. The GUI element 7828A can include a prompt 78246 through which the user can review settings associated with the emergency contacts. The GUI element 7828A can include a prompt 7821 through which the user can review settings associated with the health-care provider.

Figure 86:
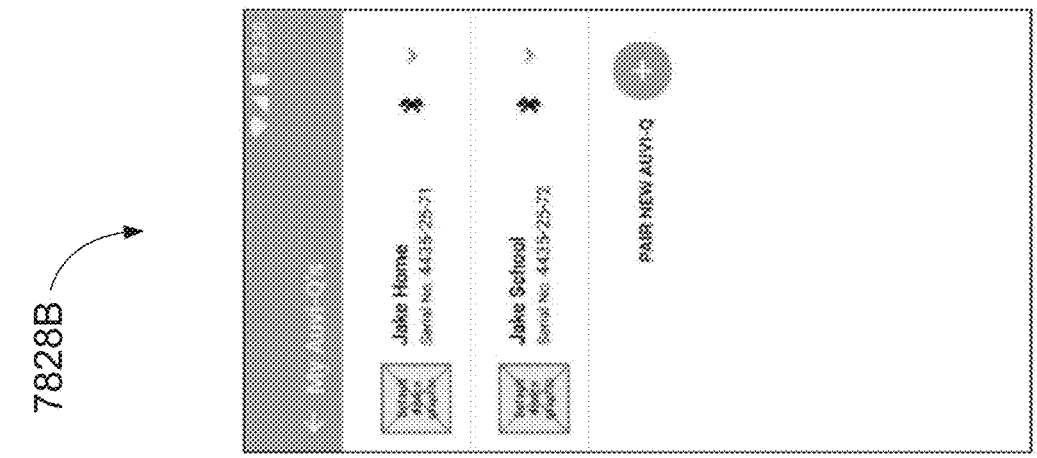
FIGS. 85-89 depict graphical user interface elements produced in connection with a method of managing multiple medicament delivery devices within a connected health medicament delivery system, according to an embodiment.
Figure 87:
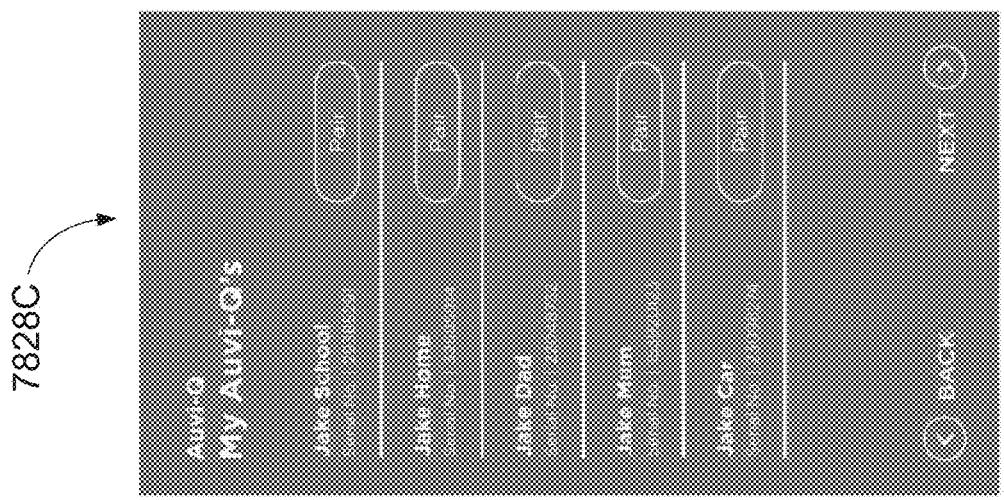
Figure 88:
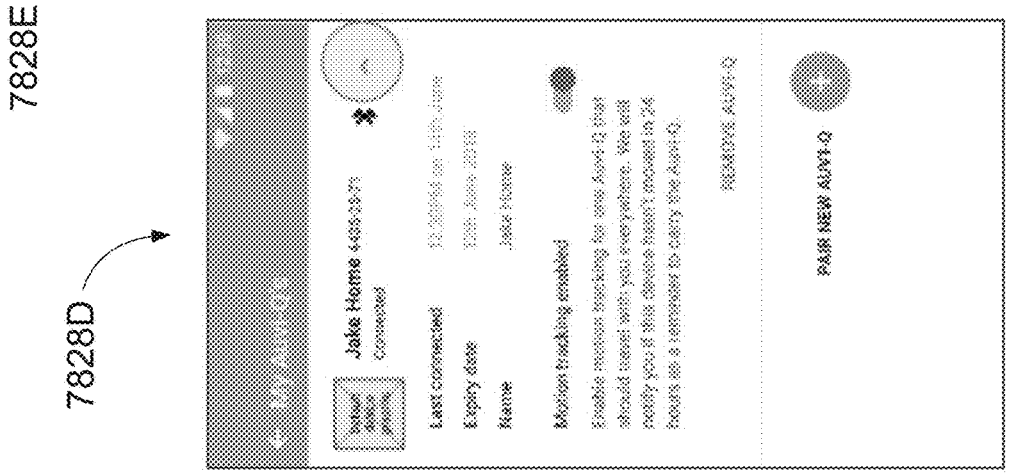
Figure 89:
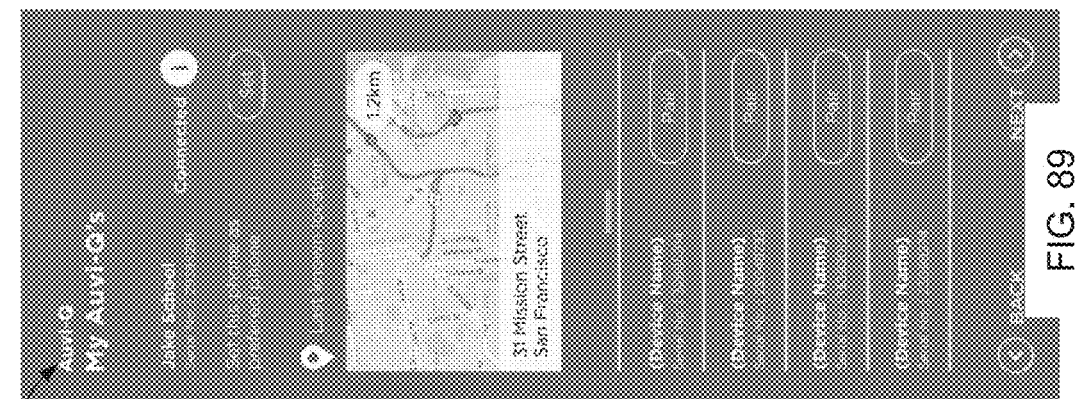

Referring to FIGS. 86 and 87, the onboarding module 7819 or any other application module can cause the remote computing device 7801 to produce the GUI element 7828B and/or the GUI element 7828C, which each provide a listing of connected medicament delivery devices and a status of each device (e.g., paired or not paired, the device "name," the device serial number, or the like). The onboarding module 7819 or any other application module can cause the remote computing device 7801 to produce the GUI element 7828D, which provides information unique to the medicament delivery device, and prompts the user to enable certain services or features available within the connected health system 7800. For example, as shown, the user can enable the "motion tracking" (also referred to as the "leash" or "soft leash") feature. As described below the soft leash feature produces reminders and notifications based on the recorded motion of the medicament delivery device and an expected or "target" motion profile. In other embodiments, the user can enable the "last known location" feature (see GUI element 7828E), which can track the last location at which the remote computing device 7801 was in wireless communication with the medicament delivery device. In yet other embodiments, the user can enable any other features described herein, such as, for example, a temperature monitoring feature, an enhanced event detection feature, or the like.

Although FIGS. 85-89 are shown from the perspective of the user (or patient's) remote computing device 7801, in other embodiments, the connected health system 7800 (and any of the connected health systems described herein) can allow a parent or "emergency contact" (e.g., via the remote computing device 7802) to review, update and/or edit certain preferences or information associated with a connected medicament delivery device. In other embodiments, the connected health system 7800 (and any of the connected health systems described herein) can allow another third party (e.g., a payer or health care provider) to review, update and/or edit certain preferences or information associated with one or more connected medicament delivery devices. For example, in some embodiments, a health-care provider can elect to receive notification when a medicament delivery device is used.

Soft Leash/Motion Tracking Methods

Figure 90:
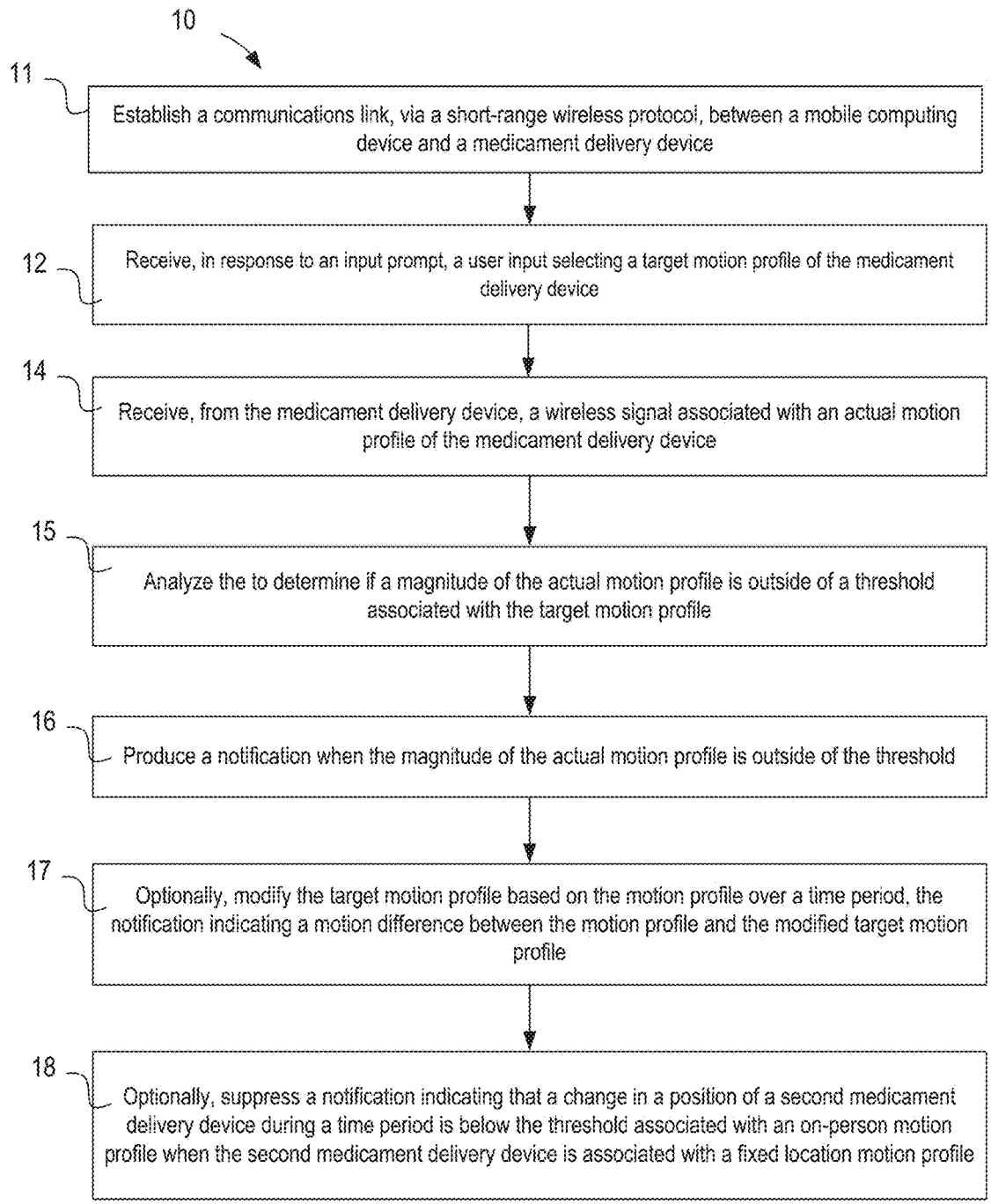
FIG. 90 is a flow chart of a method of producing a compliance notification, according to an embodiment.

FIG. 90 is a flow chart of a method 10 of producing notifications based on a motion profile of a medicament delivery device, according to an embodiment. The method 10 can be performed by the leash module 7813 or any other application modules described herein. Moreover, although the method 10 is described as being performed by and/or within the connected health system 7800, in other embodiments, the method 10 can be performed by any of the connected health systems (or components thereof) described herein. Because the method 10 does not produce notifications solely based on whether a medicament delivery device (e.g., the device 7000) is within range of a remote computing device (e.g., the remote device 7801), but rather produces notifications that are unique to the particular medicament delivery device and/or patient, the method can be referred to as a "soft leashing" method. Such soft leashing methods can limit instances of false alarms. For example, if a device (e.g., the device 7000') is designated as being intended for storage at the user's school, there will be many times when the device is not in wireless communication with the user's remote computing device (e.g., the computing device 7801), and thus notifications based on proximity are not appropriate.

The method 10 includes establishing a communications link, via a short-range wireless protocol, between a mobile computing device and a medicament delivery device, at 11. The short-range wireless protocol can be any of the protocols described herein, including the Bluetooth® wireless protocol. A user input selecting a target (or intended) motion profile of the medicament delivery device is received in response to an input prompt, at 12. The input prompt can be similar to the prompt produced by the GUI element 7826F shown and described with reference to FIG. 81 above. The user input can include, for example, the selection of an intended use profile from a drop-down list, the entry of a physical location (e.g., an address of the user's home), details of an expected daily commute, or the like. For example, in some embodiments, the target motion profile can be an on-person motion profile or a fixed location motion profile. Specifically, the target motion profile can designate that the medicament delivery device is to be kept at home (fixed location), kept at school or work (fixed location), carried with user (on-person profile), maintained as part of an emergency kit (hybrid profile), or the like. In some embodiments, as described below, the target motion profile can be modified based on a pattern of actual motion behavior tracked over a time period.

The method 10 includes receiving, from the medicament delivery device, a wireless signal associated with an actual motion profile of the medicament delivery device, at 14. The wireless signal can be received at any time and in any manner consistent with the communications link and/or wireless protocol established. For example, in some embodiments, such as when the medicament delivery device 7000 is regularly carried in proximity to the remote computing device 7801, the wireless signal can be received regularly throughout the day (e.g., every hour, every two hours, every six hours, or the like). In other embodiments, the medicament delivery device may not be in communication range regularly, and thus the wireless signal can be received at irregular intervals when the communication link is established. For example, a medicament delivery device that is to be maintained at school may only be in wireless communication with the remote communication device (e.g., the device 7801) once a week. In some embodiments, the actual motion profile can be calculated or determined by the leash module 7983 of the electronic circuit system 7900, and can include any of a position, a velocity, an acceleration, or an orientation of the medicament delivery device during a time period. The time period can be, for example, 24 hours, one week, two weeks, one month, or any other suitable time period. In this manner, the actual motion profile can be representative of the whether the medicament delivery device is being used in accordance with its intended use.

The actual motion profile is then analyzed to determine if a magnitude of the actual motion profile is outside of a threshold associated with the target motion profile, at 15. A notification is then produced when the magnitude of the actual motion profile is outside of the threshold, at 16. For example, in some embodiments, the magnitude of the actual motion profile includes an amount of a change in the position of the medicament delivery device during the time period (e.g., over a one week time period), and the notification indicates that the magnitude is outside of the threshold associated with the target motion profile. For example, in some embodiments, the target motion profile can be an "on-person" motion profile. When the actual motion profile indicates little to no change in position over the time period (i.e., the magnitude of actual motion is less than the magnitude of a target amount of motion), the wireless signal received can cause the production of a notification, at 17. The notification can be produced by a notification module (e.g., the notification module 7817), and can be, for example, the GUI element 7833A shown in FIG. 92. In other embodiments, however, the target motion profile can be a "fixed location" (or limited motion) motion profile. When the actual motion profile indicates little to no change in position over the time period, the notification can optionally be suppressed, at 18. In this manner, the notifications can be customized to the expected or targeted use for each medicament delivery device.

In some embodiments, the soft leash method can optionally include modifying the target motion profile based on the user's previous history. Said another way, the leash method can optionally include "learning" the user's behavior and updating the target motion profile based on the learned behavior. In this manner, the notifications can be customized not only to the expected use for each medicament delivery device, but also for the actual behavior of the user. For example, in some embodiments, a predictive module (e.g., the predictive module 7986 and/or the predictive module 7816) can track, record and/or analyze the motion of the medicament delivery device over a "learning" time period (one week, two weeks, one month, or more), and then modify the default target motion profile based on the actual tracked motion. For example, in some embodiments, the actual motion of an "on person" medicament delivery device can be substantially lower during a weekend than during the week. In such situations, the predictive module and/or the soft leash methods can modify the target motion profile during the weekend to reflect the expected lower amount of motion. In this manner, false notifications can be reduced.

In some embodiments, the method can include suspending one or more notifications based on a temporary change in the target motion profile. For example, in some embodiments, the user, patient and/or account administrator can indicate (e.g., in response to a GUI element) that the target motion profile should be suspended due to a vacation, temporary job assignment, illness or the like.

Although shown and described as producing leash notifications based on the difference between a target motion profile and an actual motion profile, in other embodiments, the method 10 can optionally include producing multiple notifications based on any number of different criteria. For example, in some embodiments, the method 10 can include producing a second notification indicating that the distance between the medicament delivery device and the remote computing device is greater than a threshold distance. Such distance-based notifications can be enabled, for example, only with certain medicament delivery devices (e.g., on-person devices). Specifically, in some embodiments, the method optionally includes receiving, from the medicament delivery device, a wireless signal to maintain the established communications link. A relative position between the mobile computing device and the medicament delivery device can then be determined based on the wireless signal (e.g., if the wireless signal is not received within a time period, or the like). A second notification can then be produced when the relative position exceeds a relative position threshold. The second notification can be produced by a notification module (e.g., the notification module 7817), and can be, for example, the GUI element 7833B shown in FIG. 93.

Although shown and described as producing leash notifications based on the difference between a target motion profile and an actual motion profile, in other embodiments, the method 10 can include producing a second notification indicating that the location of the device based upon a global positioning sensor (GPS) of the mobile computing device has changed. Such GPS notifications can be enabled, for example, only with certain medicament delivery devices (e.g., on-person devices). Specifically, in some embodiments, the method optionally includes receiving, from the medicament delivery device, a wireless signal to maintain the established communications link. A GPS location of the medicament delivery device when the communication link is maintained can be determined from the GPS sensor of the mobile computing device. A second notification can then be produced when the GPS location has changed or is outside of desired range. The second notification can be produced by a notification module (e.g., the notification module 7817), and can be, for example, the GUI element 7833B shown in FIG. 93.

In other embodiments, a leash method can optionally include producing a second notification indicating that a temperature (or temperature history) of the medicament delivery device is such that it may be in a location that is not consistent with the target use and/or storage location. For example, in some embodiments, a method can optionally include producing a second notification indicating that the temperature of the medicament device is approach a threshold temperature, and alerting the user, patient and/or account administrator to ensure that the device has not been left in a car. In some embodiments, the method 10 can optionally include receiving, from the medicament delivery device, a second wireless signal associated with a temperature profile of the medicament delivery device. The notification (or a second notification) can be based on both the motion difference and a temperature difference between the temperature profile and a predetermined temperature range. In this manner, if the actual motion profile (or motion difference) indicates that the medicament delivery device has recently been moving at a high rate of speed (indicative of traveling in an automobile) and then subsequently experiences an increase in temperature, then the leash module can determine that it is likely that the medicament delivery device has been left in a car.

Figure 91:
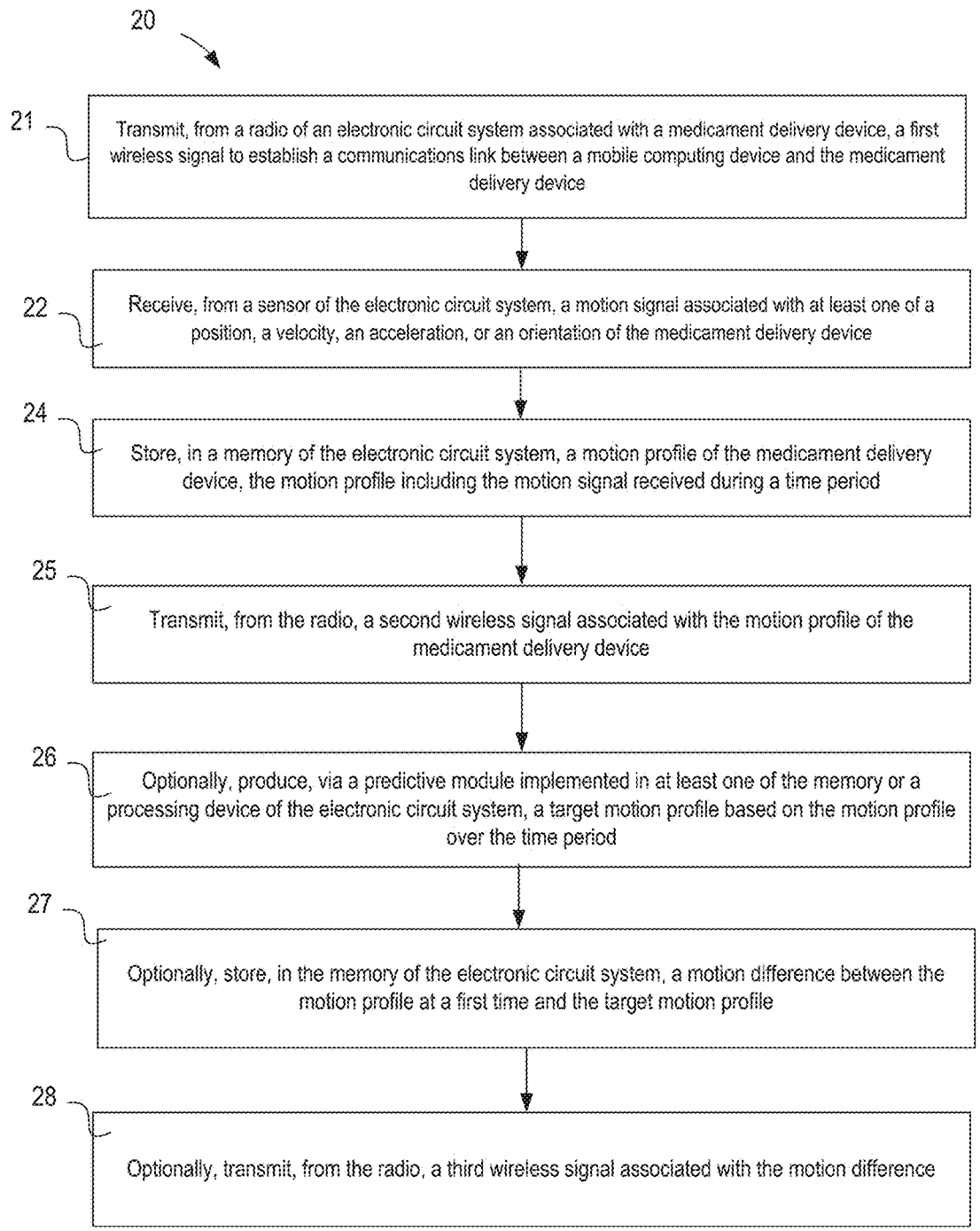
FIG. 91 is a flow chart of a method of producing a compliance notification, according to an embodiment.
Figures 92, 93:
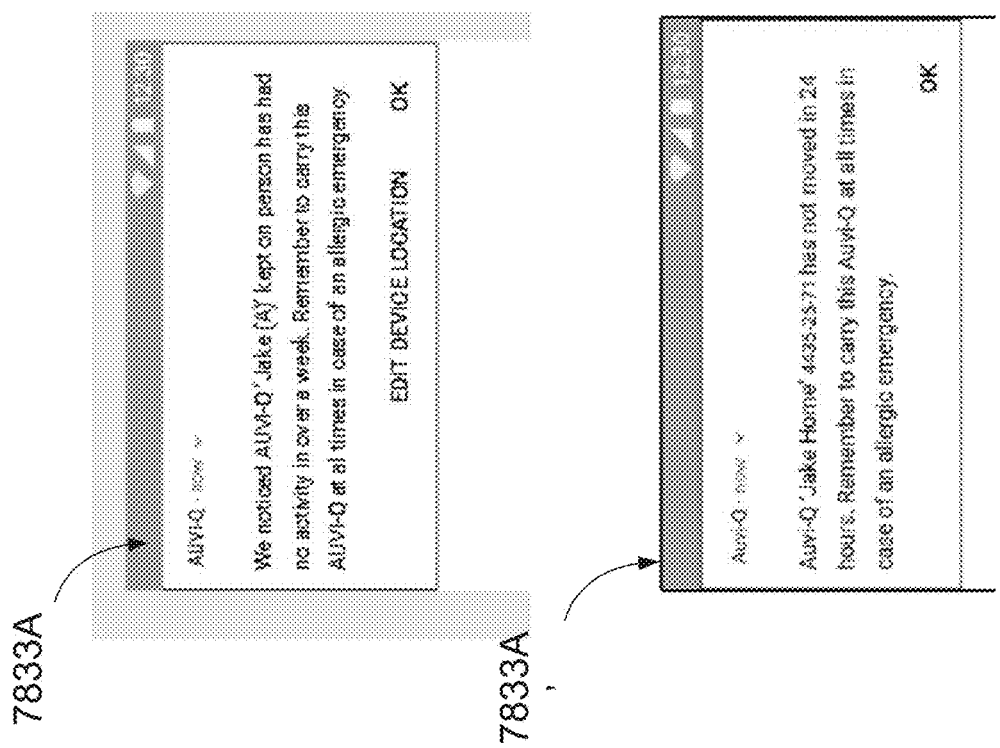
FIGS. 92-93 depict graphical user interface elements produced in connection with a method of producing a compliance notification within a connected health medicament delivery system, according to an embodiment.
Figure 94:
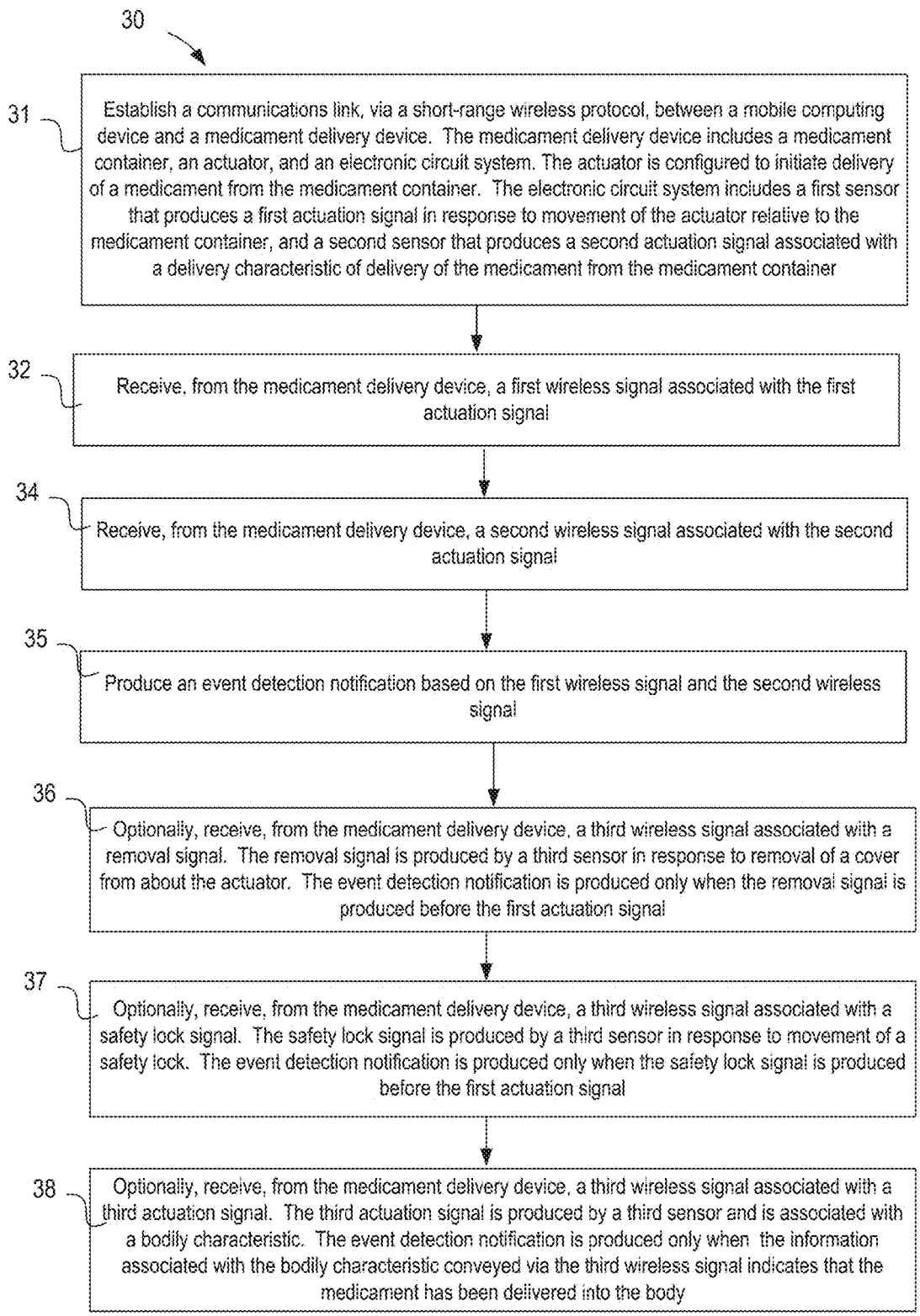
FIG. 94 is a flow chart of a method of producing an event detection notification, according to an embodiment.

Although the method 10 is shown and described being performed primarily by the leash module 7813 within the remote computing device 7801 (e.g., by receiving wireless signals from the medicament delivery device 7000), in other embodiments, all or portions of any of the leash methods described herein can be performed by the leash module 7983 (or any other module within the electronic circuit system 7900, including the predictive module 7986). For example, FIG. 91 is a flow chart of a method 20 of producing wireless signals and/or notifications based on a motion profile of a medicament delivery device, according to an embodiment. Although the method 20 is described as being performed by and/or within the medicament delivery device 7000, in other embodiments, the method 20 can be performed by any of the medicament delivery devices described herein.

The method 20 includes transmitting, from a radio of an electronic circuit system associated with a medicament delivery device, a first wireless signal to establish a communications link between a mobile computing device and the medicament delivery device, at 21. The communication link can be established using any suitable short-range wireless protocol, such as, for example, the Bluetooth® wireless protocol.

A motion signal associated with at least one of a position, a velocity, an acceleration, or an orientation of the medicament delivery device is received from a sensor of the electronic circuit system, at 22. The sensor can be, for example, any of the sensors 7970 discussed herein. For example, in some embodiments, the electronic circuit system is coupled to at least one of a housing of the medicament delivery device (e.g., the housing 5100) or a cover configured to receive at least a portion of the medicament delivery device (e.g., the cover 4200 or 5200). The sensor can be an accelerometer (e.g., the accelerometer 5971) that detects at least one of the position, the velocity, the acceleration, or the orientation of at least one of the housing or the cover. Based on the motion signal, a leash (or motion) module (e.g., the leash module 7983) can produce a motion (or "actual motion") profile of the medicament delivery device.

The motion profile is then stored in a memory of the electronic circuit system, at 24. The motion profile can include the motion signal received during a time period. For example, in some embodiments, the motion profile of the medicament delivery device is produced by a motion module that includes the sensor, an amplifier, a filter (either hardware or software), and/or an analog to digital converter. In this manner, the motion profile can exclude spurious readings or noise, and can provide a representation of the actual motion of the medicament delivery device over the time period.

The method 20 includes transmitting, from the radio, a second wireless signal associated with the motion profile of the medicament delivery device, at 25. The wireless signal can be transmitted at any time and in any manner consistent with the communications link and/or wireless protocol established. For example, in some embodiments, such as when the medicament delivery device 7000 is regularly carried in proximity to the remote computing device 7801, the wireless signal can be transmitted regularly throughout the day (e.g., every hour, every two hours, every six hours, or the like). In other embodiments, the medicament delivery device may not be in communication range regularly, and thus the wireless signal can be transmitted at irregular intervals when the communication link is established. For example, a medicament delivery device that is to be maintained at school may only be in wireless communication with the remote communication device (e.g., the device 7801) once a week. In some embodiments, the actual motion profile can be calculated or determined by the leash module 7983 of the electronic circuit system 7900, and can be transmitted with the device is in range of the remote computing device.

In some embodiments, the method 20 can optionally include producing, via a predictive module implemented in at least one of the memory or a processing device of the electronic circuit system, a target motion profile based on the motion profile over the time period, at 26. Said another way, the leash method 20 can optionally include "learning" the user's behavior and producing a target motion profile based on the learned behavior. In this manner, the notifications produced to the user can be customized not only to the expected use for each medicament delivery device, but also for the actual behavior of the user. In such embodiments, the method 20 can further optionally include storing, in the memory of the electronic circuit system, a motion difference between the motion profile at a first time and the target motion profile, 27. A third wireless signal associated with the motion difference can optionally be transmitted from the radio, at 28.

In some embodiments, the electronic circuit system is coupled to at least one of a housing of the medicament delivery device (e.g., the housing 5100) or a cover configured to receive at least a portion of the medicament delivery device (e.g., the cover 4200 or 5200). The sensor can be an accelerometer (e.g., the accelerometer 5971) that detects at least one of the position, the velocity, the acceleration, or the orientation of at least one of the housing or the cover. Based on the motion signal, a leash (or motion) module (e.g., the leash module 7983) can produce a motion (or "actual motion") profile of the medicament delivery device. Because the motion profile is associated with a time period that can be on the order of a day, a week, or longer, the motion signal can be received at a first sample rate, which can be such that the power draw from the accelerometer is minimized. For example, in some embodiments, the first sample rate can be once every 10 seconds, once every 30 seconds, once every minute, or at an even slower sample rate. Additionally, the motion signal (e.g., a vibration signal from the accelerometer) can be used in any of the "event detection" methods described herein (such as the method 30 described below). Because the event detection methods are associated with a time period that can be on the order of one second or less, when operating in an "event detection" mode, the motion signal can be received at a second sample rate, which faster than the first sample rate. For example, in some embodiments, the second sample rate can be once every second or less. To facilitate the desired variable sample rates for the accelerometer, in some embodiments, a method can include receiving, from a cover removal sensor, a removal signal indicating the that the cover has been removed from about the medicament delivery device. In response to the cover removal signal, the motion signal is then received from the accelerometer at the second sample rate, which is greater than the first sample rate.

Any of the "soft leash" methods described herein can optionally include modifying the notification based on the recorded motion of the medicament delivery device. For example, in some embodiments, any of the methods above can further include modifying a notification (or producing a notification) to reinforce desired behavior of the user based on the recorded motion data. For example, in some embodiments, a method can optionally include producing a notification indicating that that the user has successfully been carrying the device for a threshold number of consecutive days. The notification can state, for example, "congratulations—you have been carrying your delivery device for five consecutive days."

Event Detection Methods

In some embodiments, the connected health system 7800 can produce notifications (e.g., via the remote computing device 7801 and/or the remote computing devices 7802) indicating that a change in status of the medicament delivery device 7000 has occurred. For example, as described above, in some embodiments, the use module 7982 (of the medicament delivery device 7000) and/or the use module 7812 (of the remote computing device 7801) can receive and analyze signals to determine whether an actual event has occurred. Such events can include, for example, instances of the device being removed from the cover (e.g., the cover 5200 or the cover 4200), instances of the safety lock (e.g., the safety lock 4700 and 5700) being removed, or an actual medicament delivery event. Moreover, as described herein the event detection methods can include receiving multiple different signals to validate that an actual event has taken place. By requiring multiple signals, the likelihood of erroneous notifications can be reduced.

FIG. 90 is a flow chart of a method 30 of producing a notification based on multiple signals, according to an embodiment. The method 20 can be performed by the use module 7812 or any other application modules described herein. Moreover, although the method 30 is described as being performed by and/or within the connected health system 7800, in other embodiments, the method 30 can be performed by any of the connected health systems (or components thereof) described herein. Because the method 30 does not produce notifications solely based on a single signal (e.g., whether an actuator has been moved), but rather produces notifications that are based on the analysis of multiple signals, the method can be referred to as a "true event detection" method. Such true event detection methods can limit instances of false alarms.

The method 30 includes establishing a communications link, via a short-range wireless protocol, between a mobile computing device and a medicament delivery device, at 31. The short-range wireless protocol can be any of the protocols described herein, including the Bluetooth® wireless protocol. The medicament delivery device can be any of the devices described herein, such as an auto-injector (e.g., the auto-injectors 4000 and 5000), a pen injector, a medication pump, a body-worn drug delivery device, a prefilled syringe, a nasal delivery device or an inhaler. The medicament delivery device includes a medicament container, an actuator, and an electronic circuit system. The actuator (e.g., the actuator 4300 or 5300) is configured to initiate delivery of a medicament from the medicament container. The electronic circuit system can be, for example, the electronic circuit system 5900 described herein. The electronic circuit system includes a first sensor, and a second sensor. The first sensor (e.g., the switch 4973 or 5973) is configured to produce a first actuation signal in response to movement of the actuator relative to the medicament container. The second sensor (e.g., the accelerometer 5971) is configured to produce a second actuation signal associated with a delivery characteristic of delivery of the medicament from the medicament container.

Although the second sensor is described as being an accelerometer, the second actuation signal can be produced by any suitable sensor configured to detect a delivery characteristic. In some embodiments, the delivery characteristic includes at least one of a vibration signature of the medicament delivery device during actuation, a gas pressure within the medicament delivery device during actuation, a temperature change of a portion of the medicament delivery device during actuation, or a noise produced by the medicament delivery device during actuation. In other embodiments, the delivery characteristic is associated with delivery of the medicament from the medicament container into a body, the delivery characteristic including at least one of a temperature associated with the body, an ionic change associated with placing the medicament delivery device in contact with the body, or a tissue impedance associated with the body.

The method further includes receiving from the medicament delivery device a first wireless signal associated with the first actuation signal, at 32. A second wireless signal associated with the second actuation signal is received from the medicament delivery device, at 34. An event detection notification based on the first wireless signal and the second wireless signal is then produced, at 35. The event detection notification can be produced by the notification module 7817 and can include any suitable notification, such as the GUI elements 7834A and 7834B shown in FIGS. 96 and 97, respectively.

In some embodiments, producing the event detection notification is performed in an event detection module (e.g., use module 7812) and includes comparing information associated with the delivery characteristic conveyed via the second wireless signal to an actuation profile. The actuation profile can include, for example, a gas pressure within a region of the medicament delivery device as a function of time, a signature vibration of the housing during delivery, or the like. In this manner, the event detection module can verify that the event is an "actual" delivery event. In some embodiments, the event detection notification indicates an actuation error when the information associated with the second wireless signal does not indicate that a valid delivery event has occurred. For example, in some embodiments, the event detection notification can indicate an error when a time difference between the occurrence of second actuation signal and the occurrence of the first actuation signal exceeds a time threshold. Said another way, if the first signal is associated with the moving of the actuator (e.g., the actuator 5300), and the second signal is associated with a gas pressure or vibration signature, and the time lag between the occurrence of the pressure (or vibration signature) indicates a likelihood of an erroneous delivery event, then the notification can produce an error message.

In some embodiments, the method 30 can optionally include receiving a third wireless signal as a way to further validate whether event is an actual event or an erroneous or invalid event. For example, in some embodiments, the method optionally includes receiving, from the medicament delivery device, a third wireless signal associated with a removal signal, at 36. The removal signal is produced by a third sensor in response to removal of a cover from about the portion of the actuator (e.g., the cover 5200). The event detection notification is produced only when the removal signal is produced before the first actuation signal. In this manner, the use module 7812 will not produce a delivery event notification unless the cover is first removed.

In some embodiments, the method optionally includes receiving, from the medicament delivery device, a third wireless signal associated with a safety lock signal, at 37. The safety lock signal is produced by a third sensor in response to movement of a safety lock (e.g., the safety lock 5700) to arm the medicament delivery device. The event detection notification is produced only when the safety lock signal is produced before the first actuation signal. In this manner, the use module 7812 will not produce a delivery event notification unless the safety lock is first moved to arm the device for delivery.

In some embodiments, the method optionally includes receiving, from the medicament delivery device, a third wireless signal associated with a third actuation signal, at 38. The third actuation signal is produced by a third sensor and is associated with a bodily characteristic (e.g., impedance or the like). The event detection notification is produced only when the information associated with the bodily characteristic indicates that the medicament has been delivered into the body.

Figure 95:
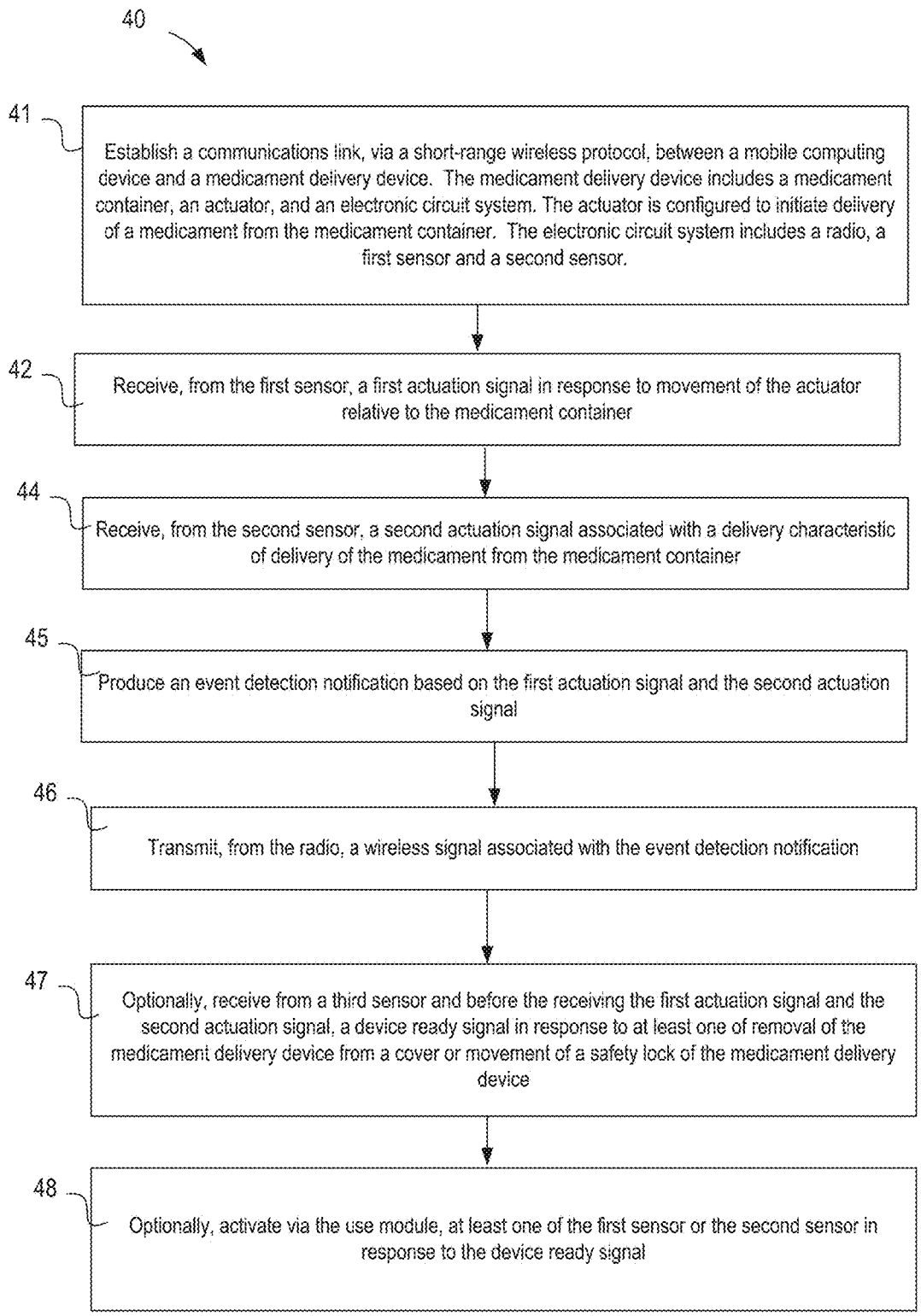
FIG. 95 is a flow chart of a method of producing an event detection notification, according to an embodiment.
Figures 96, 97, 98:
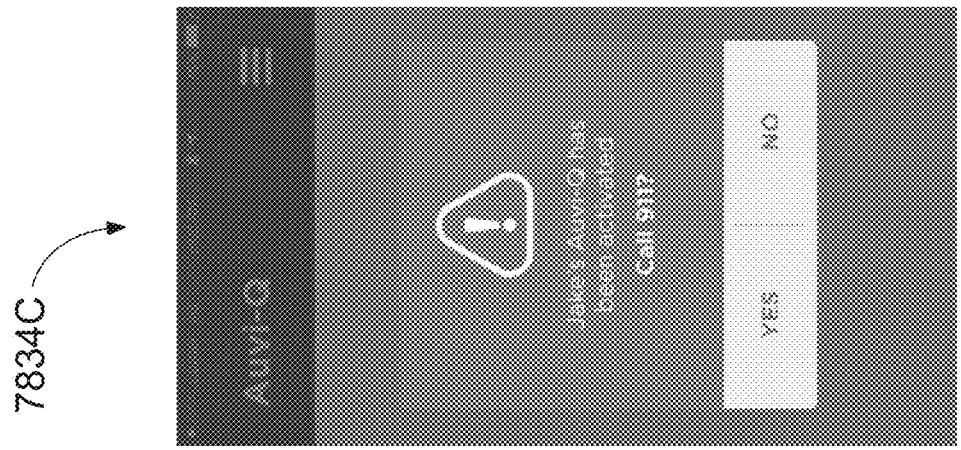
FIGS. 96-101 depict graphical user interface elements produced in connection with a method of producing an event detection notification within a connected health medicament delivery system, according to an embodiment.
Figure 101:
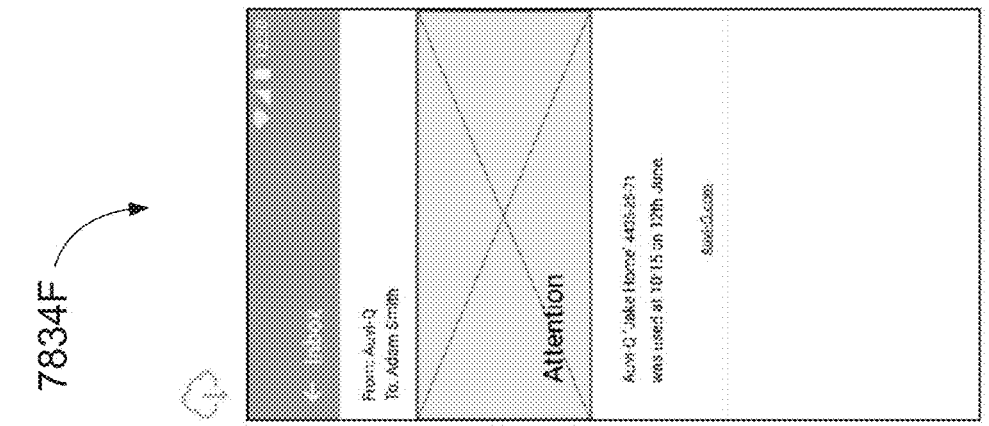
Figure 100:
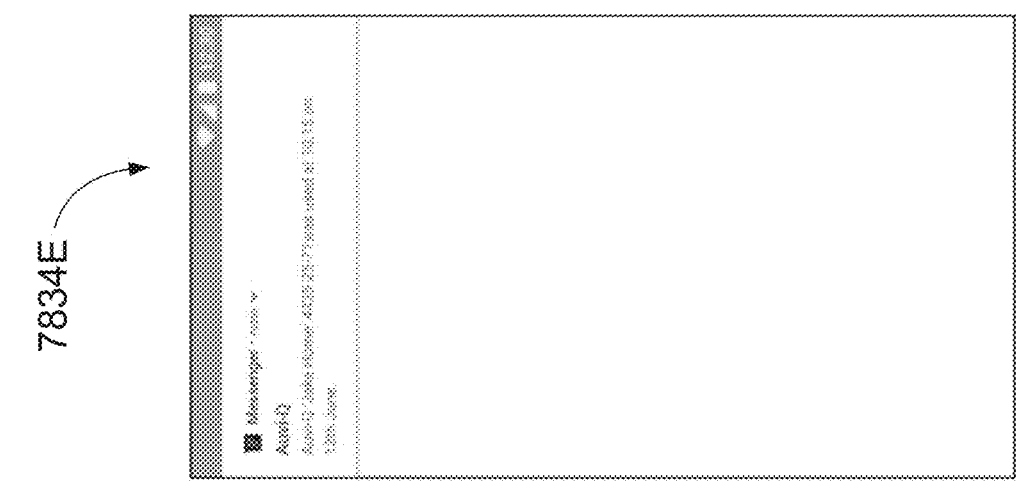
Figure 99:
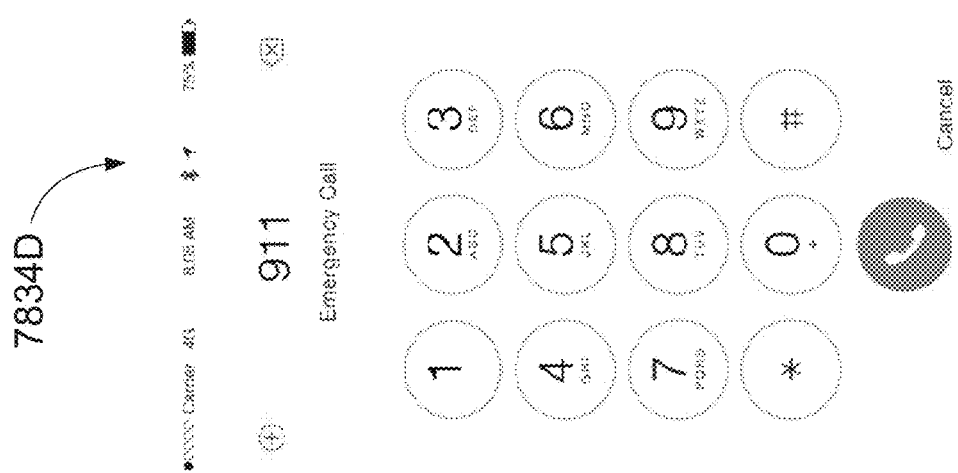

Although the method 30 is shown and described being performed primarily by the use module 7812 within the remote computing device 7801 (e.g., by receiving wireless signals from the medicament delivery device 7000), in other embodiments, all or portions of any of the event detection (or use) methods described herein can be performed by the use module 7982 (or any other module within the electronic circuit system 7900). For example, FIG. 95 is a flow chart of a method 40 of producing wireless signals and/or notifications to confirm an event of a medicament delivery device, according to an embodiment. Although the method 40 is described as being performed by and/or within the medicament delivery device 7000, in other embodiments, the method 40 can be performed by any of the medicament delivery devices described herein.

The method 40 includes establishing a communications link, via a short-range wireless protocol, between a mobile computing device and a medicament delivery device, at 41. The short-range wireless protocol can be any of the protocols described herein, including the Bluetooth® wireless protocol. The medicament delivery device can be any of the devices described herein, such as an auto-injector (e.g., the auto-injectors 4000 and 5000), a pen injector, a medication pump, a body-worn drug delivery device, a prefilled syringe, a nasal delivery device or an inhaler. The medicament delivery device includes a medicament container, an actuator, and an electronic circuit system. The actuator (e.g., the actuator 4300 or 5300) is configured to initiate delivery of a medicament from the medicament container. The electronic circuit system can be, for example, the electronic circuit system 5900 described herein. The electronic circuit system includes a radio, a first sensor, and a second sensor. The first sensor (e.g., the switch 4973 or 5973) is configured to produce a first actuation signal in response to movement of the actuator relative to the medicament container. The second sensor (e.g., the accelerometer 5971) is configured to produce a second actuation signal associated with a delivery characteristic of delivery of the medicament from the medicament container.

Although the second sensor is described as being an accelerometer, the second actuation signal can be produced by any suitable sensor configured to detect a delivery characteristic. In some embodiments, the delivery characteristic includes at least one of a vibration signature of the medicament delivery device during actuation, a gas pressure within the medicament delivery device during actuation, a temperature change of a portion of the medicament delivery device during actuation, or a noise produced by the medicament delivery device during actuation. In other embodiments, the delivery characteristic is associated with delivery of the medicament from the medicament container into a body, the delivery characteristic including at least one of a temperature associated with the body, an ionic change associated with placing the medicament delivery device in contact with the body, or a tissue impedance associated with the body.

The method further includes receiving from the first sensor a first actuation signal in response to movement of the actuator relative to the medicament container, at 42. A second actuation signal associated with a delivery characteristic of delivery of the medicament from the medicament container is received from the second sensor, at 44. An event detection notification based on the first actuation signal and the second actuation signal is then produced, at 45. The event detection notification can be produced by the notification module 7986 and can include any suitable notification for transmission to the remote computing device 7801. A wireless signal associated with the event detection notification is then transmitted (e.g., to the remote computing device 7801) by the radio, at 46.

In some embodiments, producing the event detection notification is performed in an event detection module (e.g., use module 7982) and includes comparing information associated with the delivery characteristic conveyed via the second actuation signal to an actuation profile. The actuation profile can include, for example, a gas pressure within a region of the medicament delivery device as a function of time, a signature vibration of the housing during delivery, or the like. In this manner, the event detection module can verify that the event is an "actual" delivery event. In some embodiments, the event detection notification transmitted to the remote computing device 7801 indicates an actuation error when the information associated with the second wireless signal does not indicate that a valid delivery event has occurred. For example, in some embodiments, the event detection notification can indicate an error when a time difference between the occurrence of second actuation signal and the occurrence of the first actuation signal exceeds a time threshold. Said another way, if the first signal is associated with the moving of the actuator (e.g., the actuator 5300), and the second signal is associated with a gas pressure or vibration signature, and the time lag between the occurrence of the pressure (or vibration signature) indicates a likelihood of an erroneous delivery event, then the notification can produce an error message.

In some embodiments, the method 40 can optionally include receiving a third actuation signal to further validate whether event is an actual event or an erroneous or invalid event. For example, in some embodiments, the method optionally includes receiving, from a third sensor and before the receiving the first actuation signal, a device ready signal, at 47. The device ready signal is produced in response to removal of the medicament delivery device from a cover (e.g., the cover 5200) or movement of a safety lock. In response to receiving the device ready signal, the method can optionally include activating, via the use module, one of the first sensor or the second sensor, at 48.

The event detection notifications produced by the methods described herein can include any suitable notification. For example, in some embodiments, the use module 7812 and/or the notification module 7817 of the patient's computing device (e.g., the device 7801) can produce the GUI elements 7834A and 7834B shown in FIGS. 96 and 97, respectively. In some embodiments, the use module 7812 and/or the notification module 7817 of the patient's computing device (e.g., the device 7801) can further produce a series of GUI elements to facilitate calling an emergency responder. For example, in some embodiments, the use module 7812 and/or the notification module 7817 can produce GUI element 7834C, which allows a user to bypass a lock screen to make an emergency call. Further, in response to receiving a user input to the prompts in the GUI element 7834C, the use module 7812 and/or the notification module 7817 can produce the GUI element 7834D to allow the user to place an emergency call. Such GUI elements can include pre-programmed numbers that will be called upon activation, such as, for example, the number for an emergency responder (e.g., in connection with an emergency use medicament delivery device), a health care provider (e.g., in connection with a chronic-care device), or a parent.

In other embodiments, the use module 7812 and/or the notification module 7817 of the patient's computing device (e.g., the device 7801) can transmit information to the service platform 7870 via the network 7805. In this manner, the use detection notifications described herein can be delivered (or pushed) to other remote computing devices within the system 7800 (e.g., the remote computing devices 7802). For example, in some embodiments, the service platform 7870 can cause information to be delivered to a parent's remote computing device 7802 that causes the remote computing device 7802 to produce one or more GUI elements. The GUI elements can be similar to the GUI element 7834E and GUI element 7834F.

In some embodiments, any of the use detection methods described herein can be used with a chronic-care medicament delivery device that is configured to delivery multiple doses at different times. In such embodiments, the use module can produce a use profile (e.g., an injection profile) to track the pattern of actual delivery events over time. Thus, in a similar manner as tracking the motion of the device (e.g., via the soft leash methods describe herein), the connected health system can also track the use profile and produce notifications in response to the use profile. Such notifications can state, for example, that the user's regimen has been followed for XX consecutive days, or the like.

Additional Services and Notifications

Figure 104:
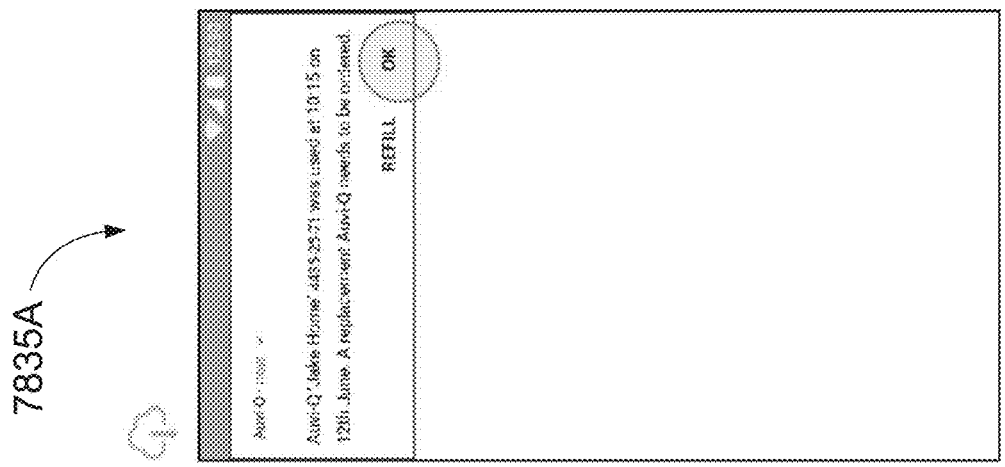
FIGS. 104-105 depict graphical user interface elements produced in connection with a method of producing a refill notification, according to an embodiment.
Figure 103:
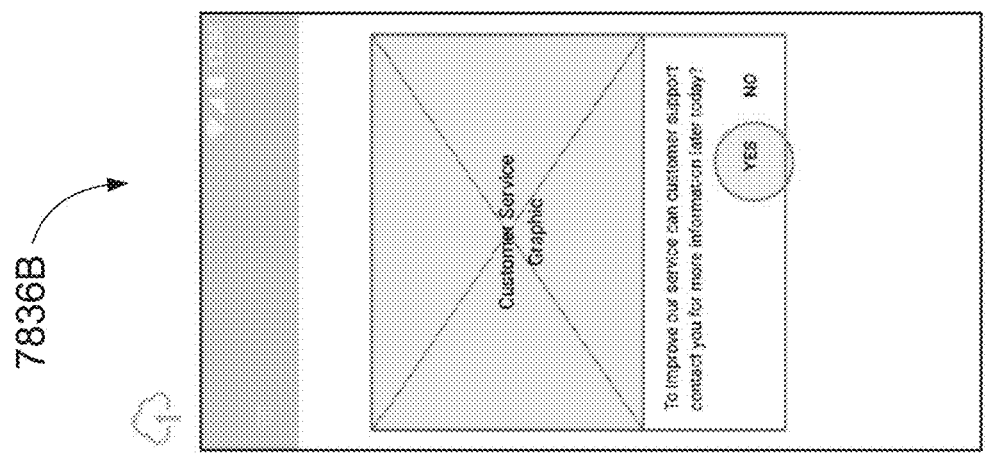
FIGS. 102-103 depict graphical user interface elements produced in connection with a method of producing post-delivery notification within a connected health medicament delivery system, according to an embodiment.
Figure 102:
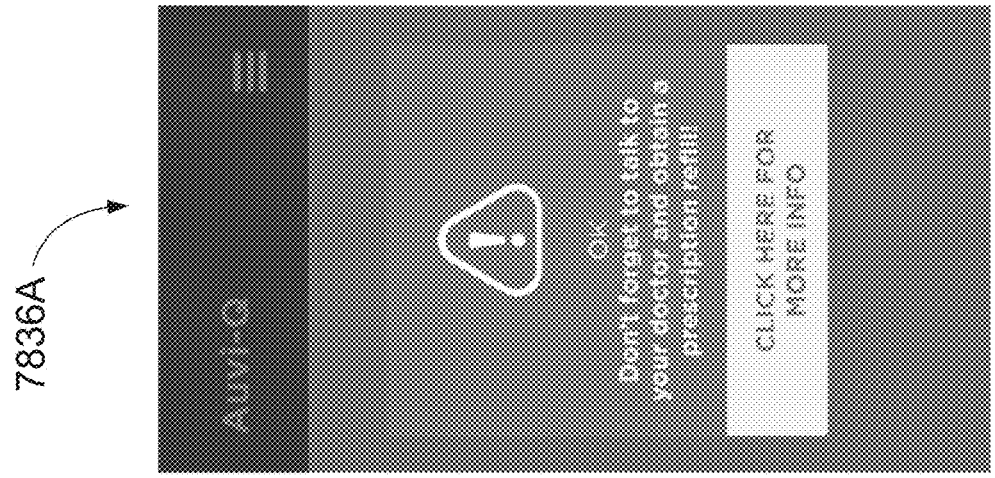
Figure 107:
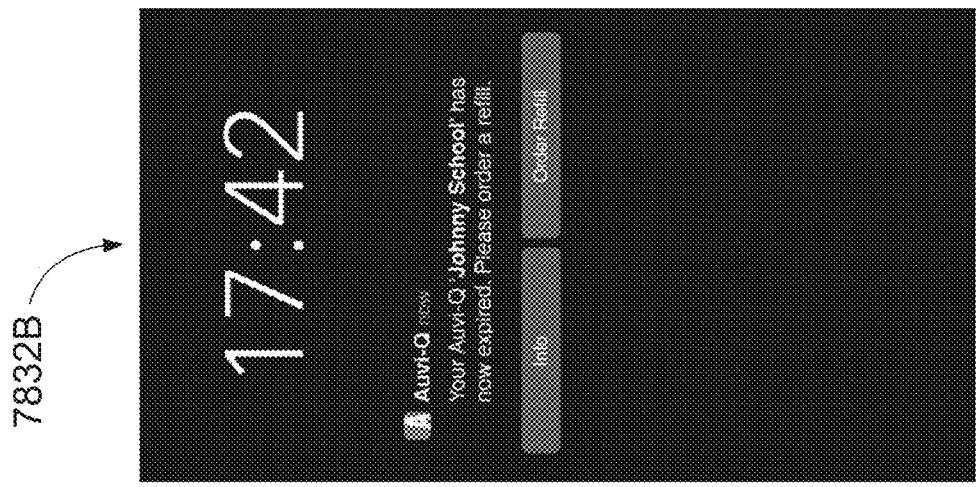
FIGS. 106-107 depict graphical user interface elements produced in connection with a method of producing an expiration notification, according to an embodiment.
Figure 106:
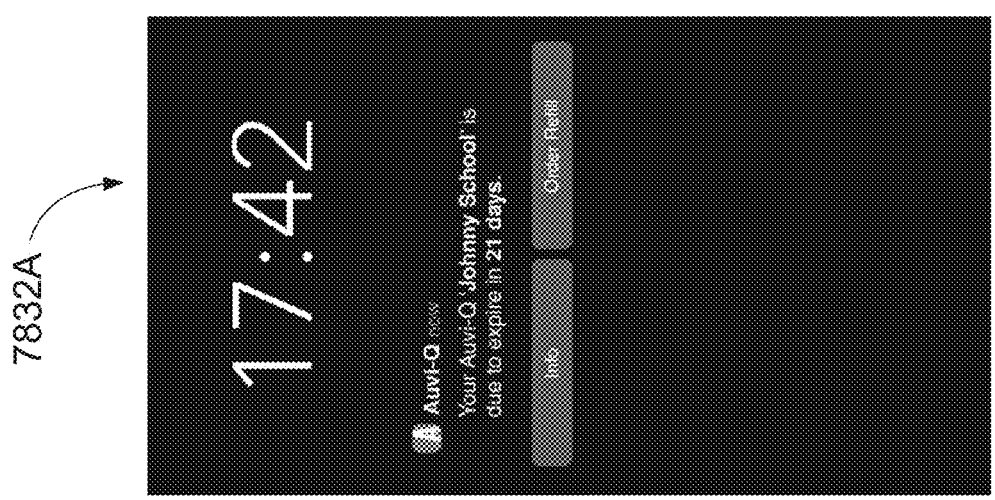
Figure 105:
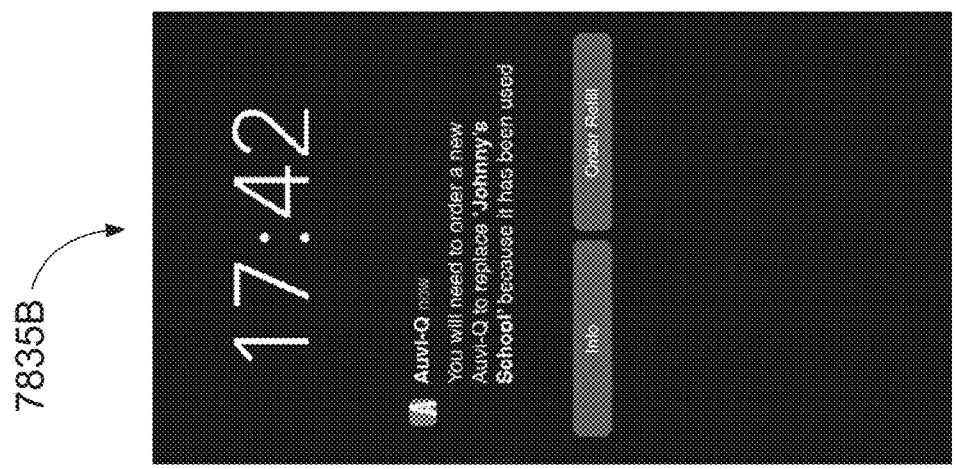
Figure 110:
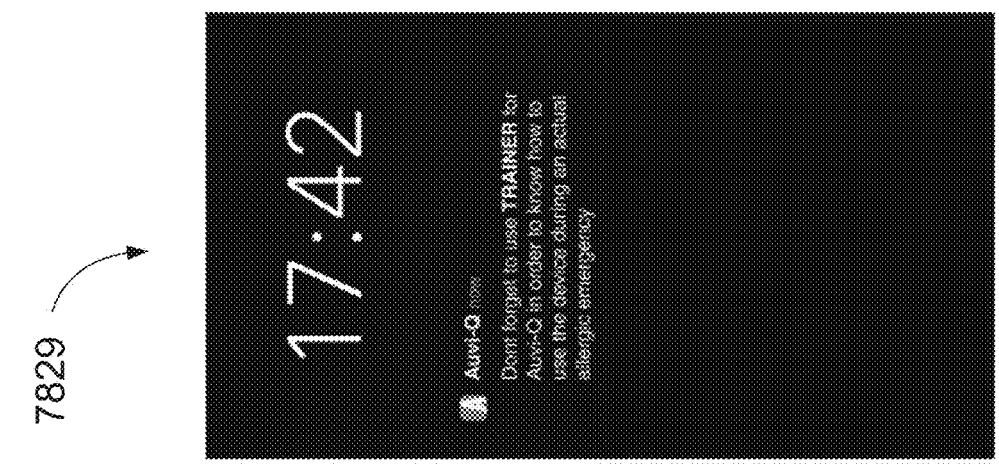
FIG. 110 depicts a graphical user interface element produced in connection with a method of producing a training reminder, according to an embodiment.

In addition to the apparatus and methods described above, the connected health system 7800 can provide additional services and notifications. For example, in some embodiments, one or more of the application modules described herein can present post-use care instructions and/or facilitate reordering a medicament delivery device after the first device has been used. FIGS. 102 and 103 are examples of GUI elements produced by an application module executed in a remote computing device 7801 that provide post-use instructions and facilitate reordering a device after use. Specifically, the GUI element 7836A prompts a user to seek follow-up care consistent with the use guidelines of the medicament delivery device. GUI element 7836B prompts a user to contact the device manufacturer after use. FIGS. 104 and 105 show GUI elements 7835A and 7835B, which facilitate reordering.

In some embodiments, the service platform 7870 can store information related to the expiration of one or more medicament delivery devices within the system, and can transmit notifications to one or more remote computing devices (e.g., the remote computing devices 7801 or 7802). In this manner, the connected health system can remind the user, patient, and/or account administrator about an upcoming expiration date. For example, in some embodiments, the notification module (e.g., the notification module 7817) can produce an expiration notification, such as the GUI element 7832A or the GUI element 7832B. In response to receiving a "refill request" from the user prompt, the connected health system 7800 can then transmit the order to a local pharmacy, to a manufacturing subsystem, or the like.

In some embodiments, a temperature history module (e.g., the temperature history module 7815 and/or the temperature history module 7985) can receive information from a temperature sensor and calculate a mean kinetic temperature based on a temperature signal. The temperature history module or a notification module (e.g., the notification module 7817) can then produce a temperature notification, such as the GUI element 7831A or the GUI element 7831B.

In some embodiments, the connected health system 7800 can produce one or more reminders to enhance the user's experience and/or improve compliance in using the medicament delivery device. For example, in some embodiments, the notification module (e.g., the notification module 7817) can produce a training reminder notification, such as the GUI element 7829.

In addition, the connected health system 7800 can be operable to provide reminders, for example, if the user is scheduled to use the medicament delivery device. In embodiments where the remote computing device is communicatively linked to the medicament delivery device, the application can receive signals from the medicament delivery device associated with use of the medicament delivery device. In this way, a reminder may only be issued if the user has not actually used the medicament delivery device according to a schedule. Any suitable methods for generating alerts and/or communicating with the medicament delivery device can be employed, such as, for example, those methods disclosed in U.S. Patent Publication No. 2014/0243749, entitled "Devices, Systems and Methods for Interacting with Medicament Delivery Systems" filed on Dec. 27, 2013, the disclosure of which is incorporated herein by reference in its entirety.

The application can also generate alerts, for example if the medicament has expired, been recalled, or if the medicament delivery device has experienced a temperature unsuitable for the medicament. Any suitable methods for tracking the temperature history of the medicament delivery device can be employed, such as, for example, those methods disclosed in U.S. Pat. No. 8,361,029, entitled "Devices, Systems and Methods for Medicament Delivery" issued Jan. 29, 2013, the disclosure of which is incorporated herein by reference in its entirety. Similarly stated, a computing device can receive signals associated with the status of the medicament delivery device from the medicament delivery device and/or from a remote computing device and the application can notify the user of the status.

Figure 111:
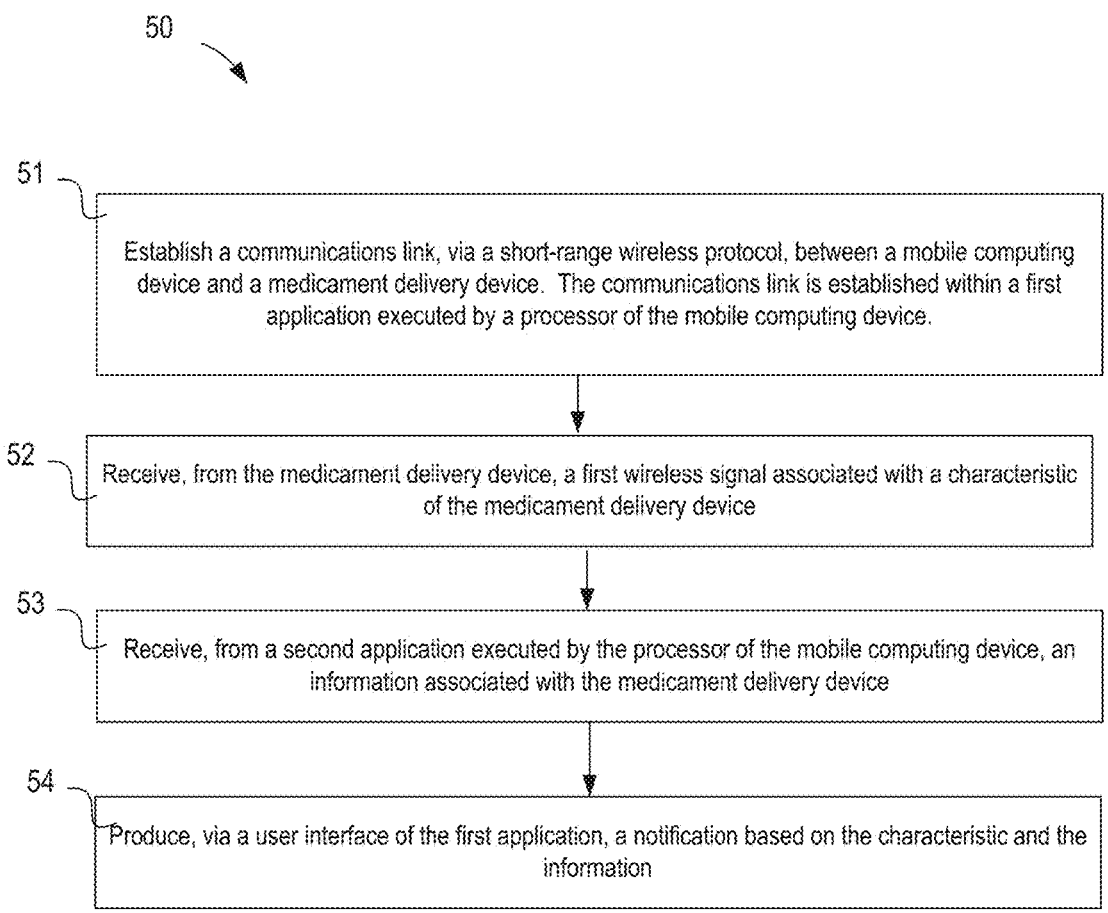
FIG. 111 is a flow chart of a method of producing a notification, according to an embodiment.

As described above, in some embodiments, the GUI elements and notifications shown above can be displayed within a first application (e.g., executed by the processor 7810), and an application interface module can exchange information from a second application (executed by the processor 7810). In this manner, the connected health system 7800 can utilize information from other computer-based applications or systems to enhance the performance of the connected health system 7800. For example, FIG. 111 is a flow chart of a method 50 of information exchange, according to an embodiment. The method 50 includes establishing a communications link, via a short-range wireless protocol, between a mobile computing device and a medicament delivery device, at 51. The communications link is established within a first application executed by a processor of the mobile computing device. The first application can be the connected health application and can include any of the application modules described herein, such as the leash module 7813, the network module 7814, the temperature history module 7815, and/or the onboarding module 7819).

A first wireless signal associated with a characteristic of the medicament delivery device is received from the medicament delivery device, at 52. The first wireless signal can be associated with input from any of the sensors 7970 described herein. For example, the first wireless signal can be associated with a temperature of the medicament delivery device, a location associated with the medicament delivery device, or an event delivery signal produced by the medicament delivery device. In other embodiments, the first wireless signal can be associated with a characteristic of the user (e.g., the type of allergy, health-care provider, etc.).

Information associated with the medicament delivery device is received from a second application executed by the processor of the mobile computing device, at 53. The second application is different from the first application. A notification is then produced via a user interface of the first application, the notification including the characteristic and the information from the second application, at 54.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the cover 4200 and the cover 5200 are shown and described as being substantially solid and covering the status apertures through which a user can view the medicament (e.g., the status apertures 4150, 4151), in other embodiments, any of the covers described herein can include one or more status windows or apertures that can allow a patient to monitor the status and/or contents of a medicament container (e.g., the medicament container 4560). For example, by visually inspecting the status apertures of the cover, a patient can determine, without removing the cover, whether the medicament container contains a medicament, whether the medicament is cloudy or discolored, and/or whether a medicament has been dispensed. In some embodiments, the cover (or any portion of a device housing) can include a label about the status apertures that minimizes the transmission of ultraviolet (UV) radiation therethrough. In this manner, the risk of exposing the medicament to UV radiation can be minimized.

Although the battery assembly 5962 is shown and described as being in continuous electronic communication with the processor 5980, in other embodiments, any of the electronic circuit systems described herein can include a switch or battery isolation tab that isolates the battery assembly from the processor during manufacturing and/or storage. When the medicament delivery device is shipped or otherwise placed in use, the battery isolation tab or switch can be transitioned to allow the battery assembly to continuously supply to the processor 5980 when the cover 5200 is disposed about the housing 5100.

For example, although electronic circuit systems are shown and described above as outputting one or more outputs directed towards a single, immediate user, in some embodiments, a locator device and/or monitoring device can output multiple outputs directed towards multiple different classes of users. For example, in some embodiments, the medicament delivery devices and systems can output a first output to the immediate user (e.g., via a short-range wireless output) and second output to a remotely located emergency response team. In such embodiments, the second output can be, for example, a phone call, SMS, a page, an e-mail or the like. For example, in some embodiments, the second output can be an e-mail to the parents and/or care-givers of a child. Moreover, such a second output can be transmitted either wirelessly or through a wired network. In some embodiments, such outputs can be managed, produced, and/or transmitted by any of the connected health medicament delivery systems shown and described herein, such as the systems 5800 and 6800 described herein.

Although the electronic circuit systems are shown and described above as outputting one or more outputs in response to one or more switches, in other embodiments an electronic circuit system can output an electronic output in response to any number of different inputs. For example, in some embodiments, an electronic circuit system can output an electronic output based on input from the user provided via a keyboard, a touch screen, a microphone or any other suitable input device. In this manner, the electronic outputs can be produced in response to direct feedback from the user. In other embodiments, the electronic outputs can be produced in response to signals produced by one or more sensors, such as the sensors 1970, or any of the sensors described in connection with the electronic circuit system 5900. For example, in some embodiments, any of the electronic outputs can be produced in response to a signal produced by an accelerometer, such as the accelerometer 5971. In other embodiments, the electronic circuit system 5900 (or any of the electronic circuit systems described herein) can include a skin sensor used to detect placement of a portion of the medicament delivery device and send an output to the processor. For example, in some embodiments, a medicament delivery device can be a wearable device having a contact portion that is maintained in contact with the user's skin. In such embodiments, a contact sensor can be used to produce signals associated with the desired placement of the contact portion against the skin. Such skin sensors can include, for example, optical sensors, resistive skin sensors, capacitive touch sensors, or thermal-based skin sensors.

The medicament delivery devices and simulated medicament delivery devices are described herein as being configured to produce one or more wireless signals in accordance with the methods described herein. Although the methods and apparatus are described herein as being configured to modify the communication mode and/or the communication interval associated with such wireless signals in response to a change in the status and/or configuration of a device (e.g., a medicament delivery device or a simulated medicament delivery device), in other embodiments, any of the apparatus and methods described herein can modify any aspect of the wireless signals based on such change in status and/or configuration. For example, in some embodiments a method can include modifying a power level of a wireless signal in response to a change in status and/or configuration of a medicament delivery device or a simulated medicament delivery device. In other embodiments, a method can include modifying the information contained within a wireless signal in response to a change in status and/or configuration of a medicament delivery device or a simulated medicament delivery device. For example, in some embodiments, a wireless signal can include information associated with a signal power level (e.g., TX Power) and/or an identification of a device. Such information can be changed in response to a change in status and/or configuration of a medicament delivery device or a simulated medicament delivery device.

In some embodiments, information included within a signal can include instructions to initiate a natural language user interface associated with (or running on) another device. Thus, any of the apparatus and methods described herein can be configured to send and/or can include the sending of a signal to initiate a natural language user interface associated with a remote computing device. For example, in some embodiments, any of the electronic circuit systems coupled to or associated with any of the medicament delivery devices (or simulated devices), such as the device 1900, 4900, or 5900, can be configured to send a wireless signal to initiate a natural language user interface associated with a remote computing device, such as, for example, the computing devices 1801, 1802, 5801 described above. In such embodiments, the computing device can be, for example, a smart phone having a natural language user interface, such as, for example, Siri (from Apple) or any other "intelligent personal assistant." The electronic circuit system can be configured to initiate the user interface via the wireless connection by sending a signal. In some embodiments, the signal can be sent in response to a change in the status and/or configuration of the medicament delivery device and/or the simulated medicament delivery device. In this manner, the electronic circuit system can initiate the interface to provide the user with additional resources during a time of activity with the medicament delivery device and/or the simulated medicament delivery device.

In some embodiments, a computing device (e.g., the user's mobile phone, or any other device, such as the computing devices 1801, 1802, 5801 described above) can send signals based on and/or produced from a natural language interface that are received by a medicament delivery device, a cover, and/or a simulator of the types shown and described herein. For example, as described above, a connected health medicament delivery system can include a computing device, such as a cell phone that has a natural language interface, and a medicament delivery device, such as an auto-injector, an inhaler, wearable injector, or a patch pump. In such embodiments, a user can provide voice commands to natural language interface of the cell phone. Such commands can include, for example, instructions to administer an additional dose, instructions to call a healthcare professional or the like. In response, the cell phone can send, via a wireless connection of the types shown and described herein, a signal to the medicament delivery device. The device can then execute the instructions. In this manner, the capability of the cell phone can be leveraged to produce a voice-activated medicament delivery device.

Any of the radios, transmitters, receivers, and/or transceivers described herein can be operable to transmit, receive, repeat, and/or otherwise interact with electromagnetic signals. Electromagnetic signals can be of any suitable frequency. For example, the radios, transmitters, receivers, and transceivers can be operable to transmit and/or receive IEEE 802.11 signals, Bluetooth® signals, FM radio signals, AM radio signals, cellular telephone signals, satellite pager signals, RFID signals, GPS signals, and/or any other suitable electromagnetic signal.

Although the computing device 7801 is described above as including a user interface 7820 that can display any of the GUI elements described herein, in other embodiments, the electronic circuit system on any of the medicament delivery devices (e.g. the electronic circuit system 5900) can include a user interface than can display any of the GUI element described herein. For example, in some embodiments, a medicament delivery device (including either the housing of the device or the cover within which the device is contained, such as the cover 5200) can include a touch screen that can display GUI elements and receive input into the electronic circuit system of the medicament delivery device.

Although the medicament delivery devices are shown and described herein as establishing a short-range connection with a remote computing device (e.g., a smart phone) via the Bluetooth® wireless protocol, in other embodiments, any of the devices and methods described herein can employ any suitable short-range communication link, such as near field communication (NFC) or infrared (IR).

Although the medicament delivery devices are shown and described herein as including a radio (e.g., the radio 7951) and/or a communication module (e.g., the communication module 7981) that establish a short-range connection with a remote computing device (e.g., a smart phone), in other embodiments, any of the radios and/or communication modules of the medicament delivery devices described herein can establish any suitable wireless connection with any suitable communication device. For example, in some embodiments, any of the medicament delivery devices described herein can include a radio and/or communication module configured to establish a wireless connection within a cellular network. In this manner, the medicament delivery device can directly access any number of remote devices (e.g., the parent's phone 7802, the service platform 7870, or the like) without requiring a short-range connection with the user's remote device (e.g., the user's phone 7801). In other embodiments, any of the medicament delivery devices described herein can include a radio and/or communication module configured to establish a wireless connection via LTE Direct protocol or any other suitable protocols.

Although some of the embodiments described herein include one "master device" (e.g., the computing device 1801, 5801, which can be, for example, a smart phone) and one "slave device" (e.g., the medicament delivery device 1000, 4000, 5000, which include an on-board electronic circuit system), in other embodiments, devices and methods can include and/or establish a piconet including any suitable number of master devices and/or slave devices. For example, in some embodiments, a computing device 1801, 5801 can be configured to be paired with and/or establish a piconet with more than one medicament delivery device. In other embodiments, a computing device and/or connected health medicament delivery system can be configured to establish a piconet with a first medicament delivery device, a simulated medicament delivery device (or trainer) associated with the first medicament delivery device (e.g., a wireless-enabled trainer of the types shown and described herein), and a second medicament delivery device (e.g., a wireless-enabled medicament delivery device). In this manner, the computing device and/or the connected health medicament delivery system can track and/or manage multiple devices owned by a user (e.g., a delivery device maintained at school, a delivery device maintained at work, a delivery device carried with the user, or the like).

In some embodiments, a medicament delivery device is shown and described as an auto-injector. In other embodiments, the medicament delivery device can be a patch configured to adhere to the patient. The patch can release a medicament, for example, after receiving a signal that medical treatment is needed. The patch can receive the signal from, for example, a monitoring device. In other embodiments, the medicament delivery device can be an injector configured to be carried in a pocket of the patient's garments. The injector can be configured to inject a medicament, for example, after receiving a signal that medical treatment is needed.

In some embodiments, any of the electronic circuit systems and/or connected health medicament delivery systems can be used in conjunction with any suitable medicament delivery device or drug product. For example, in some embodiments, any of the electronic circuit systems and/or connected health medicament delivery systems can be used in conjunction with an inhaler, a tablet delivery system, an on-body delivery system, a nasal delivery system (e.g., an intranasal sprayer), or a nebulizer.

In some embodiments, any of the medicament delivery devices described herein can include an electronic circuit system and/or any suitable sensor and be operable to output an electronic output. Such a sensor can include, for example, a proximity sensor (e.g., to determine the position of the medicament delivery device), a temperature sensor, a pressure sensor, an optical sensor or the like. For example, in some embodiments, the container can include a temperature sensor configured to sense the temperature of the medicament contained within the medicament delivery device. In this manner, as described above with reference to the "temperature alert" methods, the electronic circuit system can output an instruction and/or a status message when the medicament is too cold for effective delivery. For example, in some embodiments, when the medicament is too cold for effective delivery or the delivery of a cold medicament may cause unnecessary pain and discomfort (this may occur, for example, if the container is being used in an outdoor setting or requires refrigeration prior to use), the electronic circuit system can output a message, such as, for example, "Medicament is too cold—allow medicament to reach room temperature before using" and can alert the user when the proper temperature has been reached.

Although in some embodiments the electronic circuit systems are shown and described above as outputting a single output in response to an input (e.g., the removal of a medicament delivery device from a cover, the actuation of a medicament delivery device, etc.), in other embodiments, an electronic circuit system can output a sequence of electronic outputs in response to such an input. In some embodiments, for example, when a medicament delivery device is removed from a container, an electronic circuit system (e.g., the electronic circuit systems 1900, 4900, 5900) can output a predetermined sequence of use instructions over a predetermined time period. For example, upon removing the medicament delivery device, the first instruction can be an audible output indicating the type of medicament delivery device removed. After a predetermined time period, the electronic circuit system can then output a second instruction, which can be a visual output instructing the user in how to diagnose the patient and/or prepare the patient for the medicament. In a similar manner, the electronic circuit system can provide additional outputs to instruct the user in the use of the medicament delivery device. Moreover, in some embodiments, the electronic circuit system can output an output instructing the user in post-use procedures, such as for example, the disposal of the medicament delivery device, instructions for follow-up treatment or the like.

For example, although the electronic circuit systems are shown and described above as being configured to output primarily audible and visual outputs, in other embodiments, an electronic circuit system can be configured to produce any suitable output. For example, in some embodiments, an electronic circuit system can produce a haptic output, such as a vibratory output produced by a piezo-electric actuator. In other embodiments, an electronic circuit system can produce a thermal output, produced by a heating or cooling element.

Although some embodiments describe a recorded message output in English, in other embodiments, the electronic circuit system can output recorded speech in any language. In yet other embodiments, the electronic circuit system can output recorded speech in multiple languages. In yet other embodiments, the user can select the language in which the recorded speech is to be output.

Medicament delivery devices shown and described above can be single-use medical injectors, or any other suitable device for delivering one or more doses of a medicament into a patient's body. For example, in some embodiments, a medicament delivery device can be a pen injector containing multiple doses of a chronic-care medicament, such as, for example, insulin. In such embodiments, an electronic circuit system (of the types shown and described herein) can output instructions associated with not only an initial use of the medicament delivery device, but also associated with repeated uses, dosage monitoring or the like. In other embodiments, a medicament delivery device can include a transdermal medicament delivery device, a wearable injector or pump that dispenses drug over several hours or days, an inhaler or a nasal medicament delivery device.

For example, in some embodiments, a chronic-care medicament delivery device can include one or more sensors (e.g., the sensors 7970) that detect a status or use of the device, and can work in conjunction with a use module (e.g., the use module 7982, the use module 7812 or any of the use or "event detection" modules described herein) to produce outputs notifying a user of when certain medicament delivery events are due in accordance with a prescribed regimen. For example, in some embodiments, certain therapeutic agents (e.g., medicaments to treat diabetes, rheumatoid arthritis (RA), multiple sclerosis (MS), and/or Crohn's disease) are administered at regular intervals. Such intervals can be, for example, twice daily, once daily, once weekly, or the like. In such embodiments, a use (or event detection) module can detect an actual delivery, including a date and/or time stamp of the delivery. A notification module (e.g., the notification module 7817) or any of the other modules described herein can calculate a "next delivery" date (or time) and produce a reminder notification. The reminder notification can be similar to any of the GUI elements described herein. For example, in some embodiments, the next delivery date can be calculated based on the date and time stamp of the most recent detected usage of the medicament delivery device. The use module can then maintain a count of how many doses have been administered and determine, based on the detected use and the stored regimen, the next delivery date.

In other embodiments, a delivery interval can be irregular and/or based on information or data that is independent of a time interval. Such information can include, for example, physiological data of the patient (e.g., blood glucose levels or the like). In such embodiments, a use module (or any other module described herein) can receive information associated with the actual use (or delivery) of the device, the date and/or time stamp, and the additional information, and calculate a "next delivery" date (or time). For example, in some embodiments, a patient may log test data (e.g., blood glucose measurements) via a second application (i.e., an application executed by the processor 7810 or any other processor described herein, the application being separate from the connected health system application). In such embodiments, an application interface module (e.g., the application interface module 7818) can receive the information or test data from the second application. The information received can then be used to calculate the next delivery date or time. In this manner, the application interface module can automatically retrieve information (e.g., the patient's test data) used to accurately calculate the next delivery event.

In some embodiments, a chronic-care medicament delivery device can include a medicament container containing multiple doses of a medicament, and a dose adjustment mechanism with which the user can adjust the dosage amount to be delivered. Such dose adjustment mechanisms can include, for example, a dial adjustment mechanism that limits a stroke length of an injector plunger. In such embodiments, a notification module (e.g., the notification module 7817) or any of the other modules described herein can produce a notification reminding the user of the next delivery date, and also reminding the user of the desired dosage setting. The notification can be similar to any of the GUI elements described herein. In some embodiments, the notification can include one or more instructions for operating the dose adjustment mechanism. For example, the notification can include a video presentation that is displayed via a user interface (e.g., the user interface 7820) that guides a user step-by-step through the dose adjustment process. In other embodiments, the chronic-care medicament delivery device can include a sensor (e.g., included among the sensors 7970 described above) that senses the position of the dose adjustment mechanism. In such embodiments, the notification can include information based on the actual position of the dose adjustment mechanism. For example, in some embodiments, a notification can indicate the current setting based on feedback from the sensor (e.g., "The current setting is 0.5 mL").

In other embodiments, any of the medicament delivery devices described herein can include an actuator that limits movement of the dose adjustment mechanism. For example, in some embodiments, a chronic-care medicament delivery device can include an electronic actuator that, when actuated, can limit movement (i.e., can "lock out") the dose adjustment feature. In such embodiments, a dose control module (or any of the application modules described herein) can receive information associated with the prescribed dose and can limit movement of the dose adjustment mechanism in response to such information. In this manner, the medicament delivery device and/or the connected health system can "lock out" or otherwise prevent the user from setting the incorrect dose.

In yet other embodiments, any of the medicament delivery devices described herein can include a disarming mechanism that prevents the device from administering the medicament. For example, in some embodiments, a disarming device can reversibly prevent an activation mechanism from producing the force to deliver a dose of the medicament. This can be useful, for example, in a chronic-care application to prevent a dose from being administered before the desired delivery date or time. In such embodiments, a dose control module (or any of the application modules described herein) can receive information associated with the prescribed dose and can prevent actuation of the device in response to such information. In some embodiments, the disarming device can be a mechanism that prevents removal of a cover (e.g., the cover 4200 or the cover 5200), removal of a safety guard (e.g., the safety guard 4700 or the safety guard 5700) and/or movement of the actuator (e.g., the base 4300 or the base 5300).

In other embodiments, the disarming device can irreversibly and/or permanently prevent delivery of the medicament. For example, in some embodiments, the medicament delivery device can be irreversibly and/or permanently disabled in response to the temperature sensor indicating that the medicament has been stored above a predetermined temperature for a certain amount of time. In other embodiments, the medicament delivery device can be irreversibly and/or permanently disabled in response to a timer indicating that the medicament is expired or has been mixed for longer than a predetermined period of time. The disarming device can be any of the disarming devices shown and described in U.S. Pat. No. 8,361,026 entitled "Apparatus and Methods for Self-Administration of Vaccines and Other Medicaments," filed Nov. 19, 2009, which is incorporated herein by reference in its entirety.

Although various embodiments have been described as having particular features and/or combinations of components, other embodiments are possible having a combination of any features and/or components from any of embodiments where appropriate. For example, although some embodiments are described as having a processor, a radio, a sensor, etc. disposed on a particular portion of a device (e.g., on the electronics housing 4170), in other embodiments, any of the electronic circuit systems can be disposed on any suitable portion of a delivery device or simulated delivery. For example, in some embodiments, a removable outer cover of a medicament delivery device (such as the covers 4200 or 5200) or simulated medicament delivery device can include a processor and/or radio. Similarly, in some embodiments a kit can have a processor, audible output, etc. Any devices, structures, and/or modules associated with a medicament delivery device, therefore, can be associated with any suitable kit, adapter, cover, and/or simulated medicament delivery device.

The medicament delivery devices described herein, such as the medicament delivery device 1000, and any others described herein, can be any suitable medicament delivery device. For example, a medicament delivery device according to an embodiment can include a pen injector, an auto-injector, a wearable injector or pump that dispenses drug over several hours or days, other body-worn drug delivery devices, an inhaler or a transdermal delivery device. Where medicament delivery devices are described, it should be understood that alternative embodiments including a simulated medicament delivery device are possible, for example, the simulated medicament delivery devices shown and described in U.S. Pat. No. 9,022,980, entitled "Medical Injector Simulation Device" filed Feb. 27, 2007, the disclosure of which is incorporated herein by reference in its entirety. A simulated medicament delivery device may be suitable to train a user in the operation of a medicament device.

The simulated medicament delivery device can simulate the actual medicament delivery device in any number of ways. For example, in some embodiments, the simulated medicament delivery device can have a shape corresponding to a shape of the actual medicament delivery device, a size corresponding to a size of the actual medicament delivery device and/or a weight corresponding to a weight of the actual medicament delivery device. Moreover, in some embodiments, the simulated medicament delivery device can include components that correspond to the components of the actual medicament delivery device. In this manner, the simulated medicament delivery device can simulate the look, feel and sounds of the actual medicament delivery device. For example, in some embodiments, the simulated medicament delivery device can include external components (e.g., a housing, a needle guard, a sterile cover, a safety lock or the like) that correspond to external components of the actual medicament delivery device. In some embodiments, the simulated medicament delivery device can include internal components (e.g., an actuation mechanism, a compressed gas source, a medicament container or the like) that correspond to internal components of the actual medicament delivery device.

In some embodiments, however, the simulated medicament delivery device can be devoid of a medicament and/or those components that cause the medicament to be delivered (e.g., a needle, a nozzle or the like). In this manner, the simulated medicament delivery device can be used to train a user in the use of the actual medicament delivery device without exposing the user to a needle and/or a medicament. Moreover, the simulated medicament delivery device can have features to identify it as a training device to prevent a user from mistakenly believing that the simulated medicament delivery device can be used to deliver a medicament. For example, in some embodiments, the simulated medicament delivery device can be of a different color than a corresponding actual medicament delivery device. Similarly, in some embodiments, the simulated medicament delivery device can include a label clearly identifying it as a training device.

In some embodiments, the medicament delivery devices and/or medicament containers shown herein can include any suitable medicament, such as a vaccine. Such vaccines can include, for example, an influenza A vaccine, an influenza B vaccine, an influenza A (H1N1) vaccine, a hepatitis A vaccine, a hepatitis B vaccine, a haemophilus influenza Type B (HiB) vaccine, a measles vaccine, a mumps vaccine, a rubella vaccine, a polio vaccine, a human papilloma virus (HPV) vaccine, a tetanus vaccine, a diphtheria vaccine, a pertussis vaccine, a bubonic plague vaccine, a yellow fever vaccine, a cholera vaccine, a malaria vaccine, a cancer vaccine, a smallpox vaccine, a pneumococcal vaccine, a rotavirus vaccine, a varicella vaccine, a meningococcus vaccine and/or any combination thereof (e.g. tetanus, diphtheria and pertussis vaccine). In other embodiments, the medicament delivery devices and/or medicament containers shown herein can include epinephrine. In other embodiments, the medicament contained within any of the medicament delivery devices and/or medicament containers shown herein can be naloxone, including any of the naloxone formulations described in U.S. Pat. No. 8,627,816, entitled "Medicament Delivery Device for Administration of Opioid Antagonists Including Formulation for Naloxone," filed on Feb. 28, 2011.

In other embodiments, the medicament contained within any of the medicament delivery devices and/or medicament containers shown herein can include insulin, glucagon, human growth hormone (HGH), erythropoiesis-stimulating agents, adalimumab, other monoclonal Antibodies (mAbs'), Interferon and other chronic therapies, or the like. Such formulations can be produced using a general lyophilization process with glucagon (of recombinant or synthetic origin) using bulking agents, stabilizers, buffers, acidifying agents or other excipients comprising of, but not limited to, one or more of the following combinations: lactose, hydrochloric acid; glucose, histidine, hydrochloric acid; trehalose, mannitol, citrate; trehalose, mannitol, hydrochloric acid; trehalose, glycine, hydrochloric acid; Mannitol, ascorbic acid; and Glycine, hydrochloric acid.

In other embodiments, any of the medicament delivery devices and/or medicament containers described herein can be filled with and/or used to inject medicament formulations, including lyophilized biologics and/or biopharmaceuticals, such as, for example, canakinumab, certolizumab, golimumab, and/or interleukins, for the treatment of crypyrin associated periodic syndromes, hereditary angioedema, and other auto-immune diseases. In yet other embodiments, any of the medicament delivery devices and/or medicament containers described herein can be filled with and/or used to inject intranasal medicaments including small molecules such as epinephrine, naloxone, diazepam, midazolam, lorazepam or biologics, such as glucagon or human growth hormone, formulated for use in an auto injector, for the treatment of musculoskeletal diseases, growth disorders, diabetes or other disorders. Thus, although the medicament delivery devices shown herein are primarily injectors, in other embodiments, a medicament delivery device need not be a medical injector, but rather, can be an inhaler, a wearable pump, an intranasal delivery device or the like.

In other embodiments, any of the medicament delivery devices and/or medicament containers described herein can be filled with and/or used to inject an anti-thrombolytic, such as LMWH, ULMWH, Xa Inhibitors, biotinylated idraparinux, etc., for either the acute management and/or surgical prophylaxis of deep vein thrombosis and/or pulmonary embolism or for the management of other conditions which may require anticoagulation to prevent thromboembolism, such as its use in cardiovascular diseases including atrial fibrillation and ischemic stroke. In another example, in some embodiments an injector according to an embodiment can be filled with and/or used to inject formulations for the treatment of asthma and/or chronic obstructive pulmonary disease.

In other embodiments, any of the medicament delivery devices and/or medicament containers described herein can be filled with and/or used to inject recombinant hyaluronidase.

In other embodiments, any of the medicament delivery devices and/or medicament containers described herein can be filled with and/or used to inject depot medroxyprogesterone acetate for the treatment of infertility.

In other embodiments, any of the injectors described herein can be filled with and/or used to inject Benzodiazepines such as Midazolam, Anticoagulants, Hematopoietic agents, Adrenocortical steroids, Antidiabetic agents, Sex hormones, Somatostatin Analogs, Monoclonal Antibodies, Agents for Migraine, Antianxiety Agents, Antiemetic/Antivertigo Agents, Antipsychotic Agents, General Anesthetics, NSAIDs, Opioid Agonist-Antagonist, Opioid Analgesics, Skeletal Muscle Relaxants. Aminoglycosides, Antiprotozoals, Antiretroviral Agents, Antituberculosis Agents, Bacitracin, Cephalosporin and Related Antibiotics, Colistimethate sodium, Lincosamides, Monobactams, Penicillins, Polymyxin B Sulfate, Antirheumatologic Agents, Antimetabolites, Immune Globulins, Immulogic Agents, Monoclonal antibodies, Antimetabolites, Hematopoietic, and/or Hemin, and agents that block proprotein convertase subtilisin/kexin type 9 (PCSK9).

In other embodiments, any of the medicament delivery devices and/or medicament containers described herein can be filled with and/or used to inject environmental, food, and household allergen formulations for the treatment of allergic disease, specifically for use in immunotherapy.

Any of the devices and/or medicament containers shown and described herein can contain and/or deliver a wide array of large or macromolecular injectables that include carbohydrate-derived formulations, lipids, nucleic acids, proteins/peptides (e.g. monoclonal antibodies) and other biotechnologically-derived medicaments. For example, anti-tumor necrosis factor agents such as infliximab, etanercept, adalimumab, golimumab, natalizumab, vedolizumab, and certolizumab can be administered using the described auto-injector heroin, Other macromolecular injectable medications that can be administered using the device and/or medicament containers shown and described herein include viscous medicaments that target pro-inflammatory cytokines (e.g. IL-1, IL-2, IL-4, IL-5, IL-6, IL-12, IL-13, IL-23, IL-17, IL-21 and associated receptors) including dupilumab, sarilumab, mepolizumab, benralizumab, reslizumab, lebrikizumab, ustekinumab, anrunkinzumab, bertilimumab, and tralokinumab. Large anti-adhesion molecules to treat a variety of diseases may be administered using the device and/or medicament containers shown and described herein including etrolizumab and vatelizumab. Still other large and viscous monoclonal antibodies that may be administered using the device and/or medicament containers shown and described herein include tezepelumab, anifrolumab, omalizumab, and proprotein convertase subtilisin kexin type 9 (PCSK9) inhibitors including alirocumab and evolocumab.

In still other embodiments, the medicament contained within any of the medicament delivery devices and/or medicament containers shown herein can be a placebo substance (i.e., a substance with no active ingredients), such as water.

The medicament containers and/or medicament delivery devices disclosed herein can contain any suitable amount of any medicament. For example, in some embodiments, a medicament delivery device as shown herein can be a single-dose device containing an amount medicament to be delivered of approximately 0.4 mg, 0.8 mg, 1 mg, 1.6 mg or 2 mg. For example, in some embodiments, a connected health medicament delivery system (such as the systems 5800, 6800) can include an epinephrine auto-injector having a dosage suitable for the patient. Such epinephrine auto-injectors can include any of the injectors shown and described in U.S. application Ser. No. 15/850,157, entitled "Medicament Delivery Device and Methods for Delivering Drugs to Infants and Children," and filed on Dec. 23, 2016, which is incorporated herein by reference in its entirety. For example, in some embodiments, any of the medicament delivery devices, such as the device 5000 shown with reference to the system 5800, can be an "adult-dose" drug product configured to deliver 0.3 mL epinephrine. In other embodiments, any of the medicament delivery devices, such as the device 5000 shown with reference to the system 5800, can be a "pediatric-dose" drug product configured to deliver 0.15 mL epinephrine. In yet other embodiments, any of the medicament delivery devices, such as the device 5000 shown with reference to the system 5800, can be a "infant-dose" drug product configured to deliver 0.1 mL epinephrine. Although the phrases "adult-dose," "pediatric-dose," and "infant-dose" are used herein, it is understood that such devices and methods are applicable to any patient within the prescribed weight ranges, even if the patient may not be considered an "adult," a "pediatric patient," or an "infant" by some definitions. For example, the "infant-dose" methods, drug products, and devices described herein are applicable to a child weighing 14 kg, even if that child is considered a toddler or pediatric patient (i.e., is not considered an "infant").

As described above, the fill volume can be such that the ratio of the delivery volume to the fill volume is any suitable value (e.g., 0.4, 0.6 or the like). In some embodiments, an electronic circuit system can include a "configuration switch" (similar to any of the switches shown and described above) that, when actuated during the assembly of the delivery device, can select an electronic output corresponding to the dose contained within the medicament container. In addition, in the case of multiple-dose delivery, the user can activate, via physical movement, voice command or the like, a switch located on the medicament delivery device in order to select the specific dose required.

What is claimed is:

1. A computer-implemented method, comprising:
    establishing a communications link, via a short-range wireless protocol, between a mobile computing device and a medicament delivery device;
    receiving, in response to an input prompt, a user input selecting a target motion profile of the medicament delivery device, the target motion profile including one of an on-person motion profile or a fixed location motion profile;
    receiving, from the medicament delivery device, a wireless signal associated with an actual motion profile of the medicament delivery device, the actual motion profile including any of a position, a velocity, an acceleration, or an orientation of the medicament delivery device during a time period;
    analyzing the actual motion profile to determine if a magnitude of the actual motion profile is outside of a threshold associated with the target motion profile, the magnitude of the actual motion profile including an amount of a change in the position of the medicament delivery device during the time period; and
    producing a notification when the magnitude of the actual motion profile is outside of the threshold, the notification indicating that the magnitude is outside of the threshold associated with the target motion profile.

2. The computer-implemented method of claim 1, wherein the time period is at least one week, and the actual motion profile is a second actual motion profile, the method further comprising:
    modifying the target motion profile based on a first actual motion profile over the time period, the notification indicating a motion difference between the second actual motion profile and the modified target motion profile.

3. The computer-implemented method of claim 1, wherein the time period is at least 24 hours.

4. The computer-implemented method of claim 1, wherein the wireless signal is a first wireless signal and the notification is a first notification, the method further comprising:
    receiving, from the medicament delivery device, a second wireless signal to maintain the communications link, the second wireless signal being periodic;
    determining, based on the second wireless signal, a relative position between the mobile computing device and the medicament delivery device; and
    producing a second notification when the relative position exceeds a relative position threshold.

5. The computer-implemented method of claim 4, wherein:
    the time period is a first time period; and
    the producing the second notification includes producing the second notification when the second wireless signal is not received within a second time period.

6. The computer-implemented method of claim 1, wherein the medicament delivery device is any one of an auto-injector, a pen injector, a medication pump, a prefilled syringe, a nasal delivery device or an inhaler.

7. The computer-implemented method of claim 1, wherein the medicament delivery device is a first medicament delivery device, the input prompt is a first input prompt, the user input is a first user input, the wireless signal is a first wireless signal, the target motion profile of the first medicament delivery device is the on-person motion profile, and the notification is a first notification indicating that a change in the position of the first medicament delivery device during the time period is below the threshold associated with the on-person motion profile, the method further comprising:
    establishing a second communications link, via the short-range wireless protocol, between the mobile computing device and a second medicament delivery device;
    receiving, in response to a second input prompt, a second user input selecting the fixed location motion profile for the second medicament delivery device;
    receiving, from the second medicament delivery device, a second wireless signal associated with an actual motion profile of the second medicament delivery device; and suppressing a second notification indicating that a change in a position of the second medicament delivery device during the time period is below the threshold associated with the on-person motion profile.

8. The computer-implemented method of claim 1, wherein the wireless signal is a first wireless signal and the notification is a first notification, the method further comprising:
receiving, from the medicament delivery device, a second wireless signal associated with a temperature profile of the medicament delivery device; and
producing a second notification when the temperature profile is outside of a predetermined temperature range.

9. The computer-implemented method of claim 1, wherein the wireless signal is a first wireless signal, the method further comprising:
receiving, from the medicament delivery device, a second wireless signal associated with a temperature profile of the medicament delivery device, the notification is based on both a motion difference between the actual motion profile and the target motion profile and a temperature difference between the temperature profile and a predetermined temperature range.

10. The computer-implemented method of claim 1, wherein the producing the notification is performed by a first application that is executed by a processor of the mobile computing device, the wireless signal is a first wireless signal and the notification is a first notification, the method further comprising:
receiving, from the medicament delivery device, a second wireless signal associated with a temperature profile of the medicament delivery device;
receiving, from a second application executed by the processor of the mobile computing device, a temperature information;
determining, within the first application and based on the temperature information received from the second application, a temperature range; and
producing a second notification when the temperature profile is outside of the temperature range.

11. A computer-implemented method, comprising:
establishing a first communications link, via a short-range wireless protocol, between a mobile computing device and a first medicament delivery device;
establishing a second communications link, via the short-range wireless protocol, between the mobile computing device and a second medicament delivery device;
receiving, in response to a first input prompt, a first user input selecting an on-person target motion profile of the first medicament delivery device;
receiving, in response to a second input prompt, a second user input selecting a fixed location target motion profile for the second medicament delivery device;
receiving, from the first medicament delivery device, a first wireless signal associated with a first actual motion profile of the first medicament delivery device, the first actual motion profile including any of a position, a velocity, an acceleration, or an orientation of the first medicament delivery device during a first time period;
receiving, from the second medicament delivery device, a second wireless signal associated with a second actual motion profile of the second medicament delivery device, the second actual motion profile including any of a position, a velocity, an acceleration, or an orientation of the second medicament delivery device during a second time period;

producing a first notification indicating that a change in the position of the first medicament delivery device during the first time period is below a threshold associated with the on-person target motion profile; and
suppressing a second notification indicating that a change in the position of the second medicament delivery device during the second time period is below the threshold associated with the on-person target motion profile.

12. The computer-implemented method of claim 11, further comprising:
receiving, from the first medicament delivery device, a third wireless signal to maintain the first communications link, the third wireless signal being periodic;
determining, based on the third wireless signal, a relative position between the mobile computing device and the first medicament delivery device; and
producing a third notification when the relative position exceeds a relative position threshold.

13. The computer-implemented method of claim 12, wherein the producing the third notification includes producing the third notification when the third wireless signal is not received within a third time period.

14. The computer-implemented method of claim 11, wherein the first medicament delivery device is any one of an auto-injector, a pen injector, a medication pump, a prefilled syringe, a nasal delivery device or an inhaler.

15. The computer-implemented method of claim 11, further comprising:
receiving, from the first medicament delivery device, a third wireless signal associated with a temperature profile of the first medicament delivery device; and
producing a third notification when the temperature profile is outside of a predetermined temperature range.

16. A computer-implemented method, comprising:
establishing a communications link, via a short-range wireless protocol, between a mobile computing device and a medicament delivery device;
receiving, in response to an input prompt, a user input selecting a target motion profile of the medicament delivery device;
receiving, from the medicament delivery device, a first wireless signal associated with an actual motion profile of the medicament delivery device;
receiving, from the medicament delivery device, a second wireless signal associated with a temperature profile of the medicament delivery device;
analyzing the actual motion profile to determine if a magnitude of the actual motion profile is outside of a threshold associated with the target motion profile; and
producing a notification when the magnitude of the actual motion profile is outside of the threshold, the notification based on both a motion difference between the actual motion profile and the target motion profile and a temperature difference between the temperature profile and a predetermined temperature range.

17. A computer-implemented method, comprising:
establishing a communications link, via a short-range wireless protocol, between a mobile computing device and a medicament delivery device;
receiving, in response to an input prompt, a user input selecting a target motion profile of the medicament delivery device;
receiving, from the medicament delivery device, a first wireless signal associated with an actual motion profile of the medicament delivery device;

analyzing the actual motion profile to determine if a magnitude of the actual motion profile is outside of a threshold associated with the target motion profile; and producing by a first application that is executed by a processor of the mobile computing device a first notification when the magnitude of the actual motion profile is outside of the threshold;

receiving, from the medicament delivery device, a second wireless signal associated with a temperature profile of the medicament delivery device;

receiving, from a second application executed by the processor of the mobile computing device, a temperature information;

determining, within the first application and based on the temperature information received from the second application, a temperature range; and producing a second notification when the temperature profile is outside of the temperature range.

18. The computer-implemented method of claim 17, wherein the actual motion profile includes any of a position, a velocity, an acceleration, or an orientation of the medicament delivery device during a time period.

19. The computer-implemented method of claim 17, wherein the medicament delivery device is any one of an auto-injector, a pen injector, a medication pump, a prefilled syringe, a nasal delivery device or an inhaler.

20. The computer-implemented method of claim 17, wherein:
the second application is a weather application; and
the temperature information includes a local temperature.

* * * * *